(12) United States Patent
Fu et al.

(10) Patent No.: US 10,669,534 B2
(45) Date of Patent: Jun. 2, 2020

(54) NANOCAGED ENZYMES WITH ENHANCED CATALYTIC ACTIVITY AND INCREASED STABILITY

(71) Applicant: Arizona Board of Regents on behalf of Arizona State University, Scottsdale, AZ (US)

(72) Inventors: Jinglin Fu, Tempe, AZ (US); Zhao Zhao, Boston, MA (US); Neal Woodbury, Tempe, AZ (US); Hao Yan, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 255 days.

(21) Appl. No.: 15/649,351

(22) Filed: Jul. 13, 2017

(65) Prior Publication Data
US 2018/0016569 A1    Jan. 18, 2018

Related U.S. Application Data

(60) Provisional application No. 62/361,884, filed on Jul. 13, 2016.

(51) Int. Cl.
| | |
|---|---|
| C12N 11/04 | (2006.01) |
| C12N 9/96 | (2006.01) |
| B82Y 5/00 | (2011.01) |
| C12N 15/11 | (2006.01) |

(52) U.S. Cl.
CPC ............... *C12N 11/04* (2013.01); *C12N 9/96* (2013.01); *B82Y 5/00* (2013.01); *C12N 15/11* (2013.01); *C12N 2310/16* (2013.01); *C12N 2320/32* (2013.01); *Y10S 977/774* (2013.01); *Y10S 977/804* (2013.01)

(58) Field of Classification Search
CPC ........... B82Y 5/00; C12N 11/04; C12N 15/11; C12N 2310/16; C12N 2320/32; C12N 9/96; Y10S 977/774; Y10S 977/804
See application file for complete search history.

(56) References Cited

U.S. PATENT DOCUMENTS

| | | |
|---|---|---|
| 2012/0094271 A1 | 4/2012 | Fu et al. |
| 2015/0218204 A1* | 8/2015 | Yin .......................... C12Q 1/68 536/23.1 |

FOREIGN PATENT DOCUMENTS

| | | |
|---|---|---|
| WO | WO-2010027642 A2 | 3/2010 |
| WO | WO-2010028214 A2 | 3/2010 |

OTHER PUBLICATIONS

Zhao et al. Nature Communications, Feb. 10, 2016, pp. 1-9. http://www.nature.com/naturecommunications. (Year: 2016).*
Bellot, G., McClintock, M. A., Lin, C. X. & Shih, W. M. Recovery of intact DNA nanostructures after agarose gel-based separation. Nat. Methods. 8, 192-194 (2011). (Year: 2011).*
Bellot et al. Nat. Methods. 8, 192-194 (2011). Supplementary Material (Year: 2011).*
Abelson, J. et al. Conformational dynamics of single pre-mRNA molecules during in vitro splicing Nat. Struct. Mal. Biol. 17, 504-512 (2010).
Andersen. E. S. et al. Self-assembly of a nanoscale DNA box with a controllable lid. Nature 459, 73-76 (2009).
Bellot, G., McClintock, M. A, Lin, C. X., Shih, W. M. Recovery of intact DNA nanostructures after agarose gel-based separation. Nat. Methods. 8, 192-194 (2011).
Betancor , L., and Luckarift, H. R. Bioinspired enzyme encapsulation for biocatalysis. Trends. Biotechnol. 26, 566-572 (2008).
Blanco, M. & Walter, N. G. Analysis of Complex Single-Molecule FRET Time Trajectories. Method. Enzymol. 472, 153-178 (2010).
Bruns, N. & Tiller, J. C. Amphiphilic network as nanoreactor for enzymes in organic solvents. Nano Lett. 5, 45-48 (2005).
Castello, A et al. Insights into RNA Biology from an Atlas of Mammalian mRNABinding Proteins. Cell 149, 1393-1406 (2012).
Chapman, AD., Cortes, A, Dafforn, T. R., Clarke, AR. & Brady, R. L. Structural basis of substrate specificity in malate dehydrogenases: crystal structure of a ternary complex of porcine cytoplasmic malate dehydrogenase, alpha-ketomalonate and tetrahydoNAD. J Mal Biol. 285, 703-712 (1999).
Chen, A. H. & Silver, P. A. Designing biological compartmentalization. Trends. Cell.Biol. 12, 662-670 (2012).
Chuprina, V. P., Heinemann, U., Nurislamov, A A, Zielenkiewicz, P., Dickerson, R. E. & Saenger W. Molecular dynamics simulation of the hydration shell of a B-DNA decamer reveals two main types of minor-groove hydration depending on groove width. Proc. Nati. Acad Sci. USA 88, 593-597 (1991).
Ciesla, J. Metabolic enzymes that bind RNA: yet another level of cellular regulatory network? Acta Biochim Pol. 53, 11-32 (2006).
Comellas-Aragones, M. et al. A virus-based single-enzyme nanoreactor. Nature Nanotech. 2, 635-639 (2007).
Douglas, S. M., Bachelet, I., Church, G. M. A logic-gated nanorobot for targeted transport of molecular payloads. Science 335, 831-834 (2012).
Douglas, S. M., Dietz, H., Liedl, T., Hogberg, B., Graf, F. & Shih, W. M. Self-assembly of DNA into nanoscale three-dimensional shapes. Nature 459, 414-418 (2009).
Eanes, R.Z., and Kun, E. Separation and characterization of aconitate hydratase isoenzymes from pig tissues. Biochim. Biophys. Acta 227, 204-210 (1971).
English, B. P., et al. Ever-fluctuating single enzyme molecules: Michaelis-Menten equation revisited. Nat. Chem. Bio. 2, 87-94 (2006).
Erkelenz, M., Kuo, C. H. & Niemeyer, C. M. DNA-Mediated Assembly of Cytochrome P450 BM3 Subdomains, J Am. Chem. Soc. 133, 16111-16118 (2011).

(Continued)

*Primary Examiner* — Janet L Epps-Smith
(74) *Attorney, Agent, or Firm* — Duane Morris LLP

(57) ABSTRACT

The present disclosure describes a nanoparticle comprising a three dimensional DNA nanocage and a payload biological macromolecule, and methods of assembly thereof.

19 Claims, 67 Drawing Sheets
(65 of 67 Drawing Sheet(s) Filed in Color)
Specification includes a Sequence Listing.

(56) References Cited

OTHER PUBLICATIONS

Fiedler, J. D., Brown. S. D., Lau. J. & Finn. M. G. RNA-directed packaging of enzymes within virus-like particles. Angew. Chem. Int. Ed 49, 9648-9651 (2010).
Fu, J., Liu, M., Liu, Y. & Yan, H. Spatially-Interactive Biomolecular Networks Organized by Nucleic Acid Nanostructures, Acc. Chem. Res. 45, 1215-1226 (2012).
Fu, J., Liu, M., Liu, Y., Woodbury, N. W. & Yan, H. Interenzyme Substrate Diffusion for an Enzyme Cascade Organized on Spatially Addressable DNA Nanostructures. J. Am. Chem. Soc. 134, 5516-5519 (2012).
Fu, J., Yang, Y. R., Johnson-Buck, A, Liu, Y., Walter, N. G., Woodbury, N. W., and Yan, H. Multi-enzyme complexes on DNA scaffolds capable of substrate channeling with an artificial swinging arm, Nature Nanotechnol. 9, 531-536 (2014).
Fu, Y., et al. Single-Step Rapid Assembly of DNA Origami Nanostructures for Addressable Nanoscale Bioreactors. J Am. Chem. Soc. 135, 696-702 (2013).
Gao, Y., Roberts, C. C., Zhu, J., Lin, J., Chang, C. A & Wheeldon, I. Tuning Enzyme Kinetics through Designed Intermolecular Interactions Far from the Active Site. ACS Catal. 5, 2149-2153 (2015).
Gourevitch, B. & Eggermont, J. J. A nonparametric approach for detection of bursts in spike trains. Journal of Neuroscience Methods 160, 349-358 (2007).
Graff, A., Winterhalter, M. & Meier, W. Nanoreactors from polymer-stabilized liposomes. Langmuir 17, 919-923 (2001).
Gray M. J., et al. Polyphosphate is a primordial chaperone. Mol. Cell. 53, 689-699 (2014).
Guo, S., Cao, R., Lu, A, Zhou, Q., Lu, T., Ding, X., Li, C. and Huang, X. One of the possible mechanisms for the inhibition effect of Tb(III) on peroxidase activity in horseradish (*Armoracia rusticana*) treated with Tb(III). J. Biol. Inorg. Chem. 13, 587-597 (2008).
Hammes, G. G., Benkovic, S. J. & Hammes-Schiffer, S. Flexibility, Diversity, and Cooperativity: Pillars of Enzyme Catalysis. Biochemistry 50, 10422-10430 (2011).
Han, D., Pal, S., Nangreave, J., Deng, Z., Liu, Y. & Yan, H. DNA origami with complex curvatures in three-dimensional space. Science 332, 342-346 (2011).
Hartl, F. U. Molecular chaperones m cellular protein folding Nature 381, 571-580 (1996).
Hecht, H. J., Kalisz, H. M., Rendle, J., Schmid, R. D. & Schomburg D. Crystal structure of glucose oxidase from Aspergillus niger refined at 2.3 A resolution. J Mol Biol. 229, 153-172 (1993).
Henriksen, A, Schuller, D. J., Gajhede, M. Structural interactions between horseradish peroxidase C and the substrate benzhydroxamic acid determined by X-ray crystallography. Biochemistry 37, 8054-8060 (1998).
Horikiri, S., Aizawa, Y., Kai, T., Amachi, S., Shinoyama, H. and Fujii, T. Electron acquisition system constructed from an NAD-independent D-lactate dehydrogenase and cytochrome c2 in Rhodopseudomonas palustris No. 7. Biosci. Biotechnol. Biochem. 68, 516-522 (2004).
Hurtley, S. Location, Location, Location. Science 326, 1205 (2009).
Jacobson, R. H., Zhang, X. J., DuBose, R. F. & Matthews, B. W. Three-dimensional structure of beta-galactosidase from *E.coli*. Nature 369, 761-766 (1994).
Jana, B., Pal, S., Maiti. P. K., Lin. S., Hynes, J. T. & Bagchi, B. Entropy of Water in the Hydration Layer of Major and Minor Grooves of DNA J Phys. Chem. B 110, 19611-19618 (2006).
Jiang, Q., Song, C., Nangreave, J., Liu, X., Lin, L., Qiu, Z., Wang, Z., Zou, G., Liang, X., Yan, H., Ding, B. DNA origami as a carrier for circumvention of drug resistance. J Am. Chem. Soc. 134, 13396-13403 (2012).
Juul, S., et al. Temperature-Controlled Encapsulation and Release of an Active Enzyme in the Cavity of a Self-Assembled DNA Nanocage. ACS Nano 7, 9724-9734 (2013).
Ke, Y., Ong, L. L., Shih, W. M. & Yin, P. Three-dimensional structures self-assembled from DNA bricks. Science, 338, 1177-1183 (2012).

Kerfeld, C. A., Sawaya, M. R., Tanaka, S., Nguyen, C. V., Phillips, M., Beeby, M. & Yeates, T. 0. Protein structures forming the shell of primitive bacterial organelles. Science 309, 936-938 (2005).
Kerfeld, C. A., Heinhorst, S. & Cannon, G. C. Bacterial microcompartments. Annu. Rev.Microbial. 64, 391-408 (2010).
Kuzyk, A et al. DNA-based self-assembly of chiral plasmonic nanostructures with tailored optical response. Nature 483, 311-314 (2012).
Langecker, M., Arnaut, V., Martin, T., List, J., Renner, S., Mayer, M., Dietz, H., & Simmel, F. Synthetic lipid membrane channels by designed DNA nanostructures. Science 338, 932-936 (2012).
Leberman, R. & Soper, A K. Effect of high salt concentrations on water structure. Nature 378, 364-366 (1995).
Levy, Y. & Onuchic, J. N. Water and proteins: A love-hate relationship. Proc. Natl. Acad Sci. USA 101, 3325-3326 (2004).
Lin, J. & Wheeldon, I. Kinetic Enhancements in DNA-Enzyme Nanostructures Mimic the Sabatier Principle ACS Catal. 3, 560-564 (2013).
Linko, V., Eerikainen, M. & Kostiainen, M. A modular DNA origamibased enzyme cascade nanoreactor. Chem. Commun. 51, 5351-5354 (2015).
Liu, B., Baskin, R. J. & Kowalczykowski, S. C. NA unwinding heterogeneity by RecBCD results from static molecules able to equilibrate. Nature 500, 482-485 (2013).
Liu, M., Fu, J., Hejesen, C., Yang, Y., Woodbury, N. W., Gothelf, K., Liu, Y. & Yan, H. A DNA Tweezer-Actuated Enzyme Nanoreactor. Nature Commun. 4, 1-5 (2013).
Liu, Y. et al. Biomimetic enzyme nanocomplexes and their use as antidotes and preventive measures for alcohol intoxication. Nature Nanotech. 8, 187-192 (2013).
Lovell, S. L. & Winzor, D. J. Effects of phosphate on the dissociation and enzymic stability of rabbit muscle lactate dehydrogenase. Biochemistry 13, 3527-3531 (1974).
Marcus, Y. Effects of ions on the structure of water: structure making and breaking. Chem. Rev. 109, 1346-1370 (2009).
Mei, Q., Wei, X., Su, F., Liu, Y., Yongbull, C., Johnson, R., Lindsay, S., Yan, H., Meidrum, D. Stability of DNA origami nanoarrays in cell lysate. Nano Lett. 11, 1477-1482 (2011).
Mei, Q., Johnson, R.H., X. Wei, F. Su, Y. Liu, L. Kelbauskas, S. Lindsay, D. R. Meldrum, and H. Yan, On-chip Isotachophoresis Separation of Functional DNA Origami Capture Nanoarrays from Cell Lysate, Nano Research, 6, 712-719 (2013).
Michelotti, N. et al. A bird's eye view tracking slow nanometer-scale movements of single molecular nano-assemblies. Methods Enzymol. 475, 121-148 (2010).
Moelberta, S., Normandb, B. & Rios, P. D. L. Kosmotropes and chaotropes: modelling preferential exclusion, binding and aggregate stability. Biophys. Chem. 112, 45-57 (2004).
New England Biolabs, "M13mp18 Single-stranded DNA" [online], New England Biolabs, retrieved on Aug. 27, 2019 from archive.org, as it appeared on Mar. 16, 2016, retrieved from the internet: <URL:https://web.archive.org/web/20160316090101/neb.com/products/n4040-m13mp18-single-stranded-dna#tabselect0>.
Ramanathan, A & Agarwal P. K. Evolutionarily Conserved Linkage between Enzyme Fold, Flexibility, and Catalysis. PLoS Biol. 9, 1-17 (2011).
Ramanathan, A, Savol, A, Burger, V., Chennubhotla, C. S. & Agarwal, P. K. Protein Conformational Populations and Functionally Relevant Substates. Acc. Chem. Res. 47, 149-156 (2014).
Rinaldi, A J., Lund, P. E., Blanco, M. R. & Walter, N. G. The Shine-Dalgarno sequence of riboswitch-regulated single mRNAs shows ligand-dependent accessibility bursts. Nat. Commun., 8976 (2015), 10 pages.
Rowland, P., Basak, AK., Gover, S., Levy, H. R. & Adams, M. J. The three-dimensional structure of glucose 6-phosphate dehydrogenase from Leuconostoc mesenteroides refined at 2.0 A resolution. Structure 2(11), 1073-1087 (1994).
Rudiuk, S., Venancio-Marques, A & Baigl, D. Enhancement and modulation of enzymatic activity through higher-order structural changes of giant DNA-protein multibranch conjugates. Angew. Chem. Int. Ed 51, 12694-12698 (2012).

(56) References Cited

OTHER PUBLICATIONS

Sang, L. & Coppens, M. Effects of surface curvature and surface chemistry on the structure and activity of protein adsorbed in nanopores. Phys. Chem. Chem. Phys.13, 6689-6698 (2011).
Sung, J. Y. & Lee, Y. N. Isoforms of glucose 6-phosphate dehydrogenase in Deinococcus radiophilus. J Microbial. 45, 318-325 (2007).
Timasheff, S. N. Protein-solvent preferential interactions, protein hydration, and the modulation of biochemical reactions by solvent components. Proc. Natl. Acad Sci. 99, 9721-9726 (2002).
Timm, C. & Niemeyer, C. M. Assembly and Purification of Enzyme-Functionalized DNA Origami Structures. Angew. Chem. Int. Ed 54, 6745-6750 (2015).
Veitch, N. C. Horseradish peroxidase: a modern view of a classic enzyme. Phytochemistry 65, 249-259 (2004).
Vriezema, D. M., Aragones, M. C., Elemans, J., Cornelissen, J., Rowan, A E. & Nolte, R. J. M. Self-assembled nanoreactors. Chem. Rev. 105, 1445-1490 (2005).
Widom, J. R., Dhakal, S., Heinicke, L. A & Walter, N. G. Single-molecule tools for enzymology, structural biology, systems biology and nanotechnology: an update. Arch. Toxicol. 88, 1965-1985 (2014).
Wilner, 0. I., Weizmann, Y., Gill, R., Lioubashevski, 0., Freeman, R. & Willner, I. Enzyme cascades activated on topologically programmed DNA scaffolds. Nature Nanotechnol. 4, 249-254 (2009).
Wong, C. M., Wong, K. H. and Chen, X. D. Glucose oxidase: natural occurrence, function, properties and industrial application. Appl. Microbial. Biotechnol. 78, 927-938 (2008).
Zhao, H. Effects of ions and other compatible solutes on enzyme activity, and its implication for biocatalysis using ionic liquids. J Mal. Catal. B-Enzym. 37, 16-25 (2005).
Zhao, H., Olubajo, 0., Song, Z., Sims, AL., Person, T. E., Lawal, R. A & Holley, L. A Effect of kosmotropicity of ionic liquids on the enzyme stability in aqueous solutions. Bioorg. Chem. 34, 15-25 (2006).
Zhao, Z. et al., "Nanocaged enzymes with enhanced catalytic activity and increased stability against protease digestion", Nature Communications, Feb. 2016, vol. 7, article 10619 and supl. S1-S106 <DOI:10.1038/ncomms10619>.

* cited by examiner

Cross-sectional view

3D View

|  | $K_M$ (μM) | $k_{cat}$ (s$^{-1}$) |
|---|---|---|
| Full Cage[HRP] | 4.3±0.6 | 290±5 |
| Free HRP | 2.3±0.5 | 32±1 |

|  | $K_M$ (µM) | $K_{cat}$ (s$^{-1}$) |
|---|---|---|
| AB-GOx | 3000±600 | 1300±50 |
| GOx control | 6200±900 | 240±10 |

|  | $K_M$ (µM) | $k_{cat}$ (s$^{-1}$) |
| --- | --- | --- |
| Full[LDH] | 17.0±1.5 | 190±5 |
| LDH control | 7.2±1.3 | 46±2 |

|  | $K_M$ (μM) | $k_{cat}$ (s$^{-1}$) |
|---|---|---|
| SH-G6pDH | 411±32 | 520±10 |
| SS-G6pDH | 436±26 | 620±10 |
| DS-G6pDH | 527±37 | 900±20 |
| G6pDH control | 340±47 | 100±10 |

SEQUENCE LISTING

<160> NUMBER OF SEQ ID NOS: 1395

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtggagagg cggtttgcgt ttt                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgagttgggt aacgccaggt ttt                                            23

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttcgcca ttcagg                                                    16

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttttgccagc tttcatcaac attcgt                                         26

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tttttggagc aaacaagaga atcggaagat tagc                                34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttttgggaga agcctttatt tcaaaaaggg acag                                34

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggtggcatca attcatgggc gcgacctgtt tgtataagca aatttt                46

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atataaagta gtagatgggc gctttt                                      26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aatcatacta atagtagtag catttt                                      26

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gctgtcatag caccgagctc gaattcgttt t                                31

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttttgagga ctaaagactt tcaacactaa gg                               32

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cggttttgct ttgcgctagt gagctaactc acatttt                          37

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttttgaagga ttaggattag cggtagcaac gcga                                 34

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttttaaaagg gcgacattca accaggc                                         27

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgactaatat gtttgatgtt tgccccagca ggctttt                              37

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttttaggctt atccggtatt ctagttt                                         27

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctcaacaagt atcacataat ttattaaagt tccagtttgg aacatttt                  48

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttttagagtc cacactagaa aatt                                            24

```
<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttttgaaaat cctcagagag atttt                                            25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttttattggg cggagccacc atttt                                            25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttttaattgc gaaacaactt tt                                               22

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttttaatcat ggctcattca gtttt                                            25

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttttgttttc ccagtcattt tt                                               22

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttttatcgta accgtggcaa agcgccattt t                                     31

<210> SEQ ID NO 25
```

<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttttatttaa attgtggcct tcctgtattt t                              31

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttttgagaca gtcaaatgcc tgagagtctt tt                             32

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttttagcctc agagcataaa gcttaatact tttgctttt                      39

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttttaacatc caatattaag caataatttt                                30

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttttaaatgg tcaataagct gaaaatttt                                 29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttttattccc aatgatacat ttcgctttt                                 29

<210> SEQ ID NO 31
<211> LENGTH: 28

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttttaaatat gcaactaaca gttgtttt                                              28

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttttgcggat ggcctcaaca tgtttt                                                26

<210> SEQ ID NO 33
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttttgtttac cagacgacga taatagcaaa aaatcattga gaaaggccgt ttt                  53

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttttacataa cgccaaatca taaccctctt tt                                         32

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttttagaaag atactaatgc agatttt                                               27

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttttggaaga aaaatctatt acaggtttt                                             29

<210> SEQ ID NO 37
<211> LENGTH: 29
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 37
ttttgaatta cctgtcagga cgttgtttt                                            29

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttttgaataa ggtaaattgg gctttt                                               26

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttttcaccct cagcaggcta cagaggcttt t                                         31

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttttatattc ggtttgcggg atcgtttt                                             28

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttttgatacc gatagtcata accgatttt                                            29

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttttaattgt acttaaacag ctttt                                                25

<210> SEQ ID NO 43
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
ttttaataat tttttaagga gccttttt                                              27

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttttcaacag ttaggaattg cgaatt                                                26

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttttcggaac ctatgactcc tcaagatttt                                            30

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttttgtcagt gccccccctg cctatttt                                              28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttttcataca tggcttttaa cgggtttt                                              28

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttttcattaa agcttccagt aagcgtttt                                             29

<210> SEQ ID NO 49
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
ttttaggttg aggcagataa atcctttt                                         28

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttttccctca gagagcattg acaggtttt                                        29

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttaagtttat tttgagcgcc aaagactttt                                       30

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttttatacat acaacaccac ggaatttt                                         28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ttttgaactg gcatgaacgt agaaattt                                         28

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttttcaaagt tacgaatacc caaaatttt                                        29

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 55
ttttgcaata gctatcatag ccgaatt                                     27

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttttaaccca caaacaatg aaatatttt                                    29

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ttttcgagaa caagcaatca gatatagatt tt                               32

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttttagaaac caataccgca ctcattttt                                   29

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttttacgcgc ctgtttcgag catgttttt                                   29

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ttttataaag tacagctaat gcagatttt                                   29

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tttttgagaa tcgccataag agaattttt                                    29

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ttttagcctg tttgtagggc ttaattttt                                    29

<210> SEQ ID NO 63
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gactccaata aacaccaggg aagcgcataa gtcagcggca aatgcagca              49

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gaaccatcgt aaagcactaa acttgacg                                     28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tagggttccg aaatagggta aacaaatc                                     28

<210> SEQ ID NO 66
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggtcaaaaga atagagggcg aaaaaccgta aataagagaa ttaa                   44

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ataaaaggaa cacccaccac cgg                                            23

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gggaaagggg cgctggcaag tcgctgcgcg taaccttgac ga                       42

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agcggtcctt ttcaccctca gatttagc                                       28

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtagctcttt agagtcggaa catggcccac tacgt                               35

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cggccaacgc tttcttttct gaatggct                                       28

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctgcattgac gggcagagag tatccctt                                       28

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcacgtaagc taaacaggag gttttataat cagtggtaaa ag        42

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcccgcgcgg ggtttttcac gctgggtggt tgagtgttga acgtg        45

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtcgtttttc cagagtaatc ttg        23

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tggggtgtgt gtgacaaatc actcgaac        28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aggccatgag cgggtaacgt gctggtca        28

<210> SEQ ID NO 78
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agtctgtcac ttgcctgagt aatccagaac aatatacgct ca        42

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79

```
cacgaagtgt ccgattaggt tgctaccaca cggcg                                    35

<210> SEQ ID NO 80
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gaggatcaaa cgacaattgc tcagtttgta ggtcaaaatg tgaataatt                     49

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcaggtcatc cgcttaaagt ggaaacct                                            28

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttgcacgtca ggatgtatcg gggcggatcg tcggaaccaa ta                            42

<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgcaaggact gttggtgccg gaaaccagca tctgcccttt tgttaa                        46

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gaaatattgg taatgaagaa cacaccga                                            28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
atcgtctatt tacacagaga tagcgcac                                            28
```

<210> SEQ ID NO 86
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctgcgcacga ttaacgttgt acccgggttg tttcccctaa tgcact          46

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgatcggaaa gggggccaag c          21

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
attcacccat tttgtaccgc cataacatcc at          32

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cggcaccgac gacataga          18

<210> SEQ ID NO 90
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
aagataaccc ttctagccct aattaaaaac gctgagagct ca          42

<210> SEQ ID NO 91
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agaatacgtc tttaaccagc aaacaccgcc tgcaaaaatc ta          42

<210> SEQ ID NO 92
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tggtcggtgt catataatag gacagaccag aaaaaatcta aag                43

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aaacaggaac aaaccctcag gtccagccct cttcgctgga tt                 42

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
aacaacctga ccgtgacttc aaatat                                   26

<210> SEQ ID NO 95
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
acgaaccatg cgcgaactga tgacctgatg gccaattggc ag                 42

<210> SEQ ID NO 96
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cgcgtctaaa cgttagtttc aacgagtaaa ctttgtttt                     39

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
aatcagccag cagcaatcaa caattgagga tttagaagga ga                 42

```
<210> SEQ ID NO 98
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aagcatctca atatatatct ttcaatagat aatacacaat tc                         42

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
agttgtgtac cccgtttgtt atttttttatt ctccgtgtcg cc                        42

<210> SEQ ID NO 100
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtaaaacatc agaacagaaa acgaga                                           26

<210> SEQ ID NO 101
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atctaaactg gtcagttggc aaaatgaaca gtgccatacc ga                         42

<210> SEQ ID NO 102
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aggtcattca ccattcattt gactgcggta acggattga                             39

<210> SEQ ID NO 103
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gagagatacc gttctagctg atgcctgaga acccttggaa gg                         42

<210> SEQ ID NO 104
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
atgccgtatt agacatcatt t                                              21

<210> SEQ ID NO 105
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
gacaactttt aaaaaattat ccatcaatat aatcctgatt gtaccagaa                49

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
tgcggtaaat gcaataaatt agggtagctc aatcataaaa gg                       42

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107
ggagcgggtt tgagtaacat ttttacaaat ttgaggaagg tt                       42

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108
gaccctgaaa tcggaaagaa taaaccaagt aagagttca                           39

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 109
cctacaagat aaaaattttt agtaatgttt tgccagaggg                          40

<210> SEQ ID NO 110
<211> LENGTH: 49

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gttagaacaa aattgtagat tttcagaggc tttgcttgta ccaacatat          49

<210> SEQ ID NO 111
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tgaataacat atatttaaca agaaaacctt ggattatact tc                 42

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcatagcgtc tacgagggaa taccacagca tagttaaaaa ac                 42

<210> SEQ ID NO 113
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aagaagtgta ggtaatattc actacaaagg taatc                         35

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggtaatagta aaccaaccta aaac                                     24

<210> SEQ ID NO 115
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgaatccccc tcaaatgttc aatatgaaga ttcacgcaag acattat             47

<210> SEQ ID NO 116
<211> LENGTH: 42
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 116
tattagtttg ataaaacggc tcatacaatg attcgaggat ac         42

<210> SEQ ID NO 117
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caggtttatc tttaaacagt taagcccctg ttaaacatca aaagcgagt    49

<210> SEQ ID NO 118
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ccctgacaaa agattaagag aaatatttaa aaacagatga acggctatc    49

<210> SEQ ID NO 119
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aaagcggatt taaattgttg atatagcatg tattttt                37

<210> SEQ ID NO 120
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cccgaaaaat gggaagggga cgcttctggg aaggg                  35

<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cgcgttttaa ttga                                         14

<210> SEQ ID NO 122
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 122
ttgacgtaac tgacgagtat gggaagtgag aaaccgccca ga                          42

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagaccgtac ctttggccag tgatgtgc                                          28

<210> SEQ ID NO 124
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gaggaagcaa ggatattatc aagacgttag ttctaaagcc tc                          42

<210> SEQ ID NO 125
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gggccttgct acgccagctg gcgtgcgggc agctttc                                37

<210> SEQ ID NO 126
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gaaggcaatg tttaataaat attcat                                            26

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gaaagaggca aaagagggtt gata                                              24

<210> SEQ ID NO 128
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 128
gataaccatc ggcttgctac tggtacagtg ccagtatggg ca                          42

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tcatcttaag tacaacggaa caatcgtcga ctggaagtgc aa                          42

<210> SEQ ID NO 130
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
taccaagcgc gaaacatgac ccccagcgat ta                                     32

<210> SEQ ID NO 131
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ccatatgcga aactttaat cattgt                                             26

<210> SEQ ID NO 132
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
aagaaaaaag atcagctata ttcagaaagc gagaaaagaa ac                          42

<210> SEQ ID NO 133
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tacttaggaa ccgagtgtac acgagcttca aaggatggga ag                          42

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 134
acggtcaatg tcagaagc                                                 18

<210> SEQ ID NO 135
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gagatggttt aatttcaagg ctgtagttag agcataagag gtca                    44

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
taggcacatg aacgactgac cgacttta                                      28

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ccacaacgcc tgta                                                     14

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaccttccat taccaattgt tgactcta                                      28

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
acccacacat caaactattg cct                                           23

<210> SEQ ID NO 140
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tgaacgaggg ggttttgtat taaggattga gtcatatgag aacgcccaa            49

<210> SEQ ID NO 141
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tccattaata cgtaatgcct aaatagcgag gtttaacgtc aggggtaaa            49

<210> SEQ ID NO 142
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
aacggagtac caagttacaa ggcggagagg aagtt                          35

<210> SEQ ID NO 143
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
aagacattca tcatcagaca acattacgtt aaccattatc tgcgattcc            49

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gccgtcgaga atacactaaa gcaactac                                  28

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
taagtatagc cccaccgtca ccga                                      24

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
tttagtaccg ccaccctact taacac								26

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ccgccaccgc gacctgctcc tgagatttgt atcatcaaaa at							42

<210> SEQ ID NO 148
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ttttcggttt gctccaacac gttgcgagta gcttgcccaa a							41

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gggatagtga gtttcgtcaa aaacatgt								28

<210> SEQ ID NO 150
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gaagattggc ccagagcagc cctttaataa gcaacgccgc caacg						45

<210> SEQ ID NO 151
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcattccaca gaca										14

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gtaacgaaaa tgaacagtcg gtaaagcc					28

<210> SEQ ID NO 153
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctagaatcaa cgagccggaa gcacacaatt aagaaccact ccaaca					46

<210> SEQ ID NO 154
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tgatattctg ggccgcttcg ctgagcccac gtgcgccgta ta					42

<210> SEQ ID NO 155
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cattaagctc agtaccaaat cgcgcagaag acgga					35

<210> SEQ ID NO 156
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
atgataaaca caatagaaaa gaaatttatt tggtatta					38

<210> SEQ ID NO 157
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
agagcgtaaa aggtgaatta tggaataggt gtaggcgtaa gt					42

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cttgagccat ttcgggaggt tttg                                          24

<210> SEQ ID NO 159
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
caatgtgagt caccgtactc aggagg                                        26

<210> SEQ ID NO 160
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
attagcaagg ccggaacagt agcaccatta cc                                 32

<210> SEQ ID NO 161
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aggctctgaa tccttatacg caatatagat ataaacaa                           38

<210> SEQ ID NO 162
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gtttggtaga aaccatcgat acaccaccct catctcacag aa                      42

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tcagtagcga caacgagcgt cttt                                          24

<210> SEQ ID NO 164
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cgtttgccag ccctcataga gccccagtac aaactaggcg ca                      42

<210> SEQ ID NO 165
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tcaaatagca gcct                                                        14

<210> SEQ ID NO 166
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
accttgagcg gttaagcccg gaattatgcg ttatacaa                              38

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
accggaagcc gccaccagtg aaatgaat                                         28

<210> SEQ ID NO 168
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
agaccagagc ctgaacatag acggggcgtt atgaccta                              38

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aagattgccc tttcctcggc cag                                              23

<210> SEQ ID NO 170
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tattgaaaat tacatttaat agcgaaatgg agggaaggta aaaattatt                  49

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acctcacaat gttaatgttg agtaaataag ttttgatgtg aa                              42

<210> SEQ ID NO 172
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aagccttaaa tcgagtgaat aattttccat tcc                                       33

<210> SEQ ID NO 173
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
acacccatcc tcggctgtct ttccttatcc taagaaaa                                  38

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
caattttatc ctgaatccgc ccagcaaaat cacacgtcac                                40

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gactttaccg cagaatgcaa acaagtcaga ccaactaatc ag                             42

<210> SEQ ID NO 176
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ccagagccta atgtgaattt taacctccag acgacgacaa agtcctg                        47

<210> SEQ ID NO 177
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 177
aggtaagcag ttaccgacgc cgccccgcca caccctcacc ag					42

<210> SEQ ID NO 178
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 178
cgatttcgag aggtaaagta attctgtccg gagaggca					38

<210> SEQ ID NO 179
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 179
tttaatacac ctttagcgtc acatagcccc ctttgtgttt ca					42

<210> SEQ ID NO 180
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 180
tccaaataag aaacgaatat tatttatccc aa					32

<210> SEQ ID NO 181
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
aaaacaattc gtcaaaatg attttcataa tcacactatt ag					42

<210> SEQ ID NO 182
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182
ttacagagag aaaagaaca tttcat					26

<210> SEQ ID NO 183

```
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctcccccgaa ccgcctggcc ctgaacagct ccgcctcttt tgtcgt                         46

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcatttgtca atatattcat t                                                   21

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tagcaagcaa agccgttcgc aaagtaaagg tttagcaatt aa                             42

<210> SEQ ID NO 186
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aggaagtaag attagttgct aaacctcccg acttggggaa tt                             42

<210> SEQ ID NO 187
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aaccaagtca ataataattt aatcaacaaa taacgcaga                                 39

<210> SEQ ID NO 188
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aagaacgtca tcgtaccgcg cgaggcgttt caatt                                     35

<210> SEQ ID NO 189
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ataatattat attttgcacc cagcta                                               26

<210> SEQ ID NO 190
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aacaatattg ccagttacaa atattaccaa cgctagaatc aa                             42

<210> SEQ ID NO 191
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
catgttccga caaaccagta atatttaaag caagagaat                                 39

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gaggcatgga aataaacagc cttttttg                                             28

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cttaccagta taaaaacatg taatttacta acata                                     35

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
attcttcaat aagaacgtca acccgaga                                             28

<210> SEQ ID NO 195
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 195
ctaccggcga gaggtgccac ccaaatcaag tttt                                  34

<210> SEQ ID NO 196
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ttttgctcat ggaaatacct aagtcacata aagggacat tcaagcgta                   49

<210> SEQ ID NO 197
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tataatcgca cttaggttgg gttatacctt ttatcaaaat catagtttt                  49

<210> SEQ ID NO 198
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cttgaaatat taattaacct tgcttctgtt tt                                    32

<210> SEQ ID NO 199
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tttttagatt aagacgctga gaagagtcta gaatc                                 35

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ttttaatgct gatgcaaatc cttatcccaa                                       30

<210> SEQ ID NO 201
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 201
aatttaatta gttagcgaga aaactttt                                            28

<210> SEQ ID NO 202
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ttttccgacc gtgtgatcta tcacctaaag                                          30

<210> SEQ ID NO 203
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ttttggggtc acgtggcgag aaaggaattt t                                        31

<210> SEQ ID NO 204
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ttttagaaag cgaaggagc gccgccgcgc ttaatgcgtt tt                             42

<210> SEQ ID NO 205
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tttttacagg gcgcgtacta taagggattt tagacaggtt tt                            42

<210> SEQ ID NO 206
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ttttgtacgc cagaatcctg agcaaattaa ccgttgtatt tt                            42

<210> SEQ ID NO 207
<211> LENGTH: 43
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 207
tttttacttc tttgattagt aagccattgc aacaggaaat ttt                    43

<210> SEQ ID NO 208
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tttttacctt ttacatcgat gaatatacag tattt                            36

<210> SEQ ID NO 209
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ttttattacc tgagcaaagg cgaattattc attttt                           36

<210> SEQ ID NO 210
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ttttaaacag tacataaaaa ttaccttttt taattttt                         38

<210> SEQ ID NO 211
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ttttataaca tcacaatatt actttt                                      26

<210> SEQ ID NO 212
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ttttcgccag ccattgcaac tccagaactt gcctacttct tgattagta tttt        54

<210> SEQ ID NO 213
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 213
ttttatcgtc tgaggacatt cttttt                                              26

<210> SEQ ID NO 214
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ttttggccaa cagagataga ataaaagaat ggattacatt ttgacgctca tttt              54

<210> SEQ ID NO 215
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ttttaatatt ttttaaaaat actttt                                              26

<210> SEQ ID NO 216
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ttttcgaacg aaccaccagc tcgccatgaa tggcaatacg tggcacagac tttt              54

<210> SEQ ID NO 217
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ttttcctgca acagtgccac gtcagtatta acaccgtttt                               40

<210> SEQ ID NO 218
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ttttacctca aatcaaatca actttt                                              26

<210> SEQ ID NO 219
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 219
ttttagttga aaggagcact aacaatttt                                      29

<210> SEQ ID NO 220
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ttttctaata gattaggaag tattatttt                                      29

<210> SEQ ID NO 221
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221 ttttgactttt acaccgaacg ttatttt                                       27

<210> SEQ ID NO 222
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ttttaatttt aaaagtaacc accagtttt                                      29

<210> SEQ ID NO 223
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ttttaaggag cggggcaatt catcatttt                                      29

<210> SEQ ID NO 224
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ttttatataa tcctgatgtt tttataatttt t                                  31

<210> SEQ ID NO 225
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 225
ttttaaacat agcatagtga atttt                                          25

<210> SEQ ID NO 226
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
ttttatcaaa atcatattag agtcagatag ctcccttaga atccttgatt tt            52

<210> SEQ ID NO 227
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ttttaacctc cggctgatgc atttt                                          25

<210> SEQ ID NO 228
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ttttaatcca atcatatatt ttagtttt                                       28

<210> SEQ ID NO 229
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tttttaattt catcttcgtg tgatatttt                                      29

<210> SEQ ID NO 230
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ttttaataag gcgctagaaa aagccttttt                                     29

<210> SEQ ID NO 231
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
```
ttttgtttag tatcagagcg ggagctattt t                          31

<210> SEQ ID NO 232
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ttttggaatc attaaggctt atttt                                 25

<210> SEQ ID NO 233
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ttttccggta ttcacttgcg ggaggtttt                             29

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttttgaagcc tttacaattt t                                     21

<210> SEQ ID NO 235
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ttttatcctg aatctaattt gccagtttt                             29

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ttttacaaaa taaaaacgat ttt                                   23

<210> SEQ ID NO 237
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237

```
ttttgtttaa cgaataacat aaatttt                              27
```

<210> SEQ ID NO 238
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238

```
ttttaacagg gaagcggcgc cgctacagtt tt                        32
```

<210> SEQ ID NO 239
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239

```
ttttgacatt caaaaattat tctttt                               26
```

<210> SEQ ID NO 240
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240

```
ttttattaaa ggtggaatta gagcctttt                            29
```

<210> SEQ ID NO 241
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241

```
ttttagcaaa atcacccgtc accaatttt                            29
```

<210> SEQ ID NO 242
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242

```
ttttgaaacc attcaagttt gcctttt                              27
```

<210> SEQ ID NO 243
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243

```
ttttagcgtc agacagcccc ctttt                                25
```

<210> SEQ ID NO 244
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ttttattagc gttcagagcc accactttt                                29

<210> SEQ ID NO 245
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ttttcggaac cgcctcagcg ggcgctagtt tt                            32

<210> SEQ ID NO 246
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ttttaagaga agggcggata agtttt                                   26

<210> SEQ ID NO 247
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ttttgccgtc gagtatcacc gtactttt                                 28

<210> SEQ ID NO 248
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
ttttcaggag gtttaaccgc cacctttt                                 28

<210> SEQ ID NO 249
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ttttctcaga gcctaggaac ccatgtttt                                29

<210> SEQ ID NO 250
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
ttttaccgta acactgtagc attctttt                                          28

<210> SEQ ID NO 251
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
ttttcacaga caggtcgtct ttccatttt                                         29

<210> SEQ ID NO 252
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
ttttgacgtt agtaaagccc ccgatttatt tt                                     32

<210> SEQ ID NO 253
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
ttttaaaata cgcagcgatt atttt                                             25

<210> SEQ ID NO 254
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
ttttaccaag cggacggtca atcatttt                                          28

<210> SEQ ID NO 255
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
ttttaaggga accgagtaat cttgtttt                                          28

```
<210> SEQ ID NO 256
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ttttacaaga acccttgaga tggtttt                                              27

<210> SEQ ID NO 257
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ttttaatttc aacttctacg ttaatttt                                             28

<210> SEQ ID NO 258
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ttttaaaacg aagatacata acgctttt                                             28

<210> SEQ ID NO 259
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ttttcaaaag gaattagaac catcaccctt tt                                        32

<210> SEQ ID NO 260
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
actacgtcga ggcaaagttt tccctcataa cgcctgagtt tcgaca                         46

<210> SEQ ID NO 261
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
agtgttgagg gcgaaaaacc gctatcattg agaat                                     35

<210> SEQ ID NO 262
```

```
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gatagactgc taaagccgcc accagatccc ctcagggaag ggtgcgcgt          49

<210> SEQ ID NO 263
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
aggcctcaga acagagagtc aaaaaataag acagccattt tt                 42

<210> SEQ ID NO 264
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
aagagttgca gcaaaatcct gtttgaaaaa ccgccagcgc ta                 42

<210> SEQ ID NO 265
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tgagaccgaa caccttaatt gagaatacat tcttagtgct ttagacagg          49

<210> SEQ ID NO 266
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cgcgtcacgc aagaaagggc gaacgaaccc tcgaggtgat ggccc              45

<210> SEQ ID NO 267
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
aatcattaga ataattatta aatataccga cctga                        35

<210> SEQ ID NO 268
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
aaaatcggcc aacgagggtg gttttttaccc agtataatta tt                            42

<210> SEQ ID NO 269
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
attaaagtga gaagttgttt gggtaataag gaaaaaaata cctatttac                     49

<210> SEQ ID NO 270
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
taatgcgata atggcaattc caatcatgcc ccgggcggcc ag                            42

<210> SEQ ID NO 271
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
accgttgaag agtcagaatc cggattttcc tcgttttgac gaccgc                        46

<210> SEQ ID NO 272
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gagccggccg ctcaaagggt tagaac                                              26

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
agaactcaaa ctaccaaatt a                                                   21

<210> SEQ ID NO 274
<211> LENGTH: 32
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 274
ccttgctgat tatagattat ctatacaacg ga                                      32

<210> SEQ ID NO 275
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
acgctcgttg cggaatca                                                      18

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tgccaagcac gacgagatga atatac                                             26

<210> SEQ ID NO 277
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
attggcatca cacgacatta tattaaataa atttagaaaa ctatta                       46

<210> SEQ ID NO 278
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tgaccatcat ttgacgacaa caactataaa agaacatttt gcacgc                       46

<210> SEQ ID NO 279
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
aagtattagt ctttaatata gcccaataga ttaaa                                   35

<210> SEQ ID NO 280
<211> LENGTH: 26
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 280
ggaagggcgc catttcattt caatta                                            26

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gcgcgcagaa aggggtgaa a                                                  21

<210> SEQ ID NO 282
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gtgtttcatt aaacaaaatt ccaacaataa tcatacatag tatgtagtt                   49

<210> SEQ ID NO 283
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
aaaacgcatc tggtggaagg tgctgagata cgagccaaat cagcga                      46

<210> SEQ ID NO 284
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gcggctgaga gccagcaaat ctaacctc                                          28

<210> SEQ ID NO 285
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccagttttgg gcgcagtaca tctgtaaaca aattg                                  35

<210> SEQ ID NO 286
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 286
gcaaagtctc cagccaagag g                                              21

<210> SEQ ID NO 287
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
attctccgtg ggaacaa                                                   17

<210> SEQ ID NO 288
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
acggcggtaa atgtaaataa tttttgttaa tcagaggta                           39

<210> SEQ ID NO 289
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gataggtgaa gccagctttc atcaacatat tgaccgtaat gg                       42

<210> SEQ ID NO 290
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
aattaatttt tagattaaag ccgtccaa                                       28

<210> SEQ ID NO 291
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
atcaagatga attacctta ttttccggcg aactg                                35

<210> SEQ ID NO 292
<211> LENGTH: 14
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 292
cctgagcaaa agaa                                                        14

<210> SEQ ID NO 293
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tgaaatcaag aggcgaatta tcaggctgca ccgctgatcg cagcatctg                  49

<210> SEQ ID NO 294
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
atattgggtt ccatcctgat tagttagc                                         28

<210> SEQ ID NO 295
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gcgcatagtg ctgcacacca ggattcgata ccgagctcat gg                         42

<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
agtaacagta ccaaagtacc gaca                                             24

<210> SEQ ID NO 297
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tcggggtcaa ggtttaacgt cttgtaaaaa ggcgaagctg gcactgttg                  49

<210> SEQ ID NO 298
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 298
aaattgcgta gattttctta attcgtacat cgg                                    33

<210> SEQ ID NO 299
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tattttgaaa agaataacaa tccaatgaaa agcat                                  35

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
ctaccatatc aaaaagccaa cgct                                              24

<210> SEQ ID NO 301
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tgcacctctt ctgagtacgc ctgtccatca ttgcgctcac tggctgcat                   49

<210> SEQ ID NO 302
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggccttcctg tgtttgttaa aggaagagta acaagagcat t                           41

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
taaacgtcct tatcattaat tac                                               23

<210> SEQ ID NO 304
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
agtaccgtcg tcgctattaa tcatttaatg gaaacatcgt aacctgaaa                49

<210> SEQ ID NO 305
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
cataacggaa tacc                14

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
atgcagaacc ctgattgc                18

<210> SEQ ID NO 307
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
acaatattca gaaacaataa ccaaaatc                28

<210> SEQ ID NO 308
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
caagcaagac tgtaaatgct taggtctttta ggaattgaca gttggatca                49

<210> SEQ ID NO 309
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
cctcctttgc aacaattgga tttaagccgt ctaaacaag aagattgag                49

<210> SEQ ID NO 310
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tatttaattc gagccagtag gtcgtaaaac agaaataaag            40

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
caacagtagg gcctgaacaa agtc            24

<210> SEQ ID NO 312
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
atccgggaga agcctttgcc gccaaaaatc atctg            35

<210> SEQ ID NO 313
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cgtagatgat aattatcaca aagattgagt aaccagtaac ccttcgcgt            49

<210> SEQ ID NO 314
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
atttactcgc aaagaataga attaccat            28

<210> SEQ ID NO 315
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
atcaggtcat atgccgggta ggtattttta gaatacttga gcata            45

<210> SEQ ID NO 316
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gatgaacaaa gccccaaaaa caattcgcat taaattcgcg tct    43

<210> SEQ ID NO 317
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tagaccagcg agggagggta ttaattagcg gtgaggaaac tacgaa    46

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
taggaataat tgtataagca aat    23

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gcaacagatg tagataatat catagataag tcctgaagat ga    42

<210> SEQ ID NO 320
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ggcgtaaata caccgtcttg ctcagatata atcatcttaa gtaca    45

<210> SEQ ID NO 321
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
caaaagaact ggtg    14

<210> SEQ ID NO 322
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gaaccattac acttgagcac cctcagcccg gaactttgcg gaacga    46

<210> SEQ ID NO 323
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gcaataaaga aaaaaccaa tgaacgggta ttaactacaa ac                          42

<210> SEQ ID NO 324
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tttaagaaag gaaaccgagc tgccgacgac aataatttat ca                         42

<210> SEQ ID NO 325
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
taaagcaagg agcaccgccg ccactcattt tgaccttcca ttacc                      45

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
atagcaatag ctcacaaaca aata                                             24

<210> SEQ ID NO 327
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
aagagcaatt ctgtccagag aatataagag aatattttta ca                         42

<210> SEQ ID NO 328
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328 tttcgtctttt cgttttccag tagcgtcacc agata                                35

<210> SEQ ID NO 329
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gaattgagtt aagcccacca ccgcca                                        26

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
agagggtaat tgaccctcag agcc                                          24

<210> SEQ ID NO 331
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
atatcgcatt aactaccaca cgcacgtata cttttcacca gtctggccc               49

<210> SEQ ID NO 332
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
atggtttcaa tataaaagaa acatcgagaa caagcagaac ca                      42

<210> SEQ ID NO 333
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
accgttctga gaaacattca acgcaaggat aaaaaaagat tca                     43

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
caatatgtat aaactagcaa acg                                           23

```
<210> SEQ ID NO 335
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
cgatattcaa ttttgtcaca atcacaccac gaaaatacgg ctgtct                      46

<210> SEQ ID NO 336
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
aatcttgagt tttgcggggc ttgccaaaag acatcgcc                               38

<210> SEQ ID NO 337
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
tcagtgcgcc ccctgcctaa ggttccttat tacgcaaagg tg                          42

<210> SEQ ID NO 338
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gtaatgacaa caac                                                         14

<210> SEQ ID NO 339
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tttaacgcaa caggagtgta ccatgattaa gactttggaa ac                          42

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
aatcctcatt aatctccaaa aaaa                                              24

<210> SEQ ID NO 341
```

<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
atggaatatg gccttgatat tatcttaccg aagagatata at                          42

<210> SEQ ID NO 342
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gaacgatagc ccggaaaagt agcacctccc gtaagaacga tatagaccg                   49

<210> SEQ ID NO 343
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
cgattcgtaa gagagataac ccacaa                                            26

<210> SEQ ID NO 344
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344 ttttttcat aaactacagt tagcttggga aaacaaca                                38

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
accaccctca gacaactttc aaca                                              24

<210> SEQ ID NO 346
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
aactgccatc cggtcattgt agcgccagag ccttaccaac ccagcaaat                   49

<210> SEQ ID NO 347
<211> LENGTH: 41

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
aaagggtagc tgataaatta tgcctgagag tctggagaat c                          41

<210> SEQ ID NO 348
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
aaatcataca gcattgagga caacgaaa                                         28

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gcgaaagtct gaaacatgaa agatttcgga acctaaattc at                         42

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
aaagggtagg gccggagaca gtc                                              23

<210> SEQ ID NO 351
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
catcgcccac gcaacggtga cctgct                                           26

<210> SEQ ID NO 352
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
atataataga gttgcgccga caataagt                                         28

<210> SEQ ID NO 353
<211> LENGTH: 37
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 353
tgaatttctt aaacagcagc ttggaccagg aaagctg                          37

<210> SEQ ID NO 354
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ccgataataa agcgcagtct cgcttttgat gatttcgccc tt                    42

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355 cccectcaga gtaccgccca tttggaatta tttgacggcc ga                    42

<210> SEQ ID NO 356
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
aggctccaaa agttaagaac tgacga                                      26

<210> SEQ ID NO 357
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
taattgggtt cacgttgaaa aagccaga                                    28

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gcatgtgaat agtagtaa                                               18

<210> SEQ ID NO 359
<211> LENGTH: 40
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 359
tgcgaataat aatttttaca aaccaccacc agaggtcaga                          40

<210> SEQ ID NO 360
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gtttcagcgg agaaccctcg ttgaga                                         26

<210> SEQ ID NO 361
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
agaaaaaggg attttaaatc ggtggcgaga tggtggttcc gaagcccga               49

<210> SEQ ID NO 362
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tatcgatcta tagtaagatt caac                                           24

<210> SEQ ID NO 363
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
agaagccttt atacaaatta agcaataaca tccaataaat caaataacc                49

<210> SEQ ID NO 364
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gaggcttcgg aacgggccgc taacagtgcc                                     30

<210> SEQ ID NO 365
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 365
gaaaagaatt agcaggctac a                                              21

<210> SEQ ID NO 366
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
ggcaccaaaa cacgtttcgg tcgctgagat cgtcaccctt taccgggg                 48

<210> SEQ ID NO 367
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
tgtttagtac atttaagttt cgtagctcaa catgtagaga gt                       42

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ttgtgtctac aggcaaggcg gagggagtta                                     30

<210> SEQ ID NO 369
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tgataaaatc cgcgtaacta aagtacggtg tctggcgcaa atggtcgaa                49

<210> SEQ ID NO 370
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
acggagaact tagcaaagag ggctggctca gtatcggttt atcttgata                49

<210> SEQ ID NO 371
<211> LENGTH: 49
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 371
ccatgttttt gtatatacac taacctaata aagactttt caggcagca                49

<210> SEQ ID NO 372
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
ataacaggtt tgaccattag actatattgc attaaagcct cattgcggg                49

<210> SEQ ID NO 373
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
acctttactc caacgaagcc ctattatagt cagaacattg aa                      42

<210> SEQ ID NO 374
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
ctcattcagt gatttttaaa tatgcacact ttcgagg                            37

<210> SEQ ID NO 375
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
caaatcacag aacgtacctt acaggacggt ggaacaacta aaggaat                 47

<210> SEQ ID NO 376
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gaaacacacg taaccgcata gacagatgat aaccg                              35

<210> SEQ ID NO 377
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
attgggggat attatcaaga actgaccaat aggtgagggt tgtac                                45

<210> SEQ ID NO 378
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ttcaaataga ccggaagcaa aattgctcta atgctattcc at                                   42

<210> SEQ ID NO 379
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ttaagagagg tcaggaataa ggcttgccct gcatc                                           35

<210> SEQ ID NO 380
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
ggattggctc attaaagatt catgtcataa atattgcaaa gcaaaaaga                            49

<210> SEQ ID NO 381
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
tcccccttgg atagaccaaa atagcgag                                                   28

<210> SEQ ID NO 382
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
ttattacata ccacagcaac atctatcacc gtaaagcggt tg                                   42

<210> SEQ ID NO 383
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
tttaggaagg tagataccag ttgcgattga gcctt                35

<210> SEQ ID NO 384
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
taatgcacta acgggaaaaa ttaatcatag cccaaacca            39

<210> SEQ ID NO 385
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aggcttttaa aatgtttaga ccaaatgccc ctgacgaaag ac        42

<210> SEQ ID NO 386
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
agacgacgat aaaacgtcca atactgcgga atccagttta cc        42

<210> SEQ ID NO 387
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ttttgaacgt ggactccaac gtcaattcca gtttggaaca agagtctttt    50

<210> SEQ ID NO 388
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
ttttaaattg ttataagcat aaagtgtaaa gcctttt              37

<210> SEQ ID NO 389
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389

```
ttttggtcga ctctagagga tgtcatagct gtttcctgtt tt                    42
```

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390

```
ttttcccagt cttgcatgcc tttt                                        24
```

<210> SEQ ID NO 391
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391

```
ttttaagcgc cattcgatcg gtgctttt                                    28
```

<210> SEQ ID NO 392
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392

```
ttttcaagag cgagtaacaa cccgtttt                                    28
```

<210> SEQ ID NO 393
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393

```
ttttatgtac cccggttgat aaatttt                                     27
```

<210> SEQ ID NO 394
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394

```
ttttatcgta aaactagcat gtcatttt                                    28
```

<210> SEQ ID NO 395
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ttttcaatgc ctgagtaatg tagatttt                          28

<210> SEQ ID NO 396
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
ttttaaaaac attatgaccc tgtaaccctc atatatttta tttt         44

<210> SEQ ID NO 397
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ttttagaggg ggtaatagtg caaaagaagt tttgtttt               38

<210> SEQ ID NO 398
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
ttttcctaat gagtgagcta actcacatta attgcgcgaa catac        45

<210> SEQ ID NO 399
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ttttctcttc gctattacgc cttaagttca a                       31

<210> SEQ ID NO 400
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ttttagtatc ggcctcagga atctgtttt                          29

<210> SEQ ID NO 401
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
attatatgtc acgttggtgt agagagggga cgatttt                 37

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tttgaatacg ggtaacgcct ttt                                              23

<210> SEQ ID NO 403
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tttaatattg aataaccttg cttaaatcaa ttaacaaccg gaaacca                    47

<210> SEQ ID NO 404
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
aagctaatac taatagtagt attcatttgg ggcgcgagct gaaaatttt                  49

<210> SEQ ID NO 405
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ttttaacgag tagatttatt gattcttaat tg                                    32

<210> SEQ ID NO 406
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ctgaatactt ttgataagag gtcatttttg ctttt                                 35

<210> SEQ ID NO 407
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ttttcttcaa agcgaaccat cgcgtaaatc ag                                    32

<210> SEQ ID NO 408
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
gtctttattt aaacagttca gaaaacgaga atttt                               35

<210> SEQ ID NO 409
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ttttaaatca agttttttgg ggtaaaggga tgaatttccg g                        41

<210> SEQ ID NO 410
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
ttttgagctt gacggggaaa gcccgaa                                        27

<210> SEQ ID NO 411
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ttttggcgct ggcaagtgta gcggctt                                        27

<210> SEQ ID NO 412
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ttttggcgcg tactatggtt gctagaatca tatg                                34

<210> SEQ ID NO 413
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ttttaacagg aggccg                                                    16

```
<210> SEQ ID NO 414
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ttttcagtga ggccaccgag taatagcaat gagtaga                              37

<210> SEQ ID NO 415
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
aacagcatca ccttgctgat ttt                                             23

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
cgcttttatt ttcatcgtat ttt                                             23

<210> SEQ ID NO 417
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
caaaaggtct gagagactac ctttt                                           25

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ttgccaaaga caaaagggct ttt                                             23

<210> SEQ ID NO 419
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
cagattagga gaggctgaga ctcctctttt                                      30

<210> SEQ ID NO 420
```

```
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
ggcgcacgaa acatgacccc taatgccgtt tccattaaac gggtttt                    47

<210> SEQ ID NO 421
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
tttttaaaca ctattt                                                     16

<210> SEQ ID NO 422
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ggtataaatc aaaagaataa tcggcaaaat ccctga                               36

<210> SEQ ID NO 423
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cctgccccag caggcgaagc ggtccacgct ggttgc                               36

<210> SEQ ID NO 424
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
aagattgccc ttcaccgcga gacgggcaac agctcg                               36

<210> SEQ ID NO 425
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gcttgcgtat tgggcgcccg cggggagagg cggtaa                               36

<210> SEQ ID NO 426
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
agaaacctgt cgtgccaccc gctttccagt cggac                                35

<210> SEQ ID NO 427
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
gggagtaacg accgtg                                                     16

<210> SEQ ID NO 428
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
tgttttgaat ggctattagt ggcacagaca atattg                               36

<210> SEQ ID NO 429
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
tgtgaggcgg tcagtattga agataaaaca gaggca                               36

<210> SEQ ID NO 430
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
agaatatcaa accctcaaac cttgctgaac ctcagg                               36

<210> SEQ ID NO 431
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
ggtaatagat tagagccgta ggagcactaa caacgc                               36

<210> SEQ ID NO 432
<211> LENGTH: 36
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 432
ggcccgaacg ttattaatcg tattaaatcc tttgca                                 36

<210> SEQ ID NO 433
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
cgtcagatga tggcaattat catattcctg attaac                                 36

<210> SEQ ID NO 434
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
tcgaaataaa gaaattgcat ttgcacgtaa aacagg                                 36

<210> SEQ ID NO 435
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
acccaatagg aacgccacag ctcatttttt aaag                                   34

<210> SEQ ID NO 436
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
atgcctgatt gctttgaaaa acaataacgg attcca                                 36

<210> SEQ ID NO 437
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ttgagatcta caaaggctgg gtagctattt ttgaca                                 36

<210> SEQ ID NO 438
<211> LENGTH: 36
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 438
aatcaagaaa acaaaattga tgatgaaaca aacatg                                    36

<210> SEQ ID NO 439
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tatggcatca attcatcggt tgtaccgg                                             28

<210> SEQ ID NO 440
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
ggaatcgtcg cacatagcga tagcg                                                25

<210> SEQ ID NO 441
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
gtatggctta gagcccaatt ctgct                                                25

<210> SEQ ID NO 442
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
ggctgagaga ctataactat atgag                                                25

<210> SEQ ID NO 443
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
tcaccataaa tcaatttaat tcgta                                                25

<210> SEQ ID NO 444
<211> LENGTH: 25
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 444
tgaaatatat ttggtttgaa atacc                                            25

<210> SEQ ID NO 445
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 445
atgaccataa atcgcctgat aaatggaggg aggg                                  34

<210> SEQ ID NO 446
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 446
tgtgtcgaaa tccctcagaa ccgcggaggg aggg                                  34

<210> SEQ ID NO 447
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 447
caccctcaga gcgcagcacc gtaaggaggg aggg                                  34

<210> SEQ ID NO 448
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 448
tttaggcaga ggcattcaac gccaacatgt aaccagccag cc                         42

<210> SEQ ID NO 449
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 449
cgaacaaagt taccagaaag taagcagata gcccagccag cc                         42

<210> SEQ ID NO 450
<211> LENGTH: 42
<212> TYPE: DNA
<213> ORGANISM: Artificial Sequence
<220> FEATURE:
<223> OTHER INFORMATION: Description of Artificial Sequence: Synthetic probe

<400> SEQUENCE: 450
gtaagcgtca tacatgtgaa tttaccgttc caccagccag cc                              42

<210> SEQ ID NO 451
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ttgctttgac gagcacgta                                                        19

<210> SEQ ID NO 452
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
gccgctacag ggcgcgtggt caat                                                  24

<210> SEQ ID NO 453
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
taacgtgctt tcaattctac caccgagtaa aagtt                                      35

<210> SEQ ID NO 454
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
aacctgttta gctagcttag tttgaccatt ag                                         32

<210> SEQ ID NO 455
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
agggcgctga acgtggcgag aaaggggagc ccccgattta ggtcgagg                        48

<210> SEQ ID NO 456
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 456
ggtggcatcc tcgttagaat caaatactat gg                                    32

<210> SEQ ID NO 457
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gaaatatttt catttgagta cggtgctgaa ta                                    32

<210> SEQ ID NO 458
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
atagtagtag cctaaatcga aactatc                                          27

<210> SEQ ID NO 459
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
gcaaggcaaa gaaggagctt aattgtctgg aa                                    32

<210> SEQ ID NO 460
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
gcataaagat taacatcatg agtctgtcca tcagcaaaat cac                        43

<210> SEQ ID NO 461
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
atcttagcaa aattaacagg attaattcga gc                                    32

<210> SEQ ID NO 462
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
tgccgtaagt ctatcagtga accattggaa caagagtcca aaagaata            48

<210> SEQ ID NO 463
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
gtaccaaaaa caaaatttta ataccta                                   27

<210> SEQ ID NO 464
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gggaacgtca aagggcgcgt tttagagagt ac                             32

<210> SEQ ID NO 465
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
caaggataat tatgacccgt gctggtaata tcgcgcagtc tct                 43

<210> SEQ ID NO 466
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
gaacgtggac tccagatagt cagacgagaa tg                             32

<210> SEQ ID NO 467
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
aaccctcata taggccggag aggggggtgct tttgctattc ggttatt            47

<210> SEQ ID NO 468
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tgtggcaaaa tcccttcag aaaaagcaaa gc						32

<210> SEQ ID NO 469
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
gcccgagagc aggcgaaaat cctgagagag ttgcagcaag tttttctt						48

<210> SEQ ID NO 470
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
ggtgagaaat tttaaacagt gacgctcaat cggggatagc aag						43

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
aaatcgtaag cgtccaccag acga						24

<210> SEQ ID NO 472
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
agtcaaatca cctattttt attttgatg tcaatcatat						40

<210> SEQ ID NO 473
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
taggcccttc accgccctcg tttaatactg cg						32

<210> SEQ ID NO 474
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
gagggtagca tcaataagcg agagaatagt aa       32

<210> SEQ ID NO 475
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
tgattctgct aatgcagaga atcggaagat tgtattaact cacattaa       48

<210> SEQ ID NO 476
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
ttcaccaggc ggggagaggc ggtttgcgta tttccagtcg       40

<210> SEQ ID NO 477
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
agatctacaa aggctatcaa aactagcaat attta       35

<210> SEQ ID NO 478
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tctggagcaa aaatcggcca acgctgagac gggcaacagc       40

<210> SEQ ID NO 479
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
taatcgtagg tcattgatgc cgga       24

<210> SEQ ID NO 480
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480 gtacccggt tgataatcag aatattttga gatgcga       37

<210> SEQ ID NO 481
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
ttgcgttggt cgtgccagct gcattaatgc aagatacata acaacatt                48

<210> SEQ ID NO 482
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
aaacgttaaa agccccttca tcagttgagg gccgc                             35

<210> SEQ ID NO 483
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
ctaatgagtg agcaagagtc aggaggttta at                                32

<210> SEQ ID NO 484
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484 taaattttttg ttaaatcagc ttaattcgct tggtaac                          37

<210> SEQ ID NO 485
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
gttatccgca tagctggctt gccctcttga ca                                32

<210> SEQ ID NO 486
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
atcaaaaaca tttttttgtga attaccttaa gaagc                            35

<210> SEQ ID NO 487
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gtagccagct tcatcaaca ttccgtgggc cgaactgcgc agacgacg        48

<210> SEQ ID NO 488
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
tgccaagcac gacgttaacg gtgtgacctg ct        32

<210> SEQ ID NO 489
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
ctgcaggtaa ttcgtaatca tggtctcaca attccacaca tggggtgc        48

<210> SEQ ID NO 490
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
tcggattcta aatgtgtacc caaatcaacc tgcgg        35

<210> SEQ ID NO 491
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
ttgaccgtaa tgggataggt ccatctgccg accccca        37

<210> SEQ ID NO 492
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
taaccgtgac gttggtgaac gaggaccaac tt        32

```
<210> SEQ ID NO 493
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
tgggaaggag ctggcgaaag ggggcagggt tttcccagtc ttgcatgc                    48

<210> SEQ ID NO 494
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
gacgacagta tcggcctcag gaagatcgca ctccagcgcg catcg                       45

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
cttctggtgc cggaaagcaa ctgt                                              24

<210> SEQ ID NO 496
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
atacatttgc aactaagggc gcgatcatac ag                                     32

<210> SEQ ID NO 497
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
gtttcattga gtagatgaaa ggagccgccg cgcttaatgc                             40

<210> SEQ ID NO 498
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
taatgctgca acaggtgcaa taaaactttt gc                                     32

<210> SEQ ID NO 499
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ggcctgaagc aaactctagc tcaaccaata aagctgaaaa                             40

<210> SEQ ID NO 500
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
ctttaattgg cttagaaccc taaagaaggg aa                                     32

<210> SEQ ID NO 501
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
ccagccattc acttgcccat atttaaggct tacaatagca cgaattca                    48

<210> SEQ ID NO 502
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
ttcaaagcga ctattaagcc tttactgagt aa                                     32

<210> SEQ ID NO 503
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
catttgtctt taccctgaac cagacctgta atgcctcaga                             40

<210> SEQ ID NO 504
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ggattgcaca aatatcgaaa aaccagcact aa                                     32

<210> SEQ ID NO 505
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
tacattggtg caacagtaat tttcttaatt gaaaagccaa gaggacga                     48

<210> SEQ ID NO 506
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
accataaaga ctggatggta agaaaccgt tc                                       32

<210> SEQ ID NO 507
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
aatgtttatc aaaaattgca atgctttcaa cg                                      32

<210> SEQ ID NO 508
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
gaatcgtcta aacagtataa atcactatta aa                                      32

<210> SEQ ID NO 509
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
aacagagaag taataaggat tatatcgtcg ctagtgaata tagccctc                     48

<210> SEQ ID NO 510
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
cgataaaaac attcaaataa attacctgag ag                                      32

<210> SEQ ID NO 511
<211> LENGTH: 32
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 511
ggaataccac caaaattgat attcttcaaa ag                                    32

<210> SEQ ID NO 512
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
caaatcataa cctggccctg tttgatggtg gttccg                                36

<210> SEQ ID NO 513
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
ccctaatcct gacagatgat ctattgat                                         28

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
gcgaactgta cgtggcttct ggcc                                             24

<210> SEQ ID NO 515
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
agtcccacca gcttaaaatt cgcat                                            25

<210> SEQ ID NO 516
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
attacaggat tatacccaaa tattgtgaaa tt                                    32

<210> SEQ ID NO 517
<211> LENGTH: 40
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 517
ttttaagaac tggctctaga aagaaaaaac agatgaacgg                              40

<210> SEQ ID NO 518
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
cggtcagtaa aaatacaagg ccgcttgcgc at                                      32

<210> SEQ ID NO 519
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
ttcaactttg aataagtttc ctgtacggcc ag                                      32

<210> SEQ ID NO 520
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
aaagctgctc attcagtaat cattaaccaa tataaattgt                              40

<210> SEQ ID NO 521
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
atctatcatt ttaattttaa taaaaatc                                           28

<210> SEQ ID NO 522
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ccctcaataa atgaaaccac cagattttgc ggtttcttaa                              40

<210> SEQ ID NO 523
<211> LENGTH: 32
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 523
agaaccggga cagatggtaa aacgtcttcg ct                                      32

<210> SEQ ID NO 524
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 524
tgaaagagat attcatagcg agtaggaacg cc                                      32

<210> SEQ ID NO 525
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 525
aggttatctc aacagttaaa gactgcggaa cagtatgcgt                              40

<210> SEQ ID NO 526
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 526
ccatgttacg aaacaatgcg ggcccagctt tccggcaccg                              40

<210> SEQ ID NO 527
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 527
gtcaacacct acgaagtttt catgtttttc ac                                      32

<210> SEQ ID NO 528
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 528
gcgattatac caagcgctta gccggtagat ggacaacccg                              40

<210> SEQ ID NO 529
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
aatacattat tcgacagcac caacaagatt gctttgaata tcatttca           48

<210> SEQ ID NO 530
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
ggcaaaagaa tatagat                                             17

<210> SEQ ID NO 531
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ttggtaaaat acgtt                                               15

<210> SEQ ID NO 532
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
ctacagaggc ttccattaag tcaatcatca tctttagttt gagggggac          48

<210> SEQ ID NO 533
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
ttgtaacatt ggttt                                               15

<210> SEQ ID NO 534
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ggtagcaaaa cctcaataag ggaaaacaaa cggcgga                       37

<210> SEQ ID NO 535
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 535
gaaagacagc atcggaaaaa atctaaaagg tgagg                              35

<210> SEQ ID NO 536
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
tgaggcttgc accctcagct aaaacaggca tcaccgtctg gccttcct                48

<210> SEQ ID NO 537
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
aaccgataaa aagaagacag acaagag                                       27

<210> SEQ ID NO 538
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gacaacaacc atcgcccatt taagggacag gattatt                            37

<210> SEQ ID NO 539
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
accgatagcc gtaacaatta ccct                                          24

<210> SEQ ID NO 540
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
acagcccata tatgtgtaat ggaaagtgaa tt                                 32

<210> SEQ ID NO 541
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 541
ctttcgaggt gaagatcgtc agggagttac gaacgaattt aatgc              45

<210> SEQ ID NO 542
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
gaaattcgac cttttttctga gttttttagt ac                           32

<210> SEQ ID NO 543
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
agattttcat ttaacacatc aagattaggc gg                            32

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ggagccttta attaagacga g                                        21

<210> SEQ ID NO 545
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
tccaaaaaag ttttgtattt cattcccaaa tc                            32

<210> SEQ ID NO 546
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
gttgacagga aacaaaatta cctgtgatgc aa                            32

<210> SEQ ID NO 547
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
```
tgcgaataat aataggaagt tttgaggact gaaaggaata tcaaa       45

<210> SEQ ID NO 548
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
gcctggaata acaaccgtc tttcttgctc ag       32

<210> SEQ ID NO 549
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tttcaacatc catcgcaaga caaagttaat tttgaaacat ccaagtcc       48

<210> SEQ ID NO 550
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
tttctgtatg gtttt       15

<210> SEQ ID NO 551
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
agttagcgta aagtaaatga at       22

<210> SEQ ID NO 552
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
aacgcctgta gcattcattg tttatcagct tg       32

<210> SEQ ID NO 553
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553

```
cattttcatc tgaaattttt gccagac                                        27
```

<210> SEQ ID NO 554
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554

```
gccaccctca gagccaccaa tgaaaaacgt attaccg                             37
```

<210> SEQ ID NO 555
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555

```
agaaccgcac cagtatgaag ccag                                           24
```

<210> SEQ ID NO 556
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556

```
cgccacttca tatgcgtact agaaaaagta cc                                  32
```

<210> SEQ ID NO 557
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557

```
cgtactcagg aggcgtcacc acccatgtat tgcgccgaca at                       42
```

<210> SEQ ID NO 558
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558

```
tatcaggagt actggtttat acaattgagg ca                                  32
```

<210> SEQ ID NO 559
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559

```
ataggtctat cataatcgtt aaatcatccc tc                                  32
```

<210> SEQ ID NO 560
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ataagtgcaa ataaggaata agttccaaag gt                                  32

<210> SEQ ID NO 561
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
taccaggttt tgaaatcatc ttcttcaaca at                                  32

<210> SEQ ID NO 562
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
gattagcggg gttcagacgt tcgatctaaa aaggctccaa aa                       42

<210> SEQ ID NO 563
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
atccatcata ttattcaccg accgctcaga ac                                  32

<210> SEQ ID NO 564
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
tttccctgcc tattt                                                     15

<210> SEQ ID NO 565
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
gagtaacagt gcccgtgatc gtcgagaggg tt                                  32

<210> SEQ ID NO 566
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gaatttaccg ttccagcttc accctcagaa cc                                   32

<210> SEQ ID NO 567
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
aatggaaaca gaacaactca tggatag                                         27

<210> SEQ ID NO 568
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
aaataaatcc tcattaaatc gctgagtagt aaccgtt                              37

<210> SEQ ID NO 569
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
ttggccttag caaggctccg ggaa                                            24

<210> SEQ ID NO 570
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
ggtcagcaac cgcgccttta ttttagatta gt                                   32

<210> SEQ ID NO 571
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
gacaaccaaa gccgttcgga aacgattgac gg                                   32

```
<210> SEQ ID NO 572
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
aaagtaatac cgcactccaa gaaccgcaaa tt                                    32

<210> SEQ ID NO 573
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
agagccacac tgtagccatc gagaacattt tg                                    32

<210> SEQ ID NO 574
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
cgccagtttt atcattcaat caatccagtt ac                                    32

<210> SEQ ID NO 575
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
cagagccgcc acctgtataa acagttaatg cc                                    32

<210> SEQ ID NO 576
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
agataccgcc atctttgcgt tttccacaat ca                                    32

<210> SEQ ID NO 577
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
tgaacaaggt agaaactcat aatccgcaaa ca                                    32

<210> SEQ ID NO 578
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
tttgccccct tattt                                                          15

<210> SEQ ID NO 579
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
agtttgcctt ttttcggtca ta                                                  22

<210> SEQ ID NO 580
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
tagcagcacc gtaatcagcg agccgccgcc ag                                       32

<210> SEQ ID NO 581
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
cagtagcacc agaaaccatc ga                                                  22

<210> SEQ ID NO 582
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
ttagagccac gcaaataaga actcgtt                                             27

<210> SEQ ID NO 583
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
caccgacttg agccatttgg ttttataata agggatt                                  37

<210> SEQ ID NO 584
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
ttaaaggtat aataagtacc gaag                                            24

<210> SEQ ID NO 585
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
agggaaggta aattcaccaa tttaccattg atattcacaa ac                        42

<210> SEQ ID NO 586
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
agacaaaagg gcgacaagta gcgacagaat ca                                   32

<210> SEQ ID NO 587
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
atagataata cagagagtca aaaat                                           25

<210> SEQ ID NO 588
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
aagtttattt tgtatcggca tagcgtcagc accctcagag cc                        42

<210> SEQ ID NO 589
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
gccatatttg tttaacatac ataa                                            24

<210> SEQ ID NO 590
<211> LENGTH: 29
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 590
aggtggcaca aacgtagaca ccacggaat                                        29

<210> SEQ ID NO 591
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
ttttcagaat cctgaacttc tttagatata gaacaacgcc aacatttt                   48

<210> SEQ ID NO 592
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592 tttttgccc gactttagga gcactttt                                          29

<210> SEQ ID NO 593
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tttttcatat tccgcctgca acagttttt                                        29

<210> SEQ ID NO 594
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
ttttgaaggg ttagaacggc aattctttt                                        29

<210> SEQ ID NO 595
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tttttgcacg taaaacaaat tatcatttt                                        29

<210> SEQ ID NO 596
<211> LENGTH: 29
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 596
ttttgatgaa tatacagaag tttgatttt                                    29

<210> SEQ ID NO 597
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ttttgggaga aacaatataa atccttacaa acatgaggat ttagaagtat ttt          53

<210> SEQ ID NO 598
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ttttaagatg attacctttt acatctttt                                    29

<210> SEQ ID NO 599
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ttaattacag gtttaacgtc atttt                                        25

<210> SEQ ID NO 600
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
tttttaaatc aatatcaaaa ttatt                                        25

<210> SEQ ID NO 601
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
ttttgaaaac atagcgaacc ttgctttt                                     29

<210> SEQ ID NO 602
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 602
ttttgagaag agtcaataca gtaca                                              25

<210> SEQ ID NO 603
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
tttaacctcc ggcaaacaaa atttt                                              25

<210> SEQ ID NO 604
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
ttttatatgt aaatgcagca aaagcgaatt atccaagtta caaaatcgtt tt                52

<210> SEQ ID NO 605
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
ttttaatggt gggttatata actttt                                             26

<210> SEQ ID NO 606
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
ttttacaccg gagagagact accttttt                                           29

<210> SEQ ID NO 607
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
tttttttagt atagattaag acgctttt                                           28

<210> SEQ ID NO 608
<211> LENGTH: 29
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 608
ttttagtagg gcccttagaa tcctttttt                                   29

<210> SEQ ID NO 609
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
tttttgtaat ttaggcacgc tcaactttt                                   29

<210> SEQ ID NO 610
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
ttttaataag agaatataaa gcctgtttt                                   29

<210> SEQ ID NO 611
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ttttcgacaa taaacaaaag aataatttt                                   29

<210> SEQ ID NO 612
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
ttttacgcgc ctgtttagac ctaaaatatt ttagaacgcg agaaaacttt ttt         53

<210> SEQ ID NO 613
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
ttttgtcttt cccagctaat gcagatttt                                   29

<210> SEQ ID NO 614
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 614
ttttaaccaa gttctgtcca gacgatttt                                29

<210> SEQ ID NO 615
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
ttttgaatca tttttcgag ccagttttt                                 29

<210> SEQ ID NO 616
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616 tttttagcg aacctccagc aaatctttt                                 29

<210> SEQ ID NO 617
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ttttaagcct taaatcacat cgtagtttt                                29

<210> SEQ ID NO 618
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
tttttgaatc ttaccaaggg tattatttt                                29

<210> SEQ ID NO 619
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
ttttagagcc taatttgaat cggctacgag cataaaaata atatcccatt ttt     53

<210> SEQ ID NO 620
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 620
ttttgcagcc ttcgagcgtc tttcctttt                                29

<210> SEQ ID NO 621
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
ttttattaac tgtacaattt tatccttt                                 29

<210> SEQ ID NO 622
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
ttttagataa ccgcgggagg ttttgtttt                                29

<210> SEQ ID NO 623
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
ttttcccttt ttgccgatta cagtgaggct atttt                         35

<210> SEQ ID NO 624
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
ttagacagga acggtaatag caataacgcg aggcgttttt t                  41

<210> SEQ ID NO 625
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
gtagcaatga agtgttattc taagagctat ctagcaagaa acaatgaatt tt      52

<210> SEQ ID NO 626
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
tttttagtaa taaca                                                        15

<210> SEQ ID NO 627
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
cagattcatc tgtaaacttc tgaataatgt ttt                                     33

<210> SEQ ID NO 628
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
ttttgtcaca cgacctagaa cccatcaata taaa                                    34

<210> SEQ ID NO 629
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
tttttgacct gaaagcgtaa gaaatag                                            27

<210> SEQ ID NO 630
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
ttttacatcg ccattattaa cacctgatta taggagcggg aaataaa                      47

<210> SEQ ID NO 631
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ttttgccacg ctgagagcca gcagccaat                                          29

<210> SEQ ID NO 632
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632

```
ttttcagttg gcaaataaaa tatacgttat tactcgtata cggattc        47
```

<210> SEQ ID NO 633
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633

```
ttttaacaac taatagatta gagcc                                25
```

<210> SEQ ID NO 634
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634

```
tttttttagac tt                                             12
```

<210> SEQ ID NO 635
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635

```
ttttcgcaga gg                                              12
```

<210> SEQ ID NO 636
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636

```
tttttttcaa at                                              12
```

<210> SEQ ID NO 637
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637

```
ttttcctaat tt                                              12
```

<210> SEQ ID NO 638
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638

```
aaattcttca caagaaagcg ctaatatcag agtttt                    36
```

<210> SEQ ID NO 639
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
cacccagcaa caccctcgca ttagacggga gatttt                                 36

<210> SEQ ID NO 640
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
ttttataaga aa                                                           12

<210> SEQ ID NO 641
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
gaaaatacga ttttattta tcccaatcca atttt                                   35

<210> SEQ ID NO 642
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
ttttggaaag ccggcggcaa gtgtagtttt                                        30

<210> SEQ ID NO 643
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ttttaagttt tttgggagct tgacggtttt                                        30

<210> SEQ ID NO 644
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
ttttgttgtt ccagttcacc caaatctttt                                        30

<210> SEQ ID NO 645
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ttttggtttg ccccataggg ttgagttttt                                30

<210> SEQ ID NO 646
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
ttttcgccag ggtggcggtc cacgcttttt                                30

<210> SEQ ID NO 647
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
ttttcataaa gtgtaaagcc acatacgagc cggaagtttt                     40

<210> SEQ ID NO 648
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
ttttccgggt accgagctcg cgactctaga ggatccttttt                    40

<210> SEQ ID NO 649
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649 tttttttaagt tgggtaacgc atgtgctgca aggcgatttt                    40

<210> SEQ ID NO 650
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
tttttcgcca ttcaggctgc ccaggcaaag cgccatttt                      40

<210> SEQ ID NO 651
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ttttgagatc gttggtttt                                              19

<210> SEQ ID NO 652
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ttttgagtaa tgacgtttt                                              19

<210> SEQ ID NO 653
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
tttttccgca cagactttt                                              19

<210> SEQ ID NO 654
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ttttcggtca cgctgcgcgt aaccaccaca ccgggcgct                        39

<210> SEQ ID NO 655
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
ggaaacctcg ctcactgccc gcttttt                                     28

<210> SEQ ID NO 656
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
attacgccgc gatcggagta caacggagat ttt                              33

<210> SEQ ID NO 657

```
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
ttaaatatcg cagagcggga gctaaacagg agaagaaaag tttt              44

<210> SEQ ID NO 658
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ttttaacgga acgc                                              14

<210> SEQ ID NO 659
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
ttttgagaat agactaaaac gtaatgccat aaaacacatt gagga            45

<210> SEQ ID NO 660
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
ttttggctga gacgtttcag cgattttgcc aactaaagga at               42

<210> SEQ ID NO 661
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
ttttccagag ccagaaagta ttcggaacca gagaaggatt ag               42

<210> SEQ ID NO 662
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
tgctattcgg taattgttga gttaagcagt taccagaagg tttt             44

<210> SEQ ID NO 663
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
ttttcatatg gtcagggaag gaacaaagtc aataacggaa tacc                       44

<210> SEQ ID NO 664
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
aaaataaaga aaatacgaat aacataaaag actccttatt tttt                       44

<210> SEQ ID NO 665
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
tttttaaaag aaaaaaatca cagcgtttgg aaccgcctcc ct                         42

<210> SEQ ID NO 666
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ttttgtatgt tag                                                         13

<210> SEQ ID NO 667
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
ttttgaactg gcatgattaa attaccagcg ccaa                                  34

<210> SEQ ID NO 668
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
ttttgaggaa acgcaataga gaaccgattg aggg                                  34

<210> SEQ ID NO 669
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 669
ttttagatag ccgaacaacc agaattatca ccgt                              34

<210> SEQ ID NO 670
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
gcgtattggg cgccagggtg gttttttcttt tcaccagctt gcttc                 45

<210> SEQ ID NO 671
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
atcggccagg aaacagaatt tatccagacg ac                                32

<210> SEQ ID NO 672
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
tgtcgaaaat cctgtttgat ggtgaaagaa ta                                32

<210> SEQ ID NO 673
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
atttgaatta cctttttaa tacgcgcggc cagctgc                            37

<210> SEQ ID NO 674
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
gcccgagaag tccactatta aagagtctat cagaaccatc gtaaagca               48

<210> SEQ ID NO 675
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 675
aaacaaaaaa gatgatattt acgatgaaaa ta                                       32

<210> SEQ ID NO 676
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
ggaacaagta gggttgttca gctaagacgc tg                                       32

<210> SEQ ID NO 677
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
tttcaattac ctgagcaaaa gttaattaca ttctgtcaaa atcat                         45

<210> SEQ ID NO 678
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
tacaaaatgc ctgatttgag cgcttcaccg ac                                       32

<210> SEQ ID NO 679
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
ctaaatcgga cggggaaagc cggcaaggag cgggcgctag taaccacc                      48

<210> SEQ ID NO 680
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
gaggtgccac ccaaatgaat aacacaagaa aa                                       32

<210> SEQ ID NO 681
<211> LENGTH: 45
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 681
gggagaaaca ataacggatt ccgcgcagag tcaaaaagca tgtag                45

<210> SEQ ID NO 682
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
gaatatacag attttcagca gcactaagtt tt                              32

<210> SEQ ID NO 683
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gaaagcgaga acgtggttag agccccctga ac                              32

<210> SEQ ID NO 684
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
acagaaataa agaaattgcg tagtaacagt atcaccgaat atcag                45

<210> SEQ ID NO 685
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
acacccgcat ggttgctttg acgagagcgg gagctaaaca                      40

<210> SEQ ID NO 686
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
ctaccatatc tgaataatta agagaggagc ggccgaacgt                      40

<210> SEQ ID NO 687
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 687
tatttgcacg taaat							15

<210> SEQ ID NO 688
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
cgcgtactcg cgcttatgag taacaacgtc ac							32

<210> SEQ ID NO 689
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
cctgattgtt tggattatac ttcaaaatta ctggtaacgt aatca							45

<210> SEQ ID NO 690
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
ggaggccgat taatatctac aggg							24

<210> SEQ ID NO 691
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
atggcaatcc accagagctt atac							24

<210> SEQ ID NO 692
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
tcaagggatt ttagaccta ttattagcg							29

<210> SEQ ID NO 693
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
tcattttgcg gaacaaagaa atcatcaata taat					34

<210> SEQ ID NO 694
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
ccaccgagtt gtagcaatac ttctaagaac tcaaactatc cgccagcc					48

<210> SEQ ID NO 695
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
tattaattgt attaaagaat catgaggaag ttcag					35

<210> SEQ ID NO 696
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
attaaccgta aaagagatta ggattctgaa accagt					36

<210> SEQ ID NO 697
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
ttacaaacaa ttcgacaact cttaaaagtg accccca					37

<210> SEQ ID NO 698
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
tacatttgta gattagcaga ggccgctttt gcaat					35

<210> SEQ ID NO 699
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
attgcaacga cgctcaatcg tctgtcacac gaccagtaat ccttctga                48

<210> SEQ ID NO 700
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
aatattacgg ccttgcagga ggttgagggt tg                                 32

<210> SEQ ID NO 701
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
tttaggagca ctaacaacta aaggatttaa ctaaaga                            37

<210> SEQ ID NO 702
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
aggaattgtc agttggcatt gctt                                          24

<210> SEQ ID NO 703
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
ttcaccagaa atggataacc catgcctcag ag                                 32

<210> SEQ ID NO 704
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
aaaccctcaa tcaatatctg gaggaaggtt gcaggga                            37

<210> SEQ ID NO 705
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
cctgaaagaa tggctattag tcttcattaa aaataccgaa cgaaccac               48

<210> SEQ ID NO 706
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
aagcatcaag ccagcacagc ggag                                        24

<210> SEQ ID NO 707
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
ctgcaacagt gccacgctga gccttgctgc ggtttat                          37

<210> SEQ ID NO 708
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
cagcagaaac agacaatatt tttgcgtaag aaagttttgt ctgtagca              48

<210> SEQ ID NO 709
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
agaggtgagg cggtcagtat taacaccgc                                   29

<210> SEQ ID NO 710
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
ccattcgcga ataataaaag ctgcattcat taaacccacc                       40

<210> SEQ ID NO 711
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
cgcttctggc actccaagtg aatagccaga ggagaggctt tgcgaata        48

<210> SEQ ID NO 712
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
gggacgcata gtaaaacggt gtcttgtttt aagaaatccg                 40

<210> SEQ ID NO 713
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
gcatcgtata ggtcacttca ttccggtaaa gaaatgcaat tcagtttg        48

<210> SEQ ID NO 714
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
gaaattgtca tggtcaaccg tgtgataaa                             29

<210> SEQ ID NO 715
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
ctcacatttg gggtgcaaga caaagaacg                             29

<210> SEQ ID NO 716
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
attaatgatg taaatccaat agtgtacata aacatcaaga                 40

<210> SEQ ID NO 717
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
cgggaaacga gactaccttt ttaattagta cc                         32

<210> SEQ ID NO 718
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 718
agaagagtgt cgctattgaa taactgagac gggcaacagc tgattgcc          48

<210> SEQ ID NO 719
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 719
aggtctgact gtcgtgggag aggcggttt                              29

<210> SEQ ID NO 720
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 720
acggtccgca gaaaagtgag ctaa                                   24

<210> SEQ ID NO 721
<211> LENGTH: 42
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 721
tatataacta tatgaggcat tcaacgccaa agccgttttt at               42

<210> SEQ ID NO 722
<211> LENGTH: 32
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 722
cgagaaaact ttttatggct taattgagaa tc                          32

<210> SEQ ID NO 723
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 723
cggagaattt gttaaatcct gtgt                                   24

<210> SEQ ID NO 724
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 724
tttcatcttc tgaattctta ctttagtata gaacgcgagg cg        42

<210> SEQ ID NO 725
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 725
gaaaaagcct gcagtataaa gc        22

<210> SEQ ID NO 726
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 726
caacgctcaa cagtagttca ccgcgcccaa ta        32

<210> SEQ ID NO 727
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 727
gccatattta attcgagcca gt        22

<210> SEQ ID NO 728
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 728
aataagagaa tataaaagca tcattccaag aa        32

<210> SEQ ID NO 729
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 729
gacaataacc atcctagaaa caaataccaa gt        32

```
<210> SEQ ID NO 730
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gacaaaagca ataatcggct gtcttcgaga aacgattttt cccacaag                    48

<210> SEQ ID NO 731
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
ataatatcac aacatgagtg ttgttcaata ta                                     32

<210> SEQ ID NO 732
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
aaaccaatgt aaagtaattt aacaatttc                                         29

<210> SEQ ID NO 733
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
taacacttaa taaagcttta ggcagtaaat gc                                     32

<210> SEQ ID NO 734
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
cgggtattaa accgtcaaac agccatatta tt                                     32

<210> SEQ ID NO 735
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
cactcgaatg taccaactca gagcatcgat ga                                     32

<210> SEQ ID NO 736
```

```
<210> SEQ ID NO 736
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gaacaagcac atgtaagaag cctttcaagg gt                                   32

<210> SEQ ID NO 737
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
aacctgtttt gcgggaaaac attatcacaa at                                   32

<210> SEQ ID NO 738
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
aatggattaa cgcaagttat acaacctaaa tt                                   32

<210> SEQ ID NO 739
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
ggcttcgaat attttagata aaaattaat gc                                    32

<210> SEQ ID NO 740
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gtattctaca tatgcgttct aaac                                            24

<210> SEQ ID NO 741
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
ttttagcgaa cctcccgaag tgttggtgtt ctccgtg                              37

<210> SEQ ID NO 742
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
aatcaagatt agttgcgtaa actggcatga tt                                   32

<210> SEQ ID NO 743
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
ttgccagtta caaataggc tttttaagaa aa                                    32

<210> SEQ ID NO 744
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
tatcccaatc caaatacgtc aataataaga gc                                   32

<210> SEQ ID NO 745
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
gcagccttag ggtaatgctt tgaacgtcag at                                   32

<210> SEQ ID NO 746
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
aaagtcagta cagagacaag ttttccagt tt                                    32

<210> SEQ ID NO 747
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
agagataatg tttaacggcg aattattca                                       29

<210> SEQ ID NO 748
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 748
aattgagtca taattattca ttaaagaatc aa                                        32

<210> SEQ ID NO 749
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
attgcgcctt taattctcca acagaagtac cg                                        32

<210> SEQ ID NO 750
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
aagaaacaat gaaaaccgat tgccaaagac gtttgccatc tt                             42

<210> SEQ ID NO 751
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
agctagtcaa gcaaacgagc ttcaagtagc at                                        32

<210> SEQ ID NO 752
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
ccgaagccat tagagactaa cgagatctca at                                        32

<210> SEQ ID NO 753
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
gttcagaaaa gaggtcgtac ctttgctatc ga                                        32

<210> SEQ ID NO 754
<211> LENGTH: 32
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 754
gctttacata ccaacgaata taatatatag aa                                      32

<210> SEQ ID NO 755
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
gaaaccgagg aaaaagacac cgtggcaacc gccaccctca ga                           42

<210> SEQ ID NO 756
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
taacgggaaa ttgctgattt ttgcatttcg ca                                      32

<210> SEQ ID NO 757
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
cccaaaaggc tcaacaggac ttgc                                               24

<210> SEQ ID NO 758
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
aagactcctt attacgcata aaggcgatta gatgggc                                 37

<210> SEQ ID NO 759
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
ttattttgtc acaatccatg aaccagagcc ac                                      32

<210> SEQ ID NO 760
<211> LENGTH: 22
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 760
ggtttaccag cgagggaggg aa                                                  22

<210> SEQ ID NO 761
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
ggtaaatatt gacggacagt cagactgtag cg                                       32

<210> SEQ ID NO 762
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
ttgagccacc atcgataggt ttaagttaga ac                                       32

<210> SEQ ID NO 763
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
caatgaaatt tgggaacgag aaagttgggg tc                                       32

<210> SEQ ID NO 764
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
gtagcgacag gtgaattacc ttttacatc                                           29

<210> SEQ ID NO 765
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
gtttgcctcc tcttttgatg atacaaacaa ag                                       32

<210> SEQ ID NO 766
<211> LENGTH: 32
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 766
ataaagcgtt gagattcgac attcatagca at                                    32

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
cgttttcatc ggcccggaat t                                                21

<210> SEQ ID NO 768
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
tcataataca gatacatagg aatacaaagc gg                                    32

<210> SEQ ID NO 769
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
cttattagca aagggagca acaccgaaaa ca                                     32

<210> SEQ ID NO 770
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
ttcataatca aatcctcat tccttgatat tcggtcgaaa cagct                       45

<210> SEQ ID NO 771
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
gtgaattaat agtaagtaac gccacagtct ta                                    32

<210> SEQ ID NO 772
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 772
tttaaccgaa ccctcggaaa cgcacgcaat aa                                   32

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
caccggaacc gccgacggag g                                               21

<210> SEQ ID NO 774
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
agccggagaa atagcgttta ccagcctcaa at                                   32

<210> SEQ ID NO 775
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
ctcagaacat ataaaggggg tatg                                            24

<210> SEQ ID NO 776
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
gccaccaccc tcagagcctt cgccagcttg gggatgt                              37

<210> SEQ ID NO 777
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
gccgccagca ttgacaaagg agcctttcaa ctaaa                                35

<210> SEQ ID NO 778
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 778
ttgaggcaaa tttcttctga ggcttatcta aaatatc                              37

<210> SEQ ID NO 779
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
cagacgattg gaaagccagg ggatcgtctt tgagggaagt attagact                  48

<210> SEQ ID NO 780
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
ggaaagcgca gtctctaact acagaggcac cctca                                35

<210> SEQ ID NO 781
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
taccgttctc cattaatcat cttttttgagt aacatta                             37

<210> SEQ ID NO 782
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
taagcgtcat acatgggctt aaaacacacg ggtaa                                35

<210> SEQ ID NO 783
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
gcctatgcgc cggaagggaa                                                 20

<210> SEQ ID NO 784
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
aacggggtat gaaagtatgg aaggtcctga ttatcagatg                              40

<210> SEQ ID NO 785
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
caagcgcgag gagtgt                                                       16

<210> SEQ ID NO 786
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
tacaacggag atttgtgaat acacccatgt tataagggaa attttcgg                    48

<210> SEQ ID NO 787
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
gcgatgagac tcctcaatag cccgtccttt gcatagataa                             40

<210> SEQ ID NO 788
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
atataagtag agaaggtctg tccaaattat ca                                     32

<210> SEQ ID NO 789
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
aatacgtagc aacggctgac caaccaaata aatcatcatt                             40

<210> SEQ ID NO 790
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790 cttttttaggt gtatcactca ttttagccgt cacagttgaa         40

<210> SEQ ID NO 791
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
ccaccacccc gtactctggt aatatcacgc aa                  32

<210> SEQ ID NO 792
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
gcagcgaacc gatatattca caaagtaatc tttccctcag          40

<210> SEQ ID NO 793
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
gttaaggata gcaagcacag ccctcaaatc aaaaaatcta          40

<210> SEQ ID NO 794
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
acgcataaag acagcagtac agactttgaa agattgcccc          40

<210> SEQ ID NO 795
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
ttccacagcc aataggtatt tacatccaga ac                  32

<210> SEQ ID NO 796
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
tttcgaggtg ggttt                                     15

<210> SEQ ID NO 797
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
tgataccgtc caaaagaacc ggattcagcc ac                                   32

<210> SEQ ID NO 798
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
cagctagtta gcgtaaaaca gtttgcaaat gagataaaac                           40

<210> SEQ ID NO 799
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
aaaaaggcat agttgccatc aagacaggcg caatttcaac                           40

<210> SEQ ID NO 800
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
gggattttgc taaacaactt tccgatctaa tacgtggctt ggcaga                    46

<210> SEQ ID NO 801
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
tttgagaata gcctt                                                      15

<210> SEQ ID NO 802
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
ggaattgcca ttcaggtccg gcac                                            24

<210> SEQ ID NO 803
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 803
tttttcagga agatcgtgcc ggaaacgtaa cattttttca cgtttttt            48

<210> SEQ ID NO 804
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 804
ttttccgtaa tgggaaccgt gcactaaagt atgtttagac tggatttt            48

<210> SEQ ID NO 805
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 805
ttttctggcc ttaaaggccg gagactttt                                 29

<210> SEQ ID NO 806
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 806
ttttccaata ggtgatattc aaccgtttt                                 29

<210> SEQ ID NO 807
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 807
tttttaatat ttttgagaga tctactttt                                 29

<210> SEQ ID NO 808
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 808
ttttattgta tacctgagag tctggtttt                                 29

```
<210> SEQ ID NO 809
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
ttttagcaaa caagagaata aagctttttt                                        29

<210> SEQ ID NO 810
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
ttttaaaggc tatcaggtga ccctgtttt                                         29

<210> SEQ ID NO 811
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811 tttttttctag ctgataattt ttagatttt                                        29

<210> SEQ ID NO 812
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
ttttagtcaa atcaccagcc tgagttttt                                         29

<210> SEQ ID NO 813
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
ttttaccctc atgtagattt agttttttt                                         29

<210> SEQ ID NO 814
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
tttttaatac tttagctata ttttctttt                                         29

<210> SEQ ID NO 815
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
ttttaaatcg gtaaggtggc atcaatttt                                      29

<210> SEQ ID NO 816
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
ttttcaaggc aaagaattag caaaacctaa tcgtaaaact agcatgtttt               50

<210> SEQ ID NO 817
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817 tttttctac taatagtaag cgaactttt                                       29

<210> SEQ ID NO 818
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
ttttatttgg ggcgcgaaat tgctctttt                                      29

<210> SEQ ID NO 819
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
ttttgaccat tagatacgga tggctttt                                       29

<210> SEQ ID NO 820
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820 tttttccca attctgcata tgcaatttt                                       29

<210> SEQ ID NO 821
<211> LENGTH: 29
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821 ttttagagc ttatcgtcat aaatatttt                                29

<210> SEQ ID NO 822
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
ttttcttttg ataacgagaa tgaccttt                                29

<210> SEQ ID NO 823
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
ttttcagacc ggtttaccct gactattt                                29

<210> SEQ ID NO 824
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
ttttaagccc gaaagacttc aaatattctc caataaatca tacaggtttt        50

<210> SEQ ID NO 825
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
ttttttatag tcagaagcca cattctttt                               29

<210> SEQ ID NO 826
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
ttttataaat caaaaataaa ggaatttt                                29

<210> SEQ ID NO 827
<211> LENGTH: 29
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 827 tttttcatt gaatcccacg acgattttt                                          29

<210> SEQ ID NO 828
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
tttttagcgt ccaatacttg caaaatttt                                         29

<210> SEQ ID NO 829
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
ttttaaaaac catagtaaat tgggctttt                                         29

<210> SEQ ID NO 830
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
tttttacgag gcccttatgc gatttttt                                          29

<210> SEQ ID NO 831
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
ttttaactaa tgccagtcag gacgttttt                                         29

<210> SEQ ID NO 832
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
ttttattatt acaggtagaa agatttaaat caaaaagatt aagaggtttt                  50

<210> SEQ ID NO 833
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 833
tttttgggaa gaaaaatgaa cgaggtttt                                    29

<210> SEQ ID NO 834
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
tttttaagaa ctggctcagg acagatttt                                    29

<210> SEQ ID NO 835
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835 tttttgaga tggtttatag gctggtttt                                     29

<210> SEQ ID NO 836
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
ttttcgagaa acaccagccc aaatctttt                                    29

<210> SEQ ID NO 837
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
ttttctgacc ttgccgacaa tgacatttt                                    29

<210> SEQ ID NO 838
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
tttttgaacg gttcgtttt                                               19

<210> SEQ ID NO 839
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 839
ttttcgcaga cgacgaaggc accaatttt                                       29

<210> SEQ ID NO 840
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
ttttaaattg tgtcgaaatc cgcgattaac gaactaacgg aacaactttt               50

<210> SEQ ID NO 841
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ttttcctaaa acgaaagagg caaaaatcat cgcctgattt tt                        42

<210> SEQ ID NO 842
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
ttttgaacga gggtaatgcc actgtcaatc acttagccgc tacgttattt t              51

<210> SEQ ID NO 843
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
ttttcaggca aagcg                                                      15

<210> SEQ ID NO 844
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
gctgacgaca gtatcggaag ttttaggctt gccctgattt t                         41

<210> SEQ ID NO 845
<211> LENGTH: 15
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 845
ttttgccagt ttgag                                                    15

<210> SEQ ID NO 846
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
ggaacaaata acaaccaggg tgagcctgta gccaaaaata attcgcgttt tt           52

<210> SEQ ID NO 847
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
cggcggataa tgtgtaatat aacagttgat ttt                                33

<210> SEQ ID NO 848
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
tttttcaatc atatgtaccc cggttgatcc agt                                33

<210> SEQ ID NO 849
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
tgatgttgag caaatacccc aaaaacagga agtttt                             36

<210> SEQ ID NO 850
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
agctattttg ttaaaattta aattgtaaac gttttt                             36

<210> SEQ ID NO 851
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
taatgataaa cgccattcag ctcatttttt aatttt                36

<210> SEQ ID NO 852
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
taaggcgtta aataagaaaa acgtcggata ttaaatgtga gcgagtttt                49

<210> SEQ ID NO 853
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
ttttacaacc atcgccc                17

<210> SEQ ID NO 854
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
ttttgaaaat ctccaaa                17

<210> SEQ ID NO 855
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855 tttttttgcag caagcggtcc cctggccctg agagagtttt                40

<210> SEQ ID NO 856
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
ttttaatccc ttataaatca gttccgaaat cggcaatttt                40

<210> SEQ ID NO 857
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
ttttcaaagg gcgaaaaacc acgtggactc caacgttttt        40

<210> SEQ ID NO 858
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
ttttccccga tttagagctt gaaccctaaa gggagctttt        40

<210> SEQ ID NO 859
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
ttttgcggtc acgctgcgcg ggcgctggca agtgtatttt        40

<210> SEQ ID NO 860
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
tttttcactt gcctgagtag ttgattagta ataacatttt        40

<210> SEQ ID NO 861
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
ttttgaaata cctacatttt aggaaaaacg ctcatgtttt        40

<210> SEQ ID NO 862
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 862
ttttccaaca gagatagaac aaaagggaca ttctggtttt        40

<210> SEQ ID NO 863
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
ttttagccct aaaacatcgc taatgcgcga actgatttt 40

<210> SEQ ID NO 864
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
tttttctaga ggatcaacgc atgcctgcag gtttt 35

<210> SEQ ID NO 865
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
ttttattcgt aattatccgc ttttt 25

<210> SEQ ID NO 866
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
tttttgtaaa gccaattgcg ttttt 25

<210> SEQ ID NO 867
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
ttttagatta atgcatttt 19

<210> SEQ ID NO 868
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
ttttctgaat aaaaatttt 19

<210> SEQ ID NO 869
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
tttttgaaca agcattttt                                              19

<210> SEQ ID NO 870
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
ttttccggaa gtgccttttt                                             19

<210> SEQ ID NO 871
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
tttttcggaa aggaacggca gtgaggtttt                                  30

<210> SEQ ID NO 872
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
ttttgtcgat agtacttttt                                             19

<210> SEQ ID NO 873
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
ttttcgccac taccgtttt                                              19

<210> SEQ ID NO 874
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 874
ttttaacgcc gtctttttt                                              19

<210> SEQ ID NO 875
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
cttcaccgac gctggtttgc cccagcaggg agtaattaat tttccctttt            50

<210> SEQ ID NO 876
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 876 tttttcctc gt                                                          12

<210> SEQ ID NO 877
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 877
aatcctgata gaatcagcac gtataacgtg cttttt                               36

<210> SEQ ID NO 878
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 878
ttttgaagtg ttttataat tacgccag                                         28

<210> SEQ ID NO 879
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 879
gggcgaccac cagagaaagg aaaattgtat aacctcaaat atctttt                   47

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 880
ccagctcgta gaaaatattt t                                               21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 881
gttttcttga agccttattt t                                               21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 882
ccagtgcata attactattt t                                              21

<210> SEQ ID NO 883
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 883 tttttccac acaacatatt tatattttag ttaa                                 34

<210> SEQ ID NO 884
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 884
tttttcactg cccgctttaa tgcttaggtt gggt                                34

<210> SEQ ID NO 885
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 885
ccaatcgcct aatgagttcg cattaaacga gccggaagca tttt                     44

<210> SEQ ID NO 886
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 886
aaataccgta gctgttcagc tttcatcccc gggtaccgag tttt                     44

<210> SEQ ID NO 887
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 887
accggaatcc aagcttgacg ttgtaaaact ttt                                 33

```
<210> SEQ ID NO 888
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
gggaggttcc agtcacaagt tgggtaacgt ttt                                  33

<210> SEQ ID NO 889
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
ttagcaaagg cgaaagggcc tcttcgctat ttt                                  33

<210> SEQ ID NO 890
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
cagaaccatc ggtgcgctgc gcaactgttt ttt                                  33

<210> SEQ ID NO 891
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
gggtcccaat tctgcgaacc catataacag ttgataa                              37

<210> SEQ ID NO 892
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ttaggtcatt tttgcggatg ctccttttga taagacg                              37

<210> SEQ ID NO 893
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
ccagaagccc gaaagacttt caaaaagatt aagaggg                              37

<210> SEQ ID NO 894
```

```
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
gactccccct caaatgctta taaatattca ttgaagg                            37

<210> SEQ ID NO 895
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
tcgagtaaga gcaacactaa ggaattacga ggcatac                            37

<210> SEQ ID NO 896
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
ctcttaataa aacgaactga agaaaaatct acgga                              35

<210> SEQ ID NO 897
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
cacgtagtaa attgggctta gaaacaccag aacgaaa                            37

<210> SEQ ID NO 898
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
taagctgacc ttcatcaaca ggcgcatagg ctgag                              35

<210> SEQ ID NO 899
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
tgcataaatt gtgtcgaaat ttgtatcatc gcctggc                            37

<210> SEQ ID NO 900
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
aaaacatagc gatagctttt agaatccttg aaaga                              35

<210> SEQ ID NO 901
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
ggacaacaat agataagtcg aacgcgcctg tttatgt                            37

<210> SEQ ID NO 902
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
taagacggga gaattaacca gggaagcgca ttaga                              35

<210> SEQ ID NO 903
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
cggattacca ttagcaagga atcaccagta gcaccaa                            37

<210> SEQ ID NO 904
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
acatgccccc tgcctattcg tataaacagt taata                              35

<210> SEQ ID NO 905
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
acgcaggcgg ataagtgccg ggttttgctc agtacca                            37

<210> SEQ ID NO 906
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 906
caacgccacc ctcagaaccg ccaccctcag aacaa                                    35

<210> SEQ ID NO 907
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
aaacaccagt acaaactact aacactgagt ttcgtcc                                  37

<210> SEQ ID NO 908
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
taaatgaatt ttctgtattc cagacgttag taagc                                    35

<210> SEQ ID NO 909
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 909
gatataagta tagtgacaca gacagccctc atggagggag gg                            42

<210> SEQ ID NO 910
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 910
cttttgatga tgtcagtgcc ttggagggag gg                                       32

<210> SEQ ID NO 911
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 911
cattgacagg aggatttaag cgtcatacat ggggagggag gg                            42

<210> SEQ ID NO 912
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 912
gcaagcaaat caggcttatt ttgcacccag ctccagccag cc                             42

<210> SEQ ID NO 913
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 913
acaattttat ccagagccta atccagccag cc                                       32

<210> SEQ ID NO 914
<211> LENGTH: 42
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 914
gtaagcagat agctataata gaaaattcat atccagccag cc                            42

<210> SEQ ID NO 915
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
ttttcagtac aaactacaac cactgagttt cgtcactttt                               40

<210> SEQ ID NO 916
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
ttttaatttt ctcagctttc cggcatttt                                           29

<210> SEQ ID NO 917
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
tttttcacgt tggagatctt ttt                                                 23

<210> SEQ ID NO 918
<211> LENGTH: 40
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 918
ttttataccg atagttgcgc tttcttaaac agcttgtttt                                40

<210> SEQ ID NO 919
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
ttttccatta aacggcaagc gcgaaatttt                                           30

<210> SEQ ID NO 920
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
gattatacgt aaaatatgtt tagagtcacc ctgttaaagg ccgcttttt tt                   52

<210> SEQ ID NO 921
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
ttttcaaagt acaacaaccg aactgatttt                                           30

<210> SEQ ID NO 922
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
cataaggggg agatttaaga agttttgcct ttt                                       33

<210> SEQ ID NO 923
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
ttttccaact ttgaaaacgt aacaaatttt                                           30

<210> SEQ ID NO 924
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 924
cccaaatcag aggacaccct cgtttaccat ttt                                    33

<210> SEQ ID NO 925
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
ttttgctgct cattcatgcg attttatttt                                        30

<210> SEQ ID NO 926
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
attaccttag tgaatatacg aggcatagtt ttt                                    33

<210> SEQ ID NO 927
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
ttttagaact ggctccggtt tt                                                22

<210> SEQ ID NO 928
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
taataaaacg aactaaatta taccgattta ggaatactttt t                          41

<210> SEQ ID NO 929
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
ttttaacaac attatgcttc aaattcaaat agagagtacc tttatttt                    48

<210> SEQ ID NO 930
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
ttttcacatt caactaatga aaaagattaa gaggaatttt        40

<210> SEQ ID NO 931
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
ttttaagagc aacactagac tattaaatca aaatcaacat gttttatttt        50

<210> SEQ ID NO 932
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
ttttgacgac gataaaaacg acagttcaga aaacgatttt        40

<210> SEQ ID NO 933
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
ttttagaggg ggtaataata aatatagcgt ccagtagatt tagttttt        48

<210> SEQ ID NO 934
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
ttttgattca ttgaatcctt tt        22

<210> SEQ ID NO 935
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
ttttccctca aatgctttaa ggtgtgtctg gaagtttttt        40

<210> SEQ ID NO 936
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
ttttgaatga ccatatagtc agaagctttt                                30

<210> SEQ ID NO 937
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
ttttaaagcg gattgcatca acaggtcatt tttgcgtttt                      40

<210> SEQ ID NO 938
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
ttttgcccga aagacgcgtt tt                                         22

<210> SEQ ID NO 939
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
ttttaaccag accggacatt atgaaagcta atcaacgcaa ggattttt             48

<210> SEQ ID NO 940
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
ttttattgct ccttttgcat aaattaagca ataaagtttt                      40

<210> SEQ ID NO 941
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
ttttgatggc ttagagccca ataaatacta atatgagaaa ggccggtttt           50

<210> SEQ ID NO 942
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
ttttaatatg caactaaaaa cgcgagctga aaaggttttt                    40

<210> SEQ ID NO 943
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
tttttcattc catataagtc aataaaccat tagattt                       37

<210> SEQ ID NO 944
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944 tttttttgcct gtttagcttt tt                                      22

<210> SEQ ID NO 945
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
ttttatattt tcatttgggg tccaatatga tattcatttt                    40

<210> SEQ ID NO 946
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
ttttggcatc aattctcata caggcatttt                               30

<210> SEQ ID NO 947
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
ttttaggcaa agaattagca agcatatatt ttaaattttt                    40

<210> SEQ ID NO 948
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
ttttcctcag agcat                                                15

<210> SEQ ID NO 949
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
ttttccctgt acattttttc attaaatctg gccttcctgt tttt                 44

<210> SEQ ID NO 950
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
ttttaaaaat ttttagatcc taaacgttaa tattttttt                       40

<210> SEQ ID NO 951
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
ttttgcaatg cctgagtaaa caggaggttg ataattgacc gtaatgtttt           50

<210> SEQ ID NO 952
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
ttttagacag tcaaatctgt acccctttt                                  29

<210> SEQ ID NO 953
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
ttttaccgtt ctagctggag caaacatcag gtcactc                         37

<210> SEQ ID NO 954
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
ttgaaaaatc tcgcgaataa taatttttt tt                               32

<210> SEQ ID NO 955
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 955
ttttaaaggc taagagaatc gatttt                                          26

<210> SEQ ID NO 956
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 956
tttttgaacg gtaatcgtaa aactgcatct gccagttttt                           40

<210> SEQ ID NO 957
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 957
agattgtata atttt                                                      15

<210> SEQ ID NO 958
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 958
ttttgcaaat atttaaattg tttcccgtcg gattctttt                            40

<210> SEQ ID NO 959
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 959
ttttgttaaa attcg                                                      15

<210> SEQ ID NO 960
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 960
ttttaccaat agtcgactca gtgccaagaa attgttatcc tttt                      44

<210> SEQ ID NO 961
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
ttttagccag ctttcatata cagtcacgac gttgtatttt                                40

<210> SEQ ID NO 962
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
ttttccgtgg gaacaaacaa ggcgaagctg gcgaactcac attaattttt                     50

<210> SEQ ID NO 963
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
ttttggatag gtcacgtgct cggtgcgggc ctcttctttt                                40

<210> SEQ ID NO 964
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964 tttttttgagg ggacgacgcc attcacggaa acccgtattg ggcgtttt                      48

<210> SEQ ID NO 965
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 965
cagcgtatgg gacagacgtt agtaaatgtt tt                                        32

<210> SEQ ID NO 966
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
ttttccgctt ctggtgcggc tgcgcaactt tt                                        32

```
<210> SEQ ID NO 967
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
tttttgttgg gaagggcgat attgtcgtgc cagctgtttt                              40

<210> SEQ ID NO 968
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
ttttgctatt acgccttaag ttgggttttt                                        30

<210> SEQ ID NO 969
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
ttttaacgcc agggttttcc aaagtgtaaa gcctggtttt                              40

<210> SEQ ID NO 970
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
ttttaaacga cggcctagag gatccccgtt tt                                     32

<210> SEQ ID NO 971
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
ttttggtacc gagctcgaat tcgtacaaag ggcattaaag a                            41

<210> SEQ ID NO 972
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
ttttgctcac aattccatgt tgttcagaat agc                                    33

<210> SEQ ID NO 973
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
ttttggtgcc taatgagcga aatcggaaaa tcc                                   33

<210> SEQ ID NO 974
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
tttttgcgtt gcgctcaagc ggtcccctgg ccc                                   33

<210> SEQ ID NO 975
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
ttttcattaa tgaatcgaga cgggcaacag ctgattttt                             40

<210> SEQ ID NO 976
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
ttttccaggg tggtttttct ttttaccgta agcctgtag                             39

<210> SEQ ID NO 977
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
ttttgccctt caccgacgct ggtttgtttt                                       30

<210> SEQ ID NO 978
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
ttttccccag caggcgcaaa atccctttt                                        30

<210> SEQ ID NO 979
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
tttttataaa tcaaacagtt tggaactttt                                        30

<210> SEQ ID NO 980
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
ttttaagagt ccact                                                        15

<210> SEQ ID NO 981
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 981
ttttgaaaaa ccgtctatca tccaacgtat catgg                                  35

<210> SEQ ID NO 982
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
ccaataggaa cccatgataa cgtgttagag agg                                    33

<210> SEQ ID NO 983
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
cattccacag ttttgtttaa aaatccatca gga                                    33

<210> SEQ ID NO 984
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
tcgagaggtc agtaccaggc ggattaacag tg                                     32

<210> SEQ ID NO 985
<211> LENGTH: 48
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 985
aagtatagac cctcagagcc accaccctca ttttcaggga aagtgccg                48

<210> SEQ ID NO 986
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
cgatctaaag acagccaagg gattctttcc tcgctttgac                         40

<210> SEQ ID NO 987
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
aacaacttaa caactagaac ctactaagga gag                                33

<210> SEQ ID NO 988
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
cccgtatagg gtcagtgcct tgagcacaaa caaataaatc gattggcc                48

<210> SEQ ID NO 989
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
tagaaaggtc aacagtttca gcggtagcgt aa                                 32

<210> SEQ ID NO 990
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
ttttaacgaa cagttaatgc ccccattagc ggggttttgc gttgatat                48

<210> SEQ ID NO 991
<211> LENGTH: 34
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 991
aggctccatt gctttcattt tagttgaatt ctgc                                  34

<210> SEQ ID NO 992
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
ttatcagcaa aggagcaaca gaaacata                                         28

<210> SEQ ID NO 993
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
ttgatattcg cctccctcag agccgagcca ccaccggaac cagtagcg                   48

<210> SEQ ID NO 994
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
acaacaacct gaggctcatt accgcttatc c                                     31

<210> SEQ ID NO 995
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 995
cagaaccgtt gaggcaggtc agacctcatt aaagccagaa gtaataag                   48

<210> SEQ ID NO 996
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
ttcggtcgca tcgccctaat ggtttaat                                         28

<210> SEQ ID NO 997
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 997
aaagacagct ttgaggcact acga                                              24

<210> SEQ ID NO 998
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
acagaatcat agcagcgtga attatcaccg tcaaattatt                             40

<210> SEQ ID NO 999
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999 cttttcatg aggaaggcgg gatc                                               24

<210> SEQ ID NO 1000
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
tacagaggca tcggaaatag aaggcgccca attttt                                 36

<210> SEQ ID NO 1001
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
aaccatcgaa gtttgccttt agcgaaaatc accggaacca gccaccct                    48

<210> SEQ ID NO 1002
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
aggcaccaaa acactcgcgt tttagcgaa                                         29

<210> SEQ ID NO 1003
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1003
cgaaagagac cgtaatgcaa cggc                                              24

<210> SEQ ID NO 1004
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1004
atacactaac ctaaaaaatc agatcgaggg taccgatata                             40

<210> SEQ ID NO 1005
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1005
cattaaagtt tattttgtca caatgacacc acggaataag tacccaaa                    48

<210> SEQ ID NO 1006
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1006
attgacggac cgacttgagc cattgaaacg tcaccaatga                             40

<210> SEQ ID NO 1007
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1007
aattgtgtcg gaacgatttt gaagcctta                                         29

<210> SEQ ID NO 1008
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1008
accaggcgtt gacaagtatc ctgaatctt                                         29

<210> SEQ ID NO 1009
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1009
ggctgaccct ccatgttact tagccgaaat ccgcgacctg gcaaaaga                    48

<210> SEQ ID NO 1010
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
agaactggcg caataataac ggaaagagca agaaacaatg gttaagcc                    48

<210> SEQ ID NO 1011
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1011
agactcctat aaaagaaacg caaacaatag aaaattcata aggtaaat                    48

<210> SEQ ID NO 1012
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1012
gaaacaccta atttcatttc cagatattat ttaacg                                 36

<210> SEQ ID NO 1013
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1013
agatggttag aacgagtagt aaatttcatc aagagtaatc cataggct                    48

<210> SEQ ID NO 1014
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1014
caataataaa aacagggaag cgcattagac gggagaatta aacccaca                    48

<210> SEQ ID NO 1015
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1015
agaattgaaa atagcaatag ctataaggaa accgaggaaa catgatta        48

<210> SEQ ID NO 1016
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1016
gagagaaaca gccagcctaa tttgccagtt        30

<210> SEQ ID NO 1017
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1017
tcagttgaag tcaggacatt gtga        24

<210> SEQ ID NO 1018
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1018
acaaaataat aacatatggg cttg        24

<210> SEQ ID NO 1019
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1019
cataagtcac tttaatcgtt gggaagactt taca        34

<210> SEQ ID NO 1020
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1020
aaggaatagg cttgcattca tta        23

<210> SEQ ID NO 1021
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1021
accaacgcta acgatcctaa t                               21

<210> SEQ ID NO 1022
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1022
acaatttaac cggatcctga cga                             23

<210> SEQ ID NO 1023
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1023
tttgcactaa gatgaacgcg gtcaat                          26

<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1024
aatcaagatt agtataatcg g                               21

<210> SEQ ID NO 1025
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1025
tagcgaaggg gcgcagagtg tacag                           25

<210> SEQ ID NO 1026
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1026
ttgcaagtat catcccccca gc                              22

<210> SEQ ID NO 1027
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1027
cctcccgact tgccactcat cctgtctttg tatcatatgc gt            42

<210> SEQ ID NO 1028
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1028
cgcgagatct ttgagcctga ta            22

<210> SEQ ID NO 1029
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1029
ggtattaaac gtaatgcact aaaga            25

<210> SEQ ID NO 1030
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1030
catcaccgac cgaccggaat acgcgagaat aactattttt            40

<210> SEQ ID NO 1031
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1031
agccgttttt aagcaagca            19

<210> SEQ ID NO 1032
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1032
gagaacaaga ataaactgtg ataaataagg cg            32

<210> SEQ ID NO 1033
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1033
ttacgagcat aaagccaacg c            21

<210> SEQ ID NO 1034
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1034
tgtttatcac gccaactaat aagaattaat taaccttgct cttttta                48

<210> SEQ ID NO 1035
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1035
cgccaaacaa caaaagtacc gacaaaagag tgaata                             36

<210> SEQ ID NO 1036
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1036
taattcgata caggtagaaa gccaatctac gt                                 32

<210> SEQ ID NO 1037
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1037
aggattatcg cgtttataag tcctgcagat a                                  31

<210> SEQ ID NO 1038
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1038
ggcattttcg agccagatgt aatttaggca ga                                 32

<210> SEQ ID NO 1039
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1039
tttaacaaac aatagtaatg cagatcattc a                                  31

<210> SEQ ID NO 1040
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1040
agaatcagaa gaaaaatttt acccttcacc agct                              34

<210> SEQ ID NO 1041
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1041
tcaacagtag ggcacgctga gattttccca aac                               33

<210> SEQ ID NO 1042
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1042
ctgaatagta tgtagaaaat atcccagccg ccaa                              34

<210> SEQ ID NO 1043
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1043
tgtagcatca ggtcttccaa gaaccaaaa                                    29

<210> SEQ ID NO 1044
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1044
tatacaaatt cttcttttta aaaatcatt acaaaattga g                       41

<210> SEQ ID NO 1045
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1045
ctgtttacct tatcaaccaa tcatgctat                                    29

```
<210> SEQ ID NO 1046
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1046
actagaacga ttaaaccgaa tcgtcgtact aagaa                              35

<210> SEQ ID NO 1047
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1047 tttttttaaat aagca                                                   15

<210> SEQ ID NO 1048
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1048
ttcccaaatg taggaataag taccgggga ggctt                               35

<210> SEQ ID NO 1049
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1049
gaacgaatac tgcgtgcagg gacagcagcg                                    30

<210> SEQ ID NO 1050
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1050
cctaaattac gcataagtat cggt                                          24

<210> SEQ ID NO 1051
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1051
ttcaaaactt ttaattgcgt agatt                                         25

<210> SEQ ID NO 1052
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1052 tttttttttct tctga                                                       15

<210> SEQ ID NO 1053
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1053
ggttgggtta ttttt                                                        15

<210> SEQ ID NO 1054
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1054
ttttaagagt caata                                                        15

<210> SEQ ID NO 1055
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1055
tgcgggtact ctgtaaatac caaaaaagca aactccaata ttgttcagc                   49

<210> SEQ ID NO 1056
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1056
atggaaacct aatagattta gaagaatcaa cacaatcaat atctggtc                    48

<210> SEQ ID NO 1057
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1057
ctttattatc ggttgcttga aaaatagcca ta                                     32

<210> SEQ ID NO 1058
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1058
atcaagatta gaatctcgtc gctgaacagg tc                                      32

<210> SEQ ID NO 1059
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1059
aaaattcatt tgtttgagga ttagagccag gaaggt                                  36

<210> SEQ ID NO 1060
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1060
gatgaactcg atagcttatt aacatttaat tg                                      32

<210> SEQ ID NO 1061
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1061
caaattttaa aaacaattc caaaccctgt tg                                       32

<210> SEQ ID NO 1062
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1062
aggtaaagta ggtctgaaga ttaagttaat tg                                      32

<210> SEQ ID NO 1063
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1063
aaaaggggta gtagcgctga tgcagtaaaa gc                                      32

<210> SEQ ID NO 1064
<211> LENGTH: 32
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 1064
ggattcgcct gattgccggg agaaattcat ca                                    32

<210> SEQ ID NO 1065
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1065
agtaccatgt aaatgagact acaccataat gc                                    32

<210> SEQ ID NO 1066
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1066
acattttgaa tagagcggaa gcggaacatc taaagcatca c                          41

<210> SEQ ID NO 1067
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1067
atataatcaa tcgcaacgca aatgcagttg a                                     31

<210> SEQ ID NO 1068
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1068
ttcaggttta acgtacttct gatataatca ttaacaccgc ct                         42

<210> SEQ ID NO 1069
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1069
aatgccagat caaatatgac aaagacataa tt                                    32

<210> SEQ ID NO 1070
<211> LENGTH: 31
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1070
ggtagctata catttgaggt gaacgacaat g                                    31

<210> SEQ ID NO 1071
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1071
cacgtaactt taattagtga gaa                                             23

<210> SEQ ID NO 1072
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1072
tcaaaataat gggcagaaga taaaa                                           25

<210> SEQ ID NO 1073
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1073
tttttttaat tattt                                                      15

<210> SEQ ID NO 1074
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1074
catcaattgg tcaatagaat cagctatact tt                                   32

<210> SEQ ID NO 1075
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1075
tatctaaatt gacgct                                                     16

<210> SEQ ID NO 1076
<211> LENGTH: 32
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1076
ttcgcgtttt tgttagtatt aaaaccacaa ac                                   32

<210> SEQ ID NO 1077
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1077
agttggcata tttt                                                       14

<210> SEQ ID NO 1078
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1078
aatgttatga caactcataa tacaaataga agc                                  33

<210> SEQ ID NO 1079
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1079
gtaacaagcc cgaacagccc caaaatgtgt                                      30

<210> SEQ ID NO 1080
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1080
cttgctgaac ctccagagat agattcacct ggtaatatcc ag                        42

<210> SEQ ID NO 1081
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1081 gaaaaaaga aaccgttatt aaagaagat                                        29

<210> SEQ ID NO 1082
<211> LENGTH: 34
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1082
ccagccggat cagaaacaat cataacccag taac                             34

<210> SEQ ID NO 1083
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1083
gcaacagtgc cacagaatac ggaac                                       25

<210> SEQ ID NO 1084
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1084
gatgggagtc tgattgtacc agaagccaag attc                             34

<210> SEQ ID NO 1085
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1085
taaccgtagc atgtagagtc tgataaatt                                   29

<210> SEQ ID NO 1086
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1086
cagaggtgag gcgactgata gtggcacaga gtaaaagagt ct                    42

<210> SEQ ID NO 1087
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1087
tcggccccaa agggttattg gattatcaga tga                              33

<210> SEQ ID NO 1088
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1088
agatcgcatt gcctgaagga attcaaaaaa a                                        31

<210> SEQ ID NO 1089
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1089
tttacgaaac cgattt                                                        16

<210> SEQ ID NO 1090
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1090
ccctaaaaag gaacggcagt gaggatgcgc cgtaaccacc                              40

<210> SEQ ID NO 1091
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1091
ccttgattag taactatcgg cggcgaacga tttaga                                  36

<210> SEQ ID NO 1092
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
tcataggcct gaaatgggcc tgcagggaac gc                                      32

<210> SEQ ID NO 1093
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1093
ctgtgtgctt gcatgaccag tacaacatta                                         30

<210> SEQ ID NO 1094
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1094
aacaatatta ccgcactaaa tttttgggg                                29

<210> SEQ ID NO 1095
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1095
tacgagtgca gtcacacatt atttagaaaa ataa                          34

<210> SEQ ID NO 1096
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1096
gcataaaggg acattatgtg ctgcggagca aat                           33

<210> SEQ ID NO 1097
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1097
ttctttctga cctgctggcc aaaaagagcg a                             31

<210> SEQ ID NO 1098
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1098
tttttttact tgcct                                               15

<210> SEQ ID NO 1099
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1099
ttgtagctaa aggggtttg aatgtggtgt a                              31

<210> SEQ ID NO 1100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1100
gtccatcacg caacgctggc aaagcgaaa                                29

<210> SEQ ID NO 1101
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1101
ctttccccga caatattaaa gcgtagctga gag                            33

<210> SEQ ID NO 1102
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1102
gaaacctagt ctttacgcca ttcgacagta                                30

<210> SEQ ID NO 1103
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1103
cgcggggacc atcgccaatg cgcgagtccg catcg                          35

<210> SEQ ID NO 1104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1104 ttttttaat cctga                                                 15

<210> SEQ ID NO 1105
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1105
cggtttgagg caaagcgtct ttcttttgct a                              31

<210> SEQ ID NO 1106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1106

```
gagcacgtcg cgcttaccaa gtcgg                                              25
```

<210> SEQ ID NO 1107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1107

```
tgagagagca ccagtggcca acg                                                23
```

<210> SEQ ID NO 1108
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1108

```
acacccgccg ctagggatta accg                                               24
```

<210> SEQ ID NO 1109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1109

```
tgtttgattt gcagcactgc ccg                                                23
```

<210> SEQ ID NO 1110
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110

```
ggagcggggg gaaagccctc cggaa                                              25
```

<210> SEQ ID NO 1111
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1111

```
ccgagatagg tggttctgag caatac                                             26
```

<210> SEQ ID NO 1112
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112

```
gcttgacgcc gtaaagccac tgtttc                                             26
```

<210> SEQ ID NO 1113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
acgtggacgg gttgagcaca aca                                              23

<210> SEQ ID NO 1114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1114
ttttcaccct cagaaccgcc cccggaatag gtgtattttt                            40

<210> SEQ ID NO 1115
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
ttttcaagag aaggattagg tgcctatttc ggaacctttt                            40

<210> SEQ ID NO 1116
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
ttttatacag gagtgtactg tggaaagcgc agtctctttt                            40

<210> SEQ ID NO 1117
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1117
ttttcagcat tgacaggagg ccaccctcag agccactttt                            40

<210> SEQ ID NO 1118
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
ttttccatct tttcataatc tcagactgta gcgcgttttt                            40

<210> SEQ ID NO 1119
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1119
ttttcaaggc cgtgggaatt agagccagtt tt                              32

<210> SEQ ID NO 1120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1120
ttttccgatt gagggaggga tggtttacca gcgccatttt                      40

<210> SEQ ID NO 1121
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1121
ttttataaag gtggcaacat tattacgcag tatgtttttt                      40

<210> SEQ ID NO 1122
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1122
ttttcgaaca aagttaccag cttaccgaag cccttttttt                      40

<210> SEQ ID NO 1123
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1123
ttttctaata tcagagagat actgaacacc ctgaactttt                      40

<210> SEQ ID NO 1124
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1124
ttttgaaaat agcagcaaaa tccaaataag aaacgacgac aattttt              47

```
<210> SEQ ID NO 1125
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1125
tttttccaga cgattttttg tttt                                            24

<210> SEQ ID NO 1126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1126
ttttactaac aaagtacata tttt                                            24

<210> SEQ ID NO 1127
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1127
ttttaaagca ttggcacaat cgtcattgca acaggaaaaa tttt                      44

<210> SEQ ID NO 1128
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
ttttgagtag aagaactcaa ataacatcag ggaagaagtg tagctttt                  48

<210> SEQ ID NO 1129
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
gaagtgtttt tataattacg ccagctatgg ttgttagaat cagagcggtt tt             52

<210> SEQ ID NO 1130
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
ttttaacagg aggccgatta ctcatagtta gcaagctttt                           40

<210> SEQ ID NO 1131
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
ttttgctgcg cgctacaggg tttt                                              24

<210> SEQ ID NO 1132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
ttttgagccc ccgtggcgag tttt                                              24

<210> SEQ ID NO 1133
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1133
tcgaggtgcg atggcccact acgttttt                                          28

<210> SEQ ID NO 1134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1134
ttttatcaag ttcggaaccc tttt                                              24

<210> SEQ ID NO 1135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1135
ttttattgac ggaccgactt tttt                                              24

<210> SEQ ID NO 1136
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1136
tttttttggg aaaccattag tttt                                              24

<210> SEQ ID NO 1137
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1137
ttttcggaaa cgatcagtag tttt                                          24

<210> SEQ ID NO 1138
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1138
ttttaatcaa gtatcggcat tttt                                          24

<210> SEQ ID NO 1139
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1139
tttttcatag ccaaaatcac ctttt                                         25

<210> SEQ ID NO 1140
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1140
ttttgagcca ccaccggaac cgagccgcca ccgtaacagc aagccccaga cgt          53

<210> SEQ ID NO 1141
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1141
ttttcctcag agccaccacc ctaccagaac caccaccaga tttt                    44

<210> SEQ ID NO 1142
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1142
ttttgccagc attgacagga ggttgagaga tcagaaccgc cac                     43

<210> SEQ ID NO 1143
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1143
ttttcaaaca ataaatcct caaatggaaa gcgcagtctc tttt                    44

<210> SEQ ID NO 1144
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1144
tttttaccgt tccagtaagc gtcatacagc ggggttttgc tca                   43

<210> SEQ ID NO 1145
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1145 tttttttaa cgaaacatga agtattatt tcgagg                             36

<210> SEQ ID NO 1146
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1146
ttttggaacc tattattctg gggtcagt                                    28

<210> SEQ ID NO 1147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1147
ccgtactctt ggccttgatt tt                                          22

<210> SEQ ID NO 1148
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1148
cccatgtacc ctcagaactt tt                                          22

<210> SEQ ID NO 1149
<211> LENGTH: 38
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1149
cagcttgcag aggctgagac tcctatacag gagttttt                                  38

<210> SEQ ID NO 1150
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1150
ttttaaccat cgcccacgca tttttaagaa ctggctcatt tt                             42

<210> SEQ ID NO 1151
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1151
tattcggttt aaacagcttg atactttt                                             28

<210> SEQ ID NO 1152
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1152
ttttaaaaat ctacgttaat gaattacctt atgcgaaacc gata                           44

<210> SEQ ID NO 1153
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1153
ttttgaacga gtagatttag ttttgtaaac gttaatattt tttt                           44

<210> SEQ ID NO 1154
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1154
agatacatgg aagtttcatt ccattttt                                             28

<210> SEQ ID NO 1155
<211> LENGTH: 32
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 1155 tttttcgca ttaaattttt ctattaaatt tt                32

<210> SEQ ID NO 1156
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1156
gcaacattaa agattcaacc gattgaggga gggaagtttt                40

<210> SEQ ID NO 1157
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1157
ttttgtgctg caaggcgatt aagttggggc gatcggtgcg ggcctcttcg cttttt                56

<210> SEQ ID NO 1158
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1158
tttttggtca tagctgtttc gcatgcctgc aggtcgtttt                40

<210> SEQ ID NO 1159
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1159
ttttgctttc cagtcgggaa agcctggggt gcctaatttt                40

<210> SEQ ID NO 1160
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 1160
ttttcgcctg gccctgagag gcgccagggt ggttttttt                40

<210> SEQ ID NO 1161
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1161
ttttgttcca gtttggaaca cgaaatcggc aaaatctttt                               40

<210> SEQ ID NO 1162
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1162
ttttgcgaaa aaccgtctat caatggccca ctacgtgaag agtccagtta aatc             54

<210> SEQ ID NO 1163
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1163
gccttgagta acagtgcccg tataaatttt                                         30

<210> SEQ ID NO 1164
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1164
atagaaaaaa taagttctgg tcagaggtta t                                       31

<210> SEQ ID NO 1165
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1165
tcaccgtcaa attattagcg ccataagaac tctaataaca                              40

<210> SEQ ID NO 1166
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1166
acatataaga aaatacttgc tttgttaatc cccc                                    34

<210> SEQ ID NO 1167
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1167
gcaccatttt agagccgcc                                                19

<210> SEQ ID NO 1168
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1168
tccttattca aagaaaaat atatatggtt t                                   31

<210> SEQ ID NO 1169
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1169
gcaccgtatc accaatcagt tcagaaaac                                     29

<210> SEQ ID NO 1170
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1170
accgaggagc cgaacaccaa gaacacaagc a                                  31

<210> SEQ ID NO 1171
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1171
gcgttttctt gcctttcatc gcctgataa                                     29

<210> SEQ ID NO 1172
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1172
tcataatccc cttattact                                                19

<210> SEQ ID NO 1173
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1173
aagactcagc ctccattcag tacaaagcgt ttgactgtag c                          41

<210> SEQ ID NO 1174
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1174 acaccccgc ccagagtgac agggatactg agtttccctc ataacgc                     47

<210> SEQ ID NO 1175
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1175
cagaggcagg tcagacgaag gaggttcgga atagattttt t                          41

<210> SEQ ID NO 1176
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1176
ccaaagccag ttaaataagt atagcctagt accgagtgag aaaaca                     46

<210> SEQ ID NO 1177
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1177
ttttgatgca agagaaggat taggatacct ttaa                                  34

<210> SEQ ID NO 1178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1178
ctacaaagcc taatttgccc aat                                              23

<210> SEQ ID NO 1179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1179
gtaccaggcg gataacgaaa atc                                          23

<210> SEQ ID NO 1180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1180
atataagaaa cgatccttta                                              20

<210> SEQ ID NO 1181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
aacgccccat aacataactg a                                            21

<210> SEQ ID NO 1182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182
cctcagaacc gccgagatga att                                          23

<210> SEQ ID NO 1183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1183
cattttacaa agtcaaccca c                                            21

<210> SEQ ID NO 1184
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1184
agccgtcacg agttaagcaa tagctccatc ttt                               33

<210> SEQ ID NO 1185
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1185

```
acagttagcg taacgatcta aagt                                          24

<210> SEQ ID NO 1186
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1186
ctgtatttgt atagcgtcag cgatagca                                      28

<210> SEQ ID NO 1187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1187
tttgtcgtct ttcaatagga a                                             21

<210> SEQ ID NO 1188
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1188
tagtaacatt tataccaagc gc                                            22

<210> SEQ ID NO 1189
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1189
ggattttgct atagaaagga acaactaaag ga                                 32

<210> SEQ ID NO 1190
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1190
acttcactac gaatacacta aaagaggaag ggaaccagcg tccaatact               49

<210> SEQ ID NO 1191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1191
attgcgaata atagtgtatc a                                             21
```

<210> SEQ ID NO 1192
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192
cacgttatga gtttccatta aa                                             22

<210> SEQ ID NO 1193
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193
tccaaacggc tacaacagca tccaccaga                                      29

<210> SEQ ID NO 1194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1194
aaggctccaa aaggagtaaa gcg                                            23

<210> SEQ ID NO 1195
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195
tgaatttccg ctgaggcttg caggcaactt ta                                  32

<210> SEQ ID NO 1196
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
ttgtatttgc gggatcgtca ccgatagtaa attgggctta gaaaga                   46

<210> SEQ ID NO 1197
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
aaaggaggct tttaaggctt taacaaagta tcataaccct c                        41

<210> SEQ ID NO 1198
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1198
aacatgagca gtaccgacaa taaacaagtg cc                                    32

<210> SEQ ID NO 1199
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1199
ttttggtagc aaaaa                                                       15

<210> SEQ ID NO 1200
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1200
aaagacaggg acgacgacaa aaggtcaccc ag                                    32

<210> SEQ ID NO 1201
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1201
tgaggattca gctattcagc ggccagaggc gt                                    32

<210> SEQ ID NO 1202
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1202
cgggtaaaat acgttacaag attcatggta aaccaaacag aggggtaaga aagagcccca      60
ggaag                                                                  65

<210> SEQ ID NO 1203
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1203
aaattccaat agatatgcag aagaaagggt tg                                    32

<210> SEQ ID NO 1204
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1204
tatgctgctc aacagttaat ttacaccctc a                                     31

<210> SEQ ID NO 1205
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1205
ttttcgaaag agatg                                                       15

<210> SEQ ID NO 1206
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1206
catcttggat cccatccaag tcctgattct aag                                   33

<210> SEQ ID NO 1207
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1207
cagcgagtag aaacacagac agcgttttta tt                                    32

<210> SEQ ID NO 1208
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1208
gaaacaaagt acagccggaa cccgcgaccg ctt                                   33

<210> SEQ ID NO 1209
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1209
tgtgatttat cattcaatca atcaaccacc ct                                    32

<210> SEQ ID NO 1210
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1210
gaaatagaga gcattccaag ttaccatctt acc                           33

<210> SEQ ID NO 1211
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1211
attgtgtcga aatgaggcgc agac                                     24

<210> SEQ ID NO 1212
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1212
ggtcaatcat acagatgaaa gttttgcata gcgaggcgaa cc                 42

<210> SEQ ID NO 1213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1213
aggcgcatag gctacctaaa a                                        21

<210> SEQ ID NO 1214
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1214
tattcattac ccaaatcaac ggccctgacc ata                           33

<210> SEQ ID NO 1215
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1215
aaaggaacga gggccgcttc ggtttat                                  27

```
<210> SEQ ID NO 1216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1216
acgagtagct ttaggaacaa a                                               21

<210> SEQ ID NO 1217
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1217
atcattgtaa aacgaactaa cggactaaag tacggtgtct ttcgcaaa                  48

<210> SEQ ID NO 1218
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1218
tttaatttga gttaaa                                                     16

<210> SEQ ID NO 1219
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1219
ttcatcagga tctgtataat gtataaaagg tggcatc                              37

<210> SEQ ID NO 1220
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1220
cgtcgcagat tagattatca gtgaagagga ct                                   32

<210> SEQ ID NO 1221
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1221
tttttgcaga tagag                                                      15

<210> SEQ ID NO 1222
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1222
acgctaccac atgctgaata gctcaacatt ttcatt                               36

<210> SEQ ID NO 1223
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1223
aggatctgat aactttgaa atacaggcgc ct                                    32

<210> SEQ ID NO 1224
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1224
ggcatacaaa atttatcaga cgctgcaacg cc                                   32

<210> SEQ ID NO 1225
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1225
caacacctgc tcatcctccg gctaagttat ac                                   32

<210> SEQ ID NO 1226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1226
gtttaccaga cgacaggaag caa                                             23

<210> SEQ ID NO 1227
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1227
tgaattcttt ttaaaaaatc atagtttttt ca                                   32

<210> SEQ ID NO 1228
<211> LENGTH: 32
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228
taacaataat gggttatcaa ctttgaaaca ct                                  32

<210> SEQ ID NO 1229
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
taaaattgaa aatccaaata actattagta tca                                 33

<210> SEQ ID NO 1230
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
ctggatgaac tgacgttact taacgccgac cg                                  32

<210> SEQ ID NO 1231
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
gcggaatcgt catgactatt aaatcaaaaa atg                                 33

<210> SEQ ID NO 1232
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1232
cattgattca cttttctcg caagaacctg acccc                                35

<210> SEQ ID NO 1233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
taaagaaacc atcaccagta                                                20

<210> SEQ ID NO 1234
<211> LENGTH: 30
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1234
tcaaattgct ccatctggca tgagaaggaa                                           30

<210> SEQ ID NO 1235
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1235
gagaatgacc atatagtcag atttagaact atttcaaata ttca                           44

<210> SEQ ID NO 1236
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1236
agaccgaaaa gctaaatcgg tt                                                   22

<210> SEQ ID NO 1237
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1237
actccagcaa taaaaggca aagaatcga                                             29

<210> SEQ ID NO 1238
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1238
agagagtacc tttaattgct cgaggtcatt tttgcggatg gc                             42

<210> SEQ ID NO 1239
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1239
ttagagctta atttcaacta aattacaggt gagatgg                                   37

<210> SEQ ID NO 1240
<211> LENGTH: 40
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1240
tggtcaataa acaggaagat tgtatttta ccaataggaa                         40

<210> SEQ ID NO 1241
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1241
tagctatatg ttttaaatat gcaaacaaca tt                                32

<210> SEQ ID NO 1242
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1242
tggggcgcgc gaccccgg                                                18

<210> SEQ ID NO 1243
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1243
gaacaactgc agatgatatt atactattac ga                                32

<210> SEQ ID NO 1244
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1244
aattctacta ataagagtaa tcgtaaaact ag                                32

<210> SEQ ID NO 1245
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1245
cattaataat tgtttggggc aattctgtaa at                                32

<210> SEQ ID NO 1246
<211> LENGTH: 32
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 1246
taaatctaat ggaaacgtaa aacgatttca tt                                32

<210> SEQ ID NO 1247
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1247
cagaaaggct atgtagctat gcgcatcgta acc                               33

<210> SEQ ID NO 1248
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1248
gacaacttat ttgcgggtta gaaatgtaag ag                                32

<210> SEQ ID NO 1249
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1249
ttacaataat aaagaaaata tacaggtaat ag                                32

<210> SEQ ID NO 1250
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1250
gtaccaaaaa cataagctag ctgataaatt aa                                32

<210> SEQ ID NO 1251
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1251
ctgtaatagt cagatgattg cgtagttaca tt                                32

<210> SEQ ID NO 1252
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1252
ccttcctcat atagggtgag gtaatgtgcc ag                                    32

<210> SEQ ID NO 1253
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1253
gcgggatacc tttttttacc ctaaatatt                                        29

<210> SEQ ID NO 1254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1254
taaaaattag caaagcggat t                                                21

<210> SEQ ID NO 1255
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1255
aggagctcgc ctgaacatcg ggtgagttta ga                                    32

<210> SEQ ID NO 1256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1256
caatagcaaa atgtgaatta                                                  20

<210> SEQ ID NO 1257
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1257
ctaaaattaa tcaggtcata cataaattaa gac                                   33

<210> SEQ ID NO 1258
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1258
tgaaaaggcc ggcaccgctg atcgcaccag tgaggaatcc tga            43

<210> SEQ ID NO 1259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1259
caccatcaat atgcgcaagg a            21

<210> SEQ ID NO 1260
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1260
accgttcatc tcaggaatct ggtgcttgat tagaaactat c            41

<210> SEQ ID NO 1261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1261
tgccggagag gcaggtcatt agg            23

<210> SEQ ID NO 1262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1262
ggagcaaaca agagaattag c            21

<210> SEQ ID NO 1263
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1263
tgaacgagat gggaacagtt ggtgtggttg cttgaatcag a            41

<210> SEQ ID NO 1264
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1264
agctcattta agcaaatatt taaatgacca tt 32

<210> SEQ ID NO 1265
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1265
cgccatcaaa ataatatca gaaaagcccc aaaacctgtt 40

<210> SEQ ID NO 1266
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1266
acgtggagct gatagcccca ccagcgtagt ag 32

<210> SEQ ID NO 1267
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1267
cattaaatgt gagggagcgg gtgcgcgta 29

<210> SEQ ID NO 1268
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1268
caacccagac gaacgaacta aaacattttg cg 32

<210> SEQ ID NO 1269
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1269
tctccgtaaa acaggatcta cagcaacaat tc 32

<210> SEQ ID NO 1270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1270

```
taatgggatg cctgagagtc t                                              21
```

<210> SEQ ID NO 1271
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1271

```
tcacaacggc ggggtcacgc cgctaggg                                       28
```

<210> SEQ ID NO 1272
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1272

```
acacgacgcc tgcaaggtga ggtatcatcc aa                                  32
```

<210> SEQ ID NO 1273
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1273

```
agattctggt tttgagaaaa atctatatga cc                                  32
```

<210> SEQ ID NO 1274
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1274

```
gtgcatctgc cagtacgcca gccaccgag                                      29
```

<210> SEQ ID NO 1275
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1275

```
ggacgaacgg caaatgaaca gtgccttaga ct                                  32
```

<210> SEQ ID NO 1276
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1276

```
atcggccacc ttgcgattca aaatttatct tt                                    32

<210> SEQ ID NO 1277
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1277
acaggaatca atattgaacc tccaatactt tt                                    32

<210> SEQ ID NO 1278
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1278
tgggaaggta acgccaggcc agtgccaagc ttctgtgtga                            40

<210> SEQ ID NO 1279
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1279
caggctgcgc aactgt                                                      16

<210> SEQ ID NO 1280
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1280
ctgagtagtc gccattgctt tccggagaca gtcaaat                               37

<210> SEQ ID NO 1281
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1281
ggccttgcag ggcgaccaca atca                                             24

<210> SEQ ID NO 1282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1282
tcacttgctt tataattcca gcca                                             24
```

<210> SEQ ID NO 1283
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1283
aattgttaga agcataaagt gtaaacctgt cgtgccagct gcggtttg                48

<210> SEQ ID NO 1284
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1284
tccgctcaca attccagacg ttgtaaaacg acgggttttc ccagtcac                48

<210> SEQ ID NO 1285
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1285
taaaagagat acttctcggc attgca                                        26

<210> SEQ ID NO 1286
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1286
gaagtgttcg tgctttcctc gttatgacga gc                                 32

<210> SEQ ID NO 1287
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1287
gcgggagcag gaacggtttg agg                                           23

<210> SEQ ID NO 1288
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1288
cgtattggag ttgcagcaag cggttgtttg atggtggttc ggtgccgt                48

<210> SEQ ID NO 1289
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1289
caacgcgcgg ggagaggcat taatgaatcg gccacaacat acgagccg                48

<210> SEQ ID NO 1290
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1290
acgtataaag tgtagcattg accg                                          24

<210> SEQ ID NO 1291
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1291
accaccaccg tactatagaa ccagtc                                        26

<210> SEQ ID NO 1292
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1292
cgctggcagg gagcccccga ttta                                          24

<210> SEQ ID NO 1293
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1293
aaagcactag tttttgggg tcgaaccatc acccaaatca                          40

<210> SEQ ID NO 1294
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1294
aaatcggaac cctaaacagc aggcgaaaat ccccacgctg gtttgccc                48

```
<210> SEQ ID NO 1295
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1295
gagcttgacg gggaaaaagc gaaacgagta a                                   31

<210> SEQ ID NO 1296
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1296
catgtcaatc atatgtaacc agctttcatc aa                                  32

<210> SEQ ID NO 1297
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1297
tttttaccag cgccaaagac aaatggtaat atccagtttt                          40

<210> SEQ ID NO 1298
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1298
ttttagacac cacggttcat atggtttttt                                     30

<210> SEQ ID NO 1299
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1299
tttttagcaa acgtaaagaa acgcaatttt                                     30

<210> SEQ ID NO 1300
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1300
ttttaacgga ataccacgca gtatgttttt                                     30

<210> SEQ ID NO 1301
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1301
ttttgtaagc agataaacgc aataattttt                                           30

<210> SEQ ID NO 1302
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1302
gaagcccttg aaatagccca ataataagag catttt                                    36

<210> SEQ ID NO 1303
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1303
ttttagaaac aattttaaga aaatttt                                              27

<210> SEQ ID NO 1304
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1304
ttttctaata tcgtaggaat cattatttt                                            29

<210> SEQ ID NO 1305
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1305 tttttagac ggaatcagat atagatttt                                             29

<210> SEQ ID NO 1306
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1306
ttttaaaatg aagaacctcc cgactttt                                             29

<210> SEQ ID NO 1307
<211> LENGTH: 29
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1307
ttttcagcca tattaaatca agattttt                                              29

<210> SEQ ID NO 1308
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1308
ttttcaacgc taacgagcgt ctttccagat ggc                                         33

<210> SEQ ID NO 1309
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1309
ttttagttgc tattttgaaa gtaatttt                                              29

<210> SEQ ID NO 1310
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1310
gtcgaggcct tatttatcca gttacaaaat aaatttt                                    37

<210> SEQ ID NO 1311
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1311
tttttgcggg aggttttcgc gcctgtttt                                             29

<210> SEQ ID NO 1312
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1312
tttagcaata gcagtttttg tttaacgtca tttt                                       34

<210> SEQ ID NO 1313
<211> LENGTH: 29
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 1313
ttttaggctt atccggtaac aagaatttt                                        29

<210> SEQ ID NO 1314
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1314
gagccagcag agaattaaaa acagggaagc gcatttt                               37

<210> SEQ ID NO 1315
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1315
ttttccgcgc ccaatagaat cggcttttt                                        29

<210> SEQ ID NO 1316
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1316
ttcatcagag agatagaggg taattgagcg tttt                                  34

<210> SEQ ID NO 1317
<211> LENGTH: 53
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1317
ttttaccgca ctcatcgaga gggtattagt ctttccaaat aaggcgttat ttt             53

<210> SEQ ID NO 1318
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1318
aaccaagttt tttttt                                                      16

<210> SEQ ID NO 1319
<211> LENGTH: 29
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1319
ttttaaataa taatcataat tactatttt                                            29

<210> SEQ ID NO 1320
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1320
tttttttatc aattaccagt ataaatttt                                            29

<210> SEQ ID NO 1321
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1321
tttttctgtc cagcttaatt gagaatttt                                            29

<210> SEQ ID NO 1322
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1322
tttttttcga gccagtaata agagaatttt ttatcctgaa tcttactttt                     50

<210> SEQ ID NO 1323
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1323
tttttcgcca tatttaaaga agagttttt                                            29

<210> SEQ ID NO 1324
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1324
ttttgccaac gctcaacagg tctgatttt                                            29

<210> SEQ ID NO 1325
<211> LENGTH: 29
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1325
ttttgaaaaa gcctgttatg taaattttt                                   29

<210> SEQ ID NO 1326
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1326
ttttaataag aataaaccaa agaactttt                                   29

<210> SEQ ID NO 1327
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1327 tttttctga cctaaattta tttagttagc gagaaaattt caattacctt ttt          53

<210> SEQ ID NO 1328
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1328
atttcatctt tttttt                                                 16

<210> SEQ ID NO 1329
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1329
ttttgctgat gcaacaaaca tcaagtttt                                   29

<210> SEQ ID NO 1330
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1330
ttttgagact acacctttt taatgtttt                                    29

<210> SEQ ID NO 1331
<211> LENGTH: 29
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1331
ttttcaatag tgtatatgtg agtgattttt                                29

<210> SEQ ID NO 1332
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1332
tttttagaat ccttgaaaac atagcctcta atttaggcag aggcattttt          50

<210> SEQ ID NO 1333
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1333
ttttataacc ttgcttcatc aatatttttt                                29

<210> SEQ ID NO 1334
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1334
ttttgaaaca gtacataacc taccattttt                                29

<210> SEQ ID NO 1335
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1335
ttttaaaaca aaattaaatt ttcagttttt                                29

<210> SEQ ID NO 1336
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1336
ttttgagcaa aagaagaaga aacaattttt                                29

<210> SEQ ID NO 1337
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1337
ttttatcgcg cagaggcgaa ataccaata acggatacta acaactaatt ttt          53

<210> SEQ ID NO 1338
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1338
gttacaaatt tttttt                                                   16

<210> SEQ ID NO 1339
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1339
ttttgtttaa cgataataca tttgatttt                                     29

<210> SEQ ID NO 1340
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1340
tttttatcaa aatcgtatta aatccttttt                                    29

<210> SEQ ID NO 1341
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1341
ttttaatcct gattttaaaa gtttgtttt                                     29

<210> SEQ ID NO 1342
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1342
ttttcggaat tatcatcata ttcctttgta ttaattaatt ttcccttttt              50

<210> SEQ ID NO 1343
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1343
ttttagtaac attatcatcg ccattttt                                   29

<210> SEQ ID NO 1344
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1344
tttttttgcc cgaacgtcgg tcagtttt                                   29

<210> SEQ ID NO 1345
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1345
ttttggattt agaagtaacg ctgagtttt                                  29

<210> SEQ ID NO 1346
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1346
ttttagatta gagccgtaaa tatcattt                                   29

<210> SEQ ID NO 1347
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1347
tttttgaaag gaattgagga ttggcaaaaa ccctcaaaaa cgctcatggt ttt        53

<210> SEQ ID NO 1348
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1348
tcaacagttt tttttt                                                16

<210> SEQ ID NO 1349
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1349
```
ttttagccag cactcaatcg tctgattttt                                29

<210> SEQ ID NO 1350
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1350
ttttattaac acccagtaat aaaagtttt                                 29

<210> SEQ ID NO 1351
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1351
ttttaaaaat acgatagaac ccttctttt                                 29

<210> SEQ ID NO 1352
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1352
ttgatatcgc gtctggcctt cctgtcacag acaatatttt tgatttt             47

<210> SEQ ID NO 1353
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1353
ttttatggct attagtcttt aatgcgagag aaaccaccag aaggagtttt          50

<210> SEQ ID NO 1354
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1354
tttttgacct gaaagcgacg tggcgtttt                                 29

<210> SEQ ID NO 1355
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1355
ttttggacat tctggcccgc ttaattttt                                    29

<210> SEQ ID NO 1356
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1356
ttttaatgga ttatttaagg ccgatttt                                     29

<210> SEQ ID NO 1357
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1357
ttttaaatac ctacatttca cgcaatttt                                    29

<210> SEQ ID NO 1358
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1358
ttttaacaat attaccgcca gcaaataggt aaatattttg taggtggca               49

<210> SEQ ID NO 1359
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1359
ttttattaac cgttgtagca tctgtccatt gcgacagt                           38

<210> SEQ ID NO 1360
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1360
tttttaaagg gattttagac taaacaggca ttggc                              35

<210> SEQ ID NO 1361
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1361
ttttgcgccg ctacagggcg acccgccgaa cgtcggat                           38

<210> SEQ ID NO 1362
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1362
ttttagaaag gaagggaaga gccggcgata agaat                                    35

<210> SEQ ID NO 1363
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1363
gtataccgcc accctcagaa ccgc                                                24

<210> SEQ ID NO 1364
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1364
gagtattaag aggctgagac tcctcaccgt actcaggagg tttagaat                      48

<210> SEQ ID NO 1365
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1365
caacgtcata catggctttt gatgtattat tctgaaacat gaaagcca                      48

<210> SEQ ID NO 1366
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1366
cgaaaccacc accagagccg ccgctgaatt taccgttcca gtaagggc                      48

<210> SEQ ID NO 1367
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1367
ttttagcccc cttattagcg tttgcaccct cagagccgcc accagcag                      48

<210> SEQ ID NO 1368
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1368
ggaagtagca ccattaccat tagtttcatc ggcattttcg gtcacgg                47

<210> SEQ ID NO 1369
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1369
cgcgcgacat tcaacaaaat caccacca                                     28

<210> SEQ ID NO 1370
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1370
gccaaaatac atacaagaca aaaggcac                                     28

<210> SEQ ID NO 1371
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1371
tataagcaga tagcagcaaa cgtaggcc                                     28

<210> SEQ ID NO 1372
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1372
tgagtaattg agcgttaaga aaagttca                                     28

<210> SEQ ID NO 1373
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1373
cagaacgtca aaaat                                                   15

```
<210> SEQ ID NO 1374
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1374
gtactggtaa taagaaagtc agaggatt                                        28

<210> SEQ ID NO 1375
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1375
tttttaatgc ccctgccta tttccgatag ttgcgccgac aatgactg                   48

<210> SEQ ID NO 1376
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1376
ttatcaatat atgtggtaaa gtaattcaac                                      30

<210> SEQ ID NO 1377
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1377
aataccagtc aggacgttgg gaagataaca gttgattccc aattcagc                  48

<210> SEQ ID NO 1378
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1378
tgtataccta cattatatct ttaggtgc                                        28

<210> SEQ ID NO 1379
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1379
cgctcatgga ataaaa                                                     16

<210> SEQ ID NO 1380
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1380
attacgccag ctgcta                                                        16

<210> SEQ ID NO 1381
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1381
gaggcgaaag ggggatactc tagaggatcc ccgggtagta                              40

<210> SEQ ID NO 1382
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1382
cgcccgagct cgaattcgta atcatgagtg agctaactca cattacac                     48

<210> SEQ ID NO 1383
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1383
ggtattgcgt tgcgctcact gccctctttt caccagtgag acggggga                     48

<210> SEQ ID NO 1384
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1384
aaacaacagc tgattgccct tcacccttat aaatcaaaag aatagagg                     48

<210> SEQ ID NO 1385
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1385
taacccgaga tagggttgag tgttgaacgt ggactccaac gtcaacaa                     48

<210> SEQ ID NO 1386
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1386
tgaaccatca ccagg                                                15

<210> SEQ ID NO 1387
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1387
attcatttca attacccgcg cagaggcgaa tttttggag ggaggg               46

<210> SEQ ID NO 1388
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1388
tcagatgatg gcaacaataa cttttggagg gaggg                          35

<210> SEQ ID NO 1389
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1389
attatcattt tttatcatca tattcctgat tattttggag ggaggg              46

<210> SEQ ID NO 1390
<211> LENGTH: 65
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1390
ttctgtgcaa aagaaggcac caggctgacc gtaatcttga caagaaccgg attttccagc    60
cagcc                                                               65

<210> SEQ ID NO 1391
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1391
gcaaaagacg gtgtacagac cttttccagc cagcc                          35

<210> SEQ ID NO 1392
```

```
<211> LENGTH: 56
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1392
gcatcaaaaa gattaagagg aacttcaaat atcgcgtttt aattttccag ccagcc          56

<210> SEQ ID NO 1393
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1393
tttttccctc cctcc                                                       15

<210> SEQ ID NO 1394
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1394
tttttggctg gctgg                                                       15

<210> SEQ ID NO 1395
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1395
tttttggagg gaggg                                                       15
```

NANOCAGED ENZYMES WITH ENHANCED CATALYTIC ACTIVITY AND INCREASED STABILITY

CROSS-REFERENCE TO RELATED APPLICATIONS

This application claims the benefit of U.S. Provisional Application No. 62/361,884, filed Jul. 13, 2016, which is hereby incorporated by reference in its entirety for all purposes.

STATEMENT REGARDING FEDERALLY SPONSORED RESEARCH

This invention was made with government support under W911NF-11-1-0137 and W911NF-12-1-0420 awarded by the Army Research Office. The government has certain rights in the invention.

SEQUENCE LISTING

The instant application contains a Sequence Listing which has been filed electronically in ASCII format and is hereby incorporated by reference in its entirety. Said ASCII copy, created on Jul. 12, 2017, is named 112624_00885_SL.txt and is 331,513 bytes in size.

BACKGROUND

Common micro- and nanoscale subcellular compartments are formed from either lipids or proteins and include mitochondria, lysosomes, peroxisomes, carboxysomes and other metabolosomes, as well as multi-enzyme complexes. Compartments increase the overall activity and specificity of the encapsulated enzyme pathways by maintaining a high local concentration of enzymes and substrates, promoting substrate channeling and protecting their content from damage, as well as by segregating potentially damaging reactions from the cytosol. Spatial confinement is also an important aspect for chaperone-assisted folding of linear polypeptides into active tertiary and quaternary conformations, as well as for preventing proteins from aggregating under cellular stress conditions. A better understanding of the effects of spatial confinement on protein function will not only enhance the fundamental knowledge of cellular organization and metabolism but also increase the ability to translate biochemical pathways into a variety of noncellular applications, ranging from diagnostics and drug delivery to the production of high-value chemicals and smart materials. Over the past few decades, artificial enzymatic particles have been created using compartmentalization by virus-like protein particles, liposomes or polymersomes and chemical crosslinking. However, severe obstacles to a broader application remain, including low encapsulation yield of large proteins because of steric hindrance, insufficient access of substrates to the encapsulated enzymes, aggregation of vesicle shells and limited control over the spatial arrangement of proteins within the compartments.

SUMMARY

In a first aspect, provided herein is a nanocage, where the nanocage comprises a three dimensional body comprising a plurality of structural members comprising DNA, wherein internal surfaces of the plurality of structural members form an inner cavity. The DNA can be M13 viral DNA. Architectural arrangement of the structural members in the three dimensional body can form a honeycomb lattice. Architectural arrangement of the structural members in the three dimensional body can form a square lattice. In some cases, the architectural arrangement of the structural members in the three dimensional body can form a single-walled square lattice. In other cases, the architectural arrangement of the structural members in the three dimensional body can form a double-walled square lattice. The three dimensional body can be smaller than 100 nm×100 nm×100 nm. The three dimensional body can be smaller than 75 nm×50 nm×50 nm. The inner cavity of the three dimensional body can measure less than 50 nm×50 nm×50 nm. The three dimensional body can further comprise at least one nanopore. The at least one nanopore can have a diameter of about 1 nm to about 5 nm. The at least one nanopore has a diameter of about 1.5 nm to about 3 nm. The three dimensional body can comprise between 0.10 to 0.30 DNA helices per $nm^2$. The three dimensional body can comprise between 0.11 to 0.17 DNA helices per $nm^2$.

In another aspect, provided herein is a nanoparticle comprising a nanocage comprising a plurality of structural members comprising DNA in a three-dimensional lattice, wherein internal surfaces of the plurality of structural members form an inner cavity; and one or more payload molecules bound to internal surfaces of the inner cavity. The payload molecules can comprise enzymes, nucleic acids, polypeptides, antibodies, phospholipids, or any combination thereof. The inner cavity can encapsulate two payload molecules. The one or more payload molecules can be covalently linked to internal surfaces of the inner cavity. The nanocage can be configured to prevent proteolytic degradation of the trapped payload molecule. The nanocage can be configured to enhance the activity of the trapped payload molecule.

In another aspect, provided herein is a method of making a nanoparticle, where the method comprises trapping a payload macromolecule in an open half cage; and assembling two half cages into a closed nanocage; wherein the closed nanocage has an inner cavity; wherein the closed nanocage has nanopores; and wherein the resulting nanoparticle comprises a closed nanocage comprising nanopores and an inner cavity comprising one or more biological macromolecules. The half cage can comprise DNA. The DNA can be M13 viral DNA. The half cage comprising DNA can be constructed by folding full-length M13 viral DNA. The half cage can comprise a base and two adjoined side walls protruding from the base. The biological macromolecule can be covalently linked to the half cage. Two half cages can be assembled into a closed nanocage by adding short bridge DNA strands.

BRIEF DESCRIPTION OF DRAWINGS

The patent or patent application file contains at least one drawing in color. Copies of this patent or patent application publication with color drawings will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

DETAILED DESCRIPTION

Figure 1A:
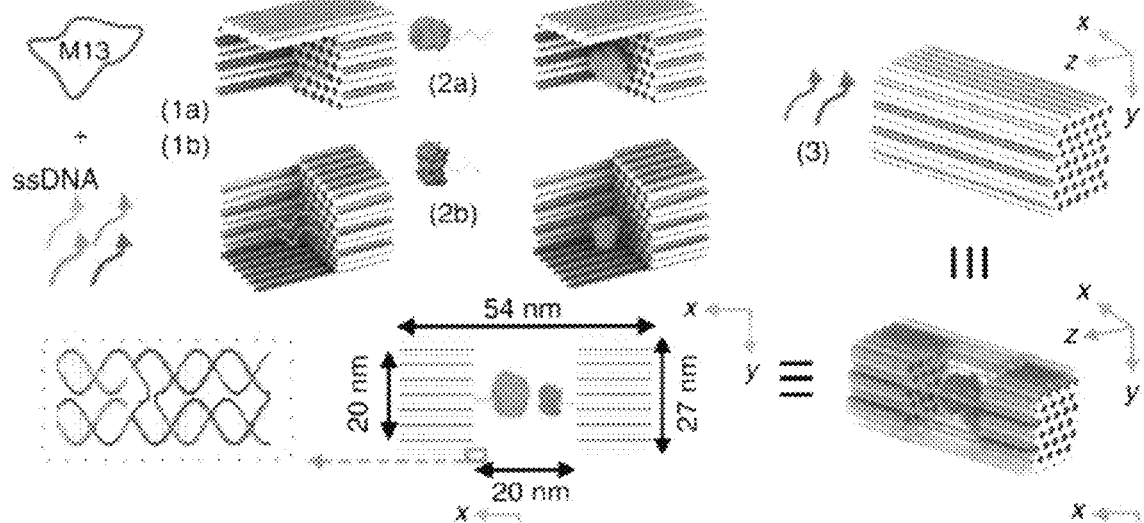
FIGS. 1A-1C show design and characterization of DNA nanocage-encapsulated enzymes with controlled stoichiometry. (A) Schematic representations of the assembly of a DNA nanocage encapsulating a pair of GOx (orange) and HRP (green) enzymes. Individual enzymes were first attached to half-cages, followed by the addition of linker strands (red) to combine the two halves into a full-cage. Small pores of honeycomb shape (~2.5 nm d.i.) were designed on the bottom of cages to facilitate the diffusion of substrate molecules in an out of the cage. (B) Negatively stained TEM images of DNA cages containing a single GOx (shown as less stained dots) and (C) a pair of GOx and HRP (shown as less stained dots). Scale bar, 50 nm.

The present disclosure describes a three dimensional nanocage assembly to encapsulate a biological macromolecule and methods of nanocage assembly. DNA nanostructures have emerged as promising molecular scaffolds to organize biomolecules at the nanoscale based on their programmable, sequence-driven self-assembly. For example, multi-enzyme cascades have been assembled on DNA nanostructures with precise control over the spatial arrangement to enhance catalytic activity by substrate channeling. Conversely, self-assembling DNA nanoboxes and cages have shown promise in the delivery of macromolecular payloads such as antibodies and enzymes. Tubular DNA nanostructures have also been used to construct efficient enzyme cascade nanoreactors. The present invention is based at least in part on the inventors' development of a simple and robust strategy for encapsulating metabolic enzymes in DNA-templated nanocages, where nanoparticles comprising the nanocaged enzymes are obtained with high assembly yield and controlled packaging stoichiometry.

Accordingly, in a first aspect, provided herein is a nanoparticle useful for the transport and administration of therapeutic agents, bioactive compounds, biomolecular reagents, biocatalysts, and other molecular compounds of interest, referred to generally herein as payload molecules (e.g., nucleic acids, polypeptides, enzymes, antibodies, or phospholipids). As used herein, the term "nanoparticle" refers to a structural composition comprising a full closed nanocage and at least one payload biological macromolecule tapped within the inner cavity of the nanocage. As used herein, "nanocage" may refer to a three dimensional body comprising an inner cavity. The three dimensional body of the nanocage is an assembly of a plurality of structural members. The internal surfaces of the structural members form the edges of the inner cavity. In one embodiment, these structural members are, tubular, rod like or linear, and may be constructed using nucleic acids. In another embodiment, the structural members are assemblies of double stranded DNA. A full closed nanocage may be formed by the assembly of two half cages.

The nanocage may be assembled using any means known in the art in which a nano-scale structure if formed. Assembly methods include, but are not limited to, DNA origami, or assembly using liposomes, polymersomes, or virus-like particles. For example, nanocages can be assembled by genetic fusion, chemical crosslinking, surface co-immobilization, and encapsulation within polymer vesicles, or virus-like particles. As used herein, "DNA origami" may refer to an assembly technique that folds a single-stranded DNA template into a 2 or 3 dimensional target structure by annealing it with short staple strands. In one embodiment, the body of the nanocage comprises between 0.10 to 0.30 DNA helices per $nm^2$. In another embodiment, the body of the nanocage comprises between 0.11 to 0.17 DNA helices per $nm^2$.

In one embodiment, the DNA used to assembly the body of the nanocage is M13mp18 single-stranded DNA. M13mp18 DNA is a circular, single-stranded virus DNA of approximately 7249 nucleotides in length and was isolated from M13mp18, a M13 lac phage vector comprising single HindIII, SphI, SbfI, PstI, SalI (AccI/HincII), XbaI, BamHI, SmaI (XmaI), KpnI (Acc65I), SacI and EcoRI sites within the gene encoding β-Galactosidase. Generally, M13mp18 DNA is useful as a standard and has been tested as a template in the dideoxy-nucleotide termination method of sequencing DNA. Detailed sequences are available at neb.com/products/n4040-m13mp18-single-stranded-dna#pd-description on the World Wide Web.

Other single-stranded circular DNA that can be used to fold a DNA nanocage include, without limitation, p7308, p7560, p7704, p8064, p8634, and pEGFP.

Figure 7:
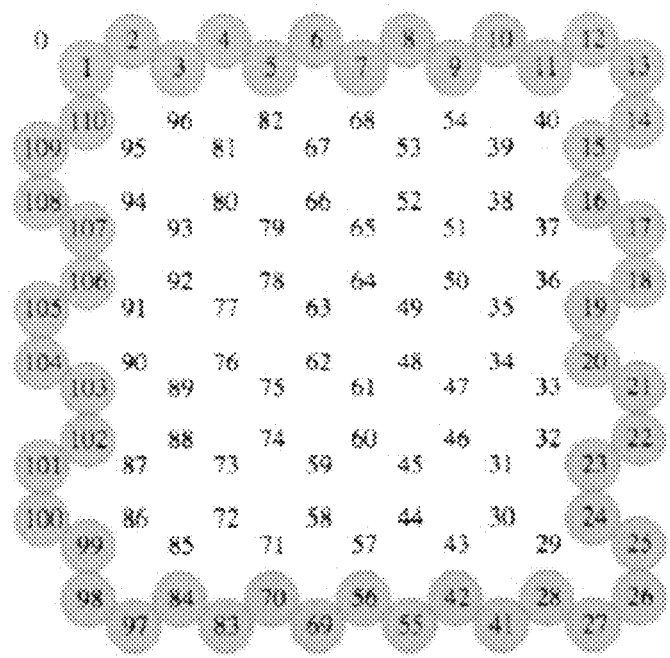
FIG. 7 illustrates an exemplary SH full-cage having a honeycomb lattice arrangement, presented in cross-sectional view and 3D view.
Figure 7:
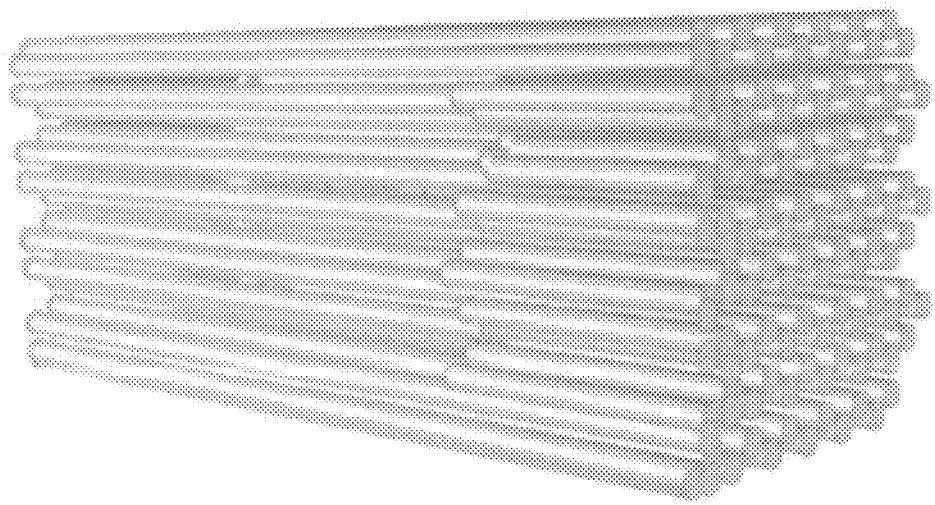
Figure 8:
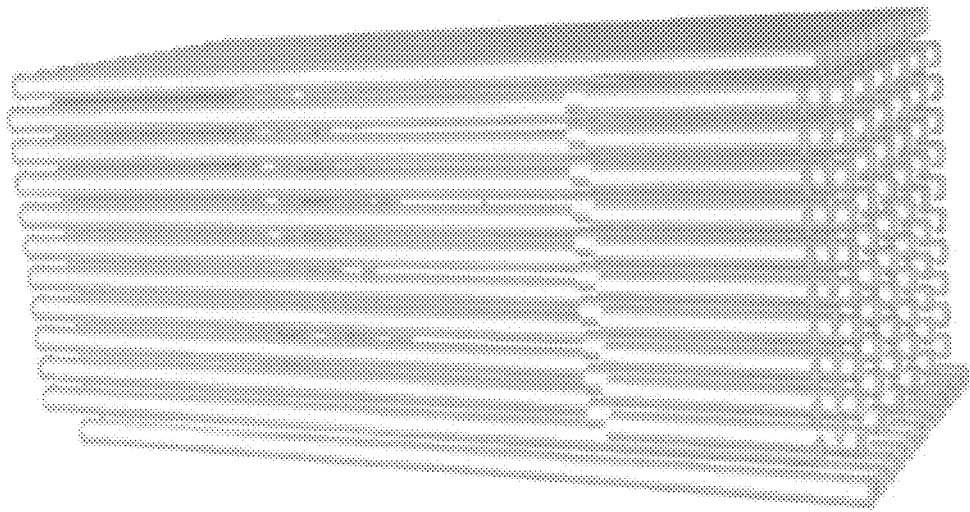
FIG. 8 illustrates an exemplary SS cage having a square lattice arrangement, presented in cross-sectional view and 3D view.
Figure 9:
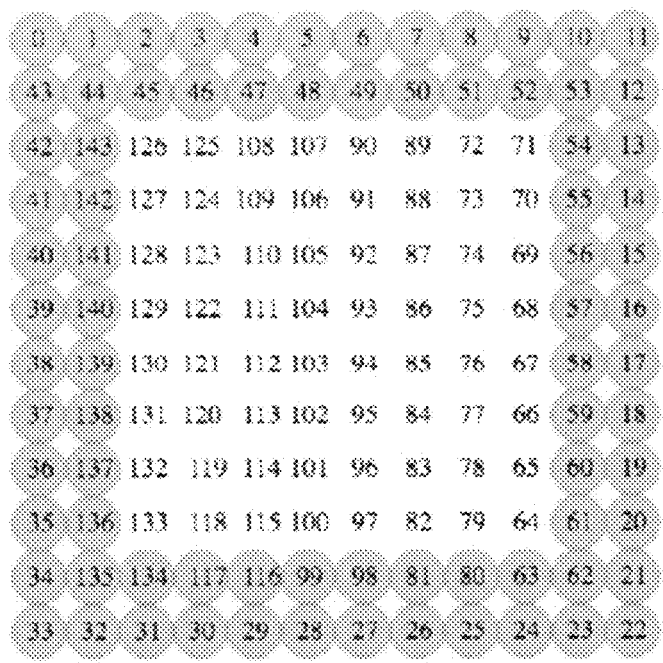
FIG. 9 illustrates an exemplary DS cage having a square lattice arrangement, presented in cross-sectional view and 3D view.
Figure 9:
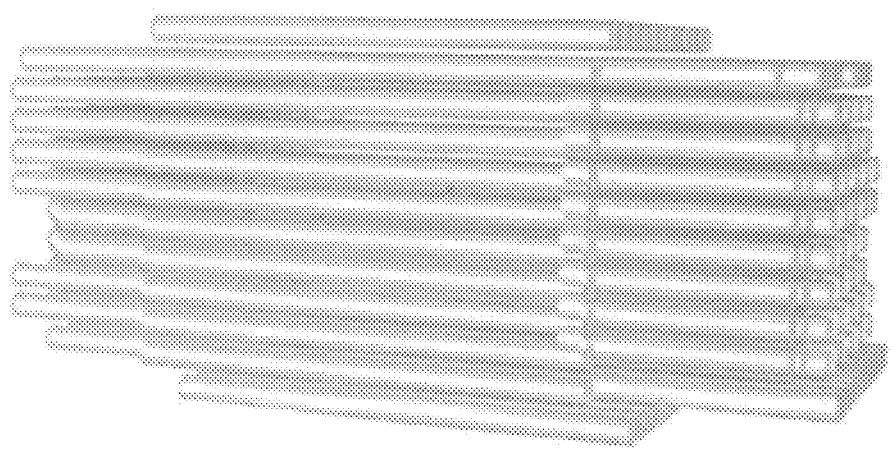

The nanocage may be formed in any architecture compatible with the chosen method of assembly. In one embodiment, the architecture of the structural members forms a square lattice, wherein the structural members and arranged in columns and rows. In another embodiment, the architecture of the structural members forms a honeycomb lattice (see FIG. 7). The architecture, assembly and three dimensional lattice of the nanocage may also accommodate variations in the number of and thickness of the walls of the nanocage. In one embodiment, the nanocage has a single walled square lattice arrangement as shown in FIG. 8, where there is a single layer of structural element between the inner cavity and the exterior of the nanocage. In one embodiment, the nanocage has a double walled square lattice arrangement as shown in FIG. 9, where there is a double layer of structural element between the inner cavity and the exterior of the nanocage. In another embodiment, the nanocage is multi-walled with several layers of structural elements between the inner cavity and the exterior of the nanocage.

The nanocage may be any size to accommodate the encapsulation of the enzyme or macromolecule of interest. In one embodiment, the dimensions of the nanocage are less than 100 nm×100 nm×100 nm. In another embodiment, the dimensions of the nanocage are less than 75 nm×50 nm×50 nm. In another embodiment, the dimensions of the nanocage are about 40-70 nm×15-40 nm×15-40 nm.

The inner cavity of the nanocage is a hollow, open space enclosed within the nanocage to contain the macromolecule or enzyme of interest. The inner cavity will have dimensions smaller than those of the nanocage. In one embodiment, the dimensions of the inner cavity are less than 50 nm×50 nm×50 nm. In one embodiment, the dimensions of the inner cavity are less than 30 nm×30 nm×20 nm.

In some cases, a nanoparticle as provided herein encapsulates a biological macromolecule within the inner cavity of the nanocage. Any biological macromolecule having any purpose or function can be encapsulated as payload within a nanocage thereby forming a nanoparticle. Exemplary biological macromolecules include, without limitation, proteins, enzymes, antibodies, protein complexes, phospholipids, nucleic acids, and combinations thereof. In one embodiment, the biological macromolecule is an enzyme. The design and structure of the nanocage may be changed and adjusted to accommodate a variety of enzymes with any size, shape, morphology or function. In one embodiment the enzyme has a molecular weight between 10-600 kilodaltons (kDa). Preferably, the nanocage accommodates enzymes having a molecular weight equal to or less than about 600 kDa.

Without being limited to one particular theory or practice, the nanocage structure may be configured for a variety of functions in regards to the encapsulated enzyme or macromolecule. In embodiments in which the macromolecule is an enzyme, the nanocage may be configured such that the catalytic activity of the enzyme may be tested while the enzyme is encapsulated within the nanocage. The nanocage may also be configured such that the catalytic activity of the enzyme is enhanced when encapsulated within the inner cavity. The nanocage may also be configured such that the enzyme is stabilized against protease digestion or proteolytic degradation when encapsulated within the inner cavity.

The nanocage structure and assembly may be designed and assembled into a nanoparticle to accommodate a variety of macromolecular configurations within the inner cavity. For example, a single nanocage may encapsulate a payload including but not limited to, a single biological macromolecule, a pair of biological macromolecules, a plurality of biological macromolecule, assemblies of biological macromolecules, multi-component complexes of biological macromolecules, or combinations thereof. When the nanoparticle comprises a payload of multiple biological macromolecules, the macromolecules may be the same, or they may be an assembly of two or more different macromolecules.

A nanocage may comprise one or more nanopores. As used herein, "nanopore" may refer to a nano-scale passage, pore or opening in the nanocage. The nanopore may be configured to allow the passage of small molecule substrates, solvents, enzyme substrates and products and the like into and out of the nanocage. The nanopores are sized such that the enzyme encapsulated within the nanocage cannot escape. In one embodiment, the nanocage comprises at least one nanopore. In another embodiment, the nanocage comprises 1-200 nanopores. In another embodiment, the nanocage comprises 10-75 nanopores. The size of the nanopores is determined by the interaction, arrangement and architecture of the structural members of the body of the nanocage, such that nanopores may be formed in the gaps between the structural members. In one embodiment, the nanopores are between 1 and 5 nm in diameter. In another embodiment, the nanopores are between 1.5 and 3 nm in diameter.

In some embodiments, the enzyme may be non-covalently linked to the internal surface of the nanocage. In another embodiment, the enzyme may be covalently connected to the internal surfaces of the nanocage. In one non-limiting, exemplary embodiment, succinimidyl 3-(2-pyridyldithio) propionate (SPDP) chemistry may be used to crosslink a surface lysine residue on the biological macromolecule to a thiol-modified oligonucleotide. Other useful methods include, without limitation, aptamer-protein noncovalent interactions, NTA-hexahistidine interactions, click chemistry, disulfide and maleimide coupling, and SPDP and SMCC (N-Succinimidyl 3-(2-pyridyldithio)-propionate) cross-linking.

A half-cage of the body of the nanocage may be assembled utilizing DNA origami. DNA structures can be designed with caDNAno and single strand DNA may be used as the scaffold. To form the half-cage, single strand DNA may be mixed with corresponding staple strands and annealed. Excess staple strands may be removed by filtration.

An enzyme molecule may be attached to the open half-cage by any appropriate covalent or non-covalent chemistry such as, for example, include, without limitation, aptamer-protein noncovalent interactions, NTA-hexahistidine interactions, click chemistry, disulfide and maleimide coupling, and SPDP and SMCC (N-Succinimidyl 3-(2-pyridyldithio)-propionate) cross-linking.

In some cases, two half-cages of the body of the nanocage are assembled by linking together half-cages. Linking may occur by incubating half-cages with DNA linkers. For example, DNA linkers may hybridize with sticky ends extending from the edge of "DNA half-cages." Preferably, DNA linkers are complimentary to these sticky ends, and can be varied for different DNA cage sequences.

The present invention has been described in terms of one or more preferred embodiments, and it should be appreciated that many equivalents, alternatives, variations, and modifications, aside from those expressly stated, are possible and within the scope of the invention.

EXAMPLE 1

The embodiment described here demonstrates a simple and robust strategy for the DNA nanocage-templated encapsulation of metabolic enzymes with high assembly yield and controlled packaging stoichiometry. With such an approach in hand, the hypothesis that the recently described, chaperone-like stabilizing impact of polyphosphate on metabolic protein enzymes together with the cryptic RNA binding properties of many enzymes may lead to beneficial effects when enzymes are surrounded by DNA nanocages, is tested.

Methods

The Design and Characterization of DNA Half-Cages and Full-Cages.

DNA origami half-cage and structures were designed with caDNAno, each used one M13mp18 ssDNA as the scaffold. Detailed design schemes are shown in FIGS. 7-9. One or both of the half-cages contained single-stranded probe strands (4 in each half-cage) extended toward the inside of the cage for binding with the DNA conjugated enzymes. Two of the half-cages can be linked together to form a fully enclosed full-cage though 24 linker strands. To form each of the half-cages, the M13mp18 ssDNA was mixed with the corresponding staples at a 1:10 molar ratio in 1×TAE-Mg2+ buffer (40 mM Tris, 20 mM acetic acid, 2 mM EDTA and 12.5 mM magnesium acetate, pH 8.0), annealed from 80° C. to 4° C. for 37 h. The excess staple strands were removed by the filtration of the DNA cages solution using 100-kD Amicon filter with 1×TAE-Mg2+ buffer for three times. To form a full-cage, 24 single-stranded DNA linkers were incubated with the two purified half-cages at a molar ratio of 5:1 for three hours at room temperature, in order to connect the two half-cages together.

Enzyme-DNA Cage Assembly.

A 15-fold molar excess of oligonucleotide-conjugated enzyme was incubated with the DNA half-cage containing capture strands. Protein assembly was performed using an annealing protocol in which the temperature was gradually decreased from 37° C. to 4° C. over 2 h and then held constant at 4° C. using an established procedure. Two Enzyme-attached half cages were then assembled into a full cage by adding DNA linkers as described above. The DNA caged-enzymes were further purified by agarose gel electrophoresis to remove excess free enzymes.

Preparation, Purification, and Characterization of Protein-DNA Conjugates.

Figure 13:
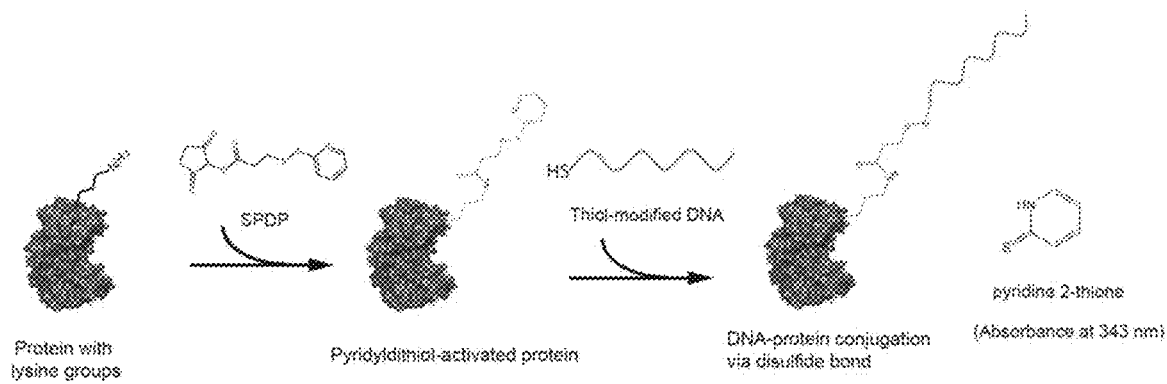
FIG. 13 shows a schematic illustration of the SPDP conjugation chemistry used for protein-DNA conjugation.
Figures 14A, 14B, 14C, 14D, 14E, 14F:
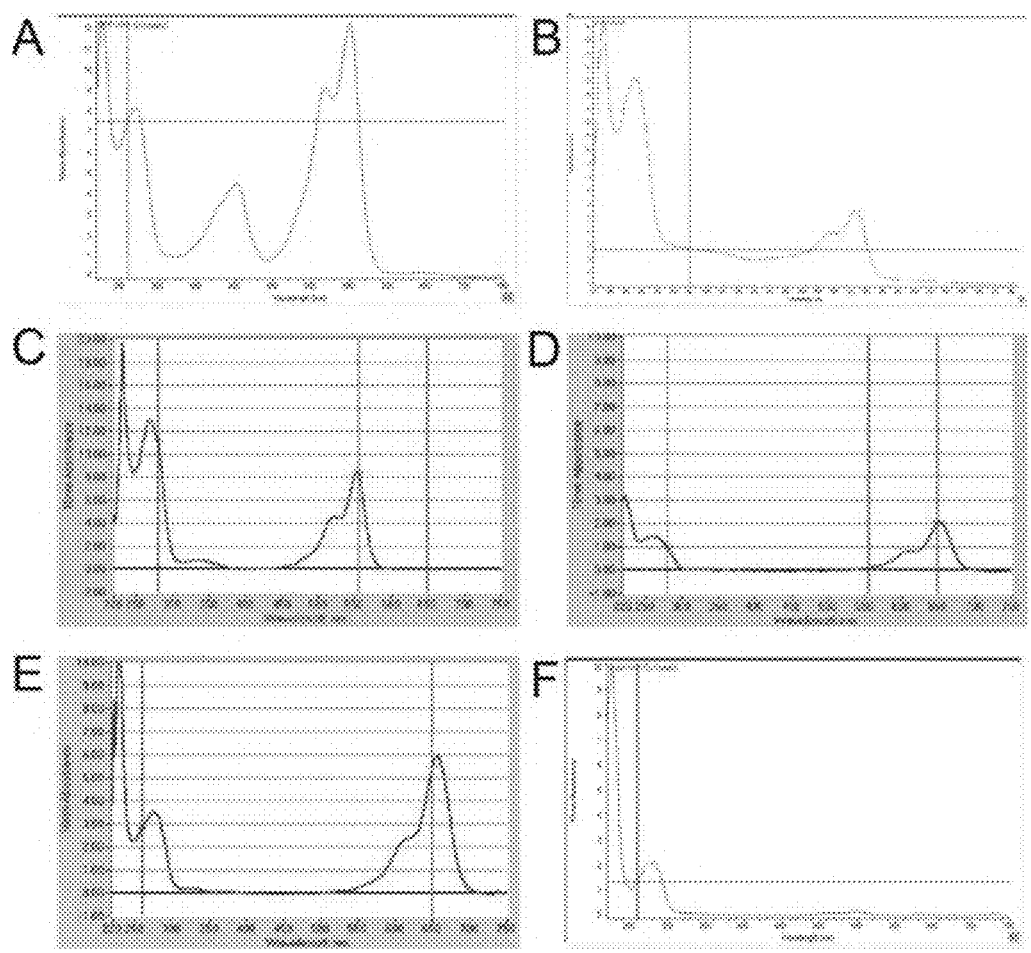
FIGS. 14A-14F show quantification of fluorescent dye-labeled enzyme-DNA conjugates using UV-Vis absorbance spectroscopy. (A) Cy3-labeled HRP-TTTTTCCCTC-CCTCC (SEQ ID NO:1393) with an average dye-to-protein ratio of 1.8; (B) Cy3-labeled GOx-TTTTTCCCTCCCTCC (SEQ ID NO:1393) with an average dye-to-protein ratio of 1.5; (C) Cy3-labeled G6pDH-TTTTTCCCTCCCTCC (SEQ ID NO:1393) with an average dye-to-protein ratio of 1.6; (D) Alexa Fluor 647-labeled MDH-TTTTTGGCTG-GCTGG (SEQ ID NO:1394) with an average dye-to-protein ratio of 1.2; (E) Alexa Fluor 647-labeled LDH-TTTTTG-GCTGGCTGG (SEQ ID NO:1394) with an average dye-to-protein ratio of 1.7; (F) Cy3-labeled (β-Gal)-TTTTTC-CCTCCCTCC (SEQ ID NO:1393) with an average dye-to-protein ratio of 0.6.
Figures 15A, 15B:
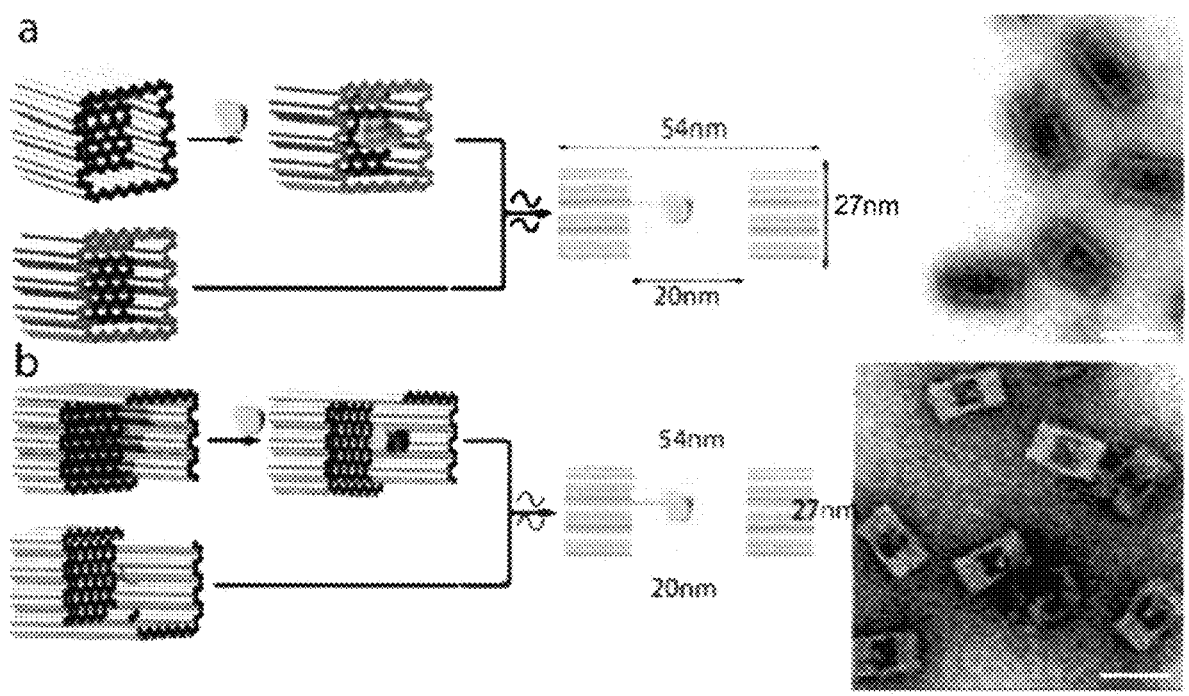
FIGS. 15A-15B shows two different designs for the cage structure with different encapsulation yields (see FIG. 16 and FIG. 17), assembled with GOx. (A) Cage with closed-wall design. (B) Cage with open-wall design.
Figure 16:
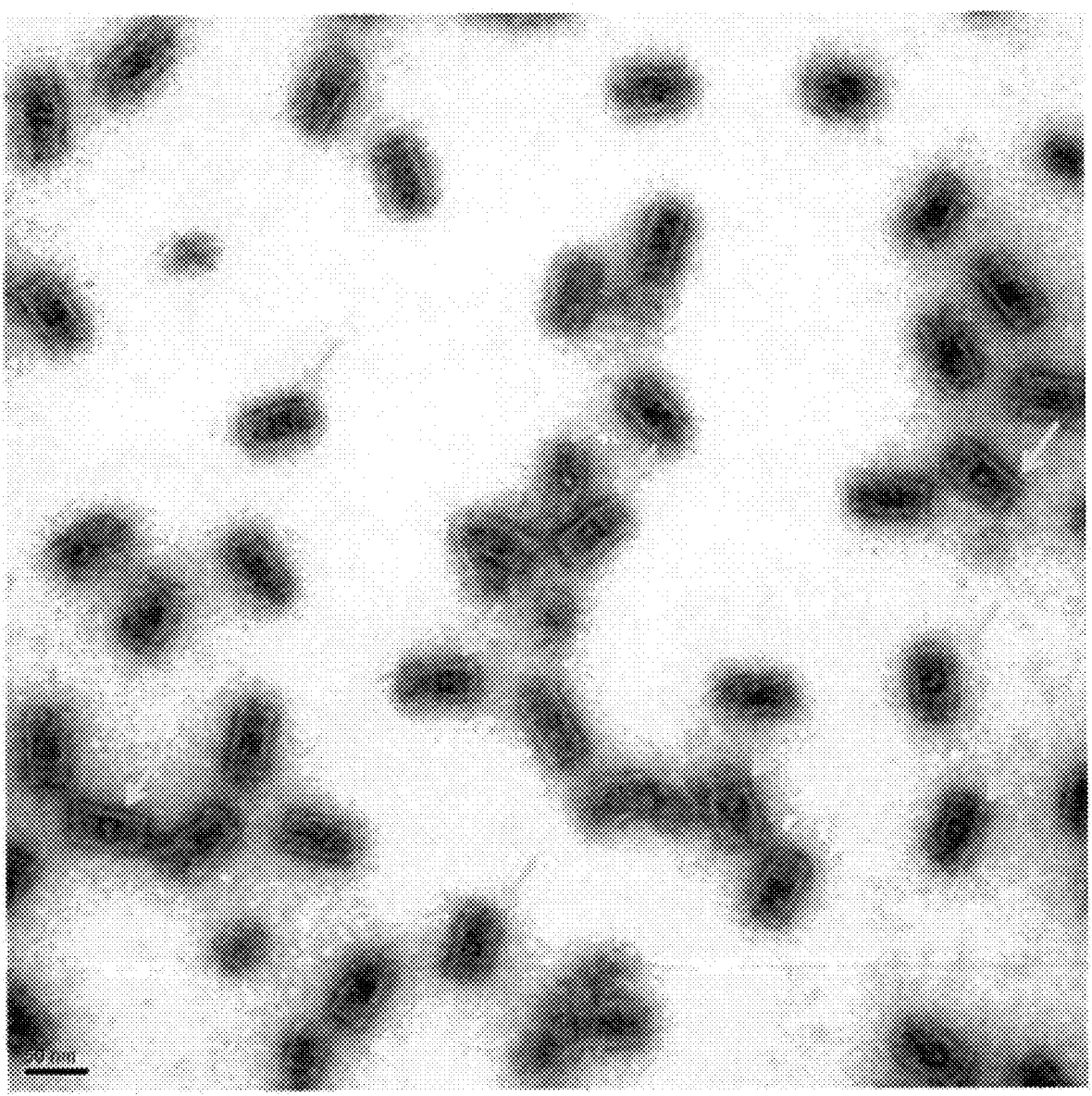
FIG. 16 shows TEM image of full-cages with closed-wall design (FIG. 15A) encapsulating GOx. An encapsulation yield of 38% was estimated from similar images containing about 230 DNA cages by dividing the number of cages with a discernible protein inside by the total number of the cages counted (yellow arrow indicates DNA cage with enzyme inside).
Figure 17:
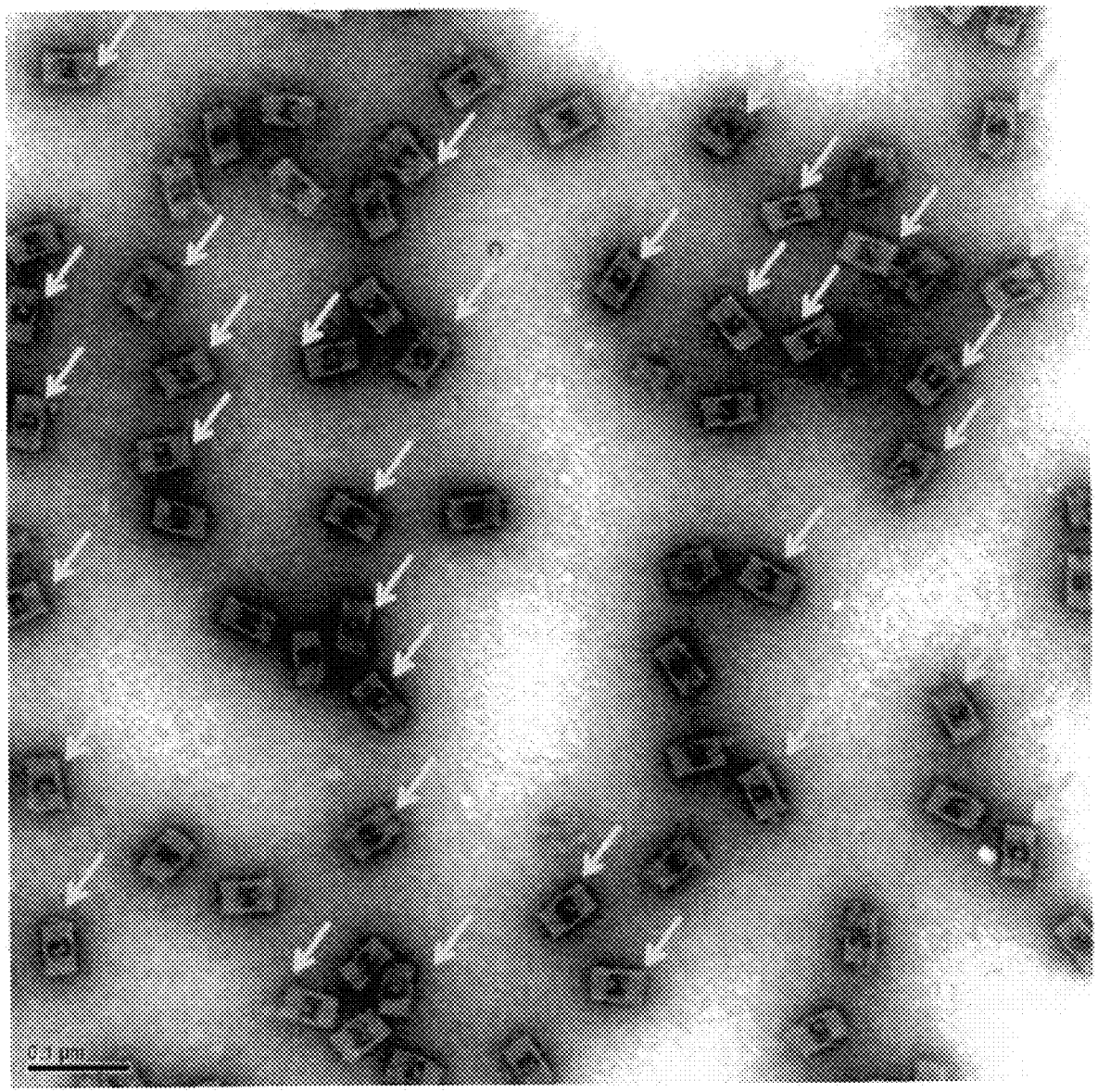
FIG. 17 shows TEM image of full-cage with open-wall design (FIG. 15B) encapsulating GOx. An encapsulation yield of 77% was estimated from similar images containing about 300 DNA cages by dividing the number of cages with a discernible protein inside by the total number of cages counted (yellow arrow indicates DNA cage with enzyme inside).

Protein-DNA conjugation—as shown in FIG. 13, SPDP conjugation chemistry was used to couple enzymes to oligonucleotides as reported previously. Enzymes (GOx, HRP, G6pDH, LDH, MDH and β-Gal) were first conjugated with SPDP at enzyme-to-SPDP ratios of 1:5, 1:20, 1:3, 1:5, 1:5, and 1:5, respectively, in HEPES buffer (50 mM HEPES, pH 8.5) for 1 h at room temperature. Different values of SPDP-to-Protein ratio were used due to the varied number of accessible surface lysine residues for each protein. Excess SPDP was removed by washing with 50 mM HEPES buffer using Amicon centrifugal filters (30 kD cutoff). The SPDP coupling efficiency was evaluated by monitoring the increase in absorbance at 343 nm due to the release of pyridine-2-thione (extinction coefficient: 8080 $M^{-1}$ $cm^{-1}$).

TCEP-treated thiolated DNA (/5ThioC6-/-TTTTTC-CCTCCCTCC (SEQ ID NO:1393) (P1), or/5ThioC6-D/-TTTTTGGCTGGCTGG (SEQ ID NO:1394) (P2) was incubated with the SPDP-modified enzymes at an enzyme-to-DNA ratio of 1:10 in 50 mM HEPES buffer (pH 7.4) for 1 h in the dark. Excess unreacted oligonucleotide was removed by ultrafiltration using Amicon 30 kD cutoff filters: washing one time with 50 mM HEPES (pH 7.4) containing 1 M NaCl and three times with 50 mM HEPES (pH 7.4). The high salt concentration in the first washing buffer helps remove DNA nonspecifically bound to the surface of the protein due to electrostatic interactions.

The absorbance values at 260 nm and 280 nm ($A_{260}$ and $A_{280}$) were recorded to quantify the enzyme-DNA complex concentrations and the labeling ratios using a Nanodrop spectrophotometer (Thermo Scientific) (FIGS. 14A-14F and Table 2). Extinction coefficients of DNA oligonucleotides were received from IDT-DNA, and extinction coefficients of enzymes were obtained from published data.

Dye labeling of DNA-conjugated proteins: The DNA-conjugated proteins were further labeled with spectrally distinct fluorescent dyes, which allow us to use native gel electrophoresis and single-molecule fluorescence to confirm the encapsulation of proteins within DNA nanocages. NETS-ester-modified dyes were reacted with the purified DNA-conjugated proteins from the above steps at a 20:1 ratio in 50 mM HEPES buffer, pH 8.5. Cy3 was directly labeled to the lysine residues on the protein surface. Excess dyes were then removed using 3-kD cutoff Amicon filters. The UV-Vis absorbance spectra of the purified dye-labeled proteins are shown in FIGS. 14A-14F and were used together with the extinction coefficients of the dye (150,000 $M^{-1}$ $cm^{-1}$ for Cy3 at 546 nm; 250,000 $M^{-1}$ $cm^{-1}$ for Alexa647 at 647 nm) and of the protein-DNA conjugates to quantify the concentration and labeling ratio of the dye-labeled proteins.

Conjugate proteins to Cy3-labeled DNA: In order to perform the single-molecule enzyme activity assay, selected enzymes (G6pDH and β-Gal) were conjugated to a Cy3-labeled DNA. First, NETS-ester-modified dyes were reacted with the 3'-amine of oligonucleotides at a 20:1 ratio in 50 mM HEPES buffer, pH 8.5. Excess dyes were then removed using 3-kD cutoff Amicon filters. Dye-modified oligonucleotides were then conjugated to proteins via the 5'-thiol using the SPDP chemistry described above. Fast Protein Liquid Chromatography (FPLC) was used to purify the protein-DNA-Cy3 conjugates for removing excess DNA-Cy3, and characterized with the UV-Vis absorbance spectra.

Enzyme-DNA Cage Assembly, Purification, and Characterization

The purified DNA half-cage containing capture strands was mixed with one of several enzyme-DNA conjugates at a 1:15 cage:enzyme ratio and annealed from 37° C. to 4° C. over 2 h in 1×TAE-$Mg^{2+}$ buffer (containing 12.5 mM Mg(OAc)$_2$). Twenty-four single-stranded DNA linkers were mixed with the two purified half-cages at a 5:1 linker: cage ratio to connect the two half-cages together by incubating at room temperature for 3 h. Agarose gel electrophoresis (2%, 1×TAE-Mg21 was employed to remove excess free enzymes (70V, 2 h). The band of the DNA cage containing the enzyme was cut from the gel and extracted using a Freeze 'N Squeeze column (Bio-Rad). The DNA origami concentration was quantified by measuring the absorbance at 260 nm ($A_{260}$) using an extinction coefficient of 0.109 $nM^{-1}cm^{-1}$.

DNA Sequences of the Designed Nanocages

Sequences of staple strands in the SH Full-Cage-Left cage are listed in SEQ ID NOs:1-210.

Sequences of staple strands in the SH-right cage are listed in SEQ ID NOs:211-420.

AB-Linker strands are listed in SEQ ID NOs:421-444.

SH-probe strands are listed in SEQ ID NOs:445-450. The BOLD portions of the sequences are complementary to the ssDNA conjugated to the enzymes, and are located in the Left (SEQ ID NOs:445-447, top) and Right (SEQ ID NOs: 448-450, bottom) half-cages.

```
34[53]
ATGACCATAAATCGCCTGATAAAT GGAGGGAGGG

48[53]
TGTGTCGAAATCCCTCAGAACCGC GGAGGGAGGG

62[53]
CACCCTCAGAGCGCAGCACCGTAA GGAGGGAGGG

51[117]
TTTAGGCAGAGGCATTCAACGCCAACATGTAA CCAGCCAGCC

61[117]
CGAACAAAGTTACCAGAAAGTAAGCAGATAGC CCAGCCAGCC

75[117]
GTAAGCGTCATACATGTGAATTTACCGTTCCA CCAGCCAGCC
```

Sequences of staple strands in the SS-left half-cage are listed in SEQ ID NOs:451-669.

Sequences of staple strands in the SS-right half-cage are listed in SEQ ID NOs:670-890.

SS-linker strands are listed in SEQ ID NOs:891-908.

SS-probes are listed in SEQ ID NOs:909-914. The BOLD portions of the sequences are complementary to the ssDNA conjugated to the enzymes, and are located in the Left (SEQ ID NOs:909-911, top) and Right (SEQ ID NOs:912-914, bottom) half-cages.

94[44]
GATATAAGTATAGTGACACAGACAGCCCTCATGGAGGGAGGG

104[50]
CTTTTGATGATGTCAGTGCCTTGGAGGGAGGG

110[44]
CATTGACAGGAGGATTTAAGCGTCATACATGGGGAGGGAGGG

87[115]
GCAAGCAAATCAGGCTTATTTTGCACCCAGCTCCAGCCAGCC

93[109]
ACAATTTTATCCAGAGCCTAATCCAGCCAGCC

103[115]
GTAAGCAGATAGCTATAATAGAAAATTCATATCCAGCCAGCC

DNA Sequences for DS Full-Cage Design, Cross Sectional View

Sequences of staple strands in the DS-left half-cage are listed in SEQ ID NOs:915-1134.

Sequences of staple strands in the DS-right half-cage are listed in SEQ ID NOs:1135-1362.

DS-linker strands are listed in SEQ ID NOs:1363-1386.

DS-probes are listed in SEQ ID NOs:1387-1392. The BOLD portions of the sequences are complementary to the ssDNA conjugated to the enzymes, and are located in the Left (SEQ ID NOs:1387-1389, top) and Right (SEQ ID NOs:1390-1392, bottom) half-cages.

64[71]
ATTCATTTCAATTACCCGCGCAGAGGCGAATTTTT
TGGAGGGAGGG

74[76]
TCAGATGATGGCAACAATAACTTTTGGAGGGAGGG

76[66]
ATTATCATTTTTTATCATCATATTCCTGATTATTT
TGGAGGGAGGG

34[149]
TTCTGTGCAAAAGAAGGCACCAGGCTGACCGTAAT
CTTGACAAGAACCGGATTTTCCAGCCAGCC

67[136]
GCAAAAGACGGTGTACAGACCTTTTCCAGCCAGCC

73[131]
GCATCAAAAAGATTAAGAGGAACTTCAAATATCGC
GTTTTAATTTTCCAGCCAGCC

Single-Molecule Fluorescence Microscopy.

All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5 k:mPEG-SVA 5 k as described previously. A flow channel was constructed as described elsewhere. To prepare the surface for enzyme or nanocage binding, a solution of 0.2 mg/mL streptavidin in T50 buffer (50 mM Tris-HCl, pH 8.0, 50 mM NaCl, 1 mM EDTA) was injected in to the flow channel, incubated for 10 min, and the excess streptavidin was flushed out thoroughly first with T50, then with 1×TAE-Mg2+.

Yield estimation by TIRF colocalization: All single-molecule measurements were performed at room temperature using a total internal reflection fluorescence (TIRF) microscope on PEGylated fused silica microscope slides. To passivate the microscope slides and functionalize the surface with biotin for selective immobilization of nanocages, a biotin- and PEG-coated surface was prepared by silylation with APTES, followed by incubation with a 1:10 mixture of biotin-PEG-SVA 5 k:mPEG-SVA 5 k as described previously[3]. A flow channel was constructed as described elsewhere[3]. To prepare the surface for enzyme or nanocage binding, a solution of 0.2 mg/mL streptavidin in TSO buffer (50 mM Tris-HCl, pH 8.0, 50 mM NaCl, 1 mM EDTA) was injected in to the flow channel, incubated for 10 min, and the excess streptavidin was flushed out thoroughly first with TSO, then with 1×TAE-Mg.

The right half of the DNA origami cage was labeled with Cy5 dye inside the cavity, via hybridization of Cy5-labeled DNA to complementary handles incorporated into the structure. Each of the ssDNA conjugated enzymes (HRP, GOx, G6pD, LDH, MDH and β-Gal) was covalently labeled with Cy3 as described in section 3 (Cy3-Enzyme-5'-TTTTTC-CCTCCCTCC, SEQ ID NO:1393), and then linked to the left half of the DNA origami cage via hybridization with complementary handles. Because Cy3 was directly labeled onto the enzyme surface, any observed Cy3 signal of the immobilized DNA nanocages came from the encapsulated enzymes. Linker strands were added to a 1:1 mixture of the two half-cages to encapsulate the enzymes in a full-cage. To capture DNA-modified enzymes in the absence of nanocage (as control) the microscope slide was incubated with 10-20 nM biotin-modified complementary DNA oligonucleotide (5'-biotin-TTTTTGGAGGGAGGG, SEQ ID NO:1395) for 3 min, followed by 10 min incubation with 20-50 pM enzyme sample in 1×TAE-Mg buffer. Excess enzyme was flushed out with 400 uL buffer (channel volume 30 μL). For the nanocage experiments, the samples were diluted to 20-50 pM in 1×TAE-Mg and immobilized on the streptavidin-coated PEG surface for 1 min, and the excess sample was flushed out with 400 μL of 1×TAE-Mg. The DNA-modified enzymes were imaged with illumination at 532 nm (15 W/cm2), and the nanocage-encapsulated enzymes were imaged with simultaneous illumination at both 532 nm (15 W/cm2) and 640 nm (40 W/cm2) as described. Particle-finding and colocalization analysis were performed using custom-written scripts in IDL and MATLAB, using a threshold of 150 counts per frame for particle identification (typical particles showed 500-1,000 counts per frame in each detection channel). The enzyme encapsulation yield, defined as the fraction of assembled nanocages containing enzyme(s), was estimated by dividing $N_{caloc}$ by the total number of particles containing a right half-cage, $N_{right}$ (Table 3).

Figures 2A, 2B, 2C, 2D, 2E:
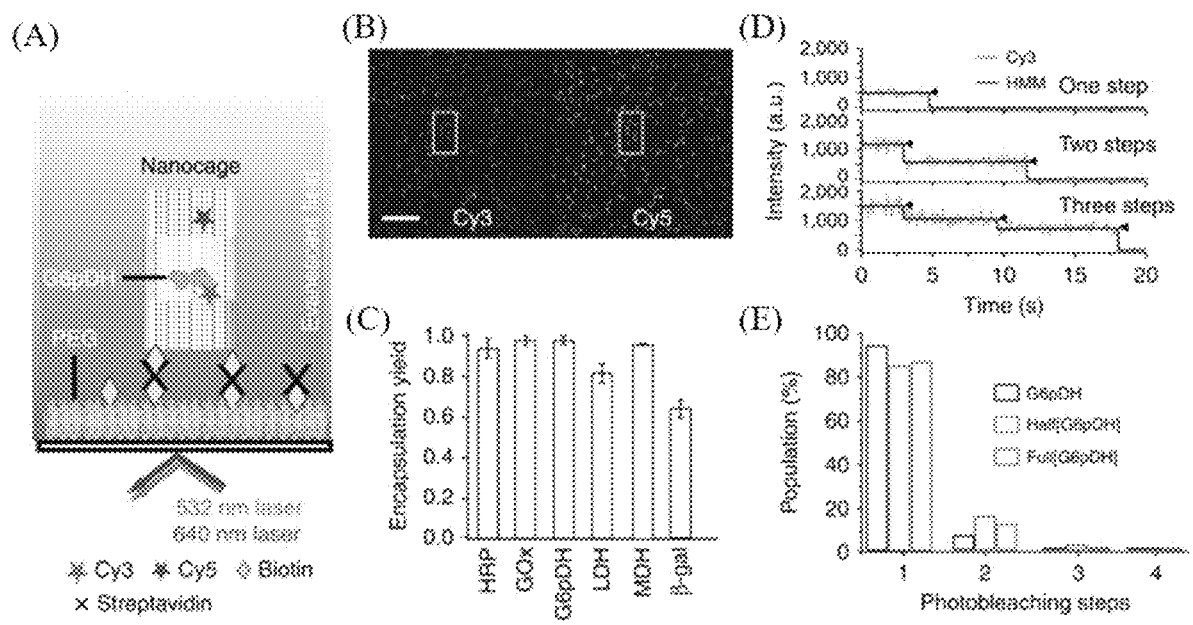
FIGS. 2A-2E show single-molecule fluorescence characterization of enzyme encapsulation. (A) Schematic illustration of single-molecule fluorescence co-localization of Cy3-labelled protein with Cy5-labelled cage using TIRF microscopy. DNA cages were captured on the surface by biotin-streptavidin interaction. (B) Representative field of view of enzyme-encapsulating cages under TIRF microscope. Examples of Cy3-Cy5 co-localization are highlighted using a pair of rectangles. Scale bar, 10 µm. (C) Quantified encapsulation yield for six different enzymes. The total number of molecules analyzed for each protein is shown in Table 3. The error bars represent the standard deviation obtained from the analysis of two to four movies of the sample from the same batch. (D) Fluorophore photobleaching trajectories with one, two, and three photobleaching steps. Photobleaching steps were quantitatively analyzed by fitting the trajectories by HMM in QUB program. (E) Photobleaching statistics for Cy3-labelled proteins encapsulated within half-cages (Half[G6pDH]) or full-cages (Full [G6pDH]), as well as for an unencapsulated protein control (G6pDH). HMM, hidden-Markov modelling.

Estimation of enzyme copy number per nanocage: The number of enzyme copies per nanocage ($N_{enz}$) was determined by single-molecule photobleaching (SMPB). First, the number of Cy3 photobleaching steps was determined separately for unencapsulated as well as half-cage and full-cage-encapsulated enzymes. For this, the donor channel data of all single molecules were idealized in QuB (http://www.qub.buffalo.edu) using a six-state model. The histogram of the photobleaching steps was then acquired using a custom-written MATLAB script. Representative intensity traces exhibiting one, two, and three photobleaching steps are shown in FIG. 2D (more than three photobleaching steps were rarely seen). Finally, the number of enzyme molecules per cage was estimated by dividing the mean number of Cy3 photobleaching steps of the full-cage ($\mu_{cy3\_Encap}$) by the mean number of Cy3 photobleaching steps for the unencapsulated enzyme ($\mu_{cy3\_Unencap}$). Results are summarized in Table 4.

Single-Molecule Enzymology

Figures 5A, 5B, 5C, 5D, 5E, 5F, 5G:
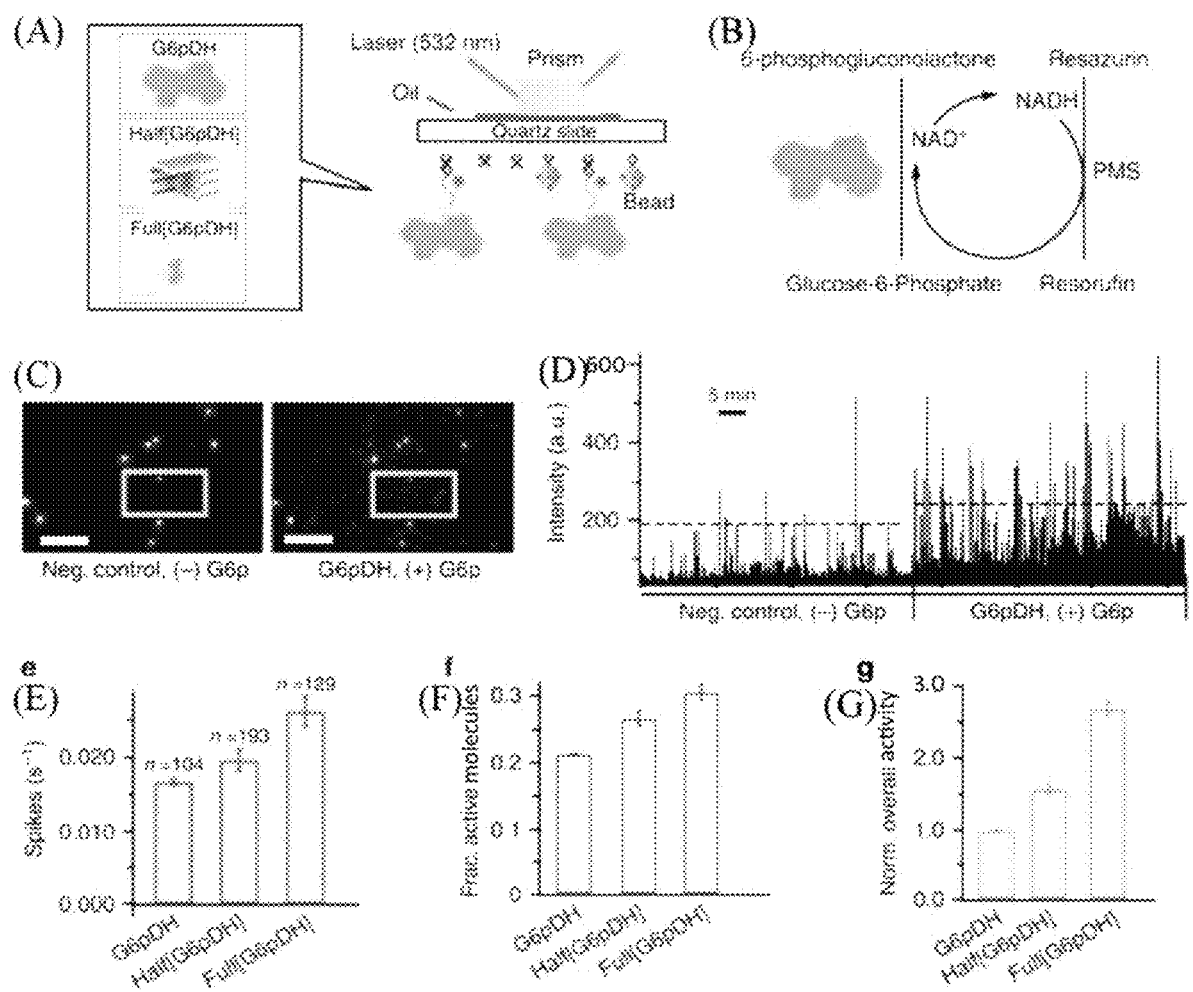
FIGS. 5A-5G show single-molecule kinetics of nanocage-encapsulated enzymes. (A) Schematic of the experimental TIRF set up for characterizing G6pDH encapsulated within a full-cage (Full[G6pDH]) and a half-cage (Half[G6pDH]), as well as an unencapsulated control. (B) A PMS/resazurin-coupled fluorescence assay used to characterize the activity of G6pDH. NAD+ is first reduced to NADH by G6pDH, followed by PMS− catalyzed electron transfer from NADH to resazurin, producing a strongly fluorescent resorufin, which has an excitation/emission maximum at 544/590 nm. (C) TIRFM snapshots captured before and after the injection of substrate G6p. In presence of G6p, the field of view showed increased fluorescence due to the formation of resorufin (compare the boxed regions). Fluorescent beads (very bright spots present in both +G6p and −G6p images) were used as reference markers to correct for the drift. Scale bars, 10 µm. (D) Real-time traces of fluorescence spikes (resorufin production) for enzymes without and with the addition of G6p substrate. Ten single-molecule traces for each condition were concatenated. (E) Statistics of spike frequency, (F) fraction of active molecules, and (G) overall observed enzyme activity for G6pDH. The number of active molecules analyzed is denoted by 'n' in (E). The standard deviations for the spike frequency were calculated after randomly assigning the active molecules into three groups; those for the fractions of active molecules were calculated from three to four independent movies, and those for the normalized overall activity were estimated from the propagation of errors. All experiments were carried out at room temperature in 1×TBS buffer, pH 7.5, in the presence of 1 mM Mg2+ and 10% (w/v) PEG 8000.

Single-molecule enzyme activity assay: Prior to single-molecule activity measurement, streptavidin-modified slides were incubated for 2 min with neutravidin-coated fluorescent beads (Invitrogen, 0.04 µm diameter, excitation/emission; 550/605 nm) at 106-fold dilution and the excess flushed out with 1×TBS buffer. These beads (5-8 per field of view) were used as fiducial markers to correct for drift of the microscope stage and/or slide (FIGS. 5A and 5C). Following complete photobleaching of Cy3 in a field of view, the activity of single unencapsulated or nanocage-encapsulated enzyme molecules was imaged on the same field of view. During analysis of the movies, the coordinates of the initial photobleaching movie were registered with those of subsequent movies using the fiducial markers (visible throughout all sequential movies) in a custom-written MATLAB script. This approach allowed us to infer the locations (x- and y-coordinates) of all individual enzymes/nanocages in the field of view even after bleaching Cy3, and to monitor enzyme turnovers (resorufin formation) at these specific coordinates.

Figure 65:
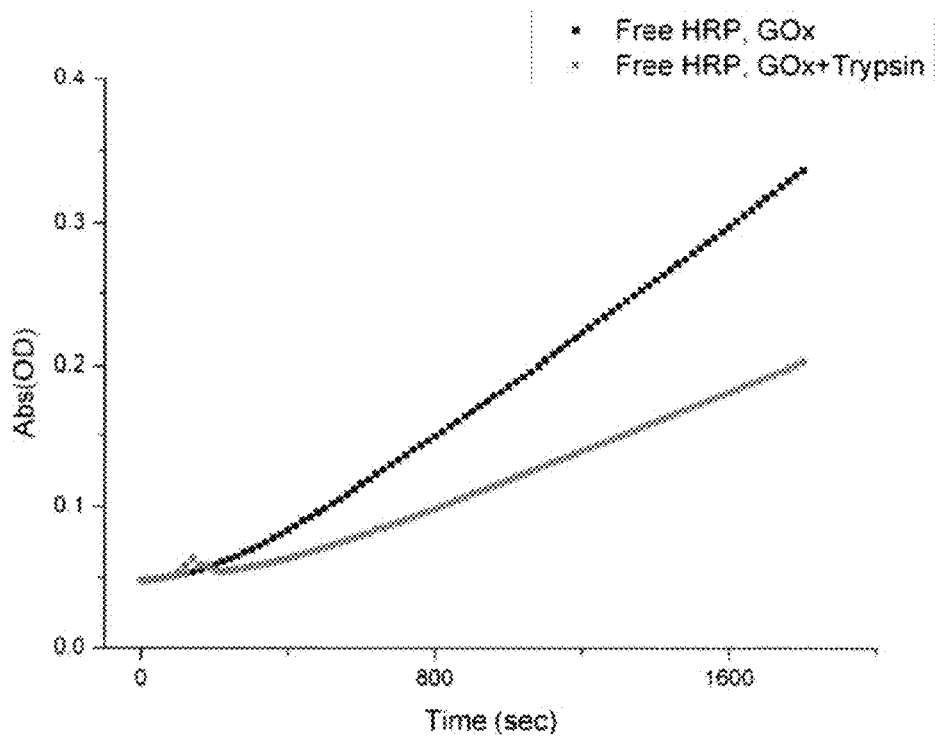
FIG. 65 shows raw activity data of a free pair of HRP and GOx (0.5 nM) before and after trypsin digestion for 24 hours at 37° C. in 1×TBS buffer (pH 7.5).
Figure 66:
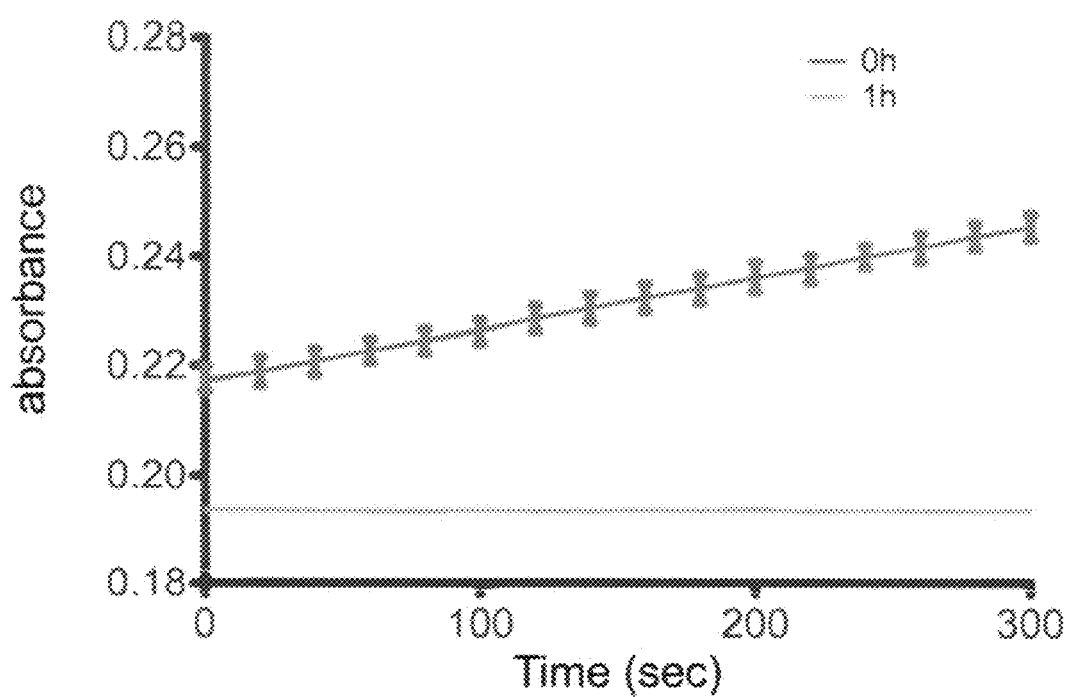
FIG. 66 shows raw activity data for free G6pDH (0.5 nM) before and after trypsin digestion for 1 h at 37° C. in 1×TBS buffer (pH 7.5). Error bars were calculated from the standard deviation of at least three replicates.

To image enzyme activity, 300 µL of substrate solution in 1×TBS buffer (pH 7.5, 1 mM $Mg^{2+}$, and 10% (w/v) PEG8000) (Table 5) was injected into the flow channel. Movies were recorded for 5 min (9,091 frames) at 35 ms frame exposure time immediately after injecting the substrate solution. In case of G6pDH, the activity was measured in the same field of view under identical laser illumination and microscope settings, with or without glucose-6-phosphate (G6p) (FIG. 5c). Enzyme activity for β-Gal was measured similarly using a 500 nM solution of resorufin β-D-galactopyranoside (RBG) as substrate, which is hydrolyzed by β-Gal into fluorescent resorufin. Fluorescence fluctuations over time were measured for unencapsulated enzyme as well as half- and full-cage-encapsulated enzyme (FIG. 65 and FIG. 66), and the fluorescence time traces were analyzed for intensity spikes using custom-written MATLAB script. The script allowed us to measure the background intensity of single-molecule traces and set a threshold (mean+8 standard deviations) to subtract from the raw intensity. Since we often observed one or two spikes above this intensity threshold in the control experiments, only those molecules with 2:4 spikes were counted as active molecules (FIG. 67) and considered for burst analysis. Due to the low concentration of resazurin (Table 5), the criteria we used to determine the fraction of active molecules might have excluded some molecules that are not highly active.

Figure 67:
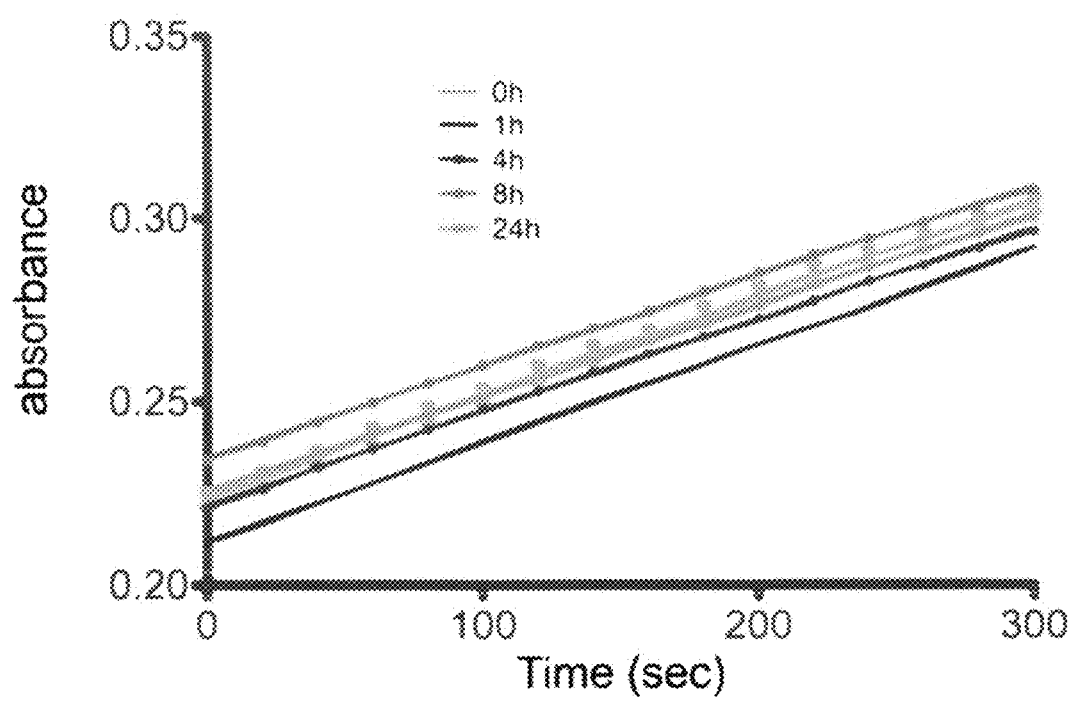
FIG. 67 shows raw activity data for Full[G6pDH] (0.5 nM) time course trypsin digestion from 0 h to 24 h at 37° C. Error bars were calculated from the standard deviation of at least three replicates.

Burst analysis: Burst analysis was carried out using a modified Rank Surprise (RS) method 6 recently utilized to analyze the binding of fluorescent DNA probes to a riboswitch. Briefly, Interspike Intervals (ISIs) were determined by calculating the time in between individual fluorescent spikes for each molecule (FIG. 67). The RS method was used to demarcate the start and end points of bursts after collecting ISIs for all molecules. Only intensity spikes characterized by an ISIs of greater than 3 seconds were considered part of a burst; any other intensity spikes are counted as non-bursts.

Comparing bulk and single-molecule enzyme activity: Unlike our single-molecule assay, the bulk measurement of enzyme activity cannot explicitly determine the fraction of active enzyme molecules present in the solution (it is well known that a fraction of enzyme molecules loses their activity during oligonucleotide conjugation, buffer exchange and the purification process). However, the observed bulk activity is contributed not only by enzyme turnover rate but also by the fraction of enzyme molecules that are still active. Both of these contributing factors need to be accounted for to directly compare the single-molecule enzyme activity with the bulk measurements. Therefore, in the single-molecule experiment, the overall activity of free, half-cage and full-cage enzymes were calculated by multiplying the turnover rate with the fraction of active molecules for the given sample.

Bulk Solution Enzyme Assay.

A 96-well-plate reader was used to monitor enzyme activity through absorbance changes of the samples. The enzyme samples and substrates were loaded in the wells of the 96-well plate with a final concentration of caged enzymes 0.5 nM in 1×TBS (Tris buffered saline with 1 mM $MgCl2$, pH 7.5) for most assays.

Enzymes and Substrates:

Glucose-6-phosphate dehydrogenase (G6pDH, *Leuconostoc mesenteroides*), malic dehydrogenase (MDH, porcine heart), lactate dehydrogenase (LDH, rabbit muscle), glucose oxidase (GOx, *Aspergillus niger*), horseradish peroxidase (HRP) and β-galactosidase (β-Gal, *E. coli*) were purchased from Sigma (St. Louis, Mo.). Pyruvate, oxaloacetate (OAA), glucose 6-phosphate (G6P), glucose, resorufin β-D-glucopyranoside (RBG), β-nicotinamide adenine dinucleotide (NAD), resazurin (RESA) and phenazine methosulfate (PMS) were obtained from Sigma-Aldrich. ABTS (2,2'-Azino-bis[3-ethylbenzothiazoline-6-sulfonic acid] diammonium salt) was purchased from Pierce (Rockford, Ill.), polyphosphate (100) is ordered from Kerafast.

DNA Strands:

Single-stranded MI3mp18 DNA was purchased from New England Biolabs. Staple strand oligonucleotides were obtained from Integrated DNA Technologies (IDT) on 96-well plates and used without further purification. Thiol-modified DNA oligonucleotides were also purchased from IDT, and were purified by denaturing PAGE before use.

Crosslinking Reagents:

N-Succinimidyl 3-(2-pyridyldithio)propionate (SPDP) and tris(2-carboxyethyl)phosphine (TCEP) were obtained from Pierce. Dimethyl sulfoxide (DMSO) was purchased from Sigma.

Buffers:

Phosphate buffered saline (PBS), HEPES sodium salt, Tris buffered saline (TB S), Tris base, acetic acid, EDTA, and magnesium acetate were purchased from Sigma. 1×TAE/$Mg^{2+}$ buffer (pH 8.0) is prepared by 40 mM Tris, 20 mM acetic acid, 2 mM EDTA and 12.5 mM magnesium acetate.

Dye-Labeling Reagents:

NHS-Cy3, Cy5 amine reactive dyes were purchased from GE Healthcare Life Sciences. NHS-AlexaFluor® 555 and AlexaFluor® 647 amine reactive dyes were obtained from Life Technologies.

Amicon centrifugal filters were purchased from Millipore.

PEG 8000 was purchased from Promega.

Surface PEGylating Reagents:

APTES (3-Aminopropyl)triethoxysilane was purchased from Sigma-Aldrich. mPEG-SV A 5 k and biotin-PEG-SY A 5 k were obtained from Laysan Bio, Inc.

TEM Imaging:

TEM grids (400 mesh, copper grid coated with ultrathin carbon, Ted Pella) were glow discharged (Emitech Kl OOX). 2 µl concentrated samples were deposited onto the grids for 1 min, washed with 10 µl DI water for 5 sec, stained with 10 µl 1% uranyl formate twice (2 sec for the first time and 15 sec for the second time), and imaged using Philips CMI2 transmission electron microscope.

Enzyme Activity Assay:

A 96-well-plate reader was used to monitor enzyme activity through absorbance changes of the samples. The enzyme samples and substrates were loaded in the wells of the 96-well plate with a final concentration of caged enzymes of 0.5 nM in 1×TBS (Tris buffered saline with 1 mM $MgCl_2$, pH 7.5) for most assays. The DNA cage concentration was determined by the $A_{260}$ value as described above. For a typical GOx and HRP assay, 1 mM Glucose and 2 mM ABTS was used as substrate and enzyme activity was measured by monitoring the increase in absorbance at 410 nm (ABTs-1). For a typical G6pDH assay, 1 mM G6P and 1 mM NAD+ were used as substrates, and enzyme activity was measured by monitoring the increased absorbance at 340 nm due to the reduction of NAD+ to NADH. For a typical LDH assay, 2 mM pyruvate and 1 mM NADH were used as substrates, and enzyme activity was measured by monitoring the decreased absorbance at 340 nm due to the oxidation of NADH to NAD+. For a typical MDH assay, 2 mM OAA and 1 mM NADH were used as substrates, and enzyme activity was measured by monitoring the decrease in absorbance at 340 nm. For a typical β-Gal assay, 100 μM RBG was used as substrate and enzyme activity was measured by monitoring fluorescence intensity, with excitation at 532 nm and emission at 590 nm.

Trypsin Assay:

Enzyme activity was measured after incubation with or without trypsin (1 μM) at 37° C. for 24 h in 1×TAE-10 mM Mg buffer (pH 8.0). Activity assay conditions: 1 mM Glucose, 1 mM ABTS, 1 nM of free GOx and HRP in pH 7.5, 1×TBS buffer containing 1 mM $MgCl_2$, and monitoring absorbance at 410 nm. In the DNA cage experiment, all conditions were the same except for incubating 1 nM DNA cage-encapsulated GOx and HRP with trypsin.

Results

Enzyme Encapsulation Strategy.

As shown in FIG. 1A, the current embodiment of the approach for enzyme encapsulation within DNA nanocages involves two steps: 1) the attachment of an individual enzyme into an open half-cage and 2) the assembly of two half-cages into a full (closed) nanocage. DNA half-cages were constructed by folding a full-length M13 viral DNA29 into the indicated shape based on a honeycomb lattice using the DNA origami technique; a shape with two open sides was chosen to improve accessibility of the internal cavity to large proteins. Two half-cages were then linked into a full-cage by adding 24 short bridge DNA strands that hybridize with the complementary ssDNA sequences extending from the edges of either half-cage. The DNA full-cage is 54 nm×27 nm×26 nm with designed inner cavity dimensions of 20 nm×20 nm×17 nm. By design, 42 small nanopores (each 2.5 nm in diameter) were introduced on each of the top and bottom surfaces of the DNA nanocage to permit the diffusion of small molecules (e.g., enzyme substrates) across the DNA walls (FIG. 7).

Figure 10:
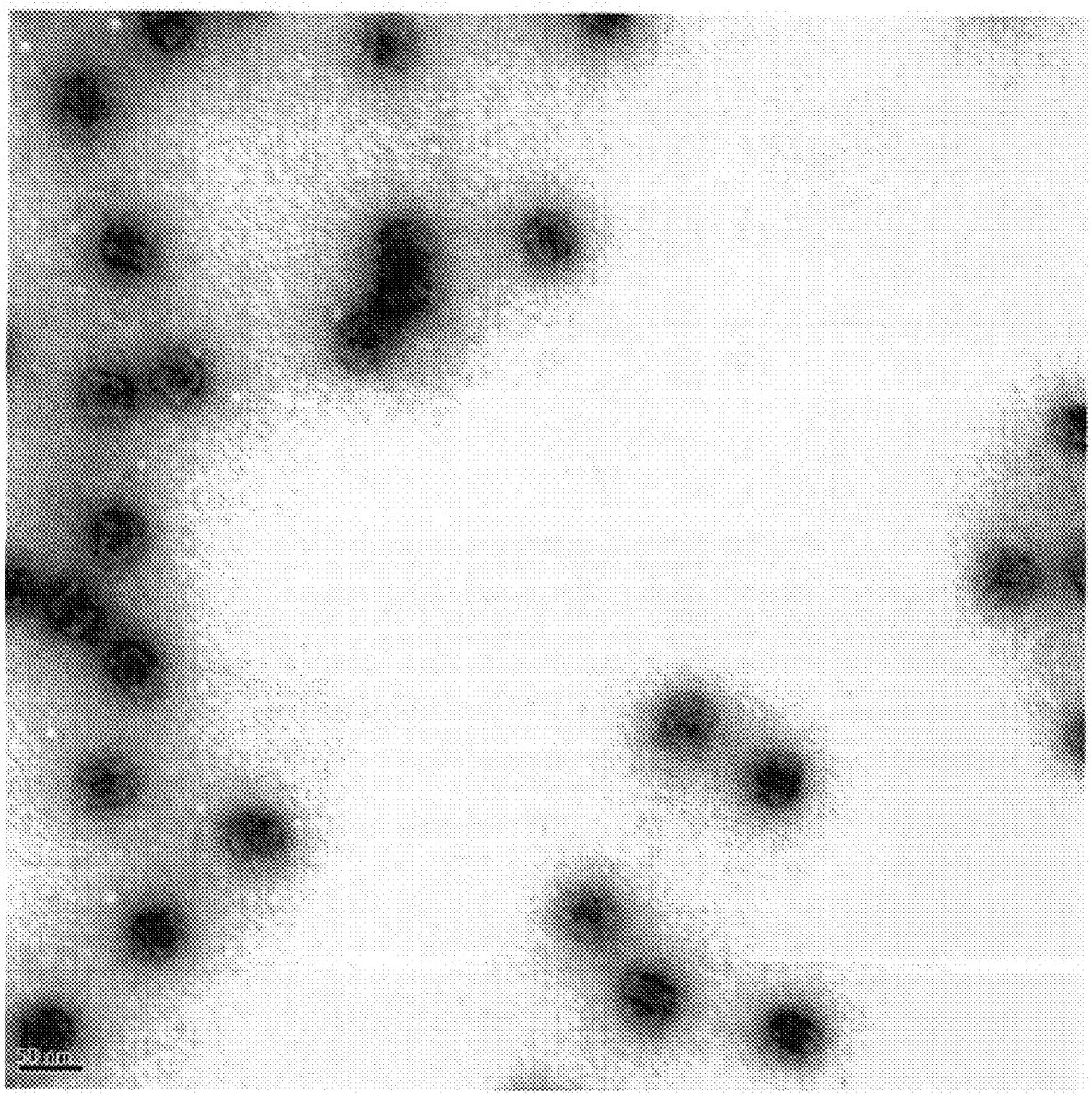
FIG. 10 shows a representative TEM image of the half-cage structure (scale bar: 50 nm).
Figure 11:
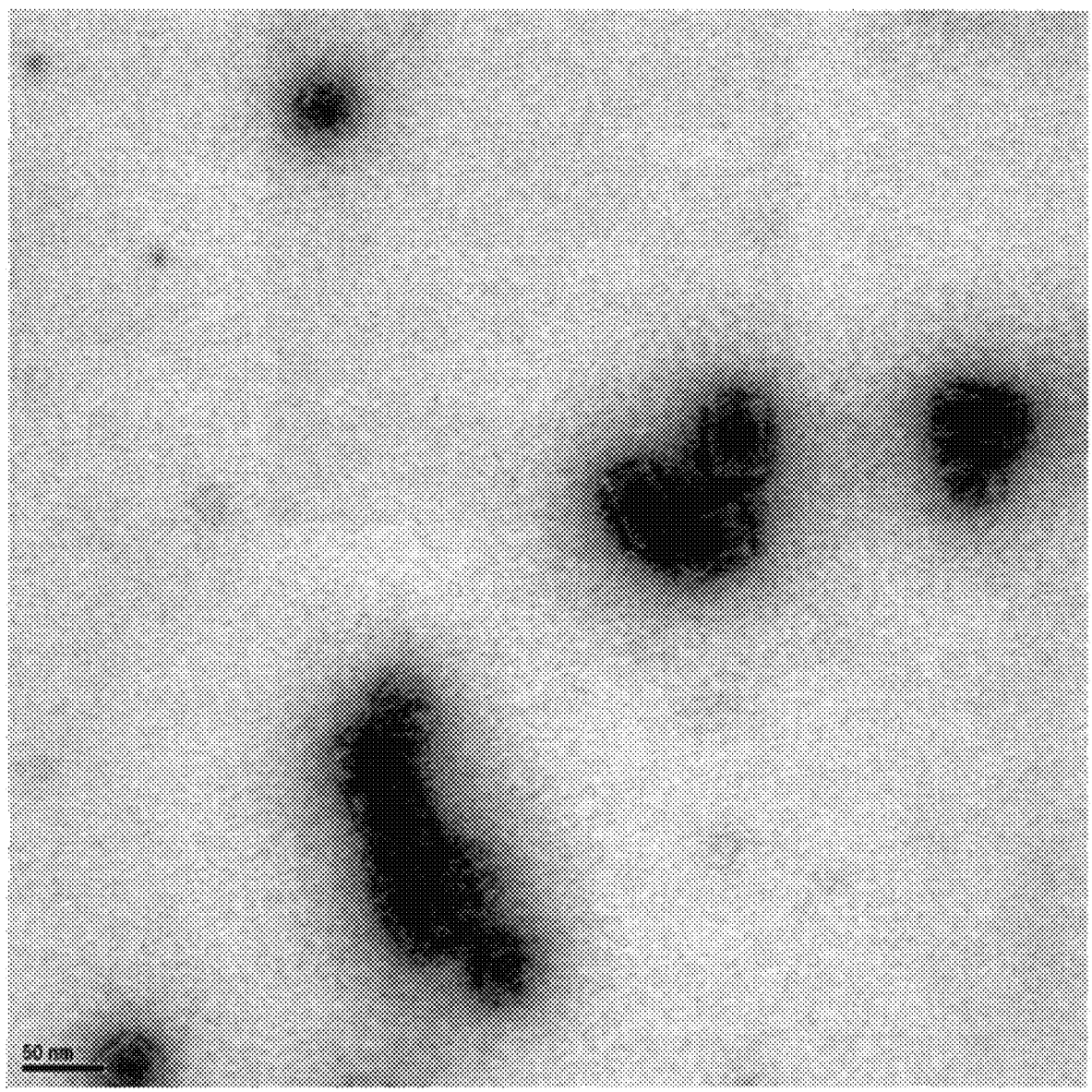
FIG. 11 shows a representative TEM image of the full-cage structure (scale bar: 50 nm).
Figure 12:
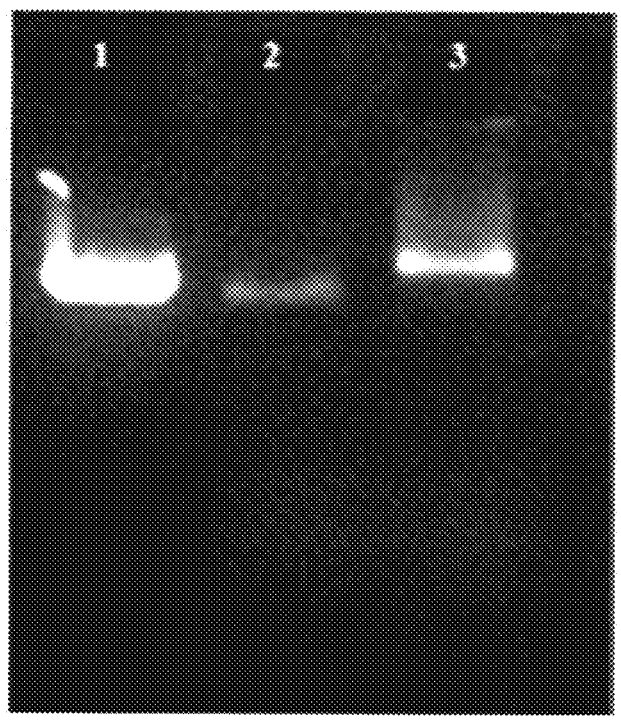
FIG. 12 shows an agarose gel electrophoresis (AGE) to characterize the full-cage structure (lane 1: MI3 DNA, lane 2: half-cage; lane 3: full-cage). According to the gel band intensity, the assembly yield of the full-cage was higher than 90%.

The formation of half and full DNA nanocages was first characterized using transmission electron microscopy (TEM) (FIG. 10 and FIG. 11) and gel electrophoresis (FIG. 12), which indicate a nearly 100% yield for half-cages and a more than 90% yield for full-cages. To capture target enzymes into a half-cage, a previously reported succinimidyl 3-(2-pyridyldithio) propionate (SPDP) chemistry was used to crosslink a lysine residue on the protein surface to a thiol-modified oligonucleotide. Two anchor probes of complementary sequence were displayed on the bottom of the half-cage cavity to capture a DNA-modified enzyme via sequence-specific DNA hybridization.

As a demonstration of an enzyme cascade, a glucose oxidase (GOx)-attached half-cage was incubated with a horseradish peroxidase (HRP)-attached half-cage at a stoichiometric ratio of 1:1, followed by the addition of bridge strands into solution to assemble a full DNA nanocage containing a GOx/HRP pair. The inner cavity of a full nanocage is of sufficient size to encapsulate this enzyme pair (GOx is 10 nm32 and HRP 5 nm in diameter33). Unencapsulated enzyme and excess short DNA strands were removed using agarose gel electrophoresis (AGE). Details of the enzyme-DNA conjugation and optimization of the assembly are shown in FIGS. 13, 14A-14F, 15A-15B, 16, 17, 18, Table 2.

Characterization of Enzyme Encapsulation.

Figure 1B:
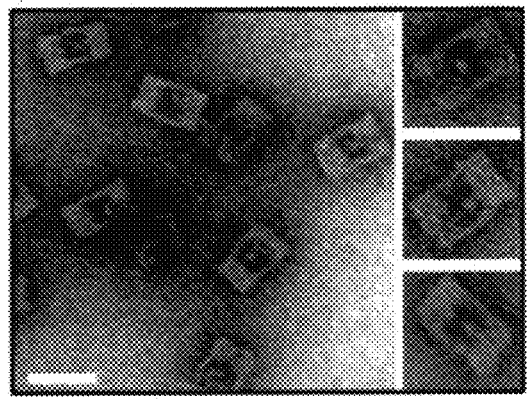
Figure 1C:
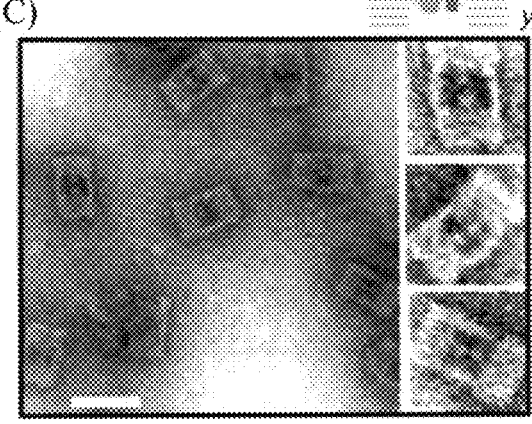
Figure 18:
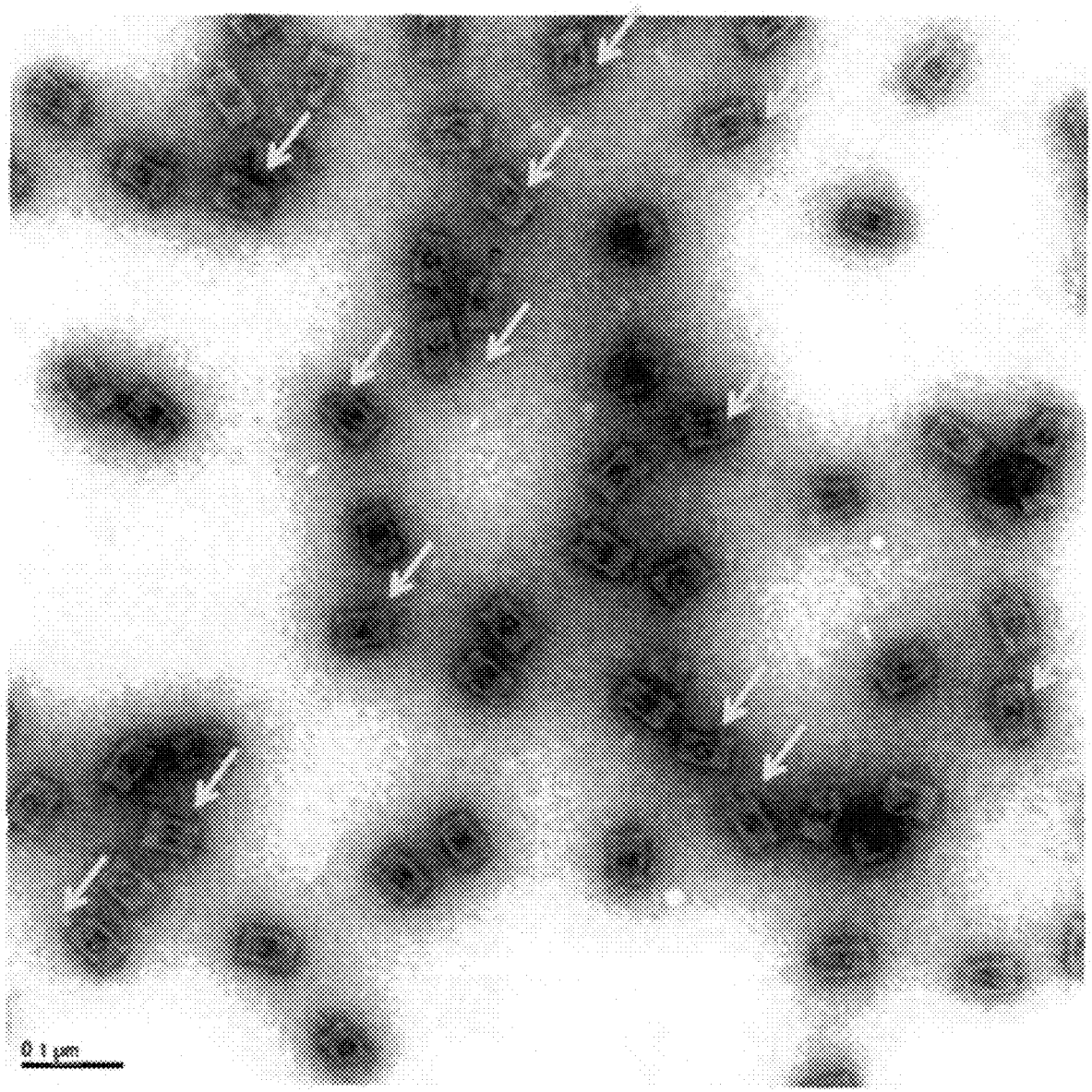
FIG. 18 shows TEM image for HRP-GOx enzyme pairs encapsulated in DNA full-cage. Despite variable quality of staining across the field of view, the inner cavity of many nanocages appeared to contain two bright spots, which we interpreted as intact HRP-GOx enzyme pairs (yellow arrow indicates DNA cage with enzyme pair inside).
Figure 19:
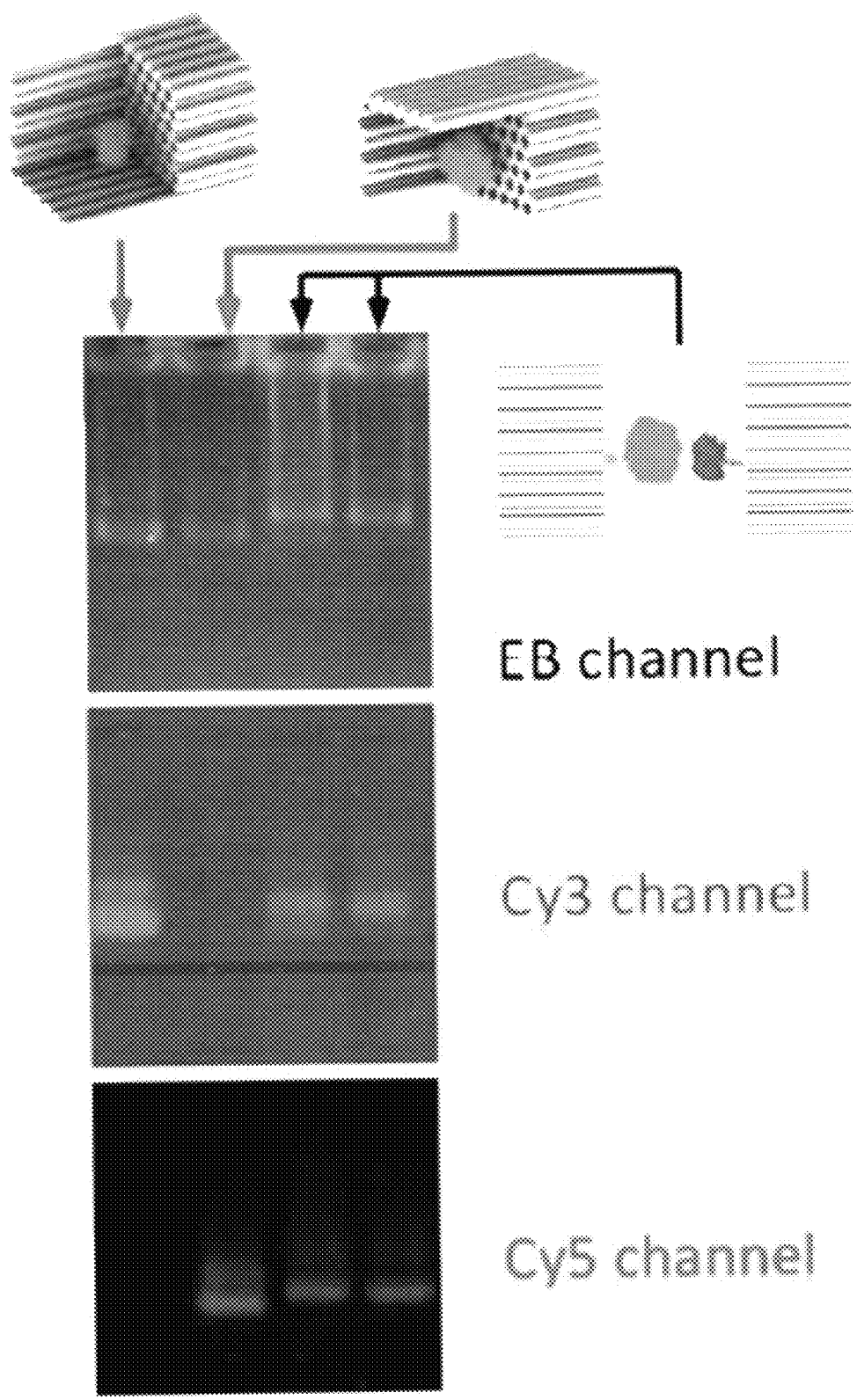
FIG. 19 shows native AGE characterization of a DNA nanocage encapsulating a GOx/HRP pair. GOx and HRP were conjugated with Cy3 and Cy5, respectively. Lane 1 (from left): half-cage assembled with GOx-Cy3, lane 2: half-cage assembled with HRP-Cy5, lanes 3 and 4: full-cage with GOx/HRP. "EB" indicates ethidium bromide staining of the gel to visualize all DNA bands.
Figure 20:
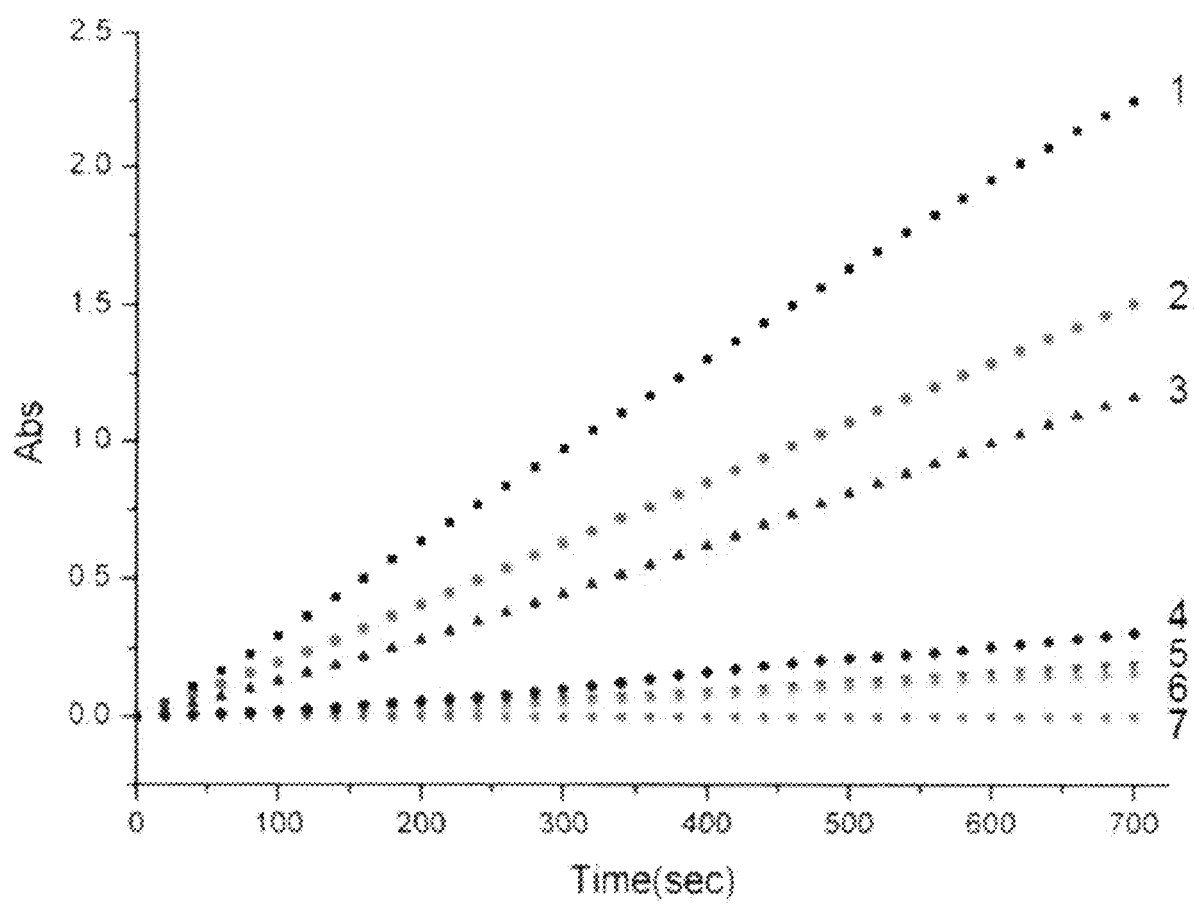
FIG. 20 shows raw activity data for a set of DNA cage-encapsulated enzymes. 1: Full[H+G], a full cage-encapsulated GOx and HRP; 2: Full[H]+Full[G], a full cage-encapsulated HRP and a full cage-encapsulated GOx; 3: half[H]+half[G], a half cage-encapsulated HRP and a half-cage encapsulated GOx; 4: Full+H+G, a full cage incubated with a pair of free HRP and GOx; 5: H+G fresh control, a fresh solution of free HRP and GOx; 6: H+G annealing control, a solution of free HRP and GOx that is incubated using the same thermal program as the DNA cage-encapsulated enzymes; 7: substrate background control. Assay conditions: 1 nM enzyme or enzyme-encapsulating DNA cage, with 1 mM Glucose, 2 mM ABTS in pH 7.5, 1×TBS buffer. Absorbance is monitored at 410 nm.
Figure 21:
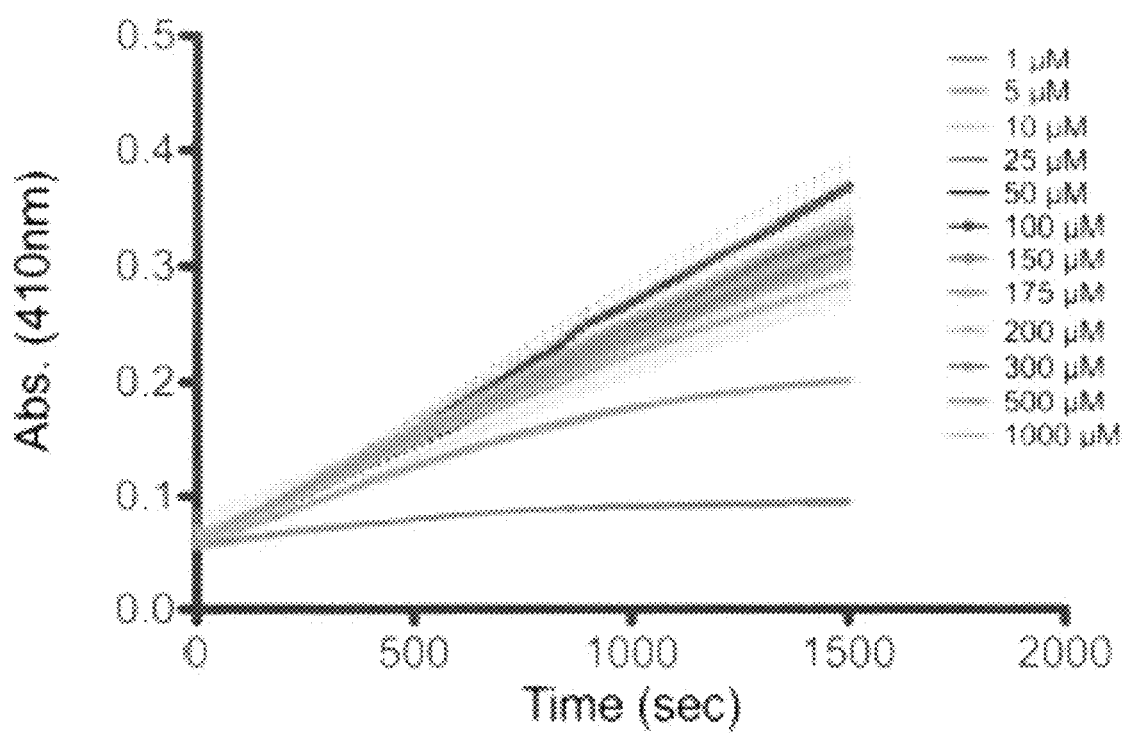
FIG. 21 shows determination of the Michaelis-Menten constants for enzymes-HRP. Raw activity data for free enzyme solution of DNA-conjugated HRP (0.5 nM) with $H_2O_2$ concentration varied from 1 μM to 1000 μM and 2 mM ABTS, monitoring absorbance at 410 nm. Error bars were calculated from the standard deviation of at least three replicates.
Figure 22:
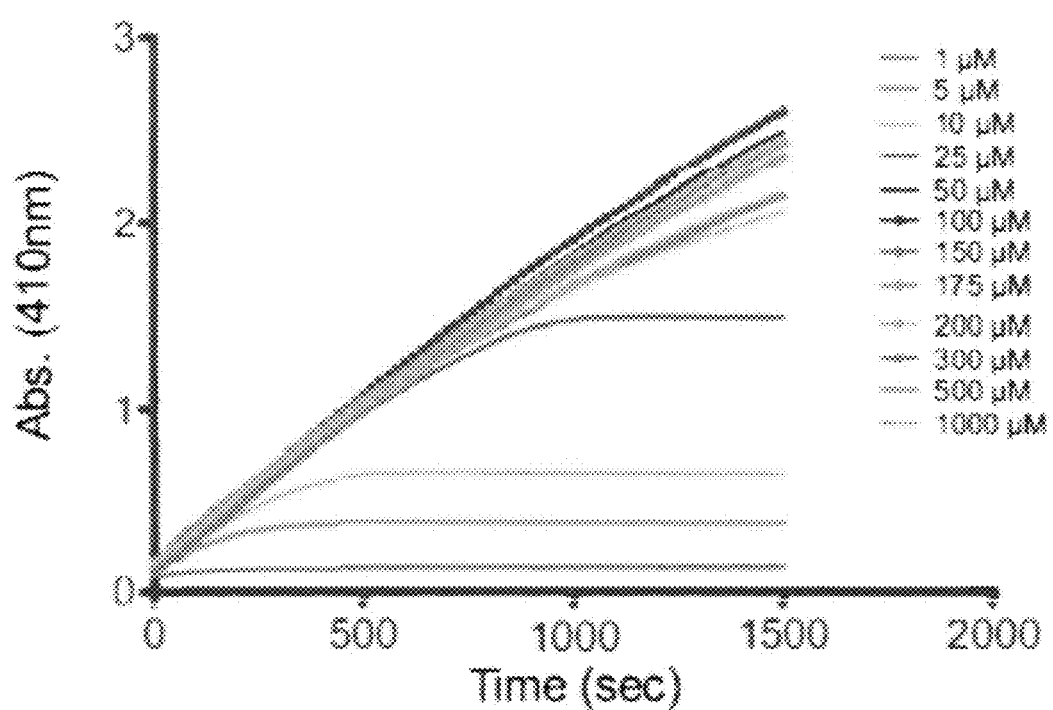
FIG. 22 shows determination of the Michaelis-Menten constants for enzymes-HRP. Raw activity data for DNA cage-encapsulating HRP (0.5 nM) with $H_2O_2$ varied from 1 μM to 1000 μM and 2 mM ABTS, monitoring absorbance at 410 nm. Error bars were calculated from the standard deviation of at least three replicates.
Figure 23:
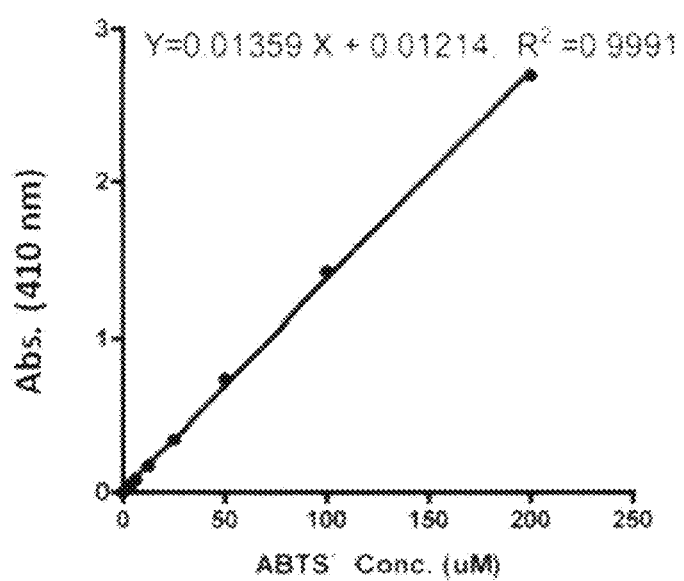
FIG. 23 shows ABTS standard curve to calculate $k_{cat}$ value (Y=0.01359x+0.01214).
Figure 24:
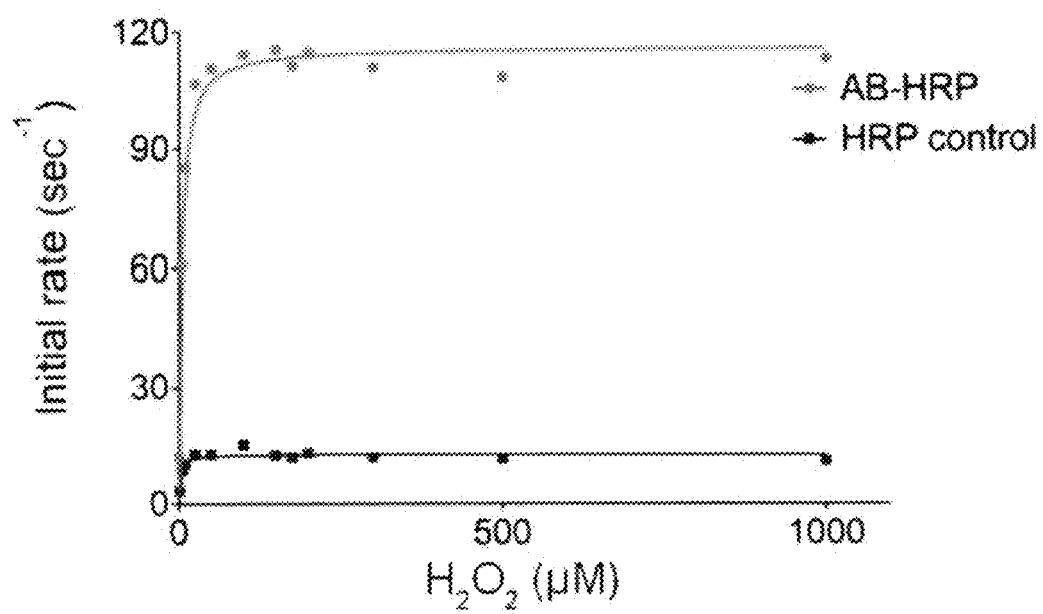
FIG. 24 shows a Michaelis-Menten plot of HRP encapsulated within a full-cage (Full-Cage[HRP], red circles), compared with that of free HRP (HRP control, black squares) using $H_2O_2$ as the substrate. The solid lines represent fits of the Michaelis-Menten model to the data. Enzyme assay conditions: 0.5 nM enzyme or DNA-cage-encapsulated enzyme, 2 mM ABTS with different concentrations of $H_2O_2$ ranging from 1 μM to 1000 μM, in 1×TBS buffer (pH 7.5, 1 mM $MgCl_2$), absorbance monitored at 410 nm. The table lists the fit parameters. Full-cage encapsulation of the enzyme caused a 2-fold increase in $K_M$ and an about 9-fold increase in $k_{cat}$.
Figure 25:
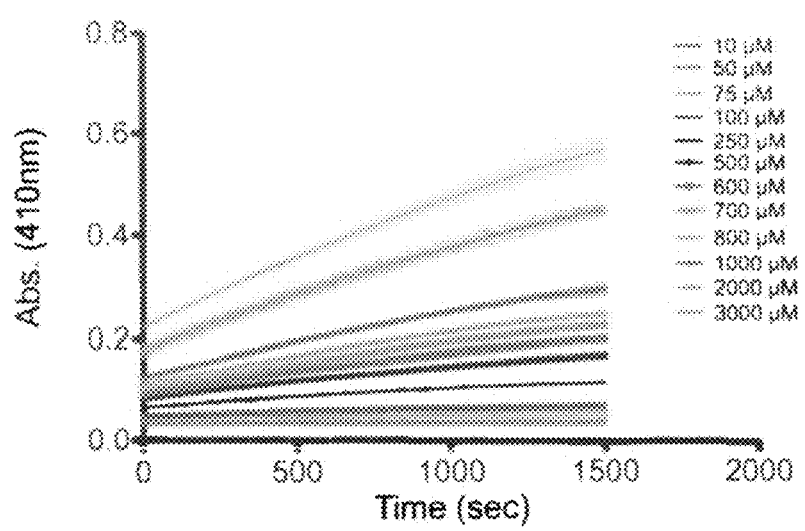
FIG. 25 shows raw activity data measurement of Full-Cage [HRP] (0.5 nM) with ABTS concentration varied from 10 μM to 3000 μM and 2000 μM $H_2O_2$, monitoring absorbance at 410 nm. Error bars were calculated from the standard deviation of at least three replicates.
Figure 26:
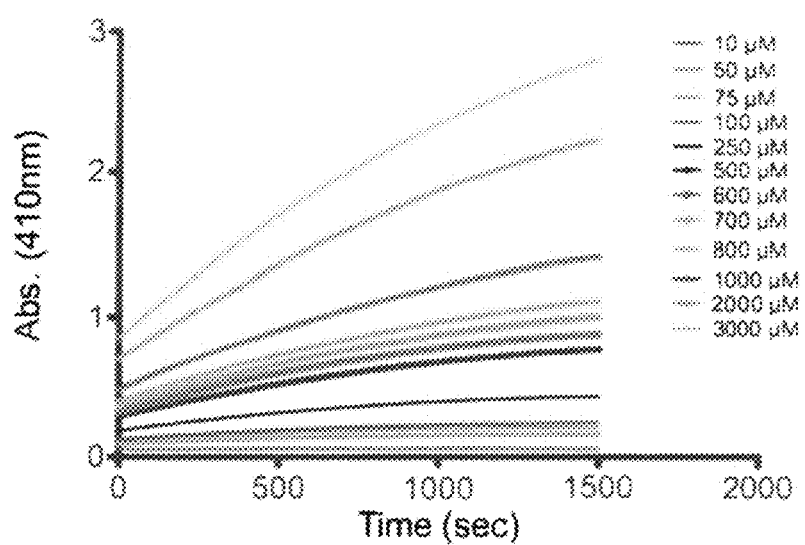
FIG. 26 shows raw activity data measurement of free DNA-conjugated HRP (0.5 nM) with ABTS concentration varied from 10 μM to 3000 μM, and 2000 μM $H_2O_2$, monitoring absorbance at 410 nm. Error bars were calculated from the standard deviation of at least three replicates.
Figure 27:
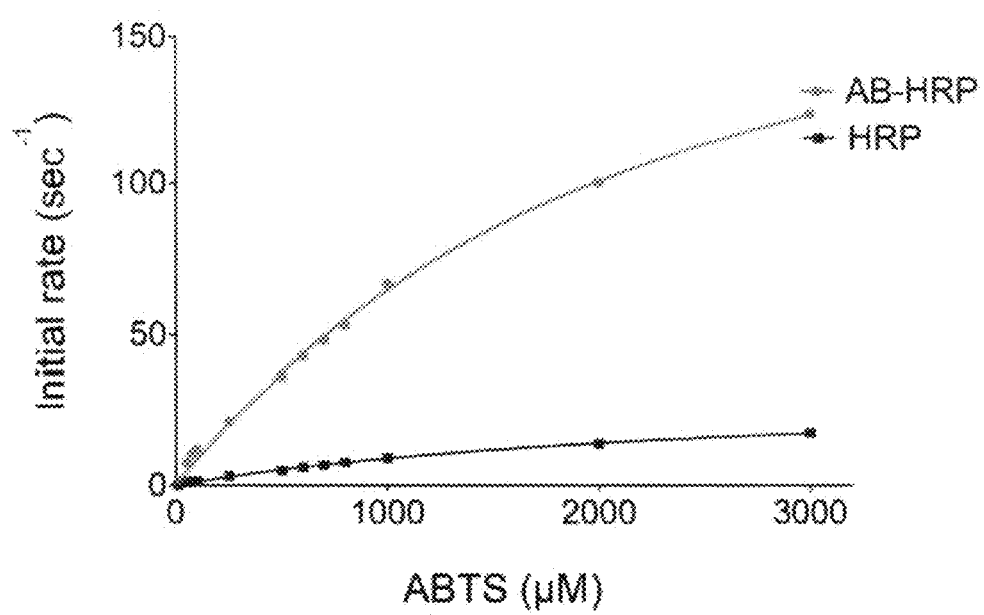
FIG. 27 shows a Michaelis-Menten plot for HRP encapsulated within a full-cage (AB-HRP, red circles), compared with that of free HRP enzyme (HRP control, black squares) using ABTS as the substrate. The solid lines represent fits of the Michaelis-Menten model to the data. Enzyme assay conditions: 0.5 nM enzyme or full-cage-encapsulated enzyme, 2000 μM $H_2O_2$ with different concentrations of ABTS, ranging from 10 μM to 3000 μM, in 1×TBS buffer (pH 7.5, 1 mM $MgCl_2$), monitoring absorbance at 410 nm. The table lists the fit parameters. DNA encapsulation of the enzyme caused no change in $K_M$ and a −9-fold increase in $k_{cat}$.
Figure 28:
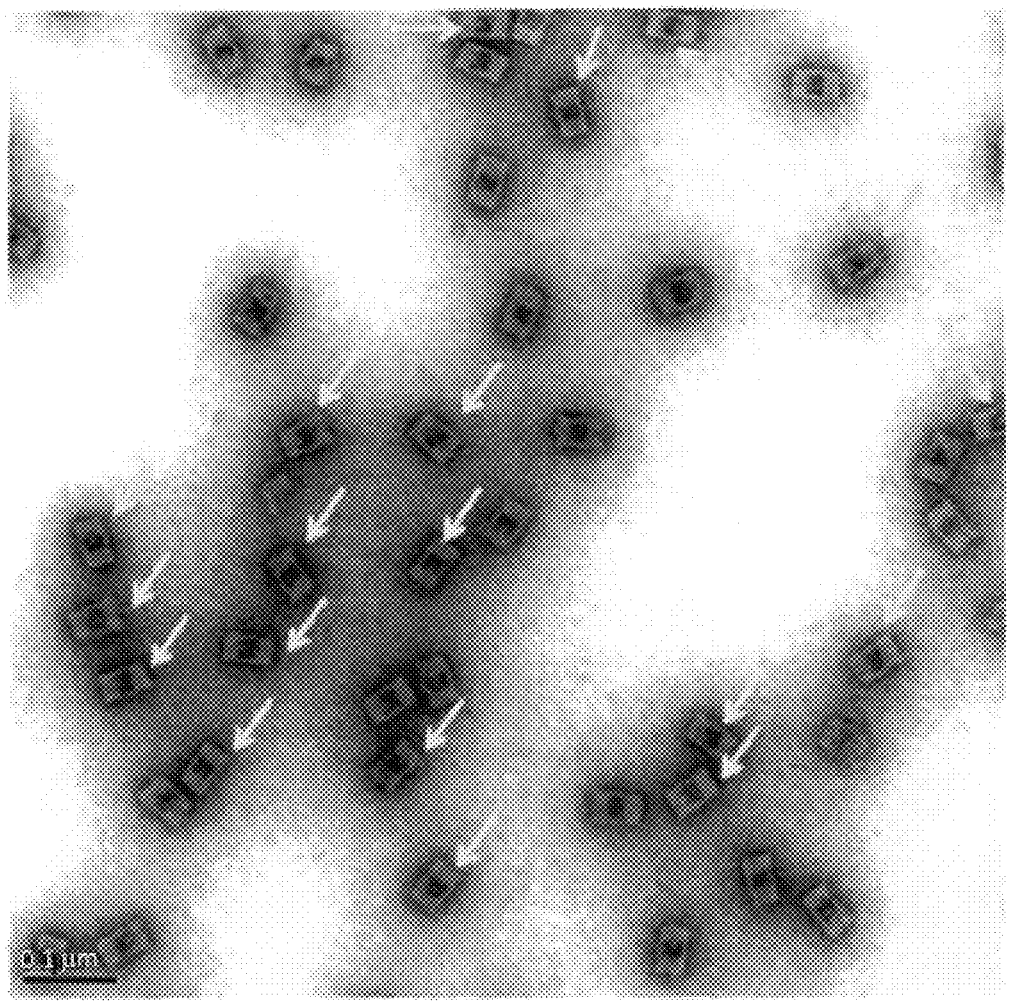
FIG. 28 shows a TEM image for the purified DNA full-cage with only HRP enzyme inside. Scale bar: 100 nm. The majority of cages showed one lighter spot inside the cavity, representing the enzyme. Despite variable quality of staining across the field of view, the inner cavity of many nanocages appeared to contain one bright spot, which we interpreted as intact one HRP enzyme (yellow arrow indicates DNA cage with enzyme inside).
Figure 29:
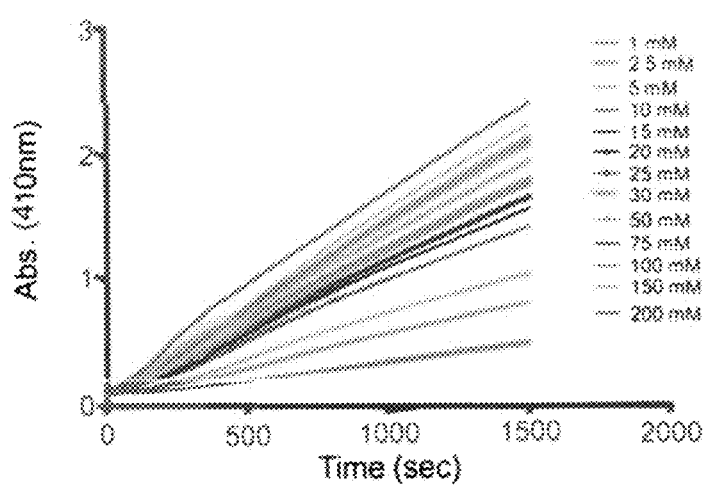
FIG. 29 shows raw activity date for free DNA-conjugated GOx (0.5 nM) with different concentrations of glucose ranging from 1 mM to 200 mM. 2 mM ABTS and 100 nM HRP were used to quickly convert $H_2O_2$ to detectable signal that was monitored at 410 nm. Error bars were calculated from the standard deviation of at least three replicates.
Figure 30:
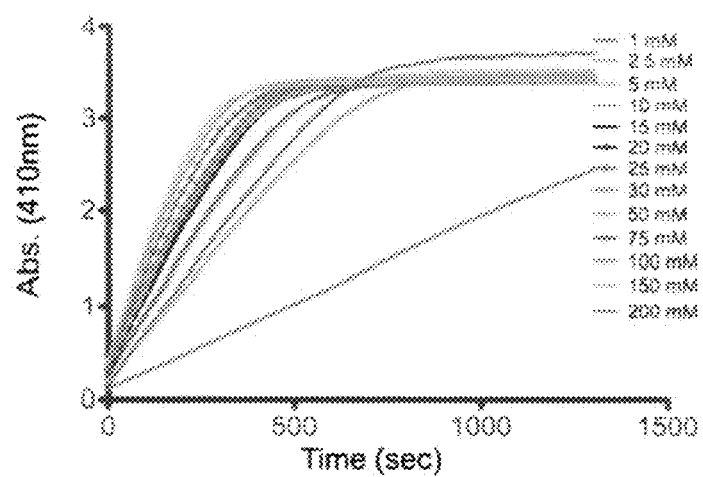
FIG. 30 shows raw activity data for DNA cage-encapsulating GOx (0.5 nM) with different concentrations of glucose ranging from 1 mM to 200 mM. 2 mM ABTS and 100 nM HRP were used to quickly convert $H_2O_2$ to detectable signal that was monitored at 410 nm. Error bars were calculated from the standard deviation of at least three replicates.
Figure 31:
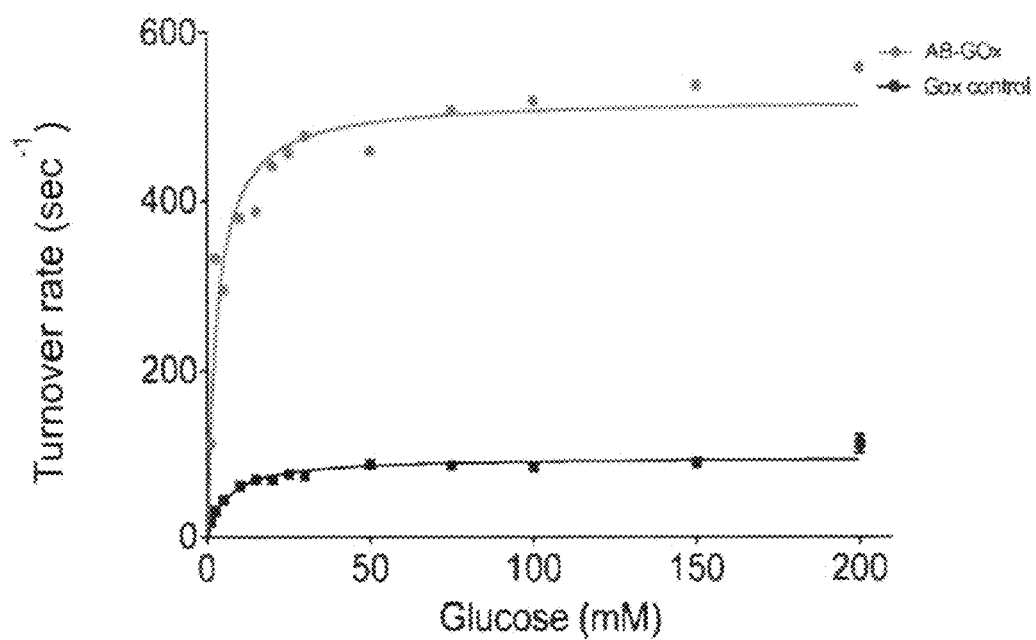
FIG. 31 shows a Michaelis-Menten plot of GOx inside the full-cage (AB-GOx, red circles), compared with that of free GOx enzyme (GOx control, black squares) using glucose as the substrate. The solid lines represent fits of the Michaelis-Menten model to the data. Enzyme assay conditions: 0.5 nM enzyme or DNA cage encapsulated enzyme, 2 mM ABTS, 100 nM HRP with different concentrations of glucose ranging from 1 mM to 200 mM, in 1×TBS buffer (pH 7.5, 1 mM $MgCl_2$) monitoring absorbance at 410 nm. The table lists the fit parameters. DNA encapsulation of the enzyme caused a 2-fold decrease in $K_M$ and a 5-fold increase in $k_{cat}$.
Figure 32:
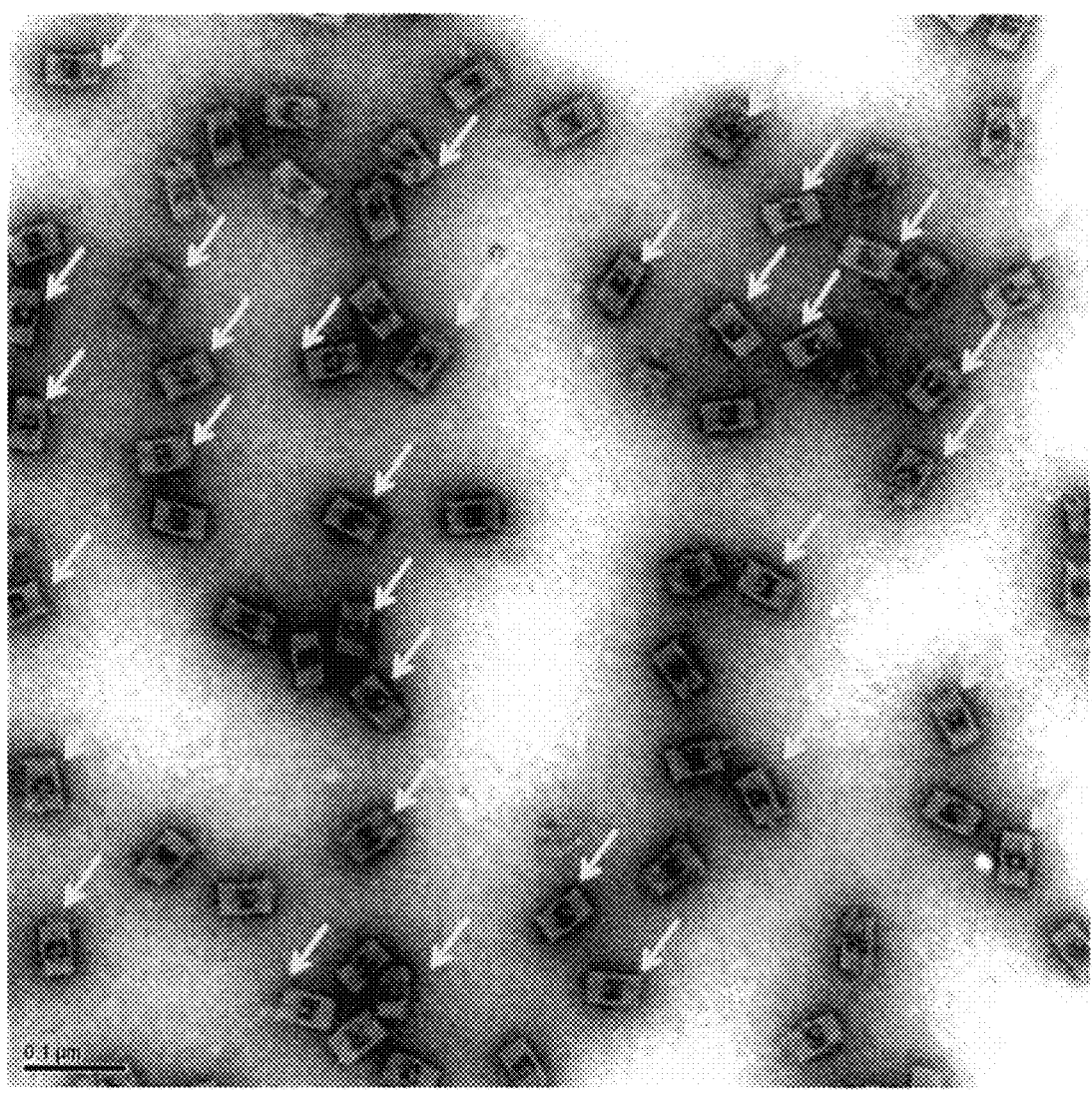
FIG. 32 shows a TEM image of the purified DNA full-cage with only GOx inside (yellow arrow indicates DNA cage with enzyme inside).
Figure 33:
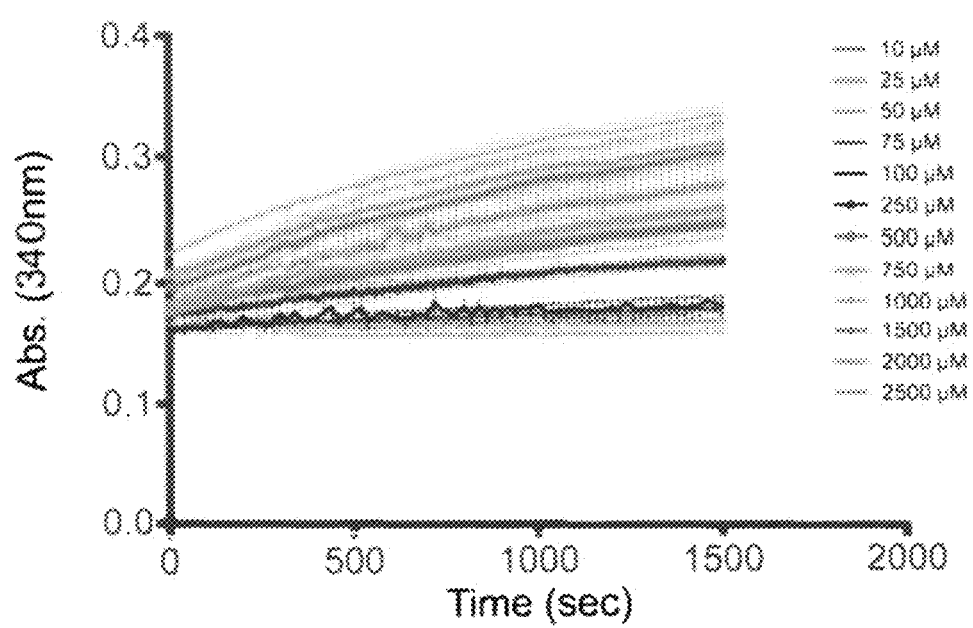
FIG. 33 determination of the Michaelis-Menten constants for enzymes-G6pDH. Raw activity data for free DNA-modified G6pDH (0.5 nM) with 10-2500 μM NAD+ and 1 mM glucose 6-phosphate, monitoring absorbance at 340 nm. Error bars were calculated from the standard deviation of at least three replicates.
Figure 34:
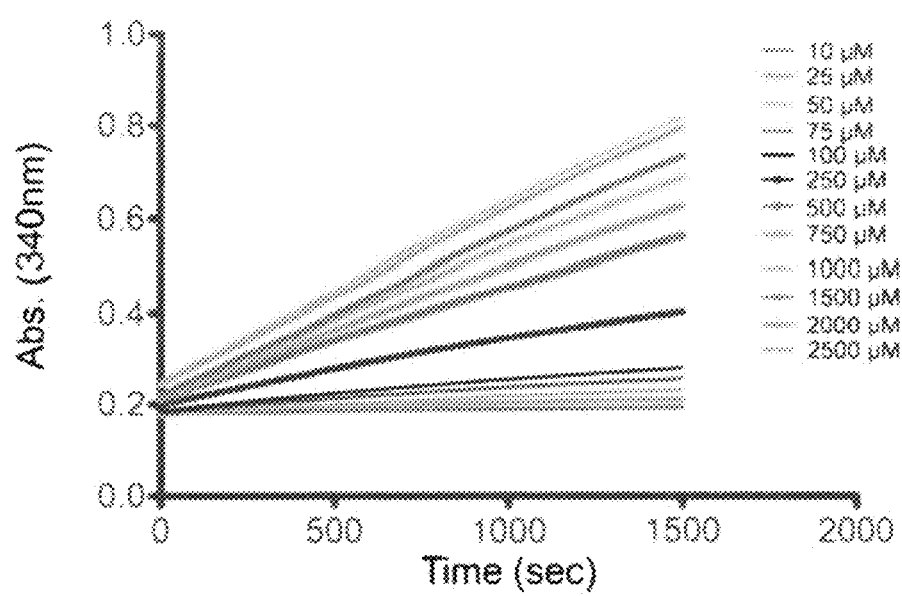
FIG. 34 shows raw activity data for Full-Cage [G6pDH] (0.5 nM) with 10-2500 μM NAD+ and 1 mM glucose 6-phosphate, monitoring absorbance at 340 nm. Error bars were calculated from the standard deviation of at least three replicates.
Figure 35:
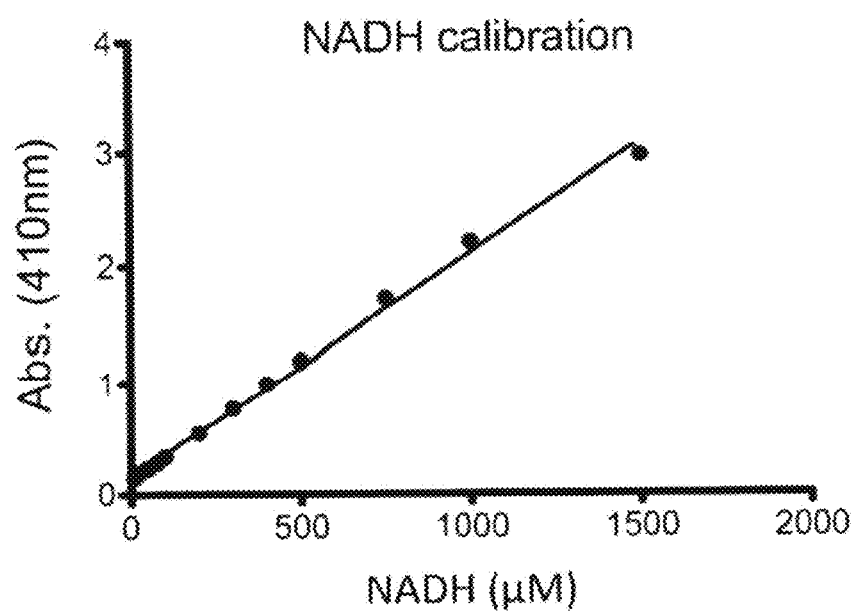
FIG. 35 shows NADH absorbance standard curve to calculate $k_{cat}$ (Y=0.001951X+0.1694).
Figure 36:
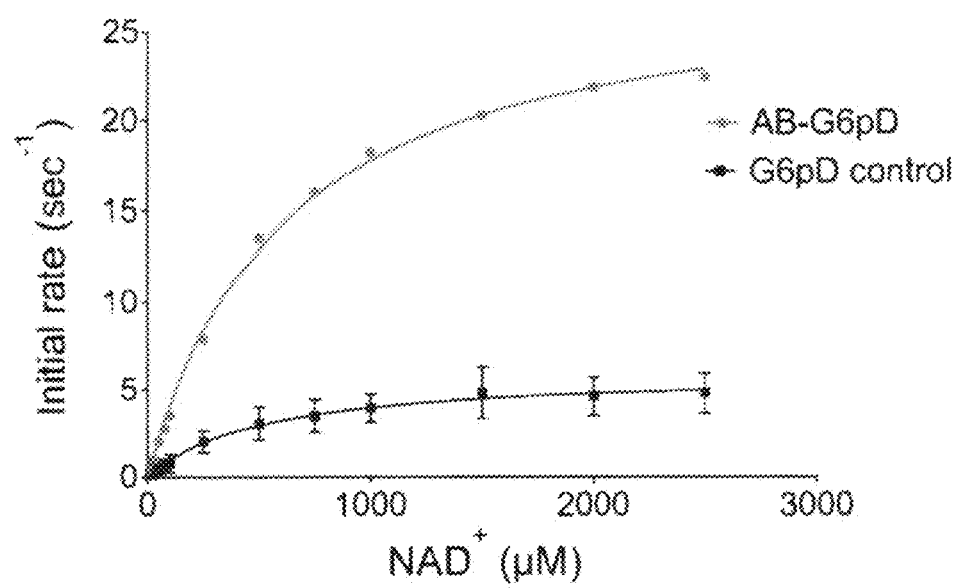
FIG. 36 shows a Michaelis-Menten plot of Full-Cage [G6pDH] (red circles) compared with that of free G6pDH (black square), using NAD+ as the varying substrate. The solid lines represent fits of the Michaelis-Menten model to the data. Enzyme assay conditions: 0.5 nM enzyme or DNA cage-encapsulated enzyme, 1 mM glucose 6-phosphate, with different concentrations of NAD+ ranging from 10 μM to 2500 μM, in 1×TBS buffer (pH 7.5, 1 mM $MgCl_2$), monitoring absorbance at 340 nm. The table lists the fit parameters. Full-cage encapsulation of the enzyme caused little change in $K_M$ and a 5-fold increase in $k_{cat}$. Error bars were calculated from the standard deviation of at least three replicates.
Figure 37:
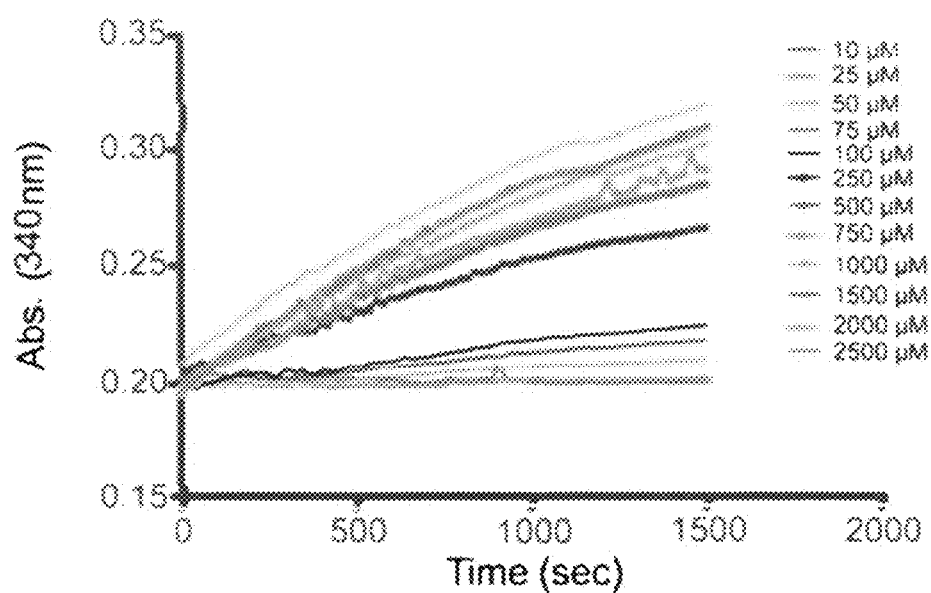
FIG. 37 shows raw activity data for free DNA-modified G6pDH (0.5 nM) with glucose 6-phosphate varied from 10 μM to 2500 μM, and 1 mM NAD+, monitoring at 340 nm. Error bars were calculated from the standard deviation of at least three replicates.
Figure 38:
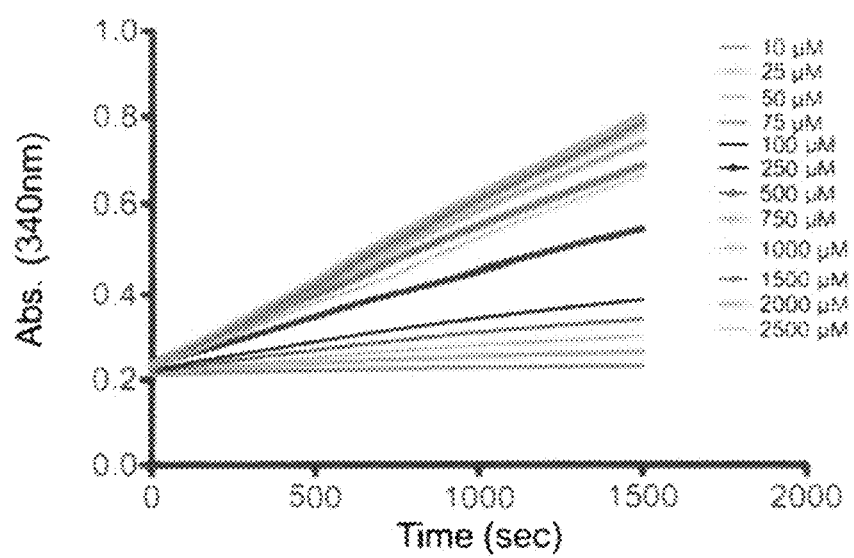
FIG. 38 shows raw activity data for Full-Cage [G6pDH] (0.5 nM) with glucose 6-phosphate varied from 10 μM to 2500 μM, and 1 mM NAD+, monitoring absorbance at 340 nm. Error bars were calculated from the standard deviation of at least three replicates.
Figure 39:
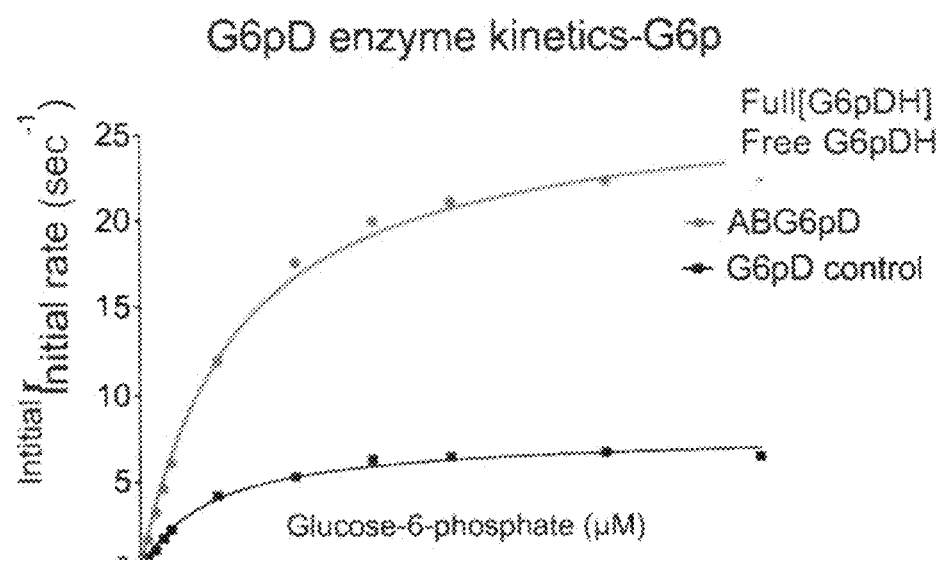
FIG. 39 shows a Michaelis-Menten plot of Full-Cage [G6pDH] (red circles), compared with that of the free G6pDH enzyme (black squares), using glucose 6-phosphate as the substrate. The solid lines represent fits of the Michaelis-Menten model to the data. Enzyme assay conditions: 0.5 nM enzyme or DNA cage-encapsulated enzyme, 1 mM NAO+, with different concentration of glucose-6-phosphate ranging from 10 μM to 2000 μM, in 1×TBS buffer (pH 7.5, 1 mM $MgCl_2$) monitoring absorbance at 340 nm. The table lists the fitting parameters. DNA encapsulation of the enzyme caused a 1.4-fold increase in $K_M$ and a 4-fold increase in $k_{cat}$.
Figure 40:
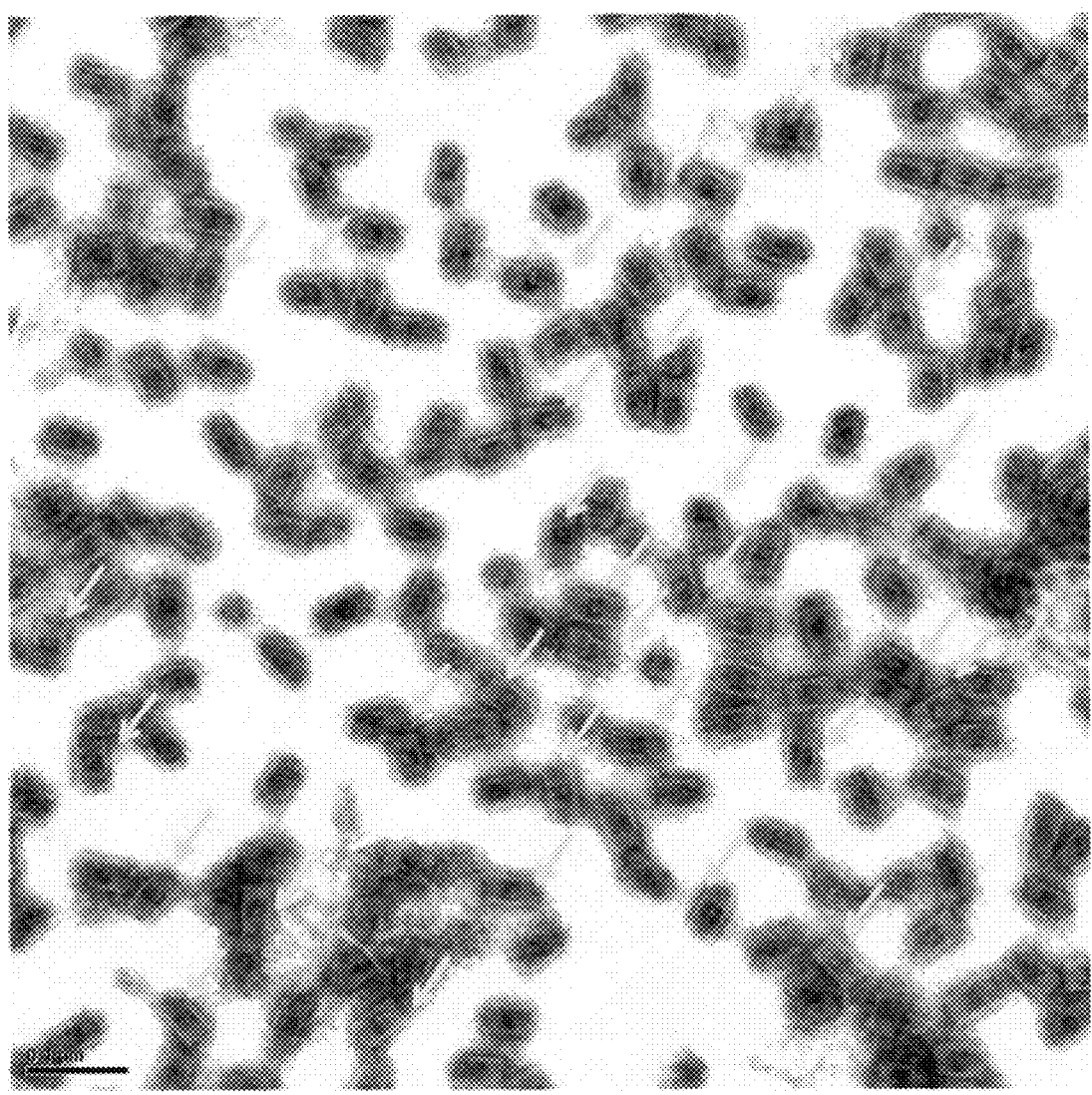
FIG. 40 shows a TEM image of AGE-purified DNA full-cages with G6pDH inside (yellow arrow indicates DNA cage with enzyme inside).
Figure 41:
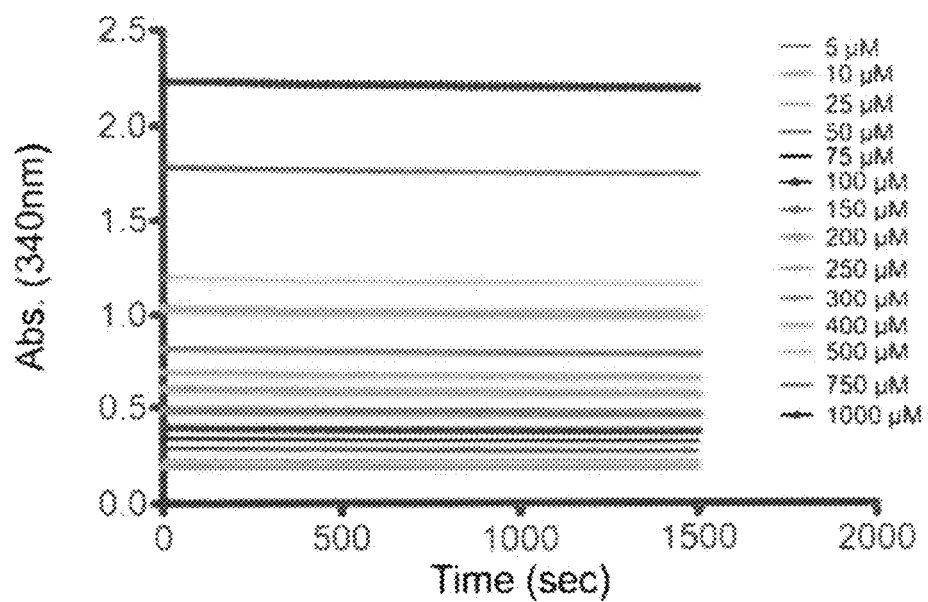
FIG. 41 shows raw activity data for free DNA-modified MDH (0.5 nM) with 5-1000 μM NADH and 2 mM OAA, monitoring absorbance at 340 nm. Error bars were calculated from the standard deviation of at least three replicates.
Figure 42:
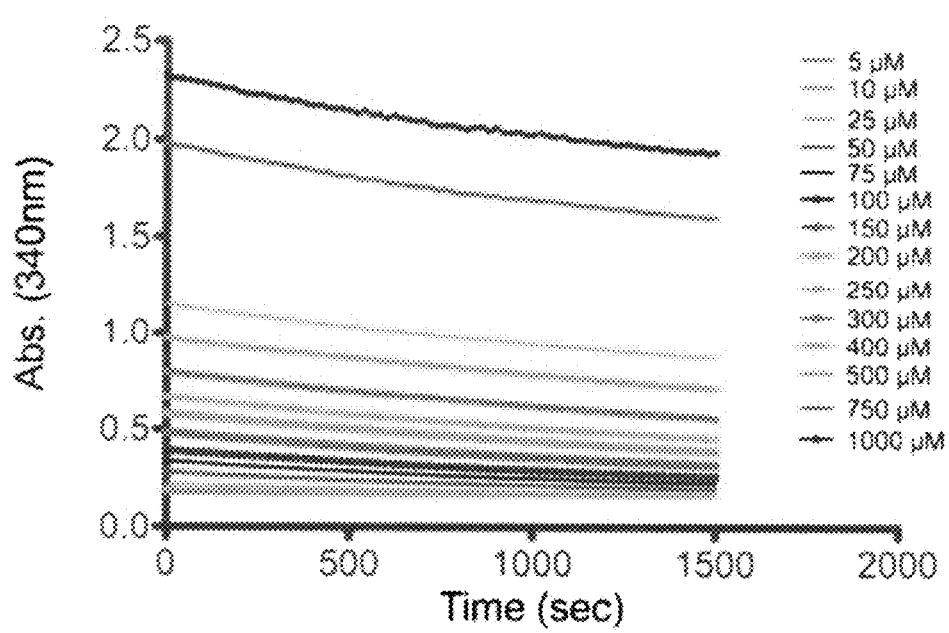
FIG. 42 shows raw activity data for Full-Cage [MDH] (0.5 nM) with 5-1000 μM NADH and 2 mM OAA, monitoring absorbance at 340 nm. Error bars were calculated from the standard deviation of at least three replicates.
Figure 43:
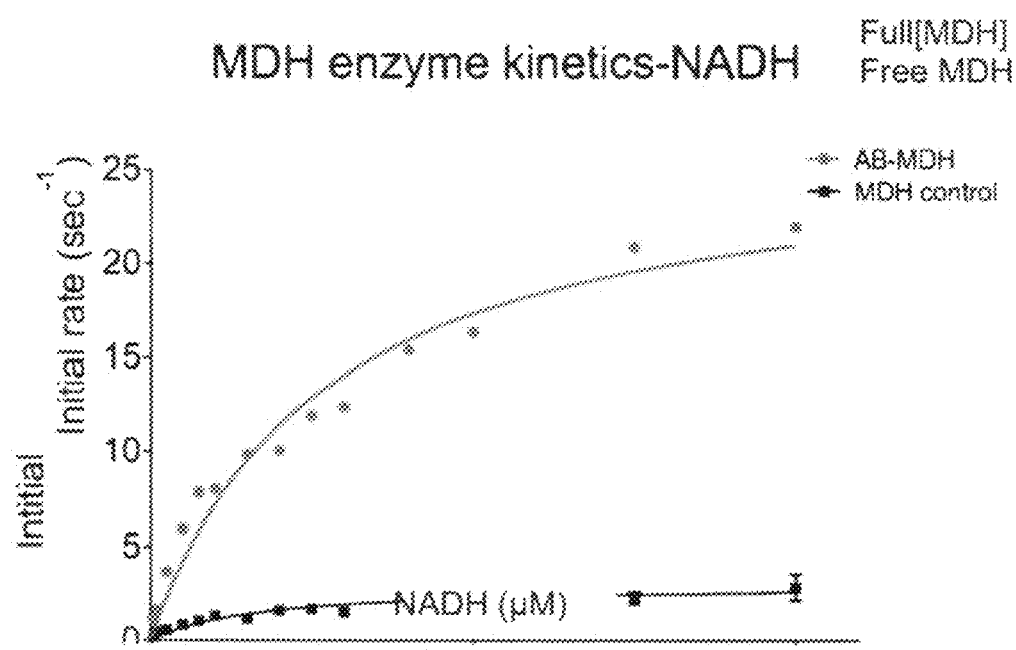
FIG. 43 shows a Michaelis-Menten plot of Full-Cage [MDH] (red circles), compared with that of free MOH (black squares) using NADH as the varying substrate. The solid lines represent fits of the Michaelis-Menten model to the data. Enzyme assay conditions: 0.5 nM enzyme or DNA cage-encapsulated enzyme, 2 mM OAA, with different concentration of NADH ranging from 5 μM to 1000 μM, in HEPES buffer (pH 7.5, 1 mM $MgCl_2$) monitoring absorbance at 340 nm. The table lists the fit parameters. DNA encapsulation of the enzyme caused a 1.5-fold increase in $K_M$ and a 9-fold increase in $k_{cat}$.
Figure 44:
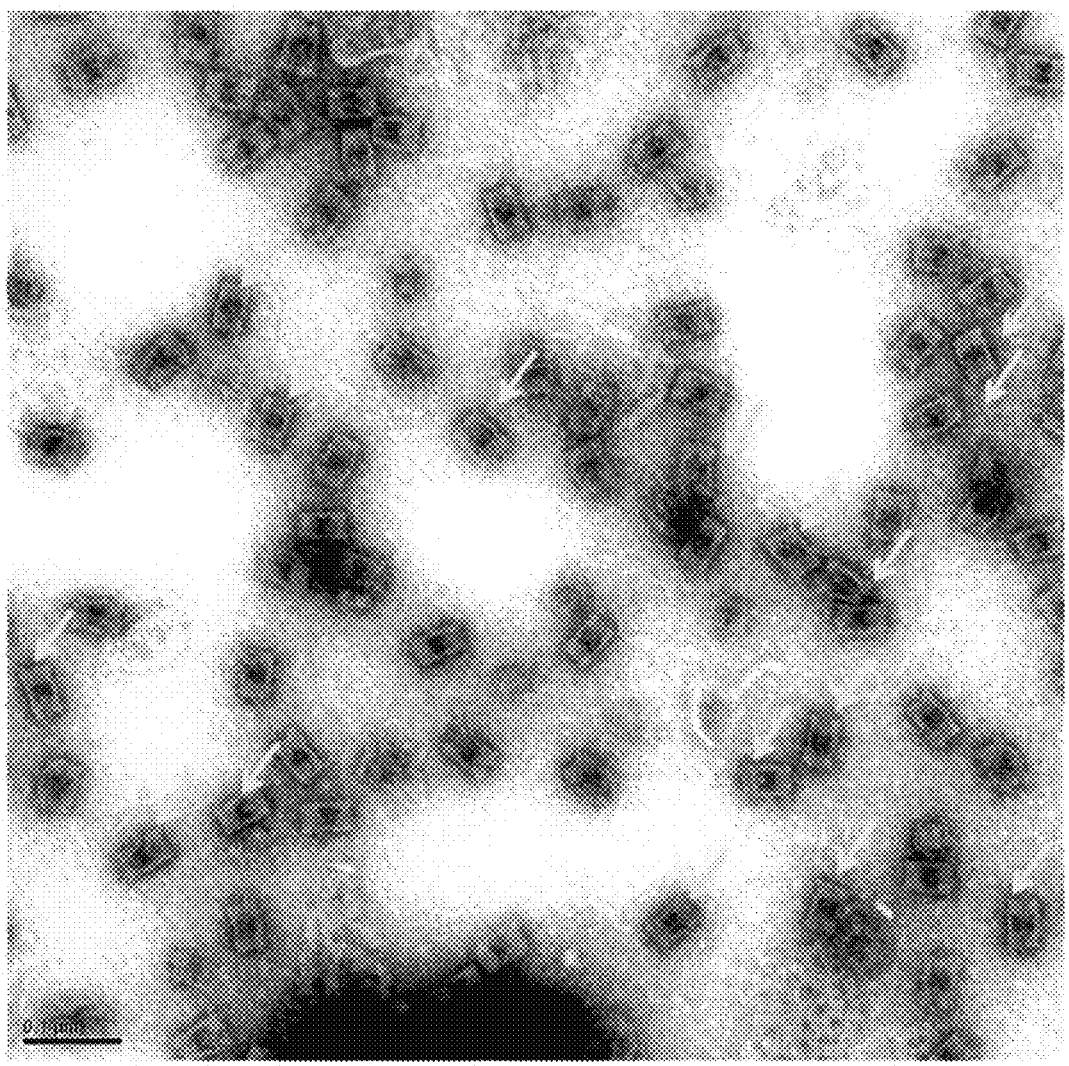
FIG. 44 shows a TEM image for DNA full-cages with MDH inside (yellow arrow indicates DNA cage with enzyme inside).
Figure 45:
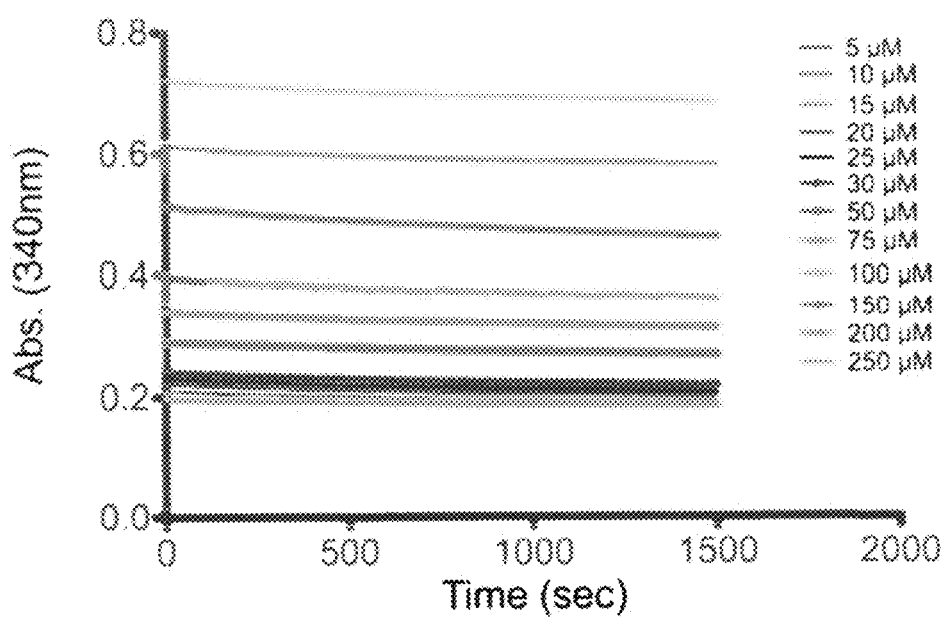
FIG. 45 shows determination of the Michaelis-Menten constants for enzymes-LDH. Raw activity for free DNA-modified LDH (0.5 nM) with 5-250 μM NADH and 2 mM pyruvate, monitoring absorbance at 340 nm. (Error bars were calculated from the standard deviation of at least three replicates)
Figure 46:
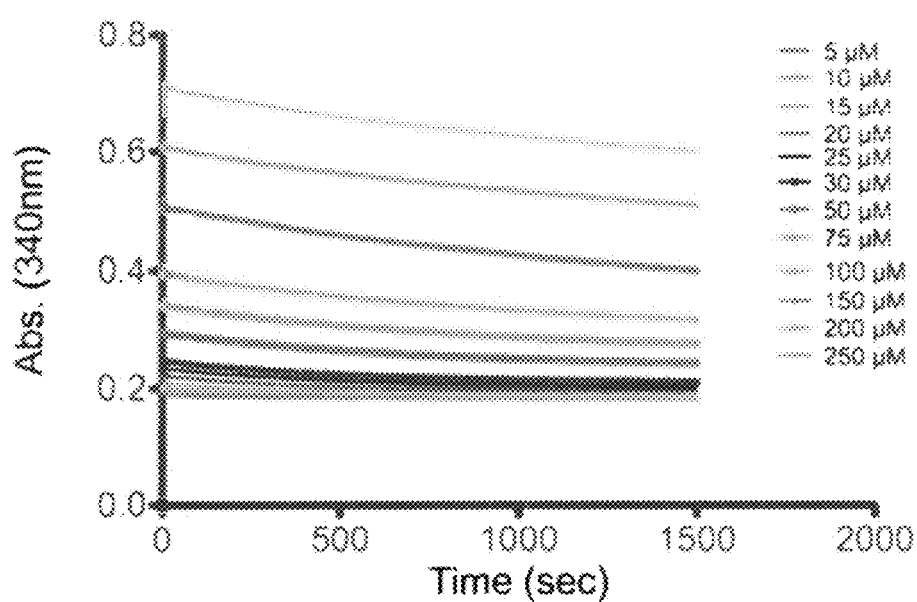
FIG. 46 shows raw activity data for full-cage [LDH] (0.5 nM) with 5-250 μM NADH and 2 mM pyruvate, monitoring absorbance at 340 nm. (Error bars were calculated from the standard deviation of at least three replicates)
Figure 47:
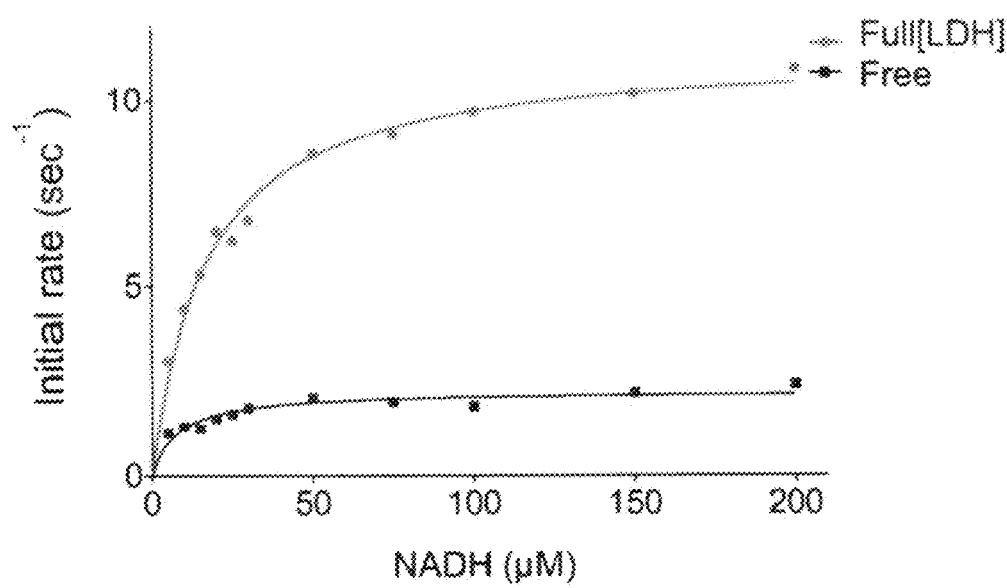
FIG. 47 shows a Michaelis-Menten plot of Full-Cage [LDH] (red circles), compared with that of free LDH (black squares), using NADH as the varying substrate. The solid lines represent fits of the Michaelis-Menten model to the data. Enzyme assay condition: 0.5 nM enzyme or DNA cage encapsulated enzyme, 2 mM pyruvate, with different concentration of NADH ranging from 5 μM to 200 μM, in HEPES buffer (pH 7.5, 1 mM $MgCl_2$) monitoring absorbance at 340 nm. The table lists the fit parameters. DNA encapsulation of the enzyme caused a 2.4-fold increase in $K_M$ and a 4-fold increase in $k_{cat}$.
Figure 48:
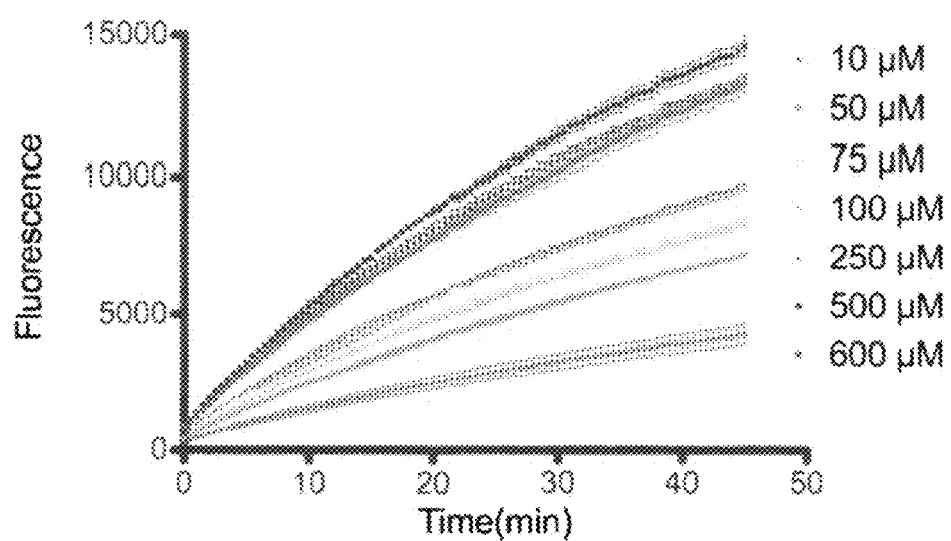
FIG. 48 shows determination of the Michaelis-Menten constants for enzymes—β-Gal. Raw activity data for free DNA-modified β-Gal (0.5 nM) with different concentration of, ranging from 10 μM to 600 μM RBG, monitoring fluorescence at 590 nm (excitation 532 nm). Error bars were calculated from the standard deviation of at least three replicates.
Figure 49:
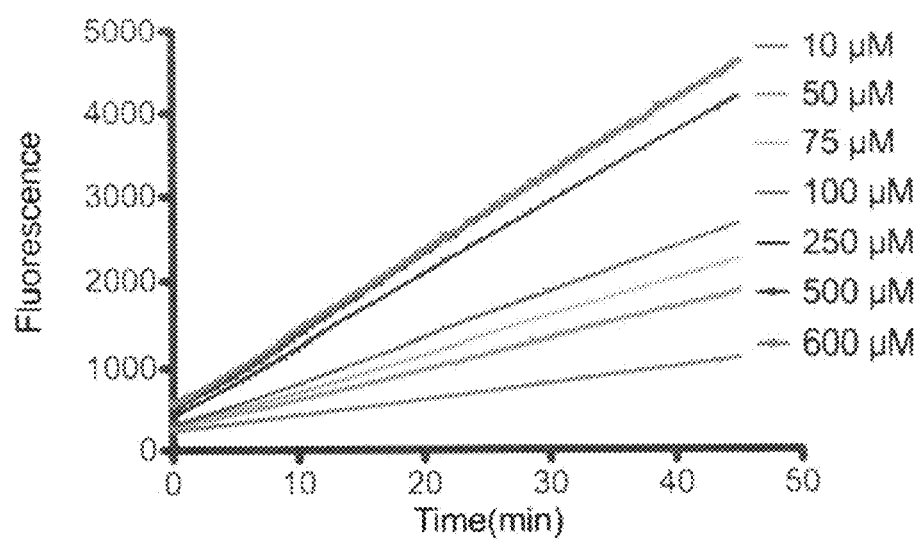
FIG. 49 shows raw activity for full-cage β-Gal (0.5 nM) with different concentration of, ranging from 10 μM to 600 μM RBG, monitoring fluorescence at 590 nm (excitation 532 nm). Error bars were calculated from the standard deviation of at least three replicates.
Figure 50:
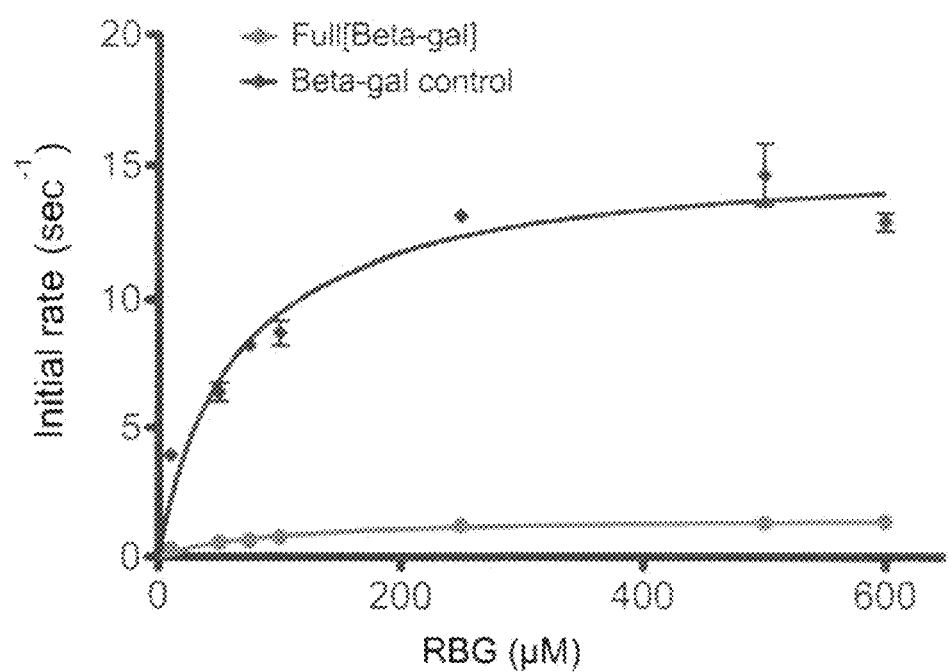
FIG. 50 shows a Michaelis-Menten plot of full-cage β-Gal (red circle), compared with that of the fresh free MDH enzyme (blue square) using RBG as the substrate. The solid line is the fitting curve using the Michaelis-Menten model. Enzyme assay condition: 0.5 nM enzyme or DNA cage encapsulated enzyme, with different concentration of RBG, ranging from 10 μM to 600 μM, in TBS buffer (pH 7.5, 1 mM $MgCl_2$) monitoring fluorescence at 532/590 nm. The table lists the fitting parameters. DNA encapsulation of the enzyme caused a −1.6-fold increase in $K_M$ and a −81% decrease in kcat. Error bars were calculated from the standard deviation of at least three replicates.
Figure 51:
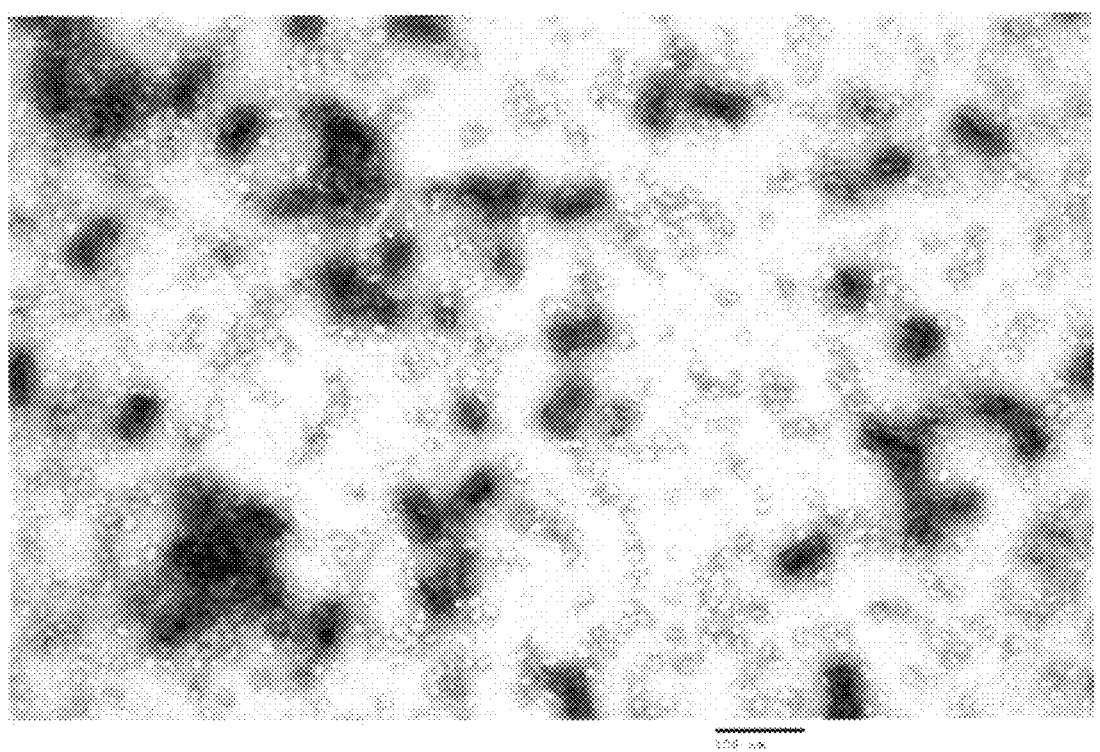
FIG. 51 shows a TEM image for the DNA full-cages with β-Gal inside (yellow arrow indicates DNA cage with enzyme inside).
Figures 52A, 52B, 52C, 52D, 52E:
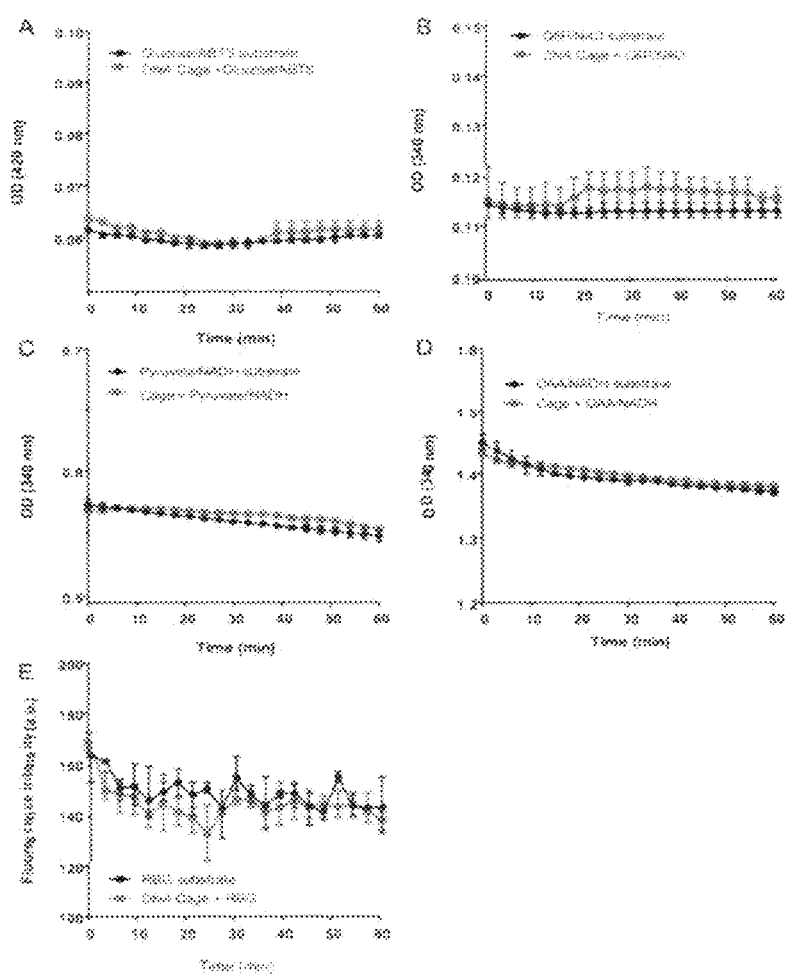
FIGS. 52A-52E show control experiments in which DNA cages were incubated with enzyme substrates. (A) Red curve: 1 nM Cage was incubated with 1 mM glucose and 2 mM ABTS (GOx/HRP substrates) in 1×TBS, pH 7.5; Black: Autocatalysis of 1 mM glucose and 2 mM ABTS (GOx/HRP substrates) in 1×TBS, pH 7.5. (B) Red: 0.5 nM Cage was incubated with 1 mM glucose-6-phosphate and 1 mM NAO+ (G6pDH substrates) in 1×TBS, pH 7.5; Black: Autocatalysis of 1 mM glucose-6-phosphate and 1 mM NAO+ in 1×TBS, pH 7.5. (C) Red: 0.5 nM Cage was incubated with 2 mM pyruvate and 0.25 mM NAOH (LOH substrates) in 1×TBS, pH 7.5; Black: Autocatalysis of 2 mM pyruvate and 0.25 mM NAOH in 1×TBS, pH 7.5. (D) Red: 0.5 nM Cage was incubated with 2 mM oxaloacetate (OAA) and 1 mM NAOH (MOH substrates) in 1×TBS, pH 7.5; Black: Autocatalysis of 2 mM OAA and 1 mM NAOH in 1×TBS, pH 7.5. (E) Red: 0.5 nM Cage was incubated with 100 µM resorufin beta-D-galactopyranoside (RBG, β-Gal substrate) in 1×TBS, pH 7.5; Black: Autocatalysis of 100 µM RBG in 1×TBS, pH 7.5, 532 nm (excitation)/590 nm (emission). Error bars were calculated from the standard deviation of at least three replicates. All above results indicate that DNA cages at our experimental concentrations do not significantly catalyze substrate conversion.
Figure 53:
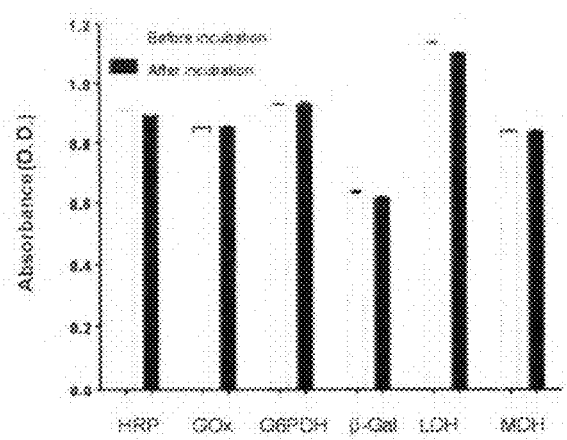
FIG. 53 shows a test of the nonspecific adsorption of enzymes onto a plastic 96-well plate. Enzyme concentrations are quantified by UV-VIS spectrometer using the following extinction coefficients: HRP ($E_{405nm}$—100,000 M-1 cm-1), GOx ($E_{280nm}$—267,200 M-1 cm-1), G6pDH ($E_{280nm}$—118,450 M-1 cm-1), β-Gal ($E_{280nm}$—972,093 M-1 cm-1), LDH ($E_{280nm}$—202,640 M-1 cm-1), MDH (E280 nm—19,600 M-1 cm-1). The UV-Vis absorbance of 100 µL of each enzyme solution was measured before adding to the plates, as well as after one hour incubation within the plates in the dark. These conditions are the same as those of the enzyme activity assay. As shown in the Figure, all enzyme solutions showed only a very slight decrease in absorbance after incubation in the plates, suggesting very weak nonspecific adsorption of enzymes onto the plastic plates. Error bars were calculated from the standard deviation of at least three replicates.
Figure 54:
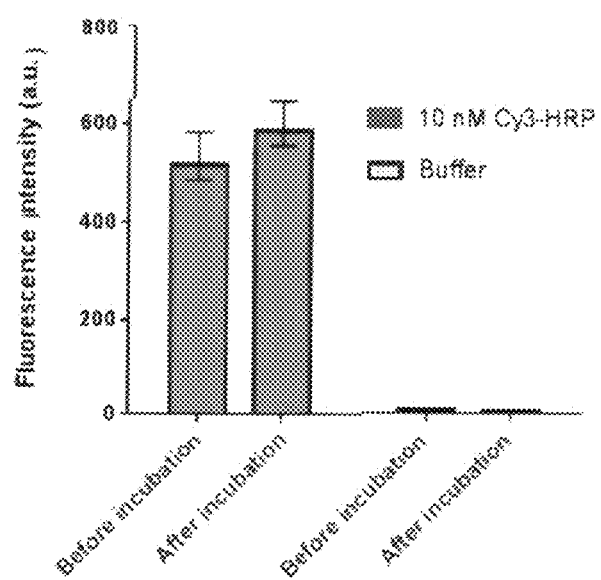
FIG. 54 shows testing for nonspecific adsorption of low nanomolar concentrations of enzymes onto plastic 96-well plates was tested using Cy3-labeled HRP. 100 µL of 10 nM Cy3-labeled HRP was assayed for fluorescence intensity, and then the plate was incubated inside a plate reader for one hour. The remaining fluorescence intensity was tested again. A slight increase of fluorescence intensity was observed, possibly due to the buffer evaporation during the incubation. This result suggests that there is very little nonspecific adsorption of Cy3-HRP onto the 96-well plate. Error bars were calculated from the standard deviation of at least three replicates.

To verify the presence of both enzymes within a DNA nanocage, the co-localization of a Cy3-labeled GOx (green emission) and a Cy5-labeled HRP (red emission) was quantified by dual-color fluorescence gel electrophoresis where a gel band with overlapped green and red color was identified (FIG. 18). By comparison, the GOx-containing half-cage (Half[GOx]) shows the presence of only Cy3 (green), whereas a HRP-half-cage (Half[HRP]) shows the presence of only Cy5 (red). In addition, negatively-stained TEM images were used to visualize DNA cages upon stoichiometrically controlled encapsulation of a single GOx (FIG. 1B) or a single GOx/HRP pair (FIG. 1C), where GOx and HRP were visible as brighter spots within the cage. To quantitatively analyze the yield of DNA nanocage encapsulation, two-color total internal reflection fluorescence (TIRF) microscopy34 (FIG. 2A) was used to characterize the fluorescence co-localization of a Cy3-labeled enzyme and a Cy5-labeled nanocage (FIG. 2B). Six different enzymes were tested and characterized for encapsulation, ranging from the smallest HRP (44 kD)35, malic dehydrogenase (MDH, 70 kD)36, glucose-6-phosphate dehydrogenase (G6pDH, 100 kD)37, lactic dehydrogenase (LDH, 140 kD)38 and GOx (160 kD)39 to the largest β-galactosidase (β-Gal, 450 kD)40. All six enzymes were successfully encapsulated within full DNA nanocages with high yields, ranging from 64-98% (FIG. 2C and Table 3). The relatively low yield of β-Gal (64%) may be due to its large size (16 nm in diameter), which is comparable to the inner diameter of the nanocage (20 nm), likely resulting in steric hindrance for encapsulation. To evaluate how many copies of the same enzyme were encapsulated per DNA nanocage, single-molecule fluorescence photobleaching (SMPB) was used to count the number of photobleaching of Cy3 fluorophores per cage (FIG. 2D). The number of copies of each enzyme per cage was estimated by normalizing the number of Cy3 fluorophores per DNA nanocage with the average number of Cy3 labels per free enzyme. A majority of nanocage-encapsulated enzymes showed only one- or two-step photobleaching of Cy3, similar to the photobleaching of single free enzymes (FIG. 2E). These results suggest that most nanocages (90%) contain exactly one enzyme per cage, as expected (FIG. 2E and Table 4).

Activity Characterization of Nano-caged Enzymes.

Figures 3A, 3B:
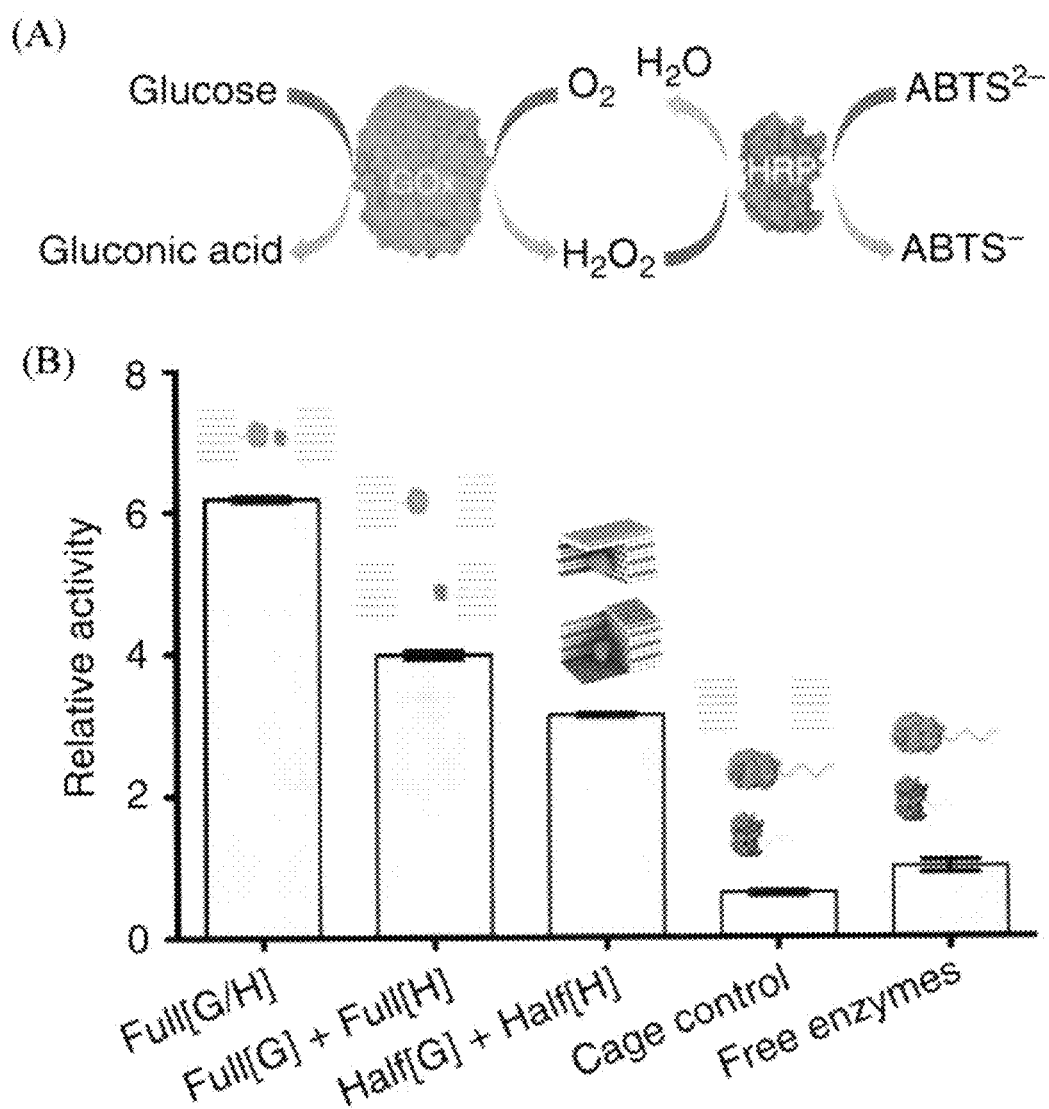
FIGS. 3A-3B show activity characterization of encapsulated GOx/HRP pairs. (A) Schematic representation of the GOx/HRP cascade. (B) Normalized cascade activities for a GOx/HRP pair encapsulated within a full-cage (Full[GOx/HRP]), two individual full-cages (Full[GOx]+Full[HRP]) and two individual half-cages (Half[GOx]+Half[HRP]), as well as unencapsulated enzyme pairs with and without the presence of DNA cages. Assay conditions: 1 nM enzyme or 1 nM enzyme-DNA cage, 1 mM glucose and 2 mM ABTS in TBS buffer (pH 7.5), and monitoring absorbance at 410 nm. Error bars were generated as the standard deviation of at least three replicates.

To evaluate the effect of DNA nanocages on enzyme activity, an encapsulated GOx/HRP pair was tested (FIG. 3A). This pair of enzymes catalyzes a reaction cascade beginning with the oxidation of glucose by GOx to generate hydrogen peroxide ($H_2O_2$). $H_2O_2$ is subsequently used by HRP to oxidize ABTS, producing a strong colorimetric signal. As shown in FIG. 3B, the overall activity of a co-assembled GOx/HRP cage (Full[GOx/HRP]) is 8-fold higher than that of a control enzyme pair incubated with the same cage but without encapsulation. Two plausible effects are hypothesized which could contribute to such a significant activity enhancement: 1) The proximity effect that brings the two enzymes close together and facilitates their substrate transfer, as described previously; and/or 2) the unique environment provided by the high charge density of DNA helices within a nanocage.

To separate the proximity effect from the charge density effect, control experiments of DNA nanocages encapsulating only a single GOx or HRP enzyme are designed, which clearly do not allow for substrate channeling between two proximal enzymes. For example, an equimolar mixture of two separate nanocages encapsulating either a single GOx or a single HRP (Full[GOx]+Full[HRP]) exhibited an 4-fold increase in overall activity compared to the unencapsulated control enzymes. Similarly, an equimolar mixture of two half-cages encapsulating either a single GOx or a single HRP already showed an increase in overall activity by 3-fold. Since there was no proximity effect in the case of two enzymes encapsulated into two different nanocages, the local environment modified by a DNA nanocage appears to be more important for the observed activity enhancement. Similarly, a half-cage was almost as effective in activity enhancement (3-fold) as a full-cage, suggesting that enzyme access to substrate does not play a role in this enhancement. Interestingly, a similar enhancement was reported previously upon conjugation of enzymes to a giant multi-branched DNA scaffold, without further explanation.

To test the generality of nanocage activity observations, the activity of six different enzymes upon encapsulation within DNA nanocages are evaluated. As shown in Table 1, five of them (GOx, HRP, G6pDH, MDH, and LDH) exhibited higher activity in nanocages than the free enzyme, with enhancements ranging from 3- to 10-fold.

Figures 4A, 4B, 4C:
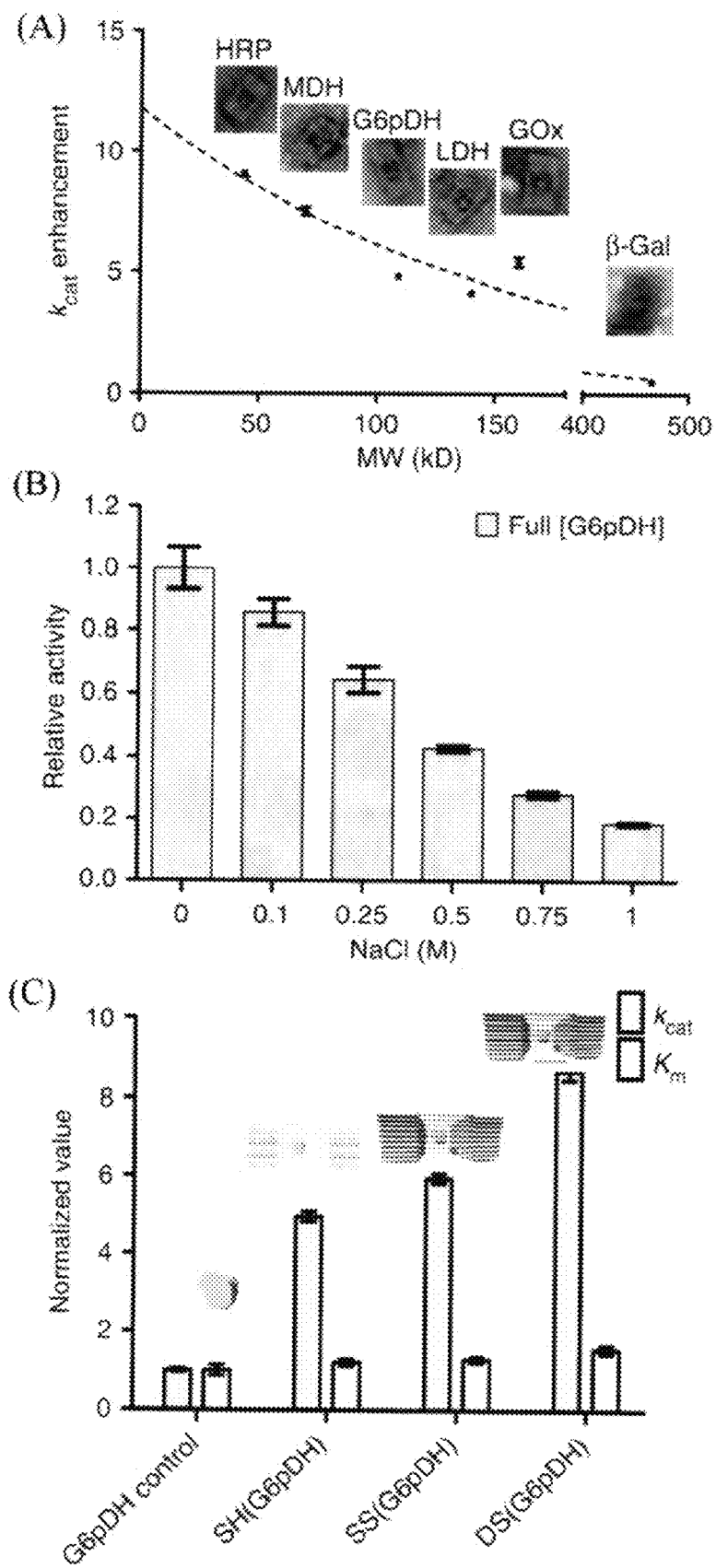
FIGS. 4A-4C show mechanistic study of the activity enhancement of DNA nanocage-encapsulated enzymes. (A) Relationship between turnover rate enhancement factor after encapsulation against enzyme molecular weight (fitted using one-phase decay function). (B) Nanocage-encapsulated G6pDH activity change after incubation with different amount of NaCl. Assay conditions: 0.5 nM enzyme-DNA cage, incubation with 1 mM glucose-6-phosphate and 1 mM NAD+ in TBS buffer (pH 7.5), and monitoring absorbance at 340 nm. (C) Normalized kcat and $K_M$ values of free G6pDH and G6pDH that is encapsulated within different DNA cage: SH(G6pDH), a honeycomb lattice origami with a single layer; SS(G6pDH), a square-lattice origami with a single layer; and DS(G6pDH), a square-lattice origami with two layers. $k_{cat}$ and $K_M$ values of caged enzymes are normalized to that of free enzymes. Error bars were generated as the standard deviation of at least three replicates.

Detailed kinetic analyses show that the $K_M$ (the Michaelis-Menten constant) varies little between encapsulated and free enzyme for most substrates (ranging from 0.5 to 2.4-fold of the free enzyme), suggesting that the porous DNA cages do not substantially hinder diffusion of small-molecule substrates. In contrast, a large increase in turnover number ($k_{cat}$) was observed for these five enzymes (ranging from 3.5- to 9.6-fold of the free enzyme), suggesting an inherently higher catalytic activity of the proteins. For all the raw kinetics data, please see FIGS. 20-54. An inverse correlation was observed between enhanced turnover and size of the encapsulated enzyme (FIG. 4A). That is, the smaller HRP (44 kD) and MDH (70 kD) exhibited relatively large increases in turnover number of 9.6±0.4 and 9.0±0.7 fold, respectively, whereas the larger enzymes G6pDH, LDH, and GOx exhibited smaller enhancements of 4.7±0.1 fold, 4.1±0.1 fold, and 5.4±0.2 fold, respectively. No correlation was observed between enhancement and isoelectric point (pI), despite the wide range of pI values for these enzymes (ranging from 4.2 to 10.0).

Figure 55:
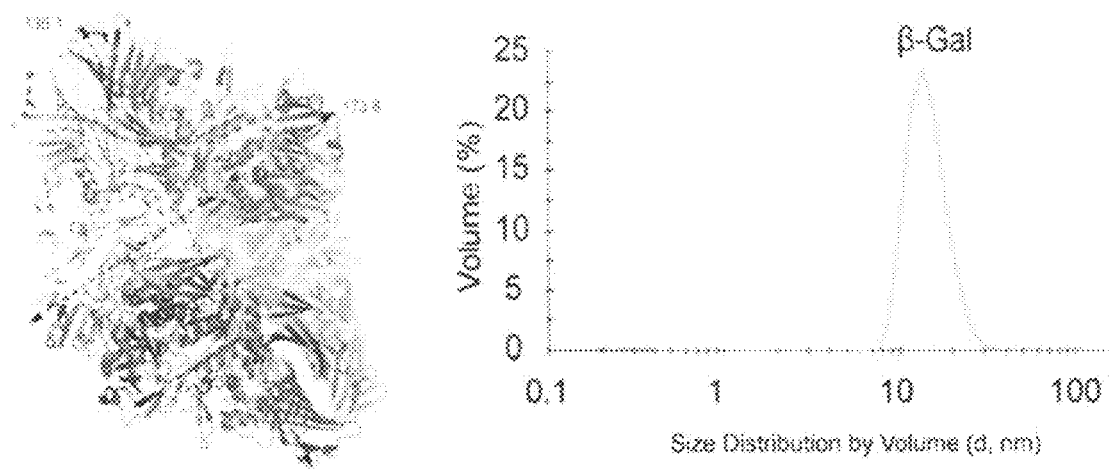
FIG. 55 shows the crystal structure of β-Gal which shows its dimensions to be 17 nm×14 nm (left) (Jacobson, R. H. et al. Nature 369, 761-766 (1994)). Dynamic Light Scattering measures a hydrodynamic diameter of 14-18 nm.
Figure 56:
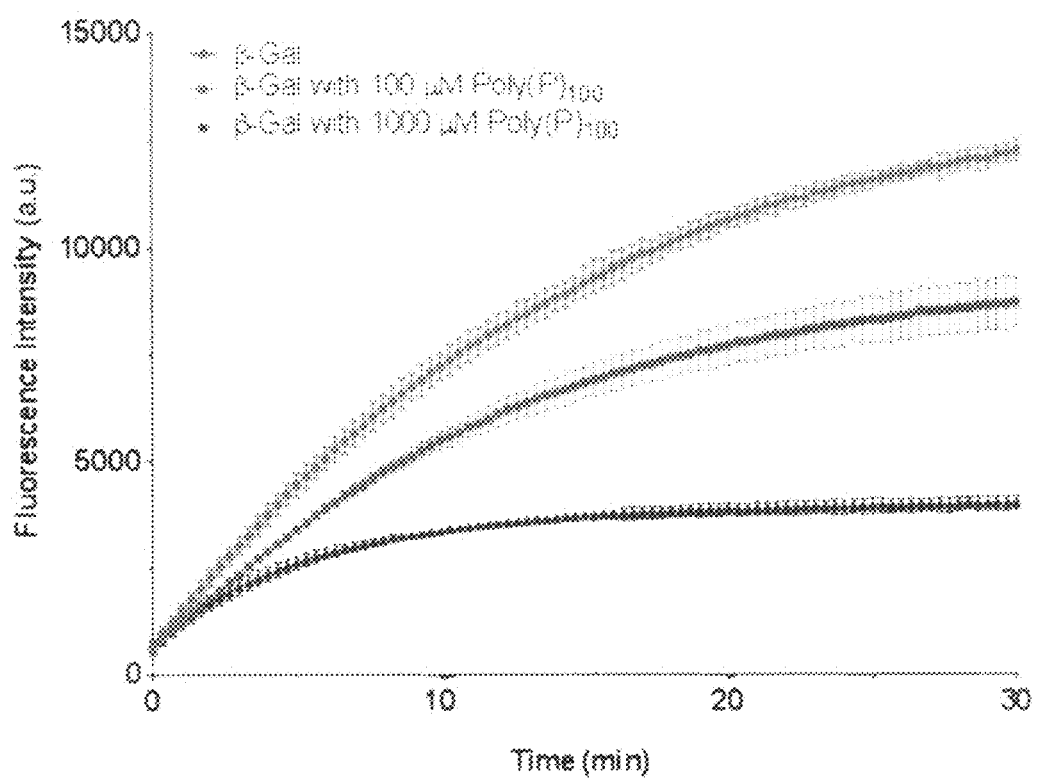
FIG. 56 shows inhibition of β-Gal activity by 100-mer polyphosphate (Poly(P)100) in solution. Assay condition: 0.25 nM β-Gal and 100 µM RBG in pH 7.4, 50 mM HEPES buffer. For inhibition assay, β-Gal was first incubated with Poly(P)100 for half an hour, then RBG substrate was added before measuring the activity. The control β-Gal was run at the same condition except for the incubation with buffer for half an hour. The activity of β-Gal was significantly inhibited by 1000 µM Poly(P)100. Error bars were calculated from the standard deviation of at least three replicates.
Figures 57A, 57B, 57C, 57D, 57E:
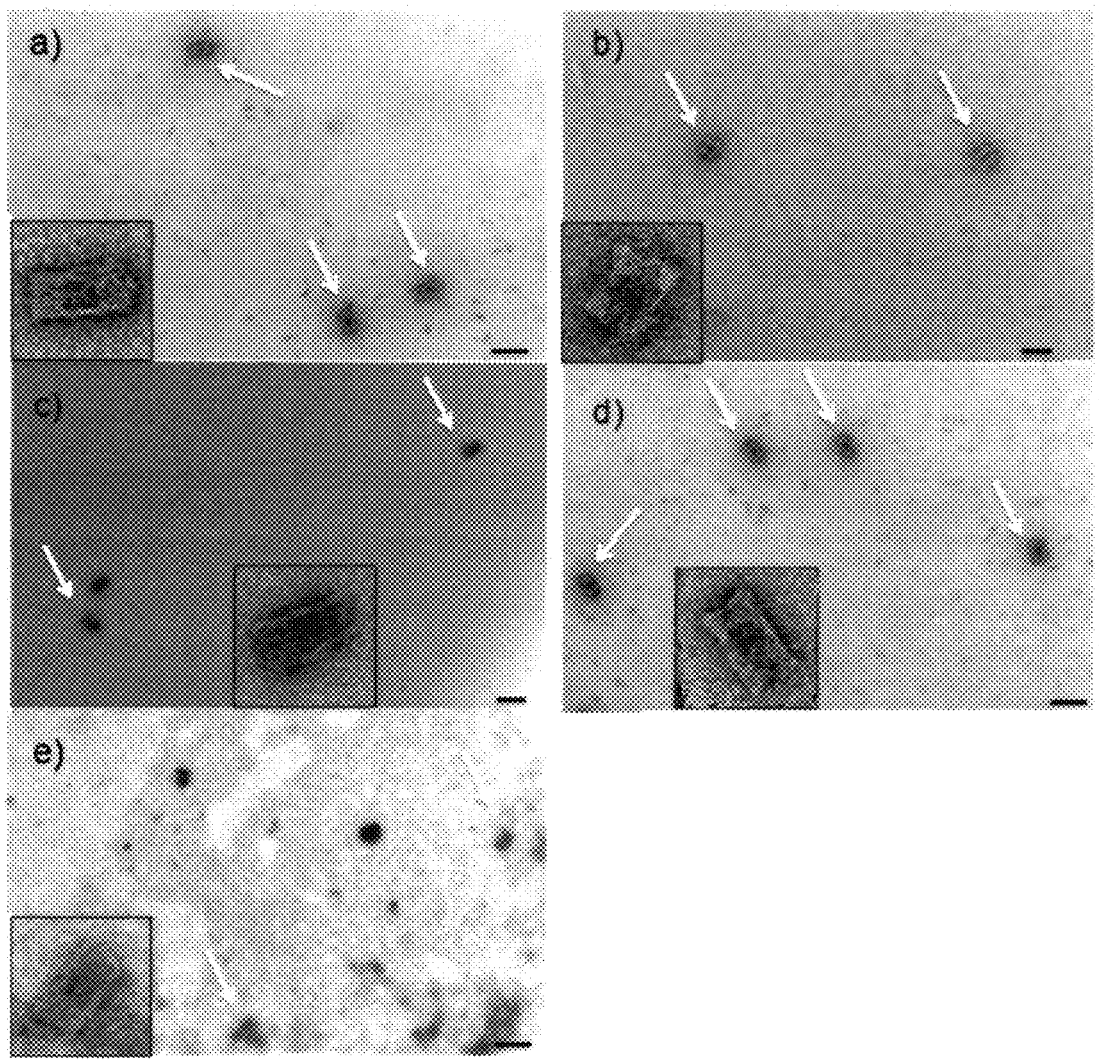
FIGS. 57A-57E show TEM images of DNA cages after 1 h incubation with a) GOx-HRP enzymatic reaction (conditions: 50 mM HEPES, pH 7.5.1 mM $MgCl_2$, 1 mM glucose, 2 mM ABTS, 1 nM GOx-HRP, 0.5 nM DNA cage), b) G6pDH enzyme reaction (conditions: 50 mM HEPES, pH 7.5.1 mM $MgCl_2$, 1 mM glucose-6-phosphate, 1 mM NAD\1 nM G6pDH, 0.5 nM DNA cage), c) MDH enzyme reaction (conditions: 50 mM HEPES, pH 7.5.1 mM $MgCl_2$, 2 mM OAA, 1 mM NADH, 1 nM MDH, 0.5 nM DNA cage), d) LDH enzyme reaction (conditions: 50 mM HEPES, pH 7.5.1 mM $MgCl_2$, 2 mM pyruvate, 1 mM NADH, 1 nM LDH, 0.5 nM DNA cage), e) β-gal enzyme reaction (conditions: 50 mM HEPES, pH 7.5.1 mM $MgCl_2$, 1 mM RBG1 nM Beta-gal, 0.5 nM DNA cage). (Scale bars: 50 nm)
Figure 58:
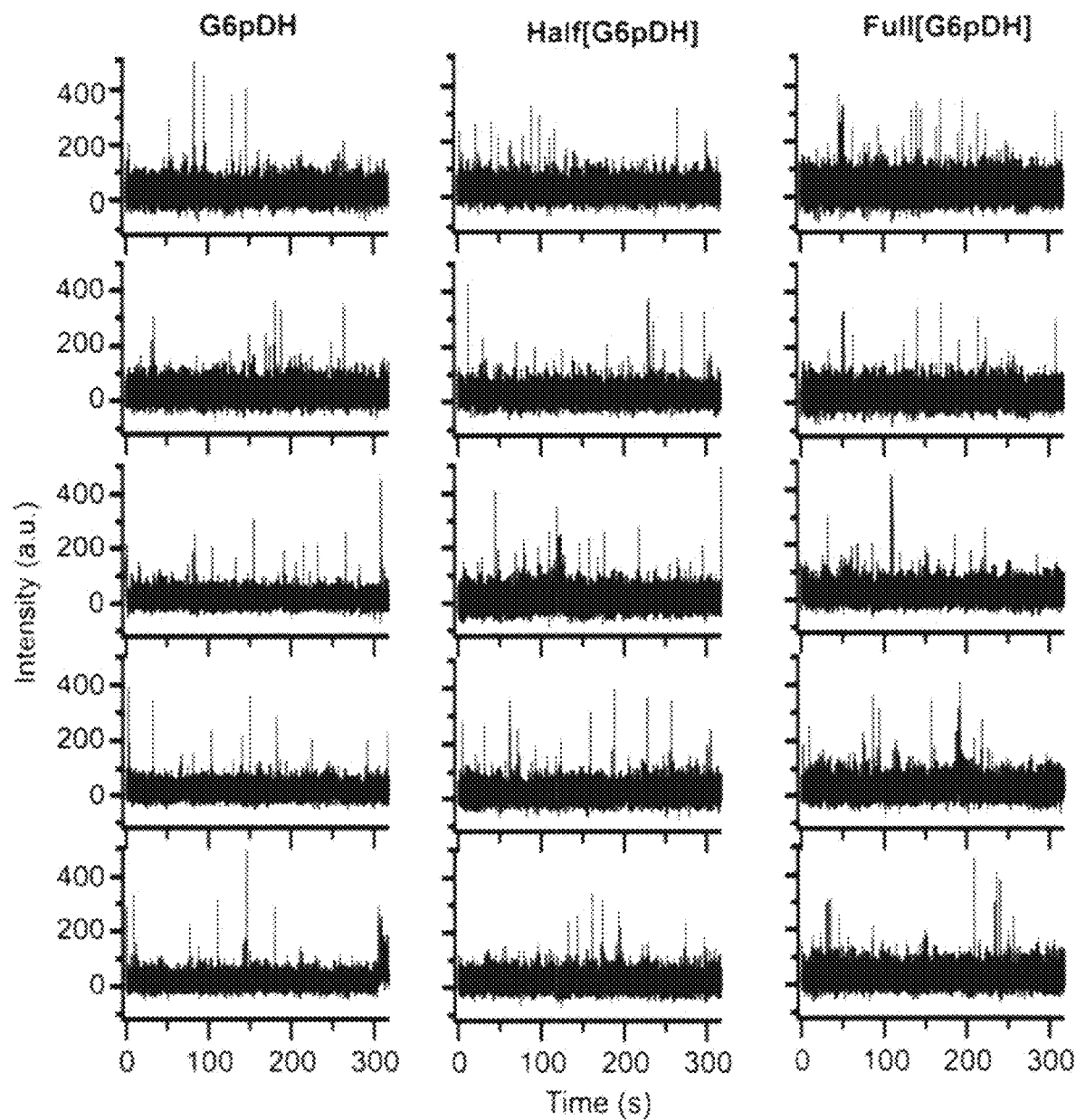
FIG. 58 shows raw enzyme activity data of single G6pDH molecules. Representative fluorescence-time traces of free-, half-cage and full-cage G6pDH. Five representative molecules are shown for each sample. The fluorescence intensity of enzyme reaction on the microscope slide was recorded for 5 min at 35 ms time resolution. The average spikes per molecule for different samples are compared in FIG. 5. All experiments were carried out at room temperature in 1×TBS buffer in presence of 1 mM Mg2+, pH 7.5 (Table 5).
Figures 59A, 59B, 59C, 59D:
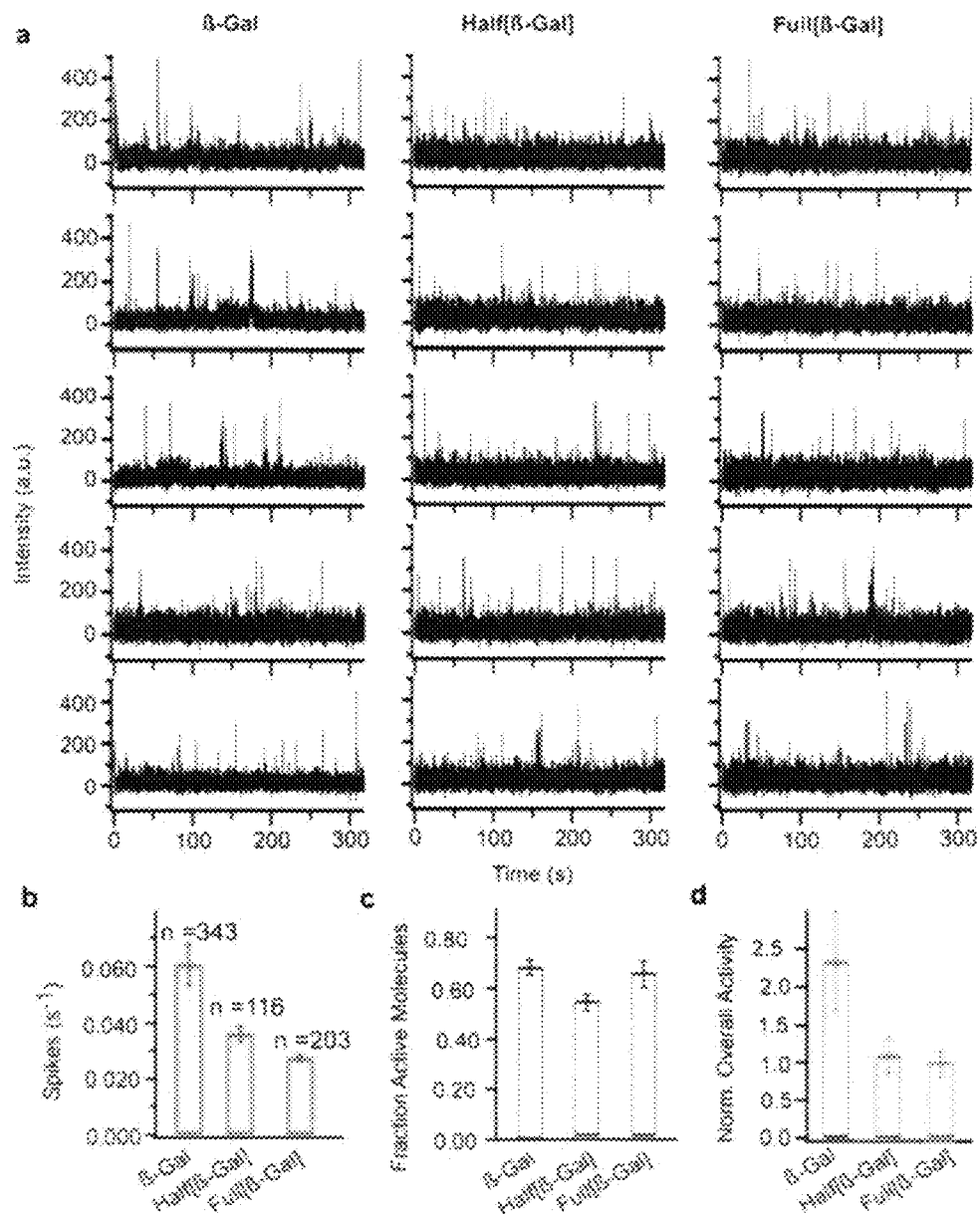
FIGS. 59A-59D show enzyme activity data of single β-Gal molecules. (A) Representative raw fluorescence-time traces of free-, half-cage and full-cage β-Gal. Five representative molecules are shown for each sample. The fluorescence intensity of enzyme reaction on the microscope slide was recorded for 5 min at 35 ms time resolution. (B, C, D) Statistics of spike frequency, fraction of active molecules, and overall observed enzyme activity. The number of active molecules analyzed is denoted by 'n' in (B). The standard deviations for spike frequency and fraction of active molecules were calculated after randomly assigning the active molecules into three groups. The standard deviation for the normalized overall activity was estimated from the propagation of errors. All experiments were carried out at room temperature in Ix TBS buffer, pH 7.5 in presence of 1 mM $Mg^{2+}$ and 10% (w/v) PEG 8000.
Figure 60:
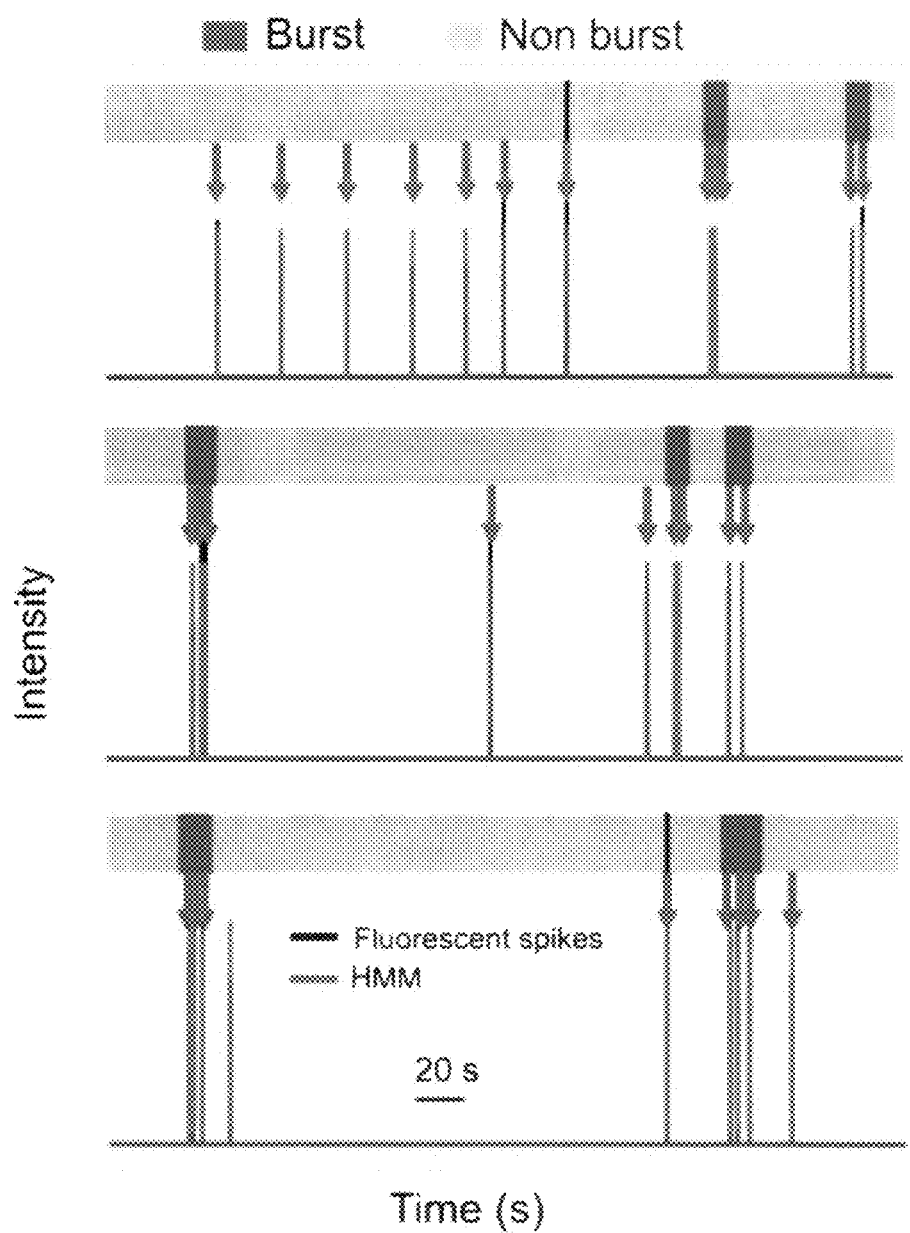
FIG. 60 shows representative intensity-time traces (black) of full-cage enzyme after background correction and Hidden Markov Model (HMM) idealization to a two-state model (red). The fluorescence-time traces of the enzyme reaction on the microscope slide were recorded at 35 ms time resolution over 5 min.
Figures 61A, 61B, 61C, 61D:
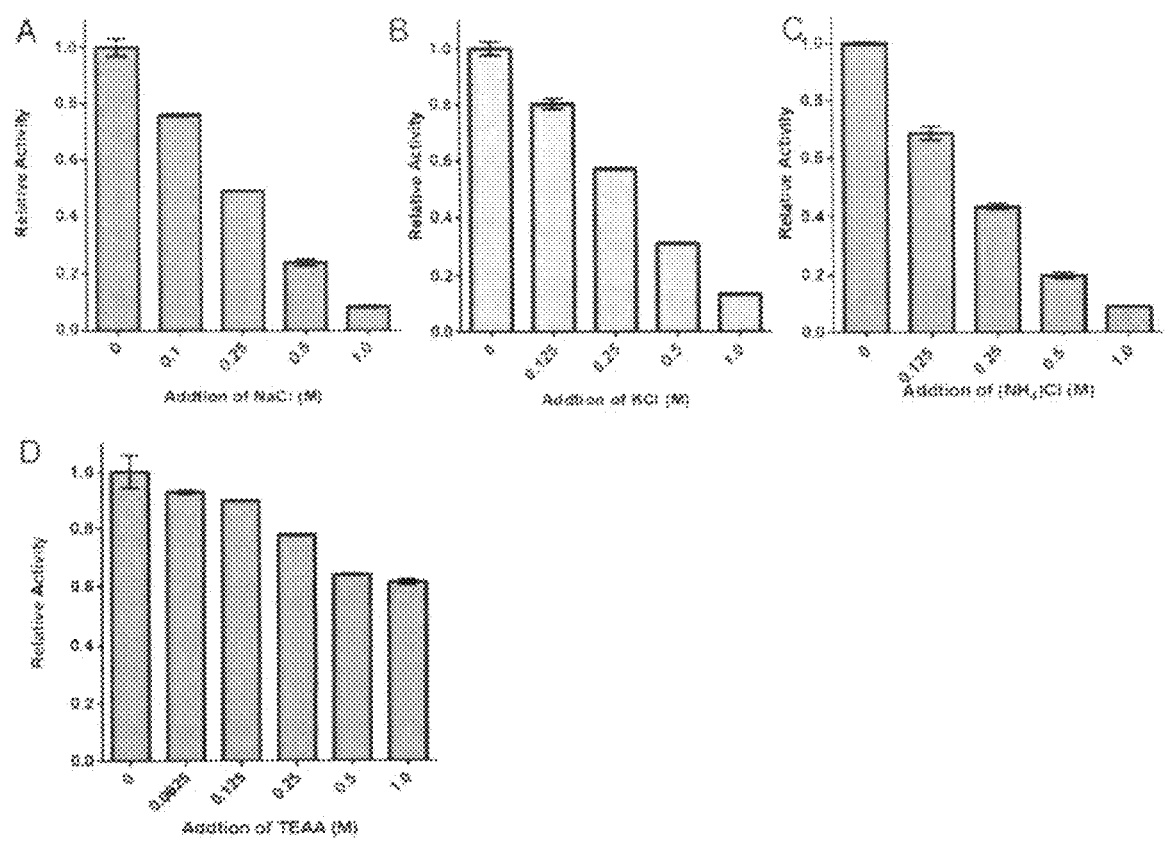
FIGS. 61A-61D show titrations showing the effects of (A) NaCl, (B) KCl, (C) NH4Cl and (D) Triethylammonium acetate (TEAA) on the activity of free G6pDH. Assay conditions: 0.5 nM enzyme was incubated with a series of ion concentrations from low to high. Enzyme activity was monitored by absorbance at 340 nm with the addition of 1 mM Glucose-6-phosphate and 1 mM NAO+ in 1×TBS buffer (pH 7.5). The results show that high concentration of salts containing small cations such as Na+, K+ and NH4+ significantly reduce the activity of G6pDH, possibly due to the chaotropic ion effect that disrupts hydrogen-bonded water structures as reported in the previous studies (Zhao, H. Journal of Molecular Catalysis B: Enzymatic 2005, 37, 16; Leberman, R. and Soper, A. K. Nature 1995, 378, 364.). Conversely, the salt containing a bulky organic cation (kosmotropic), triethylammonium, does not strongly inhibit enzyme activity, even at high concentrations. Error bars were calculated from the standard deviation of at least three replicates.

In contrast to these five enzymes, β-Gal is strongly inhibited upon encapsulation, possibly due to its large size (16 nm in diameter, FIG. 55) that is comparable to the inner cavity diameter (20 nm) of the DNA nanocage. Alternatively, the β-Gal orientation may be unfavorable and block binding of substrate to the active site. Notably, in a control experiment polyphosphate inhibited the activity of β-Gal (FIG. 56), suggesting that the local high density of backbone phosphates of the DNA nanocage might be responsible for the decrease in activity of β-Gal. The DNA cages retained their structural integrity during the enzymatic reactions (FIGS. 57A-57E).

To gain more detailed mechanistic insight into the enhancement of catalytic turnover, a novel single-molecule fluorescence assay to characterize the activity of individual enzymes with and without encapsulation was applied (FIG. 5). As shown in FIGS. 5A and 5B, TIRF microscopy is used to record the repetitive turnover of substrates by individual G6pDH enzymes over time; coupling with a PMS/resazurin reaction allowed us to detect stochastic fluctuations of enzyme turnover rates via transient spikes in intensity from the generation of the fluorescent product resorufin (FIGS. 5C-5D and FIGS. 58, 59A-59D, and 60). Such fluctuations have been observed for various enzymes before and are thought to be induced by the conformational switching between more and less active sub-states.

Compared to a control without substrate, more frequent fluorescent spikes were observed with the addition of glucose-6-phosphate substrate (FIGS. 5C and 5D). The average spike frequency was increased from 0.016±0.001 s-1 for unencapsulated enzymes, to 0.019±0.001 s-1 for the half-cage and 0.026±0.002 s-1 for the full-cage (FIG. 5E). Further analysis suggested that the fraction of active enzyme molecules was increased from 20.3% for unencapsulated enzymes to 26.6% for the half-cage and 30.5% for the full-cage (FIG. 5F). Taken together, the 1.6-fold higher spike frequency and the 1.5-fold increase in the fraction of active enzymes yield a 2.5-fold increase in G6pDH activity for the encapsulated compared to the unencapsulated enzyme (FIG. 5G), comparable to the 4-fold enhancement observed in the bulk assay. Conversely, a similar analysis of β-Gal activity showed a 3-fold lower activity of the full-cage enzyme (2.3±0.5 fold lower in spike frequency compared to free enzyme whereas the fractions of active enzymes (65%) were similar) compared to unencapsulated enzyme (FIGS. 59A-59D), also consistent with the bulk measurement.

The activity enhancement for DNA cage-encapsulated enzymes is consistent with recent reports of enhanced enzyme activity upon attachment to a long double-stranded DNA molecule (λDNA), a 2D rectangular DNA origami, or a DNA scaffold that bound to enzyme substrates, and further suggests that it may be a widespread effect of enzyme-DNA interactions. Several mechanisms have been previously proposed to explain these observed enhancements, including micro-environment composed of giant and ordered DNA molecules, molecular crowding and the substrates affinity to DNA scaffolds. We further suggested that the negatively charged phosphate backbones of DNA might also contribute to the activity enhancement. DNA is a negatively charged biopolymer due to its closely spaced backbone phosphates (leading to a linear negative charge density of 0.6 e/Å). Thus, upon encapsulation within a DNA nanocage, an enzyme is exposed to an environment full of negative charges that may resemble the relative abundance of polyanionic molecules and surfaces (including RNA and phospholipid membranes) within the cell. Phosphate is a known kosmotropic anion that increases the extent of hydrogen-bonded water structures (termed high-density or structured water). A DNA nanocage is thus expected to attract a strongly bound hydration layer of hydrogen-bonded water molecules inside its cavity. Multiple studies have described that proteins are more stable and active in a highly ordered, hydrogen-bonded water environment, possibly due to stabilization of the hydrophobic interactions of a folded protein through an increase in the solvent entropy penalty upon unfolding.

Consistent with this model, polyphosphate has been shown to act as a generic chaperone stabilizing a variety of enzymes. To further test whether this mechanism is at work in our nanocages, we titrated the concentration of NaCl (known to consist of chaotropic ions) for the purpose of interrupting hydrogen-bonded water molecules. Consistent with our hypothesis, the activity of encapsulated enzymes significantly decreased with increasing NaCl concentration (reduced to 25% activity with 1 M NaCl as shown in FIG. 4B. A high concentration of Na+ can shield the negative charge on the DNA surface, thus disrupting the surface-bound hydration layer. As a control, we observed that the bulky kosmotropic cation, triethylammonium, had a much less pronounced effect on enzymatic activity (FIGS. 61A-61D). This model also allowed us to rationalize why we observed smaller enzymes to be more activated than larger enzymes: namely, because their higher surface-to-volume ratio predicts a stronger impact of the hydration layer.

Figure 62:
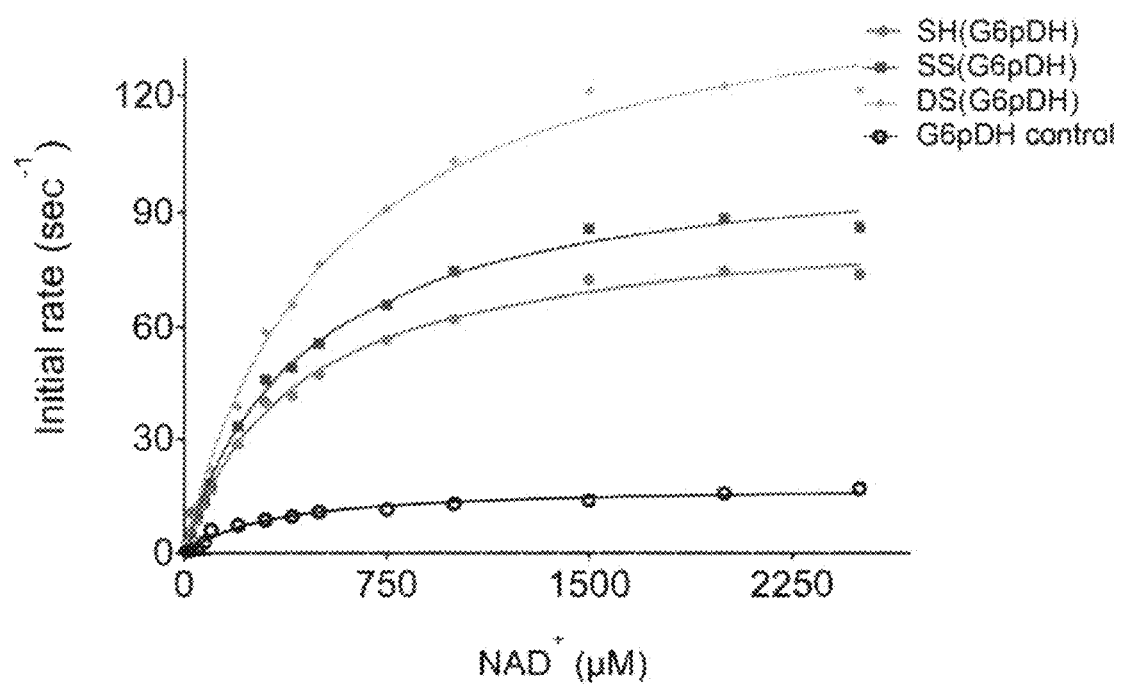
FIG. 62 shows comparison of G6pDH activity inside three different DNA full-cages, compared with that of free G6pDH, using NAO+ as the varying substrate. The SH, SS and DS cages are described in the main text. Enzyme assay conditions: 0.5 nM enzyme or DNA-cage-encapsulated enzyme, 1 mM glucose 6-phosphate, with different concentration of NAO+ ranging from 10 µM to 2500 µM, in 1×TBS buffer (pH 7.5, 1 mM $MgCl_2$) monitoring absorbance at 340 nm. The table lists the fit parameters. Encapsulation of the enzyme in different DNA full-cages caused a 1.2- to 1.5-fold increase in $K_M$ and a 5- to 9-fold increase in $k_{cat}$.
Figure 63:
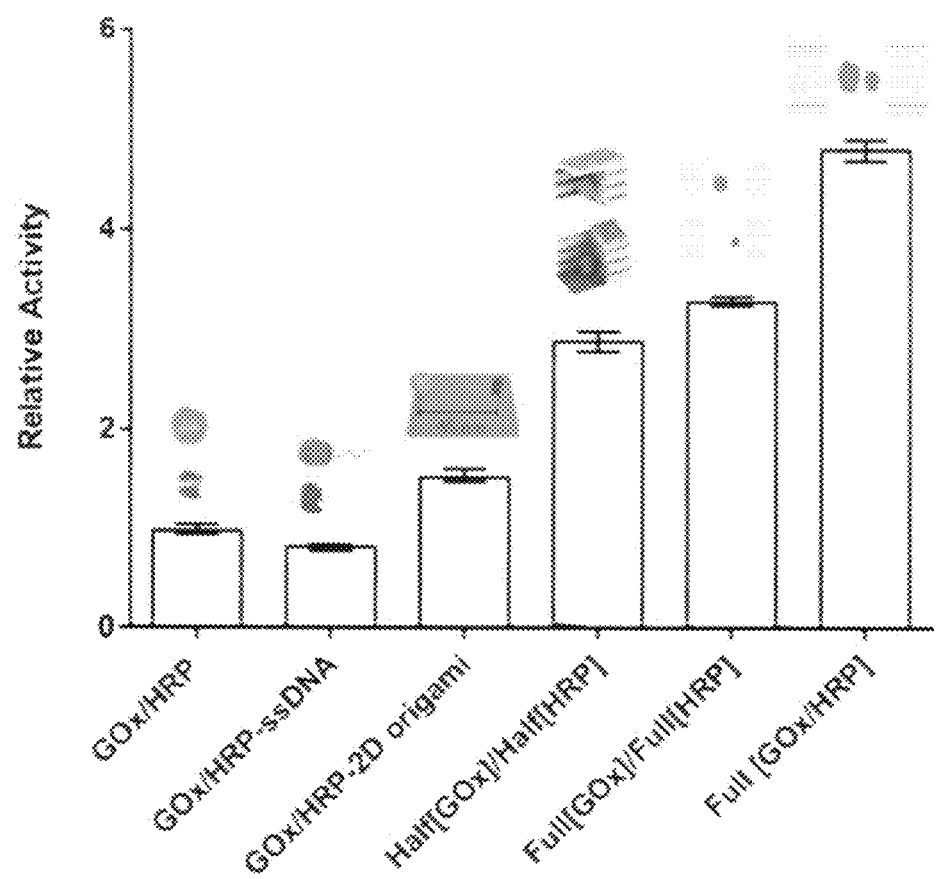
FIG. 63 The relative activity of a GOx/HRP pair when attached to a variety of DNA scaffolds: enzyme wildtypes (GOx/HRP), ssDNA (GOx/HRP-ssDNA), 2D rectangular DNA origami (GOx/HRP-2D origami), separate 3D half cages (Half[GOx]/Half[HRP]), separate full cages (Full [GOx]/Full[HRP]) and the same full cage (Full [GOx/HRP]). Enzyme activity is positively correlated to the density of DNA helices within the scaffolds, and partially or fully caged enzymes exhibit activity several-fold higher than that of free and unconjugated enzymes. Error bars were calculated from the standard deviation of at least three replicates. The value for GOx/HRP-2D origami is extracted from our previously published article (Fu, J. et al. JACS 2012, 134, 5516-5519). We concluded that the boosted activities of Full[GOx/HRP] cannot be simply attributed to a single factor of DNA density or close proximity, but may be induced by both of the high DNA density and close proximity within a DNA cage.
Figure 64:
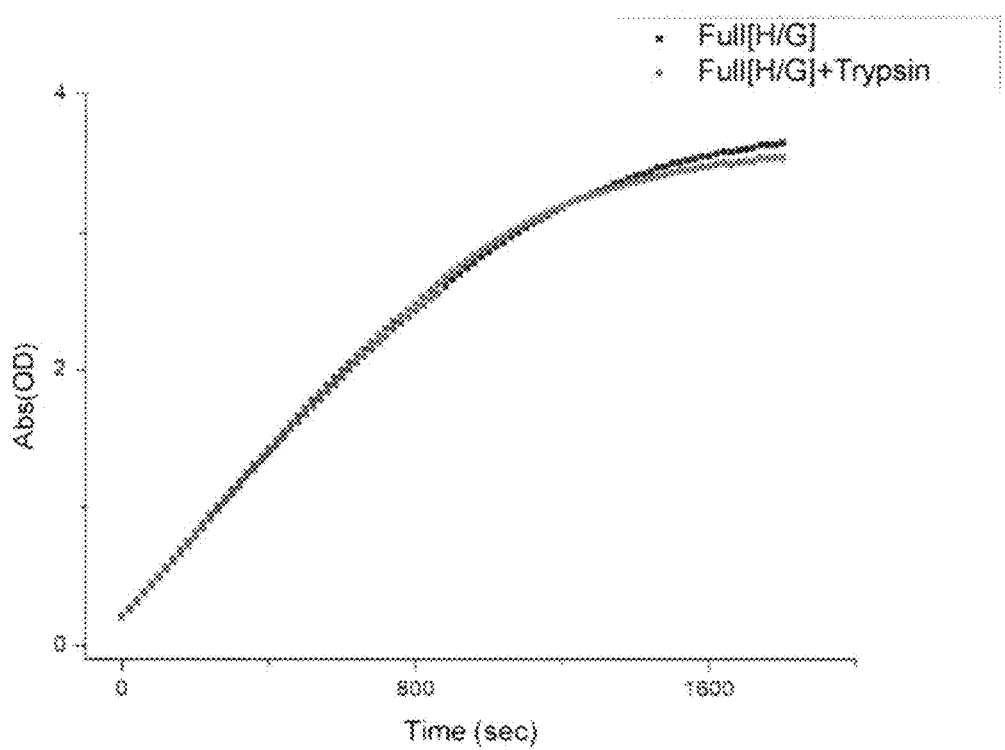
FIG. 64 shows raw activity data for full-cage [HRP/GOx] (0.5 nM) before and after trypsin digestion for 24 hours at 37° C. in 1×TBS buffer (pH 7.5).

To further test this model, we investigated the effect of DNA helix density on the encapsulated enzyme activity. As shown in FIG. 4C, we designed three nanocages with walls that systematically increase the density of DNA helices, including: 1) a single-layer honeycomb pattern (SH) with 2-3 nm pores between helices; 2) a single-layer square pattern (SS) with smaller 0.5-1 nm pores between helices, and 3) a double-layer square pattern (DS). The helix density at the top and bottom surfaces thus increased from 0.12 helices per nm2 for SH to 0.16 helices per nm2 for the SS and DS designs. The $k_{cat}$ of G6pDH encapsulated in the SH-cage was 4.7-fold higher than that of the free enzyme. As the density of DNA helices was increased, the $k_{cat}$ of encapsulated G6pDH raised to 6-fold for the SS-cage and 8-fold for the DS-cage compared to the free enzyme control. A slight increase in $K_M$ values was also observed from the SH-cage to the SS- and DS-cages, possibly due to a decrease in substrate diffusion through the DNA walls of these more tightly packed structures. For example, the $K_M$ value of G6pDH increased from 411 μM in the SH-cage to 436 μM in the SS-cage and 527 μM in the DS-cage (FIG. 62 and FIG. 4C). Additional studies showed that activities of attached enzymes were enhanced by increasing the helix packing density for various 1D, 2D and 3D DNA scaffolds (FIG. 63). These observations suggest that encapsulated enzymes exhibit higher activity within densely packed DNA cages, consistent with our model that the highly ordered, hydrogen-bonded water environment near closely spaced phosphate groups are responsible for this effect.

Figures 6A, 6B, 6C:
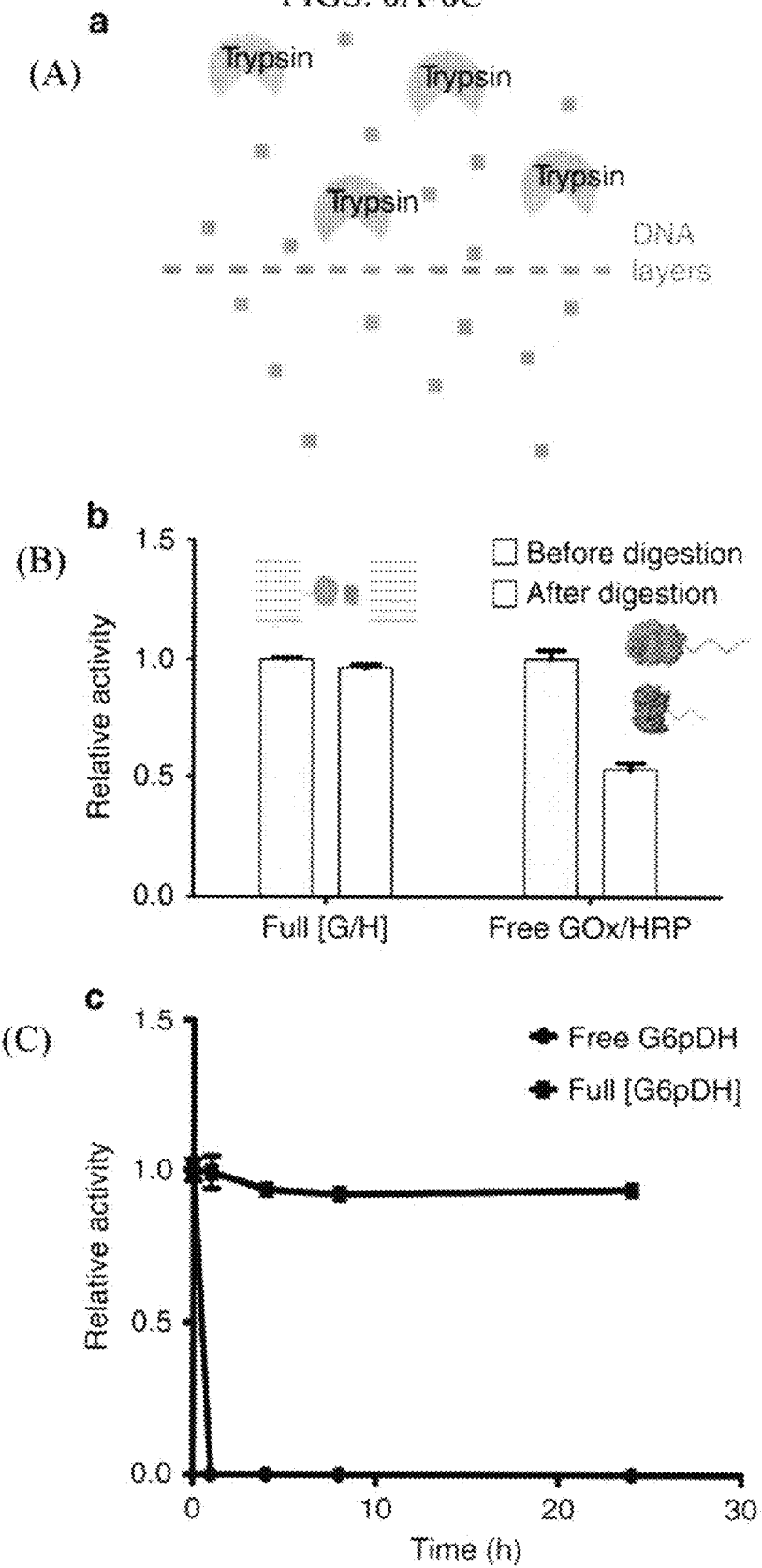
FIGS. 6A-6C show protection of nanocaged enzymes against protease-mediated degradation and aggregation. (A) Schematic representation illustrating how a DNA cage may block access of big proteins such as a protease to the interior of the cage, but still allow the penetration of small molecules. (B) Relative enzyme activity of encapsulated GOx/HRP pairs (Full [GOx/HRP]) and free GOx/HRP pairs (free GOx/HRP) before and after the addition of trypsin. Trypsin digestion conditions: enzyme or enzyme-DNA cage was incubated with 1,000× excess trypsin for 24 h at 37° C. Assay conditions: 0.5 nM enzyme or 0.5 nM enzyme-DNA cage, incubation with 1 mM glucose and 2 mM ABTS in 1×TBS buffer (pH 7.5), and monitoring absorbance at 410 nm. (C) Relative activity data for free G6pDH and Full [G6pDH] (0.5 nM) with trypsin digestion for 0, 1, 4, 8 and 24 h. Digestion by incubation sample with 1,000 times amount of trypsin at 37° C. in 1×TBS buffer (pH 7.5). Error bars were generated as the standard deviation of at least three replicates.

Nanocaged enzymes are protected from proteolysis. Self-assembled DNA nanostructures previously were found to be more resistant against nuclease degradation than single- or double-stranded DNA molecules. Similarly, DNA nanocages should protect encapsulated enzymes from deactivation and aggregation under challenging biological conditions. As shown in FIG. 6, encapsulated GOx/HRP was highly resistant to digestion by trypsin (FIG. 6B), and retained more than 95% of its initial activity after incubation with trypsin for 24 h (FIG. 6C). A time-course experiment was also performed to demonstrate the stability of caged enzymes against Trypsin digestion (FIG. 6C and FIGS. 64-67). In contrast, free GOx/HRP only retained 50% of its initial activity after a similar incubation with trypsin. This result demonstrated the potential utility of DNA nanocages for protecting encapsulated proteins from biological degradation.

TABLE 1

Enzyme kinetic data (values of $K_M$ and $k_{cat}$) for each individual enzyme encapsulated inside a DNA full-cage in comparison with the values for the free enzymes in solution.

| Enzyme | pI | Molecular weight | Substrate | Free enzyme $K_M$ (μM) | Free enzyme $k_{cat}$ (s-1) | Encapsulated enzyme $K_M$ (μM) | Encapsulated enzyme $k_{cat}$ (s-1) |
|---|---|---|---|---|---|---|---|
| GOx | 4.2 | 160 kDa | Glucose | 6,200 ± 900 | 240 ± 10 | 3,000 ± 600 | 1,300 ± 50 |
| HRP | 8.8 | 44 kDa | $H_2O_2$ | 2.3 ± 0.5 | 32 ± 1 | 4.3 ± 0.6 | 290 ± 5 |
|  |  |  | ABTS | 2,600 ± 400 | 59 ± 5 | 2,500 ± 200 | 560 ± 20 |
| G6pDH | 4.3 | 100 kDa | Glucose-6-phosphate | 220 ± 20 | 130 ± 3 | 310 ± 30 | 460 ± 10 |
|  |  |  | NAD+ | 510 ± 50 | 100 ± 3 | 590 ± 40 | 480 ± 10 |
| MDH | 10.0 | 70 kDa | NADH | 180 ± 50 | 51 ± 5 | 270 ± 50 | 460 ± 30 |
| LDH | 5.0 | 140 kDa | NADH | 7.2 ± 1.3 | 46 ± 2 | 17.0 ± 1.5 | 190 ± 5 |
| β-Gal | 4.1 | 465 kDa | RBG | 58.7 ± 16.0 | 8.5 ± 0.6* | 95.5 ± 18.9 | 1.6 ± 0.1* |

ABTS, 2,2'-azino-bis(3-ethylbenzothiazoline-6-sulphonic acid); GOx, glucose oxidase; HRP, horseradish peroxidase; LDH, lactic acid dehydrogenase; MDH, malic dehydrogenase; pI isoelectric point.
The pI values of the enzymes were obtained from brenda-enzymes.org
*$k_{cat}$ values for β-Gal groups were not calibrated

TABLE 2

Estimation of the concentration and DNA labeling ratio of the purified DNA-conjugated enzymes by measuring absorbance at 260 and 280 nm. Concentration of HRP-P1-Cy3 was estimated by the unique absorbance at 405 nm.

| DNA | A260/A280 | ε260 ($M^{-1}$ $cm^{-1}$) | ε260 ($M^{-1}$ $cm^{-1}$) | Protein | A260/A280 | ε260 ($M^{-1}$ $cm^{-1}$) | ε260 ($M^{-1}$ $cm^{-1}$) | Sample | A260/A280 | A260 | A280 | DNA-to-Protein Ratio | Protein Conc. (μM) | Dye (μM) |
|---|---|---|---|---|---|---|---|---|---|---|---|---|---|---|
| P1-Cy3 | 1.27 | 115200 | 90709 | GOx | 0.63 | 168336 | 267200 | GOx-P1-Cy3 | 1.18 | 13.50 | 14.10 | 3.09 | 25.77 | 37.00 |
| P1-Cy3 | 1.27 | 115200 | 90709 | β-Gal | 0.59 | 573534.9 | 972093 | β-Gal-P1-Cy3 | 0.63 | 1.34 | 2.11 | 0.74 | 2.03 | 1.10 |
| P1-Cy3 | 1.27 | 115200 | 90709 | G6pDH | 0.52 | 61594 | 118450 | G6pDH-P1-Gy3 | 1.00 | 11.15 | 11.17 | 2.30 | 34.17 | 53 |

TABLE 2-continued

Estimation of the concentration and DNA labeling ratio of the purified DNA-conjugated enzymes by measuring absorbance at 260 and 280 nm. Concentration of HRP-P1-Cy3 was estimated by the unique absorbance at 405 nm.

| DNA | A260/ A280 | ε260 (M$^{-1}$ cm$^{-1}$) | ε260 (M$^{-1}$ cm$^{-1}$) | Protein | A260/ A280 | ε260 (M$^{-1}$ cm$^{-1}$) | ε260 (M$^{-1}$ cm$^{-1}$) | Sample | A260/ A280 | A260 | A280 | DNA-to-Protein Ratio | Protein Conc. (μM) | Dye (μM) |
|---|---|---|---|---|---|---|---|---|---|---|---|---|---|---|
| P2-AF647 | 1.60 | 130100 | 81313 | MDH | 0.72 | 14112 | 19600 | MDH-P2-AF647 | 1.49 | 1.47 | 0.99 | 1.63 | 6.49 | 8 |
| P2-AF647 | 1.60 | 130100 | 81313 | LDH | 0.57 | 115504.8 | 202640 | LDH-P2-AF647 | 0.83 | 2.83 | 3.41 | 0.84 | 12.59 | 22 |

$A_{260}$ (DNA-protein) = $\epsilon_{260}$ (protein) * Conc. (protein) + $\epsilon_{260}$ (DNA) * Conc. (DNA)
$A_{280}$ (DNA-protein) = $\epsilon_{280}$ (protein) * Conc. (protein) + $\epsilon_{280}$ (DNA) * Conc. (DNA)
$$\text{Ratio}\left(\frac{\text{DNA}}{\text{protein}}\right) = \frac{\text{Conc. (DNA)}}{\text{Conc. (protein)}}$$

TABLE 3

Enzyme encapsulation efficiency calculation. Enzyme encapsulation was calculated by taking the ratio of the number of colocalized molecules (i.e., both enzyme and right half-cage) to the total number of molecules containing the right half-cage. N is the number of particles analyzes, $N_{coloc}$ is the number of particles containing both fluorophores, and $N_{right}$ is the number of particles showing evidence of the right half-cage.

| | N | $N_{coloc}$ | $N_{right}$ | $N_{coloc}/N_{right}$ |
|---|---|---|---|---|
| HRP | 176 | 156 | 165 | 0.94 |
| GOx | 205 | 197 | 201 | 0.98 |
| G6pDH | 218 | 209 | 214 | 0.98 |
| LDH | 1229 | 826 | 1008 | 0.82 |
| MDH | 363 | 335 | 348 | 0.96 |
| β-Gal | 284 | 115 | 179 | 0.64 |

TABLE 4

Calculation of enzyme copies per DNA nanocage. The percentage of molecules exhibiting a given number Cy3 photobleaching steps "Cy3 Steps" for both the encapsulated and unencapsulated enzymes are provided. The mean number of enzymes per cage ($N_{enz}$) was calculated by taking the ratio of $\mu_{Cy3\_Encap}$ to $\mu_{Cy3\_Unencap}$. N is the total number of particles analyzed.

| | N | Cy3 Steps (% molecules) | | | $\mu_{Cy3\_Encap}$ | Cy3 Steps (% molecules) | | | $\mu_{Cy3\_Unencap}$ | $N_{enz}$ |
|---|---|---|---|---|---|---|---|---|---|---|
| | | One | Two | Three | | One | Two | Three | | |
| HRP | 176 | 86 | 13 | 1 | 1.15 | 92 | 8 | 0 | 1.08 | 1.0 |
| G6pDH | 218 | 87 | 10 | 3 | 1.16 | 93 | 7 | 0 | 1.07 | 1.1 |
| β-Gal | 284 | 93 | 6 | 1 | 1.08 | 88 | 9 | 3 | 1.15 | 0.9 |

TABLE 5

Conditions for the single-molecule enzyme activity assay

| Solution | Concentration |
|---|---|
| 10X TBS, pH 7.5 | 1X |
| Resazurin Glucose-6-phosphate (G6p) | 50 nM |
| | 1 nM |
| Phenazine Methosulfate (PMS) | 12.5 μM |
| Mg$^{2+}$ (MgCl$_2$) | 1 mM |
| NAD$^+$ | 1 mM |
| PEG 8000 | 10% (w/v) |

Discussion

In summary, we have developed a method for using a DNA nanocage to efficiently encapsulate enzymes with high yield. Using single-molecule characterization, we were able to quantify the copies of encapsulated enzymes per cage with demonstrated one enzyme per cage. Upon encapsulation, five of six tested metabolic enzymes exhibit turnover numbers 4- to 10-fold higher than that of the free enzyme. Conversely, the $K_M$ values remain similar between encapsulated enzymes and free enzymes, indicating an uninterrupted diffusion of small-molecule substrates and products through the nanopores in the DNA cage. Application of a novel single-molecule enzyme assay showed that both the fraction of active enzyme molecules and their individual turnover numbers increase as a consequence of encapsulation.

It is therefore proposed, without being bound to any particular theory or mechanism of action, that the unique local environment created within a DNA nanocage, particularly the high density of negatively charged phosphate groups, enhances the activity of encapsulated enzymes, where the tightly bound, highly structured water layers on DNA surface may stabilize the active enzyme conformations. This effect appears consistent with recent independent evidence that many conserved metabolic enzymes are stabilized by polyphosphate and associate nonspecifically with nucleic acids through cryptic binding sites thus taking advantage of the high polyanionic DNA and RNA contents of the cell. DNA nanocages therefore may serve as a molecular tool to precisely sculpt the properties of the local environment of enzymes in smart-material and biotechnological application. DNA nanocages also demonstrated their value in protecting encapsulated enzymes from biological degradation through proteases.

REFERENCES

1. Chen, A. H. & Silver, P. A. Designing biological compartmentalization. *Trends. Cell. Biol.* 12, 662-670 (2012).

2. Hurtley, S. Location, Location, Location. *Science* 326, 1205 (2009).
3. Kertelf, C. A., Heinhorst, S. & Cannon, G. C. Bacterial microcompartments. *Annu. Rev. Microbiol.* 64, 391-408 (2010).
4. Kerfelf, C. A., Sawaya, M. R., Tanaka, S., Nguyen, C. V., Phillips, M., Beeby, M. & Yeates, T. O. Protein structures forming the shell of primitive bacterial organelles. *Science* 309, 936-938 (2005).
5. Graff, A., Winterhalter, M. & Meier, W. Nanoreactors from polymer-stabilized liposomes. *Langmuir* 17, 919-923 (2001).
6. Hartl, F. U. Molecular chaperones in cellular protein folding *Nature* 381, 571-580 (1996).
7. Comellas-Aragones, M. et al. A virus-based single-enzyme nanoreactor. *Nature Nanotech.* 2, 635-639 (2007).
8. Liu, Y. et al. Biomimetic enzyme nanocomplexes and their use as antidotes and preventive measures for alcohol intoxication. *Nature Nanotech.* 8, 187-192 (2013).
9. Sang, L. & Coppens, M. Effects of surface curvature and surface chemistry on the structure and activity of protein adsorbed in nanopores. *Phys. Chem. Chem. Phys.* 13, 6689-6698 (2011).
10. Vriezema, D. M., Aragones, M. C., Elemans, J., Cornelissen, J., Rowan, A. E. & Nolte, R. J. M. Self-assembled nanoreactors. *Chem. Rev.* 105, 1445-1490 (2005).
11. Bruns, N. & Tiller, J. C. Amphiphilic network as nanoreactor for enzymes in organic solvents. *Nano Lett.* 5, 45-48 (2005).
12. Betancor, L., and Luckarift, H. R. Bioinspired enzyme encapsulation for biocatalysis. *Trends. Biotechnol.* 26, 566-572 (2008).
13. Fiedler, J. D., Brown. S. D., Lau. J. & Finn. M. G. RNA-directed packaging of enzymes within virus-like particles. *Angew. Chem. Int. Ed.* 49, 9648-9651 (2010).
14. Douglas, S. M., Dietz, H., Liedl, T., Hogberg, B., Graf, F. & Shih, W. M. Self-assembly of DNA into nanoscale three-dimensional shapes. *Nature* 459, 414-418 (2009).
15. Han, D., Pal, S., Nangreave, J., Deng, Z., Liu, Y. & Yan, H. DNA origami with complex curvatures in three-dimensional space. *Science* 332, 342-346 (2011).
16. Ke, Y., Ong, L. L., Shih, W. M. & Yin, P. Three-dimensional structures self-assembled from DNA bricks. *Science,* 338, 1177-1183 (2012).
17. Kuzyk, A. et al. DNA-based self-assembly of chiral plasmonic nanostructures with tailored optical response. *Nature* 483, 311-314 (2012).
18. Langecker, M., Arnaut, V., Martin, T., List, J., Renner, S., Mayer, M., Dietz, H., & Simmel, F. Synthetic lipid membrane channels by designed DNA nanostructures. *Science* 338, 932-936 (2012).
19. Fu, J., Liu, M., Liu, Y., Woodbury, N. W. & Yan, H. Interenzyme substrate diffusion for an enzyme cascade organized on spatially addressable DNA nanostructure. *J. Am. Chem. Soc.* 134, 5516-5519 (2012).
20. Fu, J., Liu, M., Liu, Y. & Yan, H. Spatially-Interactive Biomolecular Networks Organized by Nucleic Acid Nanostructures, *Acc. Chem. Res.* 45, 1215-1226 (2012).
21. Wilner, O. I., Weizmann, Y., Gill, R., Lioubashevski, O., Freeman, R. & Willner, I. Enzyme cascades activated on topologically programmed DNA scaffolds. *Nature Nanotechnol.* 4, 249-254 (2009).
22. Andersen. E. S. et al. Self-assembly of a nanoscale DNA box with a controllable lid. *Nature* 459, 73-76 (2009).
23. Douglas, S. M., Bachelet, I., Church, G. M. A logic-gated nanorobot for targeted transport of molecular payloads. *Science* 335, 831-834 (2012).
24. Juul, S., et al. Temperature-Controlled Encapsulation and Release of an Active Enzyme in the Cavity of a Self-Assembled DNA Nanocage. *ACS Nano* 7, 9724-9734 (2013).
25. Fu, Y., et al. Single-Step Rapid Assembly of DNA Origami Nanostructures for Addressable Nanoscale Bioreactors. *J. Am. Chem. Soc.* 135, 696-702 (2013).
26. Linko, V., Eerikainen, M. & Kostiainen, M. A modular DNA origami-based enzyme cascade nanoreactor. *Chem. Commun.* 51, 5351-5354 (2015).
27. Gray M. J., et al. Polyphosphate is a primordial chaperone. *Mol. Cell.* 53, 689-699 (2014).
28. Cieśla, J. Metabolic enzymes that bind RNA: yet another level of cellular regulatory network? *Acta Biochim Pol.* 53, 11-32 (2006).
29. Bellot, G., McClintock, M. A., Lin, C. X., Shih, W. M. Recovery of intact DNA nanostructures after agarose gel-based separation. *Nat. Methods.* 8, 192-194 (2011).
30. Liu, M., Fu, J., Hejesen, C., Yang, Y., Woodbury, N. W., Gothelf, K., Liu, Y., and Yan, H. A DNA Tweezer-Actuated Enzyme Nanoreactors, *Nat. Commun.* 6, 712-719 (2013).
31. Fu, J., Yang, Y. R., Johnson-Buck, A., Liu, Y., Walter, N. G., Woodbury, N. W., and Yan, H. Multi-enzyme complexes on DNA scaffolds capable of substrate channeling with an artificial swinging arm, *Nature Nanotechnol.* 9, 531-536 (2014).
32. Hecht, H. J., Kalisz, K., Hendle, J., Schmid, R. D., Schomburg, D. Crystal structure of glucose oxidase from *Aspergillus niger* refined at 2-3 Å resolution. *J. Mol. Biol.* 229, 153-172 (1993).
33. Henriksen, A., Schuller, D. J., Gajhede, M. Structural interactions between horseradish peroxidase C and the substrate benzohydroxamic acid determined by X-ray crystallography. *Biochemistry* 37, 8054-8060 (1998).
34. Widom, J. R., Dhakal, S., Heinicke, L. A. & Walter, N. G. Single-molecule tools for enzymology, structural biology, systems biology and nanotechnology: an update. *Arch. Toxicol.* 88, 1965-1985 (2014).
35. Veitch, N. C. Horseradish peroxidase: a modern view of a classic enzyme. *Phytochemistry* 65, 249-259 (2004).
36. Chapman, A. D., Cortes, A., Dafforn, T. R., Clarke, A. R. & Brady, R. L. Structural basis of substrate specificity in malate dehydrogenases: crystal structure of a ternary complex of porcine cytoplasmic malate dehydrogenase, alpha-ketomalonate and tetrahydoNAD. *J Mol Biol.* 285, 703-712 (1999).
37. Rowland, P., Basak, A. K., Gover, S., Levy, H. R. & Adams, M. J. The three-dimensional structure of glucose 6-phosphate dehydrogenase from *Leuconostoc mesenteroides* refined at 2.0 A resolution. *Structure* 15, 1073-1087 (1994).
38. Lovell, S. L. & Winzor, D. J. Effects of phosphate on the dissociation and enzymic stability of rabbit muscle lactate dehydrogenase. *Biochemistry* 13, 3527-3531 (1974).
39. Hecht, H. J., Kalisz, H. M., Hendle, J., Schmid, R. D. & Schomburg D. Crystal structure of glucose oxidase from *Aspergillus niger* refined at 2.3 A resolution. *J Mol Biol.* 229, 153-172 (1993).

40. Jacobson, R. H., Zhang, X. J., DuBose, R. F. & Matthews, B. W. Three-dimensional structure of beta-galactosidase from *E. coli. Nature* 369, 761-766 (1994).
41. Erkelenz, M., Kuo, C. H. & Niemeyer, C. M. DNA-Mediated Assembly of Cytochrome P450 BM3 Subdomains, *J Am. Chem. Soc.* 133, 16111-16118 (2011).
42. Rudiuk, S., Venancio-Marques, A. & Baigl, D. Enhancement and modulation of enzymatic activity through higher-order structural changes of giant DNA-protein multibranch conjugates. *Angew. Chem. Int. Ed.* 51, 12694-12698 (2012).
43. English, B. P., et al. Ever-fluctuating single enzyme molecules: Michaelis-Menten equation revisited. *Nat. Chem. Bio.* 2, 87-94 (2006).
44. Liu, B., Baskin, R. J. & Kowalczykowski, S. C. NA unwinding heterogeneity by RecBCD results from static molecules able to equilibrate. *Nature* 500, 482-485 (2013).
45. Ramanathan, A., Savol, A., Burger, V., Chennubhotla, C. S. & Agarwal, P. K. Protein Conformational Populations and Functionally Relevant Substrates. *Acc. Chem. Res.* 47, 149-156 (2014).
46. Hammes, G. G., Benkovic, S. J. & Hammes-Schiffer, S. Flexibility, Diversity, and Cooperativity: Pillars of Enzyme Catalysis. *Biochemistry* 50, 10422-10430 (2011).
47. Ramanathan, A. & Agarwal P. K. Evolutionarily Conserved Linkage between Enzyme Fold, Flexibility, and Catalysis. *PLoS Biol.* 9, 1-17 (2011).
48. Timm, C. & Niemeyer, C. M. Assembly and Purification of Enzyme-Functionalized DNA Origami Structures. *Angew. Chem. Int. Ed.* 54, 6745-6750 (2015).
49. Lin, J. & Wheeldon, I. Kinetic Enhancements in DNA-Enzyme Nanostructures Mimic the Sabatier Principle *ACS Catal.* 3, 560-564 (2013).
50. Gao, Y., Roberts, C. C., Zhu, J., Lin, J., Chang, C. A. & Wheeldon, I. Tuning Enzyme Kinetics through Designed Intermolecular Interactions Far from the Active Site. *ACS Catal.* 5, 2149-2153 (2015).
51. Zhao, H. Effects of ions and other compatible solutes on enzyme activity, and its implication for biocatalysis using ionic liquids. *J. Mol. Catal. B-Enzym.* 37, 16-25 (2005).
52. Moelberta, S., Normandb, B. & Rios, P. D. L. Kosmotropes and chaotropes: modelling preferential exclusion, binding and aggregate stability. *Biophys. Chem.* 112, 45-57 (2004).
53. N Leberman, R. & Soper, A. K. Effect of high salt concentrations on water structure. *Nature* 378, 364-366 (1995).
54. N Jana, B., Pal, S., Maiti. P. K., Lin. S., Hynes, J. T. & Bagchi, B. Entropy of Water in the Hydration Layer of Major and Minor Grooves of DNA. *J. Phys. Chem. B* 110, 19611-19618 (2006).
55. N Chuprina, V. P., Heinemann, U., Nurislamov, A. A., Zielenkiewicz, P., Dickerson, R. E. & Saenger W. Molecular dynamics simulation of the hydration shell of a B-DNA decamer reveals two main types of minor-groove hydration depending on groove width. *Proc. Natl. Acad. Sci. USA* 88, 593-597 (1991).
56. Zhao, H., Olubajo, O., Song, Z., Sims, A. L., Person, T. E., Lawal, R. A. & Holley, L. A. Effect of kosmotropicity of ionic liquids on the enzyme stability in aqueous solutions. *Bioorg. Chem.* 34, 15-25 (2006).
57. Timasheff, S. N. Protein-solvent preferential interactions, protein hydration, and the modulation of biochemical reactions by solvent components. *Proc. Natl. Acad. Sci.* 99, 9721-9726 (2002).
58. N Levy, Y. & Onuchic, J. N. Water and proteins: A love-hate relationship. *Proc. Natl. Acad. Sci. USA* 101, 3325-3326 (2004)
59. N Grey, M. J. et al. Polyphosphate is a Primordial Chaperone. *Mol. Cell.* 53, 689-699 (2014).
60. Marcus, Y. Effects of ions on the structure of water: structure making and breaking. *Chem. Rev.* 109, 1346-1370 (2009).
61. Mei, Q., Wei, X., Su, F., Liu, Y., Yongbull, C., Johnson, R., Lindsay, S., Yan, H., Meidrum, D. Stability of DNA origami nanoarrays in cell lysate. *Nano Lett.* 11, 1477-1482 (2011).
62. Jiang, Q., Song, C., Nangreave, J., Liu, X., Lin, L., Qiu, Z., Wang, Z., Zou, G., Liang, X., Yan, H., Ding, B. DNA origami as a carrier for circumvention of drug resistance. *J. Am. Chem. Soc.* 134, 13396-13403 (2012).
63. Castello, A. et al. Insights into RNA Biology from an Atlas of Mammalian mRNA-Binding Proteins. *Cell* 149, 1393-1406 (2012)
64. Wong, C. M., Wong, K. H. and Chen, X. D. Glucose oxidase: natural occurrence, function, properties and industrial application. *Appl. Microbiol. Biotechnol.* 78, 927-38 (2008).
65. Guo, S., Cao, R., Lu, A., Zhou, Q., Lu, T., Ding, X., Li, C. and Huang, X. One of the possible mechanisms for the inhibition effect of Tb(III) on peroxidase activity in horseradish (*Armoracia rusticana*) treated with Tb(III). *J. Biol. Inorg. Chem.* 13, 587-597 (2008).
66. Sung, J. Y. & Lee, Y. N. Isoforms of glucose 6-phosphate dehydrogenase in Deinococcus radiophilus. *J. Microbiol.* 45, 318-325 (2007).
67. Horikiri, S., Aizawa, Y., Kai, T., Amachi, S., Shinoyama, H. and Fujii, T. Electron acquisition system constructed from an NAD-independent D-lactate dehydrogenase and cytochrome c2 in *Rhodopseudomonas palustris* No. 7. *Biosci. Biotechnol. Biochem.* 68, 516-522 (2004).
68. Eanes, R. Z., and Kun, E. Separation and characterization of aconitate hydratase isoenzymes from pig tissues. *Biochim. Biophys. Acta* 227, 204-210 (1971).
69. Fu, J., Liu, M., Liu, Y., Woodbury, N. W. & Yan, H. Interenzyme Substrate Diffusion for an Enzyme Cascade Organized on Spatially Addressable DNA Nanostructures. J. Am. Chem. Soc. 134, 5516-5519 (2012).
70. Liu, M., Fu, J., Hejesen, C., Yang, Y., Woodbury, N. W., Gothelf, K., Liu, Y. & Yan, H. A DNA Tweezer-Actuated Enzyme Nanoreactor. Nature Commun. 4, 1-5 (2013).
71. Abelson, J. et al. Conformational dynamics of single pre-mRNA molecules during in vitro splicing Nat. Struct. Mal. Biol. 17, 504-512 (2010).
72. Michelotti, N. et al. A bird's eye view tracking slow nanometer-scale movements of single molecular nanoassemblies. Methods Enzymol. 475, 121-148 (2010).
73. Blanco, M. & Walter, N. G. Analysis of Complex Single-Molecule FRET Time Trajectories. Method. Enzymol. 472, 153-178 (2010).
74. Gourevitch, B. & Eggermont, J. J. A nonparametric approach for detection of bursts in spike trains. Journal of Neuroscience Methods 160, 349-358 (2007).
75. Rinaldi, A. J., Lund, P. E., Blanco, M. R. & Walter, N. G. The Shine-Dalgamo sequence of riboswitch-regulated single mRNAs shows ligand-dependent accessibility bursts. Nat. Commun., 8976 (2015).

We claim:

1. A nanocage comprising:
a plurality of structural members comprising M13 viral DNA, wherein internal surfaces of the plurality of structural members form an inner cavity, wherein architectural arrangement of the structural members forms a three-dimensional body having an arrangement selected from the group consisting of a honeycomb lattice, a single-walled square lattice, and a double-walled square lattice; and
one or more payload molecules in said inner cavity.

2. The nanocage of claim 1, wherein the three dimensional body is smaller than 100 nm×100 nm×100 nm.

3. The nanocage of claim 2, wherein the three dimensional body is smaller than 75 nm×50 nm×50 nm.

4. The nanocage of claim 1, wherein the inner cavity of the three dimensional body measures less than 50 nm×50 nm×50 nm.

5. The nanocage of claim 1, wherein the three dimensional body further comprises at least one nanopore.

6. The nanocage of claim 5, wherein the at least one nanopore has a diameter of about 1 nm to about 5 nm.

7. The nanocage of claim 5, wherein the at least one nanopore has a diameter of about 1.5 nm to about 3 nm.

8. The nanocage of claim 1, wherein the three dimensional body comprises between 0.10 to 0.30 DNA helices per $nm^2$.

9. The nanocage of claim 1, wherein the three dimensional body comprises between 0.11 to 0.17 DNA helices per $nm^2$.

10. A nanoparticle comprising:
a nanocage comprising a plurality of structural members comprising DNA in a three-dimensional lattice, wherein internal surfaces of the plurality of structural members form an inner cavity; and
one or more payload molecules bound to internal surfaces of the inner cavity, wherein the one or more payload molecules comprise enzymes, nucleic acids, polypeptides, antibodies, or any combination thereof,
wherein a first structural member of the plurality of structural members is linked to a second structural member of the plurality of structural members by short bridge DNA strands,
wherein said enzymes, polypeptides, or antibodies comprise at least one lysine residue.

11. The nanoparticle of claim 10, wherein the inner cavity encapsulates two payload molecules.

12. The nanoparticle of claim 10, wherein the one or more payload molecules is covalently linked to internal surfaces of the inner cavity.

13. The nanoparticle of claim 10, wherein the nanocage blocks access of a protease to the interior of the cage to prevent proteolytic degradation of the trapped payload molecule.

14. The nanoparticle of claim 10, wherein the nanocage enhances the activity of the trapped payload molecule.

15. A method of making a nanoparticle comprising:
trapping a payload macromolecule in an open half cage comprising M13 viral DNA; and
assembling two of said open half cages into a closed nanocage having an inner cavity and nanopores; wherein the inner cavity comprises the payload macromolecule.

16. The method of claim 15, wherein the half cage comprising DNA is constructed by folding full-length M13 viral DNA.

17. The method of claim 15, wherein the half cage comprises a base and two adjoined side walls protruding from the base.

18. The method of claim 15, wherein the payload macromolecule is covalently linked to at least one of the two half cages.

19. The method of claim 15, wherein two half cages are assembled into a closed nanocage by adding short bridge DNA strands.

* * * * *